US008142994B2

(12) United States Patent
Moorhouse et al.

(10) Patent No.: US 8,142,994 B2
(45) Date of Patent: Mar. 27, 2012

(54) CLASSIFICATION, DIAGNOSIS AND PROGNOSIS OF ACUTE MYELOID LEUKEMIA BY GENE EXPRESSION PROFILING

(75) Inventors: Michael John Moorhouse, Rotterdam (NL); Petrus Jacobus Maria Valk, Rotterdam (NL); Hendrik Rudolf Delwel, Westmaas (NL); Bob Lowenberg, Rotterdam (NL); Petrus Johannes van der Spek, Lille (BE)

(73) Assignee: Erasmus University Medical Center Rotterdam, Rotterdam (NL)

( * ) Notice: Subject to any disclaimer, the term of this patent is extended or adjusted under 35 U.S.C. 154(b) by 1252 days.

(21) Appl. No.: 10/590,385

(22) PCT Filed: Feb. 23, 2005

(86) PCT No.: PCT/NL2005/000134
§ 371 (c)(1),
(2), (4) Date: Jun. 19, 2007

(87) PCT Pub. No.: WO2005/080601
PCT Pub. Date: Sep. 1, 2005

(65) Prior Publication Data
US 2008/0305965 A1    Dec. 11, 2008

(30) Foreign Application Priority Data

Feb. 23, 2004   (EP) .................................... 04075570

(51) Int. Cl.
C12Q 1/00       (2006.01)
C12Q 1/68       (2006.01)
G01N 33/53      (2006.01)
G01N 33/567     (2006.01)
G01N 33/574     (2006.01)

(52) U.S. Cl. .......... 435/4; 435/6.1; 435/6.11; 435/6.14; 435/7.1; 435/7.21; 435/7.23

(58) Field of Classification Search ..................... None
See application file for complete search history.

(56) References Cited

OTHER PUBLICATIONS

Golub et al. Molecular classification of cancer: class discovery and class prediction by gene expression monitoring. Science, vol. 286, 1999, pp. 531-537.*
Schoch et al. (PNAS Jul. 23, 2002, 99(15): 10,008-10,013.*
Kohlmann et al. (Genes, Chromosomes, & Cancer 2003 37: 396-405).*
Affymetrix (http://www.affymetrix.com/estore/, 2009).*
UniGene (HS.356623, Feb. 8, 2011).*
UniGene (HS.454253, Feb. 8, 2011).*
Human Genome Expression Profiles, Adipose Tissue Liposarcoma, available at http://telethon.bio.unipd.it/bioinfo/HGXP_170/Tissues/adipose_t_lib886.html, (last visited Jun. 2, 2011).
Human Genome Expression Profiles, Ovary Papillary Serous Carcinoma, available at http://telethon.bio.unipd.it/bioinfo/HGXP_170/Tissues/ovary_t_lib510.html (last visited Jun. 2, 2011).

* cited by examiner

Primary Examiner — Peter J Reddig
(74) Attorney, Agent, or Firm — TraskBritt

(57) ABSTRACT

The present invention relates to methods of genetic analysis for the classification, diagnosis and prognosis of acute myeloid leukemia (AML). The invention provides a method for producing a classification scheme for AML comprising the steps of a) providing a plurality of reference samples, the reference samples comprising cell samples from a plurality of reference subjects affected by AML; b) providing reference profiles by establishing a gene expression profile for each of the reference samples individually; c) clustering the individual reference profiles according to similarity; and d) assigning an AML class to each cluster. The invention further relates to a method for classifying the AML of an AML-affected subject, to a method for diagnosing AML in a subject, and to a method of determining the prognosis for an AML-affected subject.

9 Claims, 12 Drawing Sheets
(12 of 12 Drawing Sheet(s) Filed in Color)

CLASSIFICATION, DIAGNOSIS AND PROGNOSIS OF ACUTE MYELOID LEUKEMIA BY GENE EXPRESSION PROFILING

TECHNICAL FIELD

The present invention is in the field of medicine. The invention relates in particular to methods of genetic analysis for the classification, diagnosis and prognosis of acute myeloid leukemia. Also, the invention relates to nucleic acid expression profiles as obtained from cells of AML patients, which profiles by similarity group into a plurality of distinct and defined clusters that characterize different classes of AML. The invention relates to the use of such expression profiles and compositions in diagnosis and therapy of AML and specifically in the prediction of prognostically important AML classes.

The invention further relates to methods for the diagnosis of AML and for the determination of the prognosis of a subject affected by AML and to kits of parts comprising sets of nucleic acid probes suitable for performing methods of the invention either by means of genomics or proteomics.

BACKGROUND OF THE INVENTION

Acute myeloid leukemia (AML) is a collection of neoplasms with heterogeneous pathophysiology, genetics and prognosis. Based on cytogenetics and molecular analysis, AML patients are presently classified into groups or subsets of AML with markedly contrasting prognosis. For instance, the genetic translocations inv(16), t(8;21) and t(15;17) characterize AML with a relatively favorable prognosis, whereas the cytogenetically bad-risk leukemia's include patients with abnormalities involving 11q23, loss of 5(q) or 7(q), t(6;9) and t(9;22) (Löwenberg et al., 1999).

The most common molecular abnormality in AML is the internal tandem duplication (ITD) in the fms-like tyrosine kinase-3 gene (FLT3), a hematopoietic growth factor receptor (Levis & Small, 2003). FLT3 ITD mutations confer a bad prognosis to AML patients (Levis & Small, 2003). AML patients with mutations in the transcription factor cEBPa have been associated with good outcome (Preudhomme et al., 2002; van Waalwijk van Doorn-Khosrovani et al., 2003), while elevated expression of the transcription factor EVI1 predicts for notoriously poor survival (van Waalwijk van Doorn-Khosrovani et al., 2003). These examples of novel molecular prognostic markers underscore the importance of an extension of molecular analyses in AML.

Approximately thirty percent of all patients with acute myeloid leukemia (AML) are currently classified based on specific abnormal karyotypes in groups with either good or bad prognosis. The remaining seventy percent of patients, however, are not classifiable because of the lack of cytogenetic markers.

One of the aims of the present invention is to provide more accurate risk assessment tools for the diagnosis of AML. It is another aim to classify AML patients in which specific abnormal karyotypes have not been found and to distinguish these groups not only from the molecularly well-defined AML classes, but also to define prognostic subgroups within these unclassified AML types. The presence of additional prognostic classes in AML, not recognizable with currently available methods, may provide important insights into their pathophysiology. Therefore, it is an aim of the present invention to provide a more complete way of prognostication to patients with AML.

SUMMARY OF THE INVENTION

The present invention is based on the discovery that unique correlations within gene expression profiles and also with cytogenetic aberrations can be recognized with high accuracy within a representative cohort of AML patients. It has, for instance, been found that gene expression profiles obtained from a large number of AML patients can be clustered according to similarity. This enables the recognition of distinct classes of AML with similar expression profiles characterizing such a class. It was thus found that AML could be classified into distinct subclasses, each subclass being characterized by a specific clustering of gene expression profiles. Further, it was found that truly discriminative genes for most of these classes or clusters could be identified, a cluster, for instance, being characterized therein that the expression of multiple genes is up-regulated or down-regulated in that cluster whereas their expression in another cluster is unaffected.

Based on these findings, the present invention now provides in a first aspect a method for producing a classification scheme for AML comprising the steps of:
  a) providing a plurality of reference samples, the reference samples comprising cell samples from a plurality of reference subjects affected by AML;
  b) providing reference profiles by establishing a gene expression profile for each of the reference samples individually;
  c) clustering the individual reference profiles according to similarity, and
  d) assigning an AML class to each cluster.

In a preferred embodiment of such a method, the clustering of reference profiles is performed based on the information of genes that are differentially expressed between profiles, and in an even more preferred embodiment of such a method, the clustering of the reference profiles is performed on the basis of the information of the genes of Table 1, still more preferably of the genes of Table 2, which tables are provided hereinbelow.

In a further aspect, the present invention provides a method for classifying the AML of an AML-affected subject, comprising the steps of:
  a) providing a classification scheme for AML by producing such a scheme according to the method of any one of claims 1-3;
  b) providing a subject profile by establishing a gene expression profile for the subject;
  c) clustering the subject profile together with the reference profiles;
  d) determining in the scheme the clustered position of the subject profile among the reference profiles, and
  e) assigning to the AML of the subject the AML class that corresponds to the clustered position in case the subject profile is within any cluster of reference profiles, or assigning to the AML of the subject a new AML class.

In yet a further aspect, the present invention provides a method for diagnosing AML in an AML-affected subject comprising:
  a) producing a classification scheme for AML according to a method of the invention;
  b) defining cluster-specific genes for each cluster by selecting those genes of which the expression level characterizes the clustered position of the corresponding AML class among the various AML classes within the scheme;

c) determining the level of expression of a sufficient number of the cluster-specific genes in an AML-affected subject;

d) establishing whether the level of expression of the cluster-specific genes in the subject shares sufficient similarity to the level of expression that characterizes an individual AML class to thereby determine the presence of AML corresponding to the class in the subject.

In one embodiment of such a method for diagnosing AML, the cluster-specific genes may comprise all genes comprised in the gene expression profile. In a preferred embodiment of such a method, the cluster-specific genes comprise a set of 1 to 3000 genes of the genes of Table 1, more preferably 1 to 600 genes of the genes of Table 1, still more preferably 1 to 50 genes of the genes of Table 1. In an even more preferred embodiment the cluster-specific genes comprise a set of 1 to 600 genes of the genes of Table 2, still more preferably 1 to 50 genes of the genes of Table 2, and even more preferably 1 to 25 genes of the genes of Table 2. Most preferred in such a method is the use of the differentially expressed genes as shown in Table 3 for the diagnosis of a specific AML class in a subject.

In yet another aspect, the present invention provides a method of determining the prognosis for an AML-affected subject, the method comprising the steps of:

a) providing a classification scheme for AML by producing such a scheme according to a method of the invention;

b) determining the prognosis for each AML class in the scheme based on clinical records for the AML subjects comprised in the class;

c) establishing the AML class of an AML-affected subject by diagnosing and/or classifying AML in the subject according to a method of the invention, and d) assigning to the subject the prognosis corresponding to the established AML class of the AML-affected subject.

The present invention further provides a classification scheme for AML, the scheme comprising a plurality of distinct AML classes that are differentiated on the basis of similarity clustering of gene expression profiles obtained from a plurality of reference subjects affected by AML.

The classification scheme is, for instance, obtainable by a method of the invention for producing such a scheme. Preferably, the classification scheme is obtained by a method involving K-means clustering of gene expression profiles based on, for instance, gene chip array-acquired values for hybridization intensities for each gene, such as, for instance, those obtainable by using an Affymetrix gene chip.

Analysis of gene expression profiles obtained by using such gene chips preferably involves log 2 transformation of all intensity values in order to detect subtle modulations between the various genes. For each gene the geometric mean (i.e., the mean expression value determined for all individual genes in all profiles to be analyzed) is calculated. Deviation from this geometric mean is termed differential expression. Genes that are expressed at values allowing assignment of being differentially expressed are used for hierarchical clustering. Subsequently the gene signatures (characteristic expression profiles) of all samples/patients are compared with each other by means of a Pearson correlation coefficient analysis showing the (pathway) resemblance within clinical distinct groups of the total patient population.

The present invention further provides genes that are modulated (up- and down-regulated) in AML compared to the geometric mean calculated from all patients. Such genes and the proteins they encode are useful for diagnostic and prognostic purposes, and may also be used as targets for screening therapeutic compounds that modulate AML, such as antibodies. The methods of detecting nucleic acids of the invention or their encoded proteins can be used for a number of purposes. Examples include early detection of AML, monitoring and early detection of relapse following treatment of AML, monitoring response to therapy of AML, determining prognosis of AML, directing therapy of AML, selecting patients for postoperative chemotherapy or radiation therapy, selecting therapy, determining tumor prognosis, treatment, or response to treatment, and early detection of precancerous condition. Other aspects of the invention will become apparent to the skilled artisan by the following description of the invention.

In one aspect, the present invention provides a method of detecting an AML-associated transcript in one or more cells from a patient, the method comprising contacting a biological sample from the patient with a polynucleotide, such as an oligonucleotide, that selectively hybridizes to a sequence at least 80% identical to a sequence of a gene as shown in Tables 1 or 2. In one embodiment, the polynucleotide selectively hybridizes to a sequence at least 95% identical to a sequence of a gene as shown in Tables 1 or 2. In another embodiment, the polynucleotide comprises a sequence of a gene as shown in Tables 1 or 2.

In one embodiment, the biological sample used in such methods of detection is a tissue sample. In another embodiment, the biological sample comprises isolated nucleic acids, e.g., mRNA. In one embodiment, the polynucleotide is labeled, e.g., with a fluorescent label. In one embodiment, the polynucleotide is immobilized on a solid surface.

DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
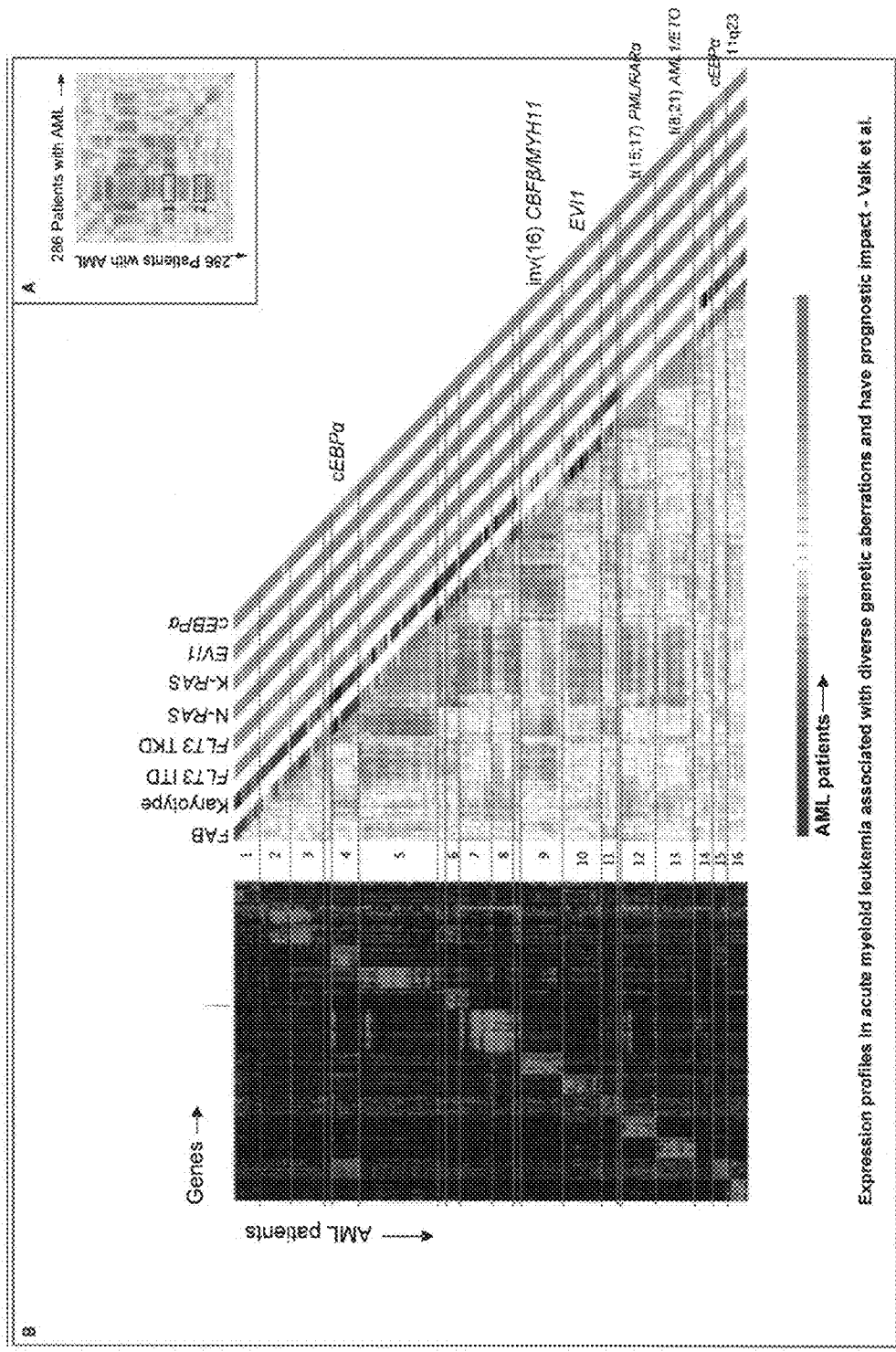
FIG. 1 shows, in panel (A), a Correlation View of 286 AML patients. The Correlation Visualization tool displays pairwise correlations between the samples. The patient samples in the visualization are colored by Pearson's correlation coefficient values with deeper colors indicating higher positive (red) or negative (blue) correlations, indicating similarity in the underlying pathway indicative for the subgroups reflecting the heterogeneity within the patient population. The scale bar indicates 100% correlation (red) towards 100% anti correlation (blue). In order to reveal correlation patterns, a matrix ordering method is applied to rearrange the samples. The ordering algorithm starts with the most correlated sample pair and, through an iterative process, sorts all the samples into correlated blocks. Each sample is joined to a block in an ordered manner so that a correlation trend is formed within a block with the most correlated samples at the center. The blocks are then positioned along the diagonal of the plot in a similar ordered manner.

Panel (B) of FIG. 1 shows an adapted Correlation View of 286 AML patients (right panel) and top40 genes defining the 16 individual clusters of patients (left panel). All 16 clusters identified on the basis of the Correlation View are indicated (1 to 16). FAB classification and karyotype based on cytogenetics are depicted in the columns along the original diagonal of the Correlation View (FAB M1-green, M2-purple, M3-orange, M4-yellow, M5-blue, M6-grey; karyotype: normal-green, inv(16)-yellow, t(8;21)-purple, t(15;17)-orange, 11q23 abnormalities-blue, other-grey). FLT3 ITD, FLT3 TKD, N-RAS, K-RAS and cEBRα mutations and EVI1 over-expression are depicted in the same set of columns (red bar: positive and green bar: negative). The expression levels of the top40 genes identified by Significance Analysis of Microarrays (SAM) analyses of each of the 16 clusters are visualized in the left panel. The scale bar indicates four-fold up-regulation-(red) towards four-fold down-regulation (green) relative to the geometric mean of all samples.

Figure 2:
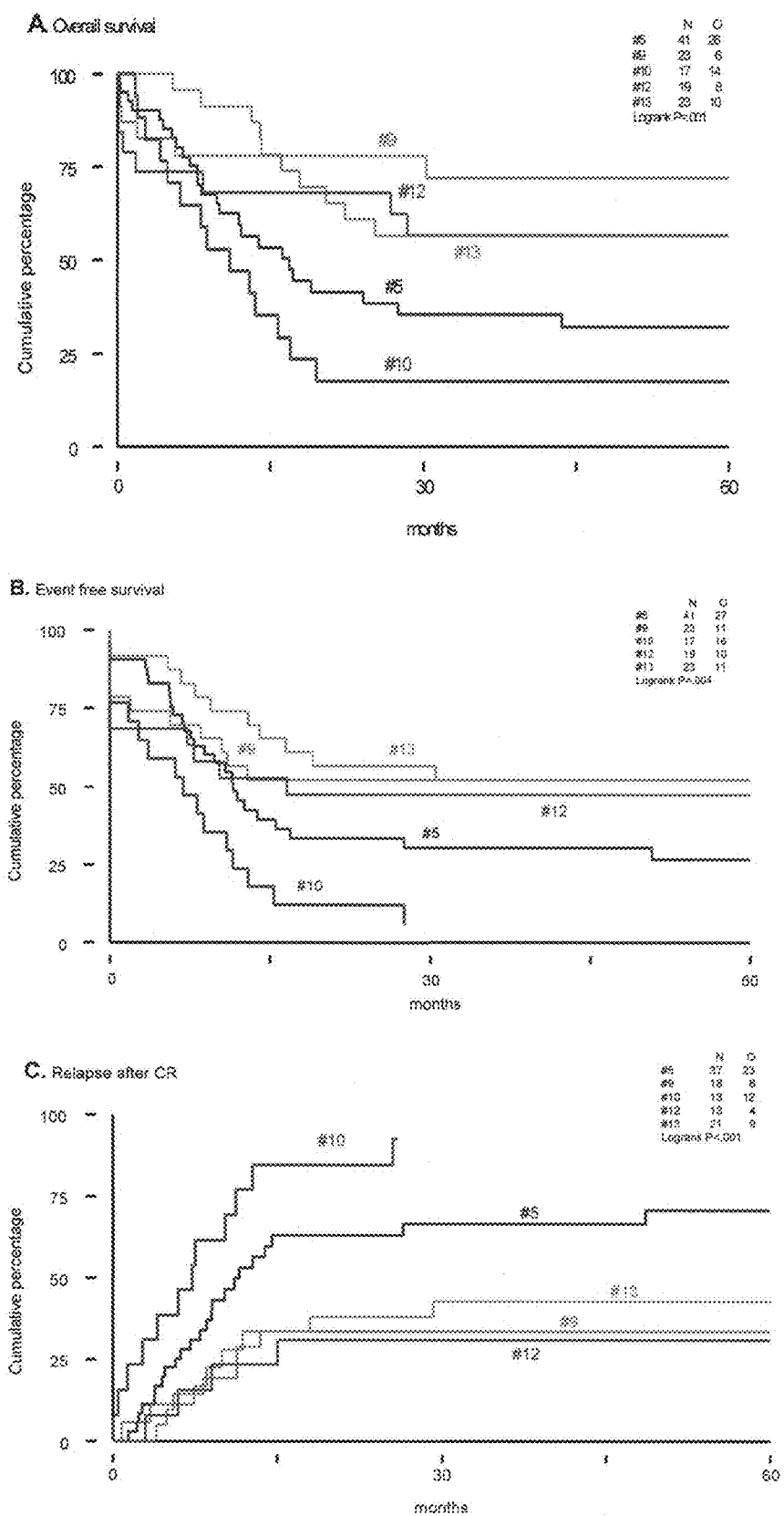

FIG. 2 shows the overall survival (panel A), event free survival (panel B) and relapse rate after CR (panel C) of AML patients in cluster #5 (M4/M5), cluster #9 (inv(16)), cluster #10 (EVI1/monosomy 7), cluster #12 (t(15;17)) and cluster #13 (t(8;21)), indicating that expression profiles in acute myeloid leukemia associate with diverse genetic aberrations and have prognostic impact.

Figure 3:
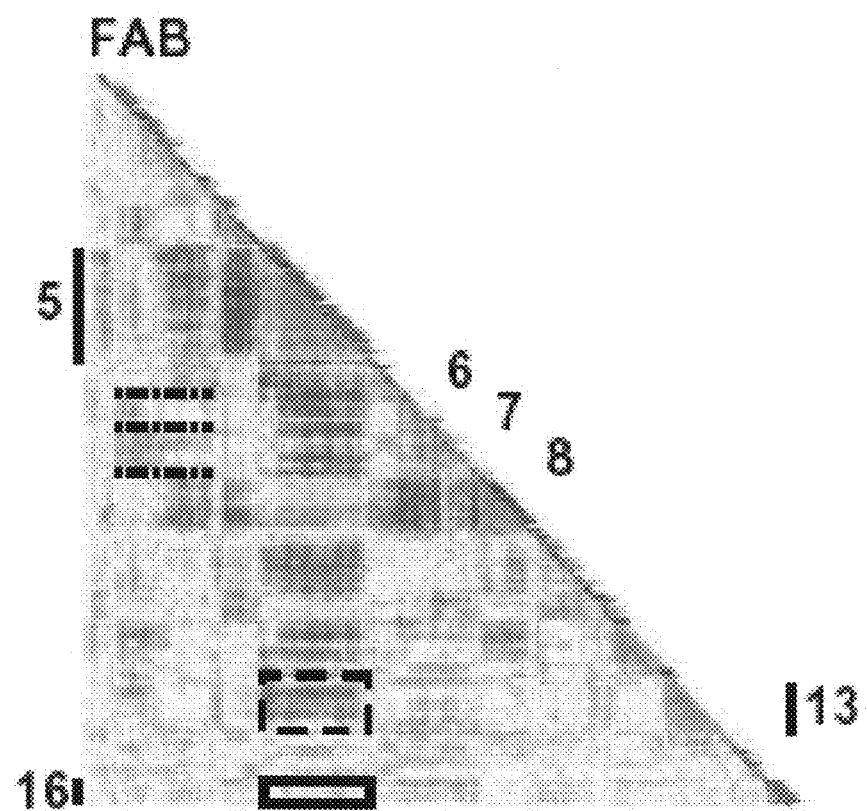

FIG. 3 provides a guideline on how to read the Omniviz Correlation View. The figure shows the Correlation View and FAB classification (right-hand edge of figure) of the cohort of 286 AML patients (2856 probe sets). A total of 16 distinct cluster can be identified on the right edge of the figure. X-axis and Y-axis show the regions of the various clusters 1-16 from top to bottom and from left to right, respectively. An exemplary correlation between cluster #5 and #16 is indicated by rectangle. Both clusters predominantly consist of AML-M5 (not visible) and correlate. However, they do form separate clusters. Anti-correlation, for instance, between cluster 5 and cluster #13, which merely contains AML-M2, is indicated by the dashed rectangle. Correlation and anti-correlation between every individual (sub)cluster can be extracted from the Correlation View and (sub)clusters can subsequently be assigned, e.g., cluster #6, #7 and #8 (dotted lines). FAB: M0-bright green, M1-green, M2-pink, M3-orange, M4-purple, M5-turquoise, M6-yellow (with number).

Figure 4:
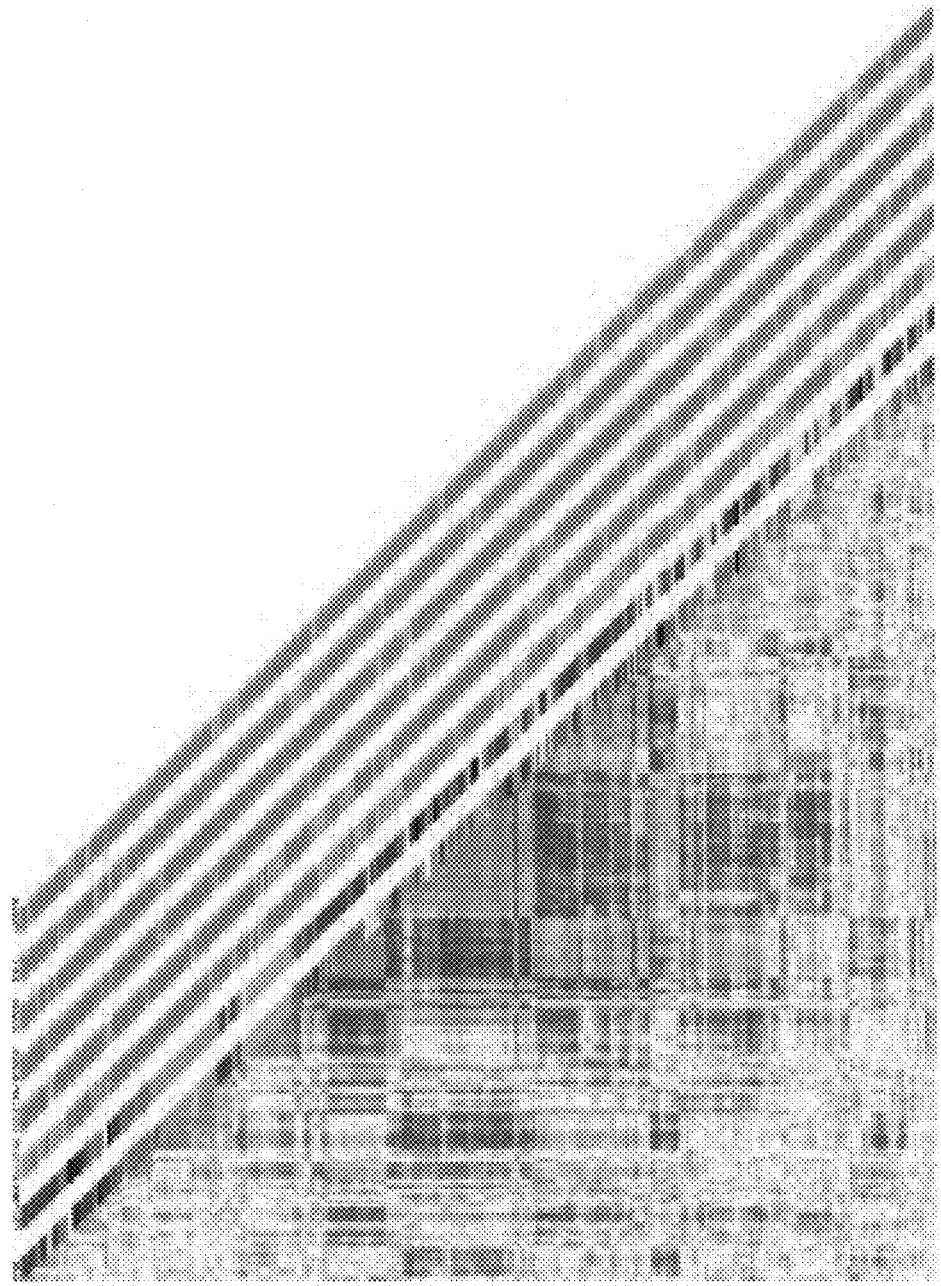
Figure 5:
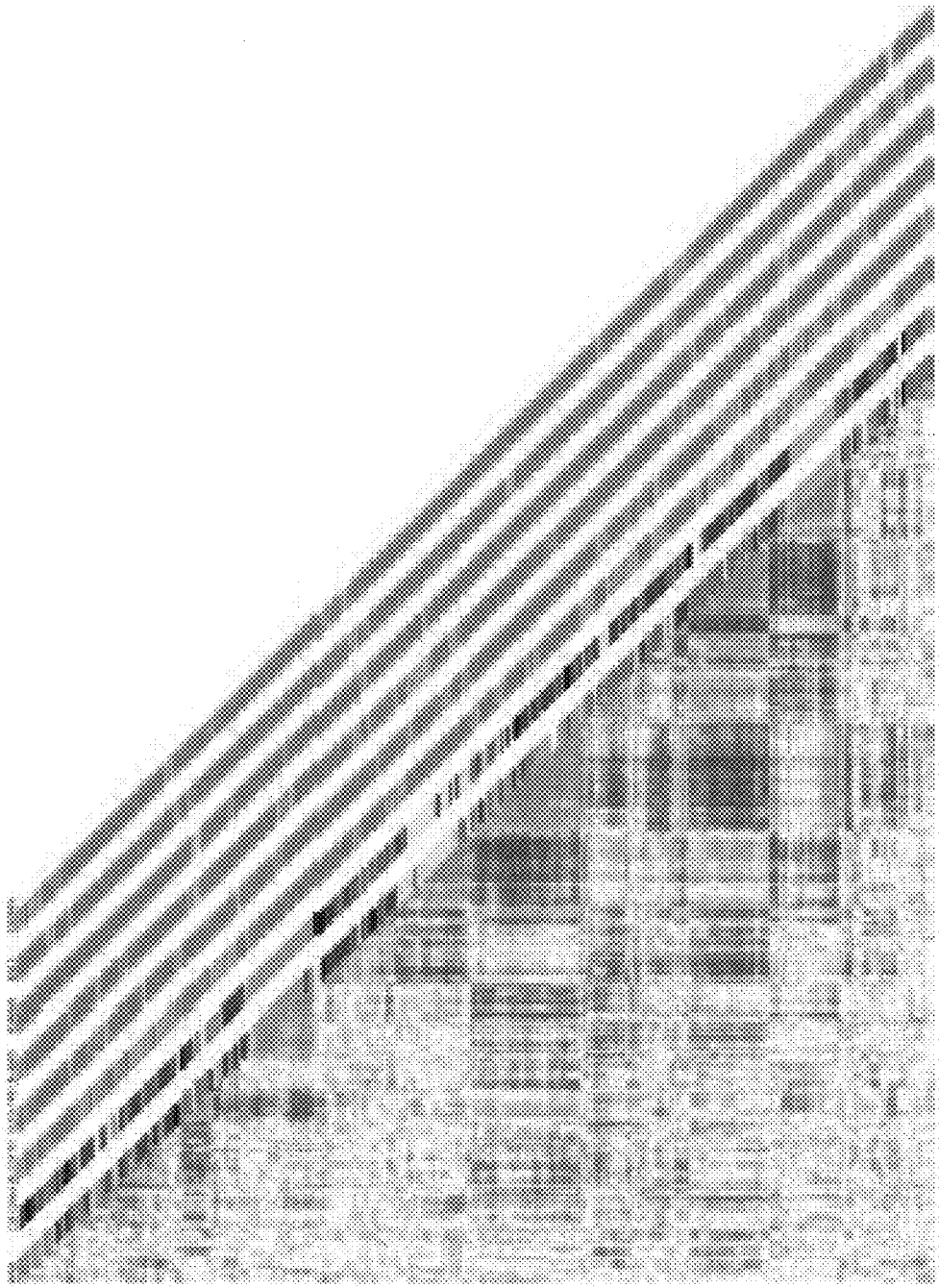
Figure 6:
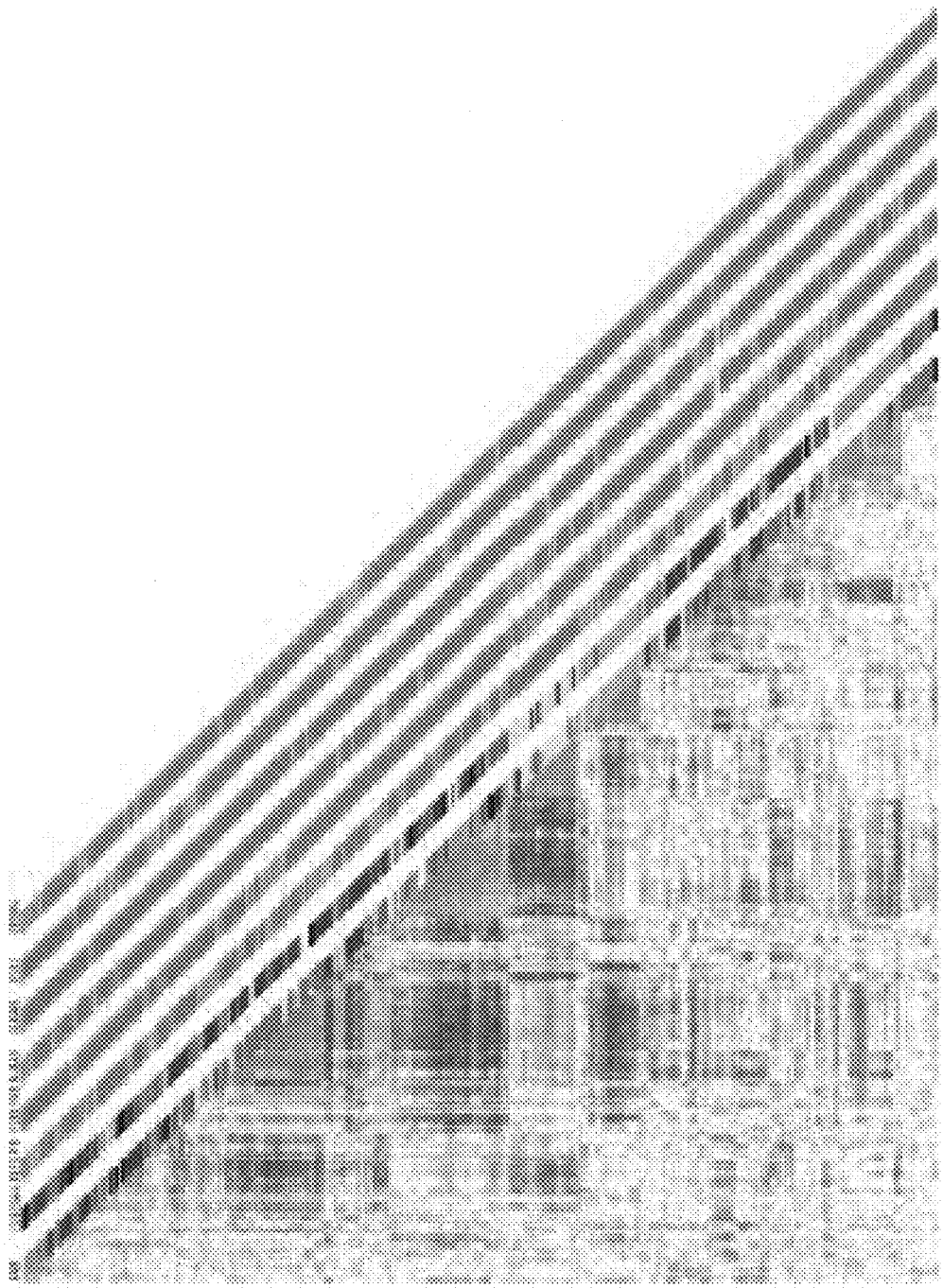
Figure 7:
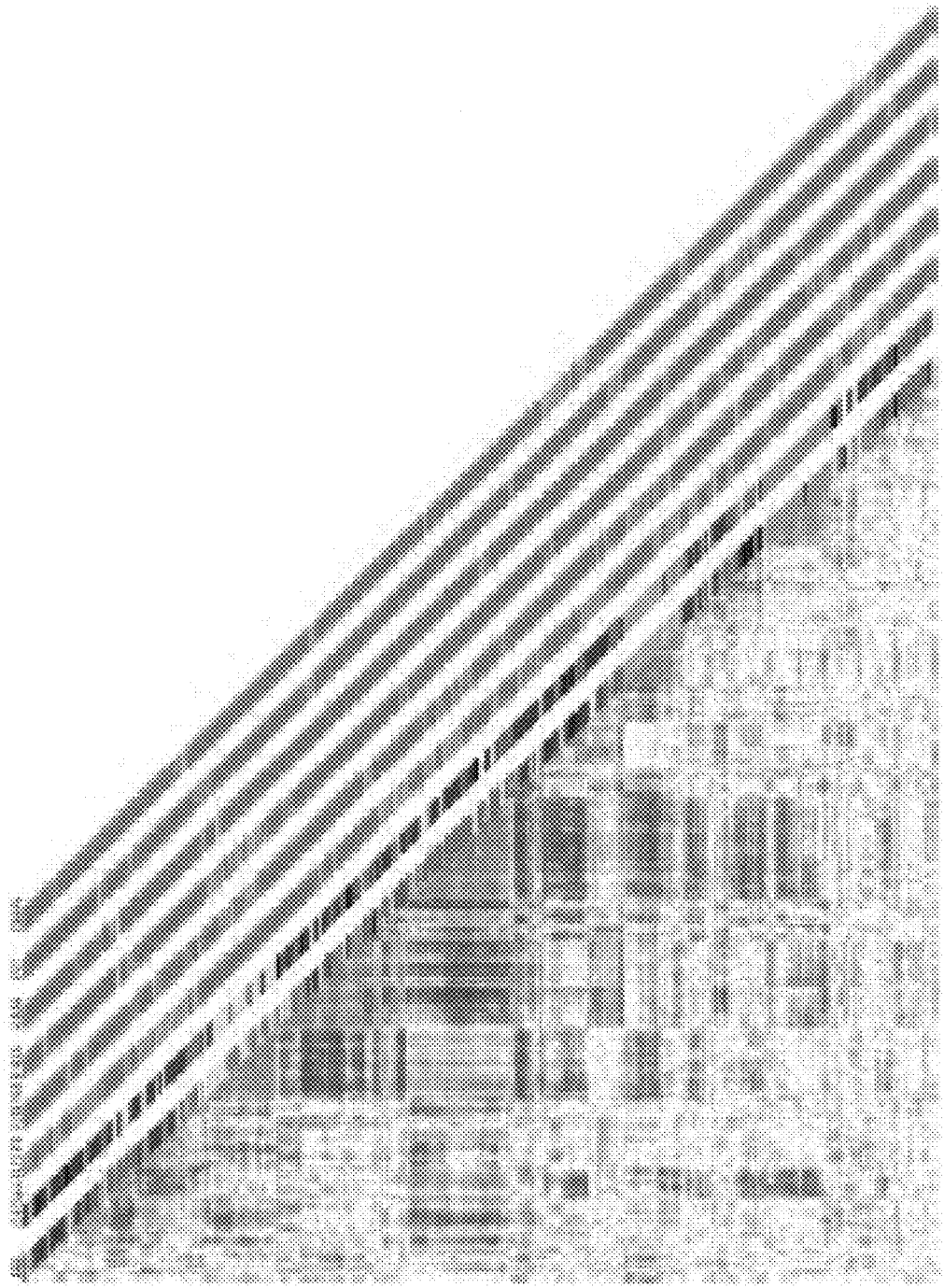
Figure 8:
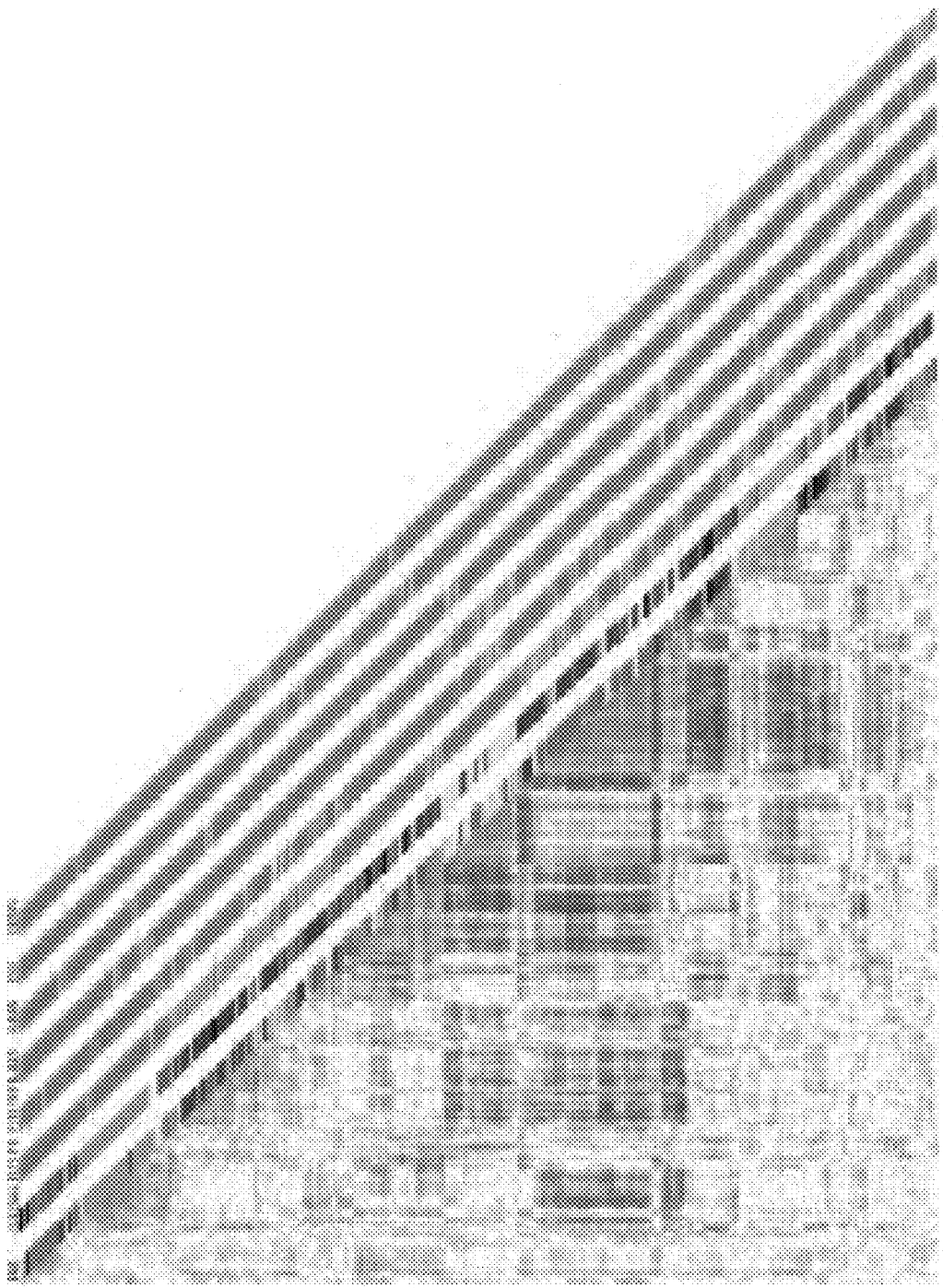
Figure 9:
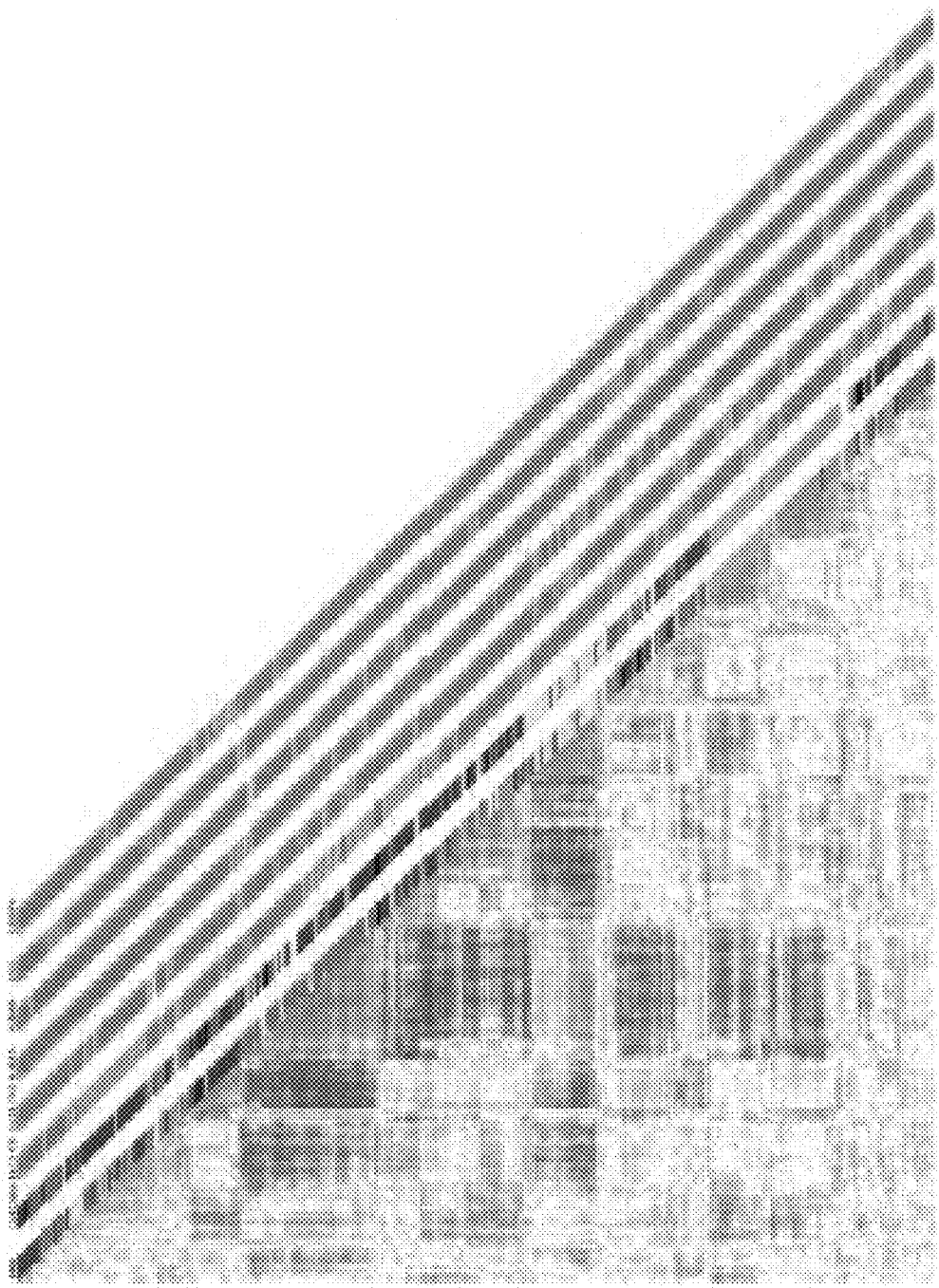
Figure 10:
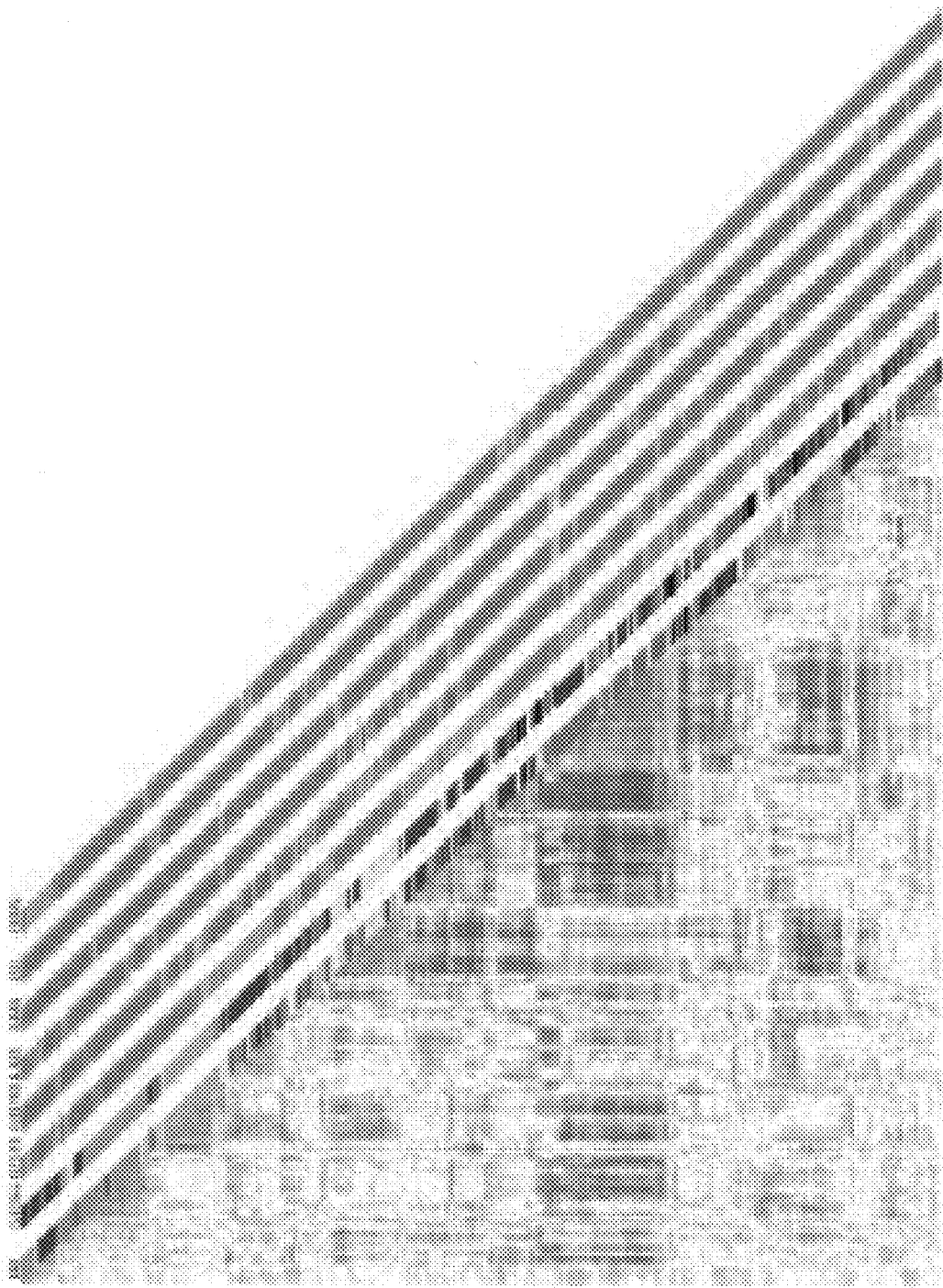

FIGS. 4-10 provide supporting results of the Pearson's correlation coefficient analyses using Omniviz with different probe subsets. In the Correlation View all 286 patients are plotted against all 286 AML patients. FAB classification and karyotype based on cytogenetics are depicted in the columns along the original diagonal (left-hand edge) of the Correlation View (FAB M0-red, M1-green, M2-purple, M3-orange, M4-yellow, M5-blue, M6-grey; karyotype: normal-green, inv (16)-yellow, t(8;21)-purple, t(15;17)-orange, 11q23 abnormalities-blue, 7(q) abnormalities-red, +8-pink, complex-black, other-grey). FLT3 ITD, FLT3 TKD, N-RAS, K-RAS and cEBPα mutations and EVI1 overexpression are depicted in the same set of columns (red bar: positive and green bar: negative). FIG. 4: 147 probe; FIG. 5: 293 probe sets; FIG. 6: 569 probe sets; FIG. 7: 984 probe sets; FIG. 8: 1692 probe sets; FIG. 9: 2856 probe sets; FIG. 10: 5071 probe sets.

Figure 11:
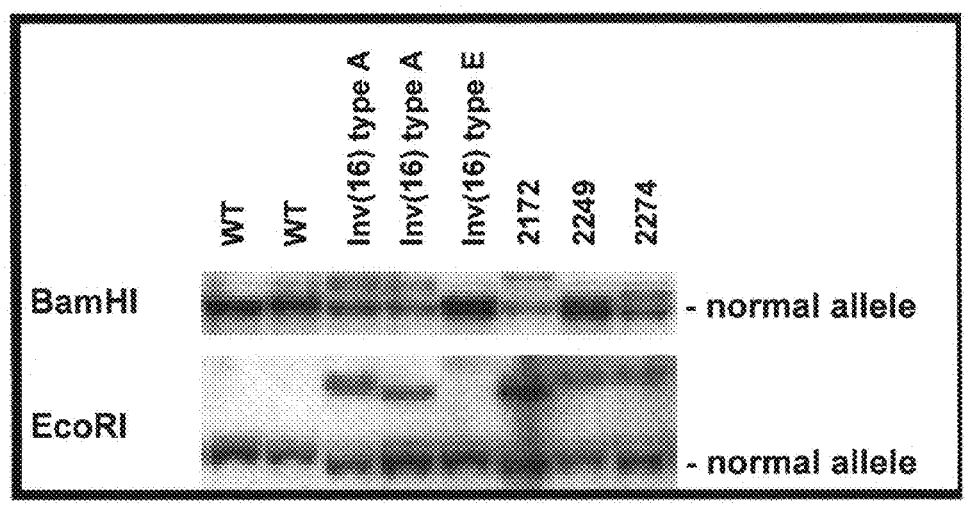

FIG. 11 shows the Southern blot analyses AML patients with cryptic inv(16). Southern blot analyses was carried out with a myosine heavy chain 11 specific probe (NT 010393, 136753-137404 nt) on material of AML (WT, no inv(16)), AML with known inv(16) breakpoint (type A and E) and three patients that clustered with all known AML and inv(16) patients in the Correlation View (FIG. 1).

Figure 12:
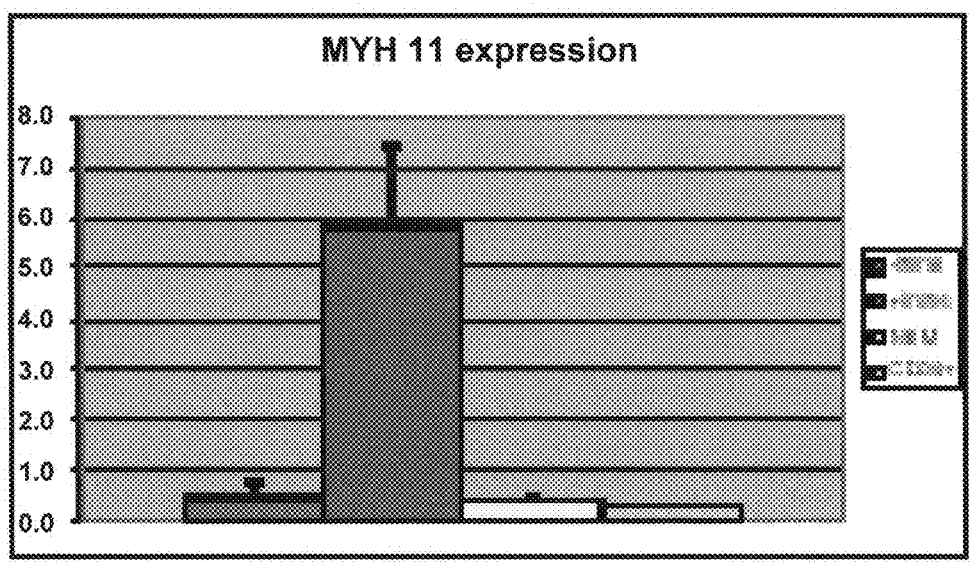

FIG. 12 shows the Expression of MYH11 as determined by Affymetrix GeneChip analyses in 286 cases of AML and controls. Expression levels of MYH11 were high in AML patients and inv(16), whereas low levels were detected in the other AML patients, CD34-positive cells and normal bone marrow.

Figure 13:
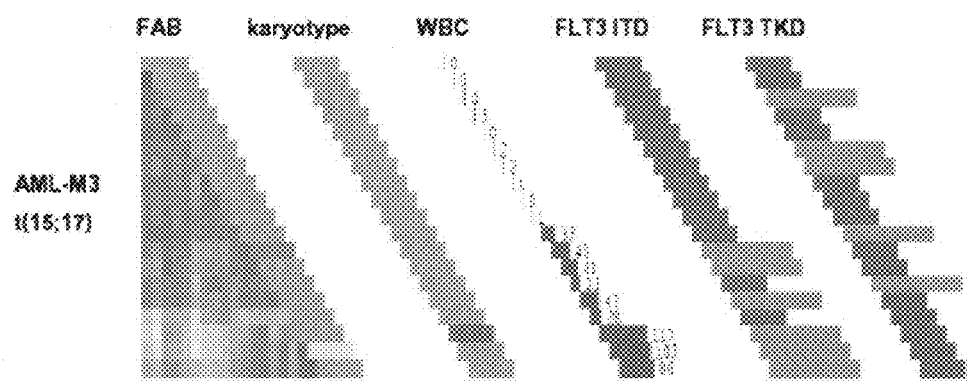

FIG. 13 shows a snapshot of Correlation View showing the AML-M3 t(15;17) patients. FAB M2-purple, M3-orange, M4-yellow. Karyotype: normal-green, t(15;17)-orange, other-grey. The AML-M3 t(15;17) patients are divided into two groups, i.e., low white blood cell count (WBC) and FLT3 ITD negative (green bar) versus high WBC/FLT3 ITD positive (red bar). Karyotype is based on cytogenetics and WBC is depicted as 10 (cells/1).

Figure 14:
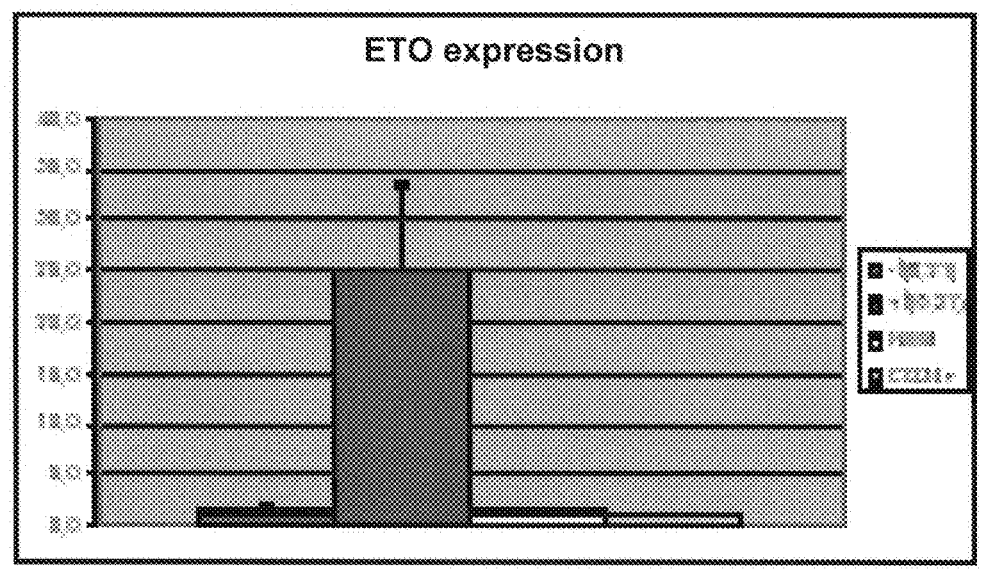

FIG. 14 shows the Expression of ETO as determined by Affymetrix GeneChip analyses in 286 cases of AML and controls. Expression levels of ETO were high in AML patients and t(8;21), whereas low levels were detected in the other AML patients, CD34-positive cells and normal bone marrow.

DETAILED DESCRIPTION OF THE INVENTION

The term "classifying" is used in its art-recognized meaning and thus refers to arranging or ordering items, i.e., gene expression profiles, by classes or categories or dividing them into logically hierarchical classes, subclasses, and sub-subclasses based on the characteristics they have in common and/or that distinguish them. In particular "classifying" refers to assigning, to a class or kind, an unclassified item. A "class" then being a grouping of items, based on one or more characteristics, attributes, properties, qualities, effects, parameters, etc., which they have in common, for the purpose of classifying them according to an established system or scheme.

The term "classification scheme" is used in its art-recognized meaning and thus refers to a list of classes arranged according to a set of pre-established principles, for the purpose of organizing items in a collection or into groups based on their similarities and differences.

The term "clustering" refers to the activity of collecting, assembling and/or uniting into a cluster or clusters items with the same or similar elements, a "cluster" referring to a group or number of the same or similar items, i.e., gene expression profiles; gathered or occurring closely together based on similarity of characteristics. "Clustered" indicates an item has been subjected to clustering.

The term "clustered position" refers to the location of an individual item, i.e., a gene expression profile, in amongst a number of clusters, the location being determined by clustering the item with at least a number of items from known clusters.

The process of clustering used in a method of to the present invention may be any mathematical process known to compare items for similarity in characteristics, attributes, properties, qualities, effects, parameters, etc. Statistical analysis, such as, for instance, multivariance analysis, or other methods of analysis may be used. Preferably, methods of analysis such as self-organizing maps, hierarchical clustering, multidimensional scaling, principle component analysis, supervised learning, k-nearest neighbors, support vector machines, discriminant analyze, partial least square methods and/or Pearson's correlation coefficient analysis are used. In another preferred embodiment of a method of the present invention Pearson's correlation coefficient analysis, significance analysis of microarrays (SAM) and/or prediction analysis of microarrays (PAM) are used to cluster gene expression profiles according to similarity. A highly preferred method of clustering comprises similarity clustering of gene expression profiles, wherein the expression level of differentially expressed genes, having markedly lower or higher expression than the geometric mean expression level determined for all genes in all profiles to be clustered, is log(2) transformed, and wherein the transformed expression levels of all differentially expressed genes in all profiles to be clustered is clustered by using K-means. A numerical query may then be used to select a subset of genes used in the process of hierarchical clustering (Eisen et al., 1998), thus, numerical queries may be run to select differentially expressed genes relative to the calculated geometric mean to select a smaller group of genes for hierarchical clustering.

Unsupervised sample clustering using genes obtained by numerical or threshold filtering is used to identify discrete clusters of samples as well as the gene-signatures associated with these clusters. The term gene signatures is used herein to refer to the set of genes that define the discrete position of the cluster apart from all other clusters, and includes cluster-specific genes. A numerical or threshold filtering is used to select genes for the analysis that are most likely of diagnostic relevance. Hierarchical clustering allows for visualization of large variation in gene expression across samples or present in most samples, and these genes could be used for unsupervised clustering so that clustering results are not affected by the noise from absent or non-changed genes.

Thus, while, K-means clustering may be performed on all genes, the Pearson correlation is preferably calculated based on a subset of genes and patients. Generally speaking the larger the threshold for accepting a deviation or change from the geometric mean, the smaller the number of genes that is selected by this filtering procedure. Different cut-off or threshold values were used to prepare lists with different numbers of genes. The higher the number of genes selected and included on such lists, the more noise is generally encountered within the dataset, because there will be a relatively large contribution of non-leukemia pathway related genes in such lists. The filtering and selection procedure is preferably optimized such that the analysis is performed on as much genes as possible, while minimizing the noise.

All genes with changed expression values higher than or equal to 1.5 times the log(2) transformed expression values and genes with changed expression values lower than or equal to −1.5 times the log(2) transformed expression values are selected for hierarchical clustering.

The subset of genes showing a markedly higher or lower expression than the geometric mean may, for instance, be a value that is more than 1.5 times the geometric mean value, preferably more than 2 times the geometric mean value, even more preferably more than 3 times the geometric mean value. Likewise, a markedly lower expression than the geometric mean expression level may, for instance, be a value that is less than 0.8 times the geometric mean value, preferably less than 0.6 times the geometric mean value, more preferably less than 0.3 times the geometric mean value.

The same selection of genes that is used for the hierarchical clustering, is used for clustering of the patients by Pearson correlation coefficient analysis.

Gene expression profiling has previously been demonstrated to be useful in distinguishing myeloid from lymphoid malignancies as well as subclasses within these diseases (Alizadeh et al., 2000; Armstrong et al., 2002; Debernardi et al., 2003; Ross et al., 2003; Yeoh; Schoch et al., 2002; Golub et al., 1999), but it was hitherto unknown whether suitable distinctions on the basis of gene expression alone could be made between various types of AML, let alone whether such distinctions could bear any relevance to prognosis of the disease.

The present invention now provides several methods to accurately identify known as well as newly discovered diagnostically, prognostically and therapeutically relevant subgroups of acute myeloid leukemia (AML), herein below also addressed as AML classes, as well as methods that can predict which approaches in treatment are likely to be effective. The basis of these methods resides in the measurement of (AML-specific) gene expression in AML-affected subjects. The methods and compositions of the invention thus provide tools useful in choosing a therapy for AML patients, including methods for assigning an AML patient to an AML class or AML cluster, methods of choosing a therapy for an AML patient, methods of determining the efficacy of a therapy in an AML patient, and methods of determining the prognosis for an AML patient.

The methods of the invention comprise in various aspects the steps of establishing a gene expression profile of subject samples, for instance, of reference subjects affected by AML or of a subject diagnosed or classified for AML. The expression profiles of the present invention are generated from samples from subjects affected by AML, including subjects having AML, subjects suspected of having AML, subjects having a propensity to develop AML, or subjects who have previously had AML, or subjects undergoing therapy for AML. The samples from the subject used to generate the expression profiles of the present invention can be derived from a variety of sources including, but not limited to, single cells, a collection of cells, tissue, cell culture, bone marrow, blood, or other bodily fluids. The tissue or cell source may include a tissue biopsy sample, a cell sorted population, cell culture, or a single cell. Sources for the sample of the present invention include cells from peripheral blood or bone marrow, such as blast cells from peripheral blood or bone marrow.

In selecting a sample, the percentage of the sample that constitutes cells having differential gene expression in AML classes should be considered. Samples may comprise at least 20%, at least 30%, at least 40%, at least 50%, at least 55%, at least 60%, at least 70%, at least 75%, at least 80%, at least 85%, at least 90%, or at least 95% cells having differential expression in AML classes, with a preference for samples having a high percentage of such cells. In some embodiments, these cells are blast cells, such as leukemic cells. The percentage of a sample that constitutes blast cells may be determined by methods well known in the art; see, for example, the methods described in WO 03/083140.

"Gene expression profiling" or "expression profiling" is used herein in its art-recognized meaning and refers to a method for measuring the transcriptional state (mRNA) or the translational state (protein) of a plurality of genes in a cell. Depending on the method used, such measurements may involve the genome-wide assessment of gene expression, but also the measurement of the expression level of selected genes, resulting in the establishment of a "gene expression profile" or "expression profile," which terms are used in that meaning hereinbelow. As used herein, an "expression profile" comprises one or more values corresponding to a measurement of the relative abundance of a gene expression product. Such values may include measurements of RNA levels or protein abundance. Thus, the expression profile can comprise values representing the measurement of the transcriptional state or the translational state of the gene. In relation thereto, reference is made to U.S. Pat. Nos. 6,040,138, 5,800,992, 6,020135, 6,344,316, and 6,033,860.

The transcriptional state of a sample includes the identities and relative abundance of the RNA species, especially mRNAs present in the sample. Preferably, a substantial fraction of all constituent RNA species in the sample are measured, but at least a sufficient fraction to characterize the transcriptional state of the sample is measured. The transcriptional state can be conveniently determined by measuring transcript abundance by any of several existing gene expression technologies.

Translational state includes the identities and relative abundance of the constituent protein species in the sample. As is known to those of skill in the art, the transcriptional state and translational state are related.

Each value in the expression profiles as determined and embodied in the present invention is a measurement representing the absolute or the relative expression level of a differentially expressed gene. The expression levels of these genes may be determined by any method known in the art for assessing the expression level of an RNA or protein molecule in a sample. For example, expression levels of RNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, to which explicit reference is made. The gene expression monitoring system may also comprise nucleic acid probes in solution.

In one embodiment of the invention, microarrays are used to measure the values to be included in the expression profiles. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, the Experimental section. See also, U.S. Pat. Nos. 6,040,138, 5,800,992 and 6,020,135, 6,033,860, and 6,344,316, to which explicit reference is made. High-density oligonucleotide arrays are particularly useful for determining the gene expression profile for a large number of RNAs in a sample.

In one approach, total mRNA isolated from the sample is converted to labeled cRNA and then hybridized to an oligonucleotide array. Each sample is hybridized to a separate array. Relative transcript levels are calculated by reference to appropriate controls present on the array and in the sample. See, for example, the Experimental section.

In another embodiment, the values in the expression profile are obtained by measuring the abundance of the protein products of the differentially expressed genes. The abundance of these protein products can be determined, for example, using antibodies specific for the protein products of the differentially expressed genes. The term "antibody" as used herein refers to an immunoglobulin molecule or immunologically active portion thereof, i.e., an antigen-binding portion. Examples of immunologically active portions of immunoglobulin molecules include F(ab) and F(ab')2 fragments which can be generated by treating the antibody with an enzyme such as pepsin. The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent. A full-length protein product from a differentially expressed gene, or an antigenic peptide fragment of the protein product can be used as an immunogen. Preferred epitopes encompassed by the antigenic peptide are regions of the protein product of the differentially expressed gene that are located on the surface of the protein, e.g., hydrophilic regions, as well as regions with high antigenicity. The antibody can be used to detect the protein product of the differentially expressed gene in order to evaluate the abundance and pattern of expression of the protein. These antibodies can also be used diagnostically to monitor protein levels in tissue as part of a clinical testing procedure, e.g., to, for example, determine the efficacy of a given therapy. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, (3-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Once the values comprised in the subject expression profile and the reference expression profile or expression profiles are established, the subject profile is compared to the reference profile to determine whether the subject expression profile is sufficiently similar to the reference profile. Alternatively, the subject expression profile is compared to a plurality of reference expression profiles to select the reference expression profile that is most similar to the subject expression profile. Any method known in the art for comparing two or more data sets to detect similarity between them may be used to compare the subject expression profile to the reference expression profiles. In some embodiments, the subject expression profile and the reference profile are compared using a supervised learning algorithm such as the support vector machine (SVM) algorithm, prediction by collective likelihood of emerging patterns (PCL) algorithm, the k-nearest neighbor algorithm, or the Artificial Neural Network algorithm. To determine whether a subject expression profile shows "statistically significant similarity" or "sufficient similarity" to a reference profile, statistical tests may be performed to determine whether the similarity between the subject expression profile and the reference expression profile is likely to have been achieved by a random event. Any statistical test that can calculate the likelihood that the similarity between the subject expression profile and the reference profile results from a random event can be used. The accuracy of assigning a subject to an AML class based on similarity between differentially expressed genes is affected largely by the heterogeneity within the patient population, as is reflected by the deviation from the geometric mean. Therefore, when more accurate diagnoses are required, the stringency in evaluating the similarity between the subject and the reference profile should be increased by changing the numerical query.

The method used for comparing a subject expression profile to one or more reference profiles is preferably carried out by re-running the subsequent analyses in a (n+1) modus by performing clustering methods as described herein. Also, in order to identify the AML class reference profile that is most similar to the subject expression profile, as performed in the methods for establishing the AML class of an AML-affected subject, i.e., by diagnosing AML in a subject or by classifying the AML in a subject, profiles are clustered according to similarity and it is determined whether the subject profile corresponds to a known class of reference profiles. In assigning a subject AML to a specific AML class, for instance, this method is used wherein the clustered position of the subject profile, obtained after performing the clustering analysis of the present invention, is compared to any known AML class. If the clustered position of the subject profile is within a cluster of reference profiles, i.e., forms a cluster therewith after performing the similarity clustering method, it is said that the AML of the subject corresponds to the AML class of reference profiles. If a subject profile is not within a cluster of reference profiles, i.e., does not form a cluster therewith after performing the similarity clustering method, then a new AML class may be assigned to that subject profile, one of such classes being subjects not having AML.

In some embodiments of the present invention, the expression profiles comprise values representing the expression levels of genes that are differentially expressed in AML classes. The term "differentially expressed" as used herein means that the measured expression level of a particular gene in the expression profile of one subject differs at least n-fold from the geometric mean calculated from all patient profiles. The expression level may be also be up-regulated or down-regulated in a sample from a subject having a particular form of AML in comparison with a sample from a subject having a different form of AML. For example, in one embodiment, the differentially expressed genes of the present invention may be expressed at different levels in different AML classes. Examples of genes that are differentially expressed in the various AML classes are shown in Tables 1 and 2.

It should be noted that many genes will occur, of which the measured expression level differs at least n-fold from the geometric mean expression level for that gene of all reference profiles. This may, for instance, be due to the different physiological state of the measured cells, to biological variation or to the present of other diseased states. Therefore, the presence of a differentially expressed gene is not necessarily informative for determining the presence of different AML classes, nor is every differentially expressed gene suitable for performing diagnostic tests. Moreover, a cluster-specific differential gene expression, as defined herein, is most likely to be informative only in a test among subjects having AML. Therefore, a diagnostic test performed by using cluster-specific gene detection should preferably be performed on a subject in which the presence of AML is confirmed. This confirmation may, for instance, be obtained by performing the method for classifying an AML in an AML-affected subject according to the present invention, or by any other test.

The present invention provides groups of genes that are differentially expressed in diagnostic AML samples of patients in different AML classes. Some of these genes were identified based on gene expression levels for 13,000 probes in 286 AML samples. Values representing the expression levels of the nucleic acid molecules detected by the probes were analyzed as described in the Experimental section using Omniviz, SAM and PAM analysis tools. Omniviz software was used to perform all clustering steps such as K-means, Hierarchical and Pearson correlation tests. SAM was used specifically to identify the genes underlying the clinically relevant groups identified in the Pearson correlation analysis. PAM is used to decide the minimum number of genes necessary to diagnose all individual patients within the given groups of the Pearson correlation.

In short, expression profiling was carried out on AML blasts from 286 de novo AML patients. Unsupervised clustering was used to identify novel (sub)groups within the Pearson correlation following the hierarchical clustering. The Pearson correlation test resulted in the identification of 16 groups or classes of AML patients with distinct molecular signatures.

The hierarchical clustering and Pearson correlation allow the detection of the genetic heterogeneity (16 clusters). This may provide for a mechanistic signature of AML. After running the SAM and PAM analysis, the diagnostic gene-signatures (including cluster-specific genes) were obtained.

While several of the molecularly assigned classes correspond to the well-defined AML subgroups with favorable cytogenetics, such as the well-recognized genetic lesions AML1/ETO, PML/RARα and CBFβ/MYH11, we identified several additional distinct classes of patients that were not identified as distinct classes of AML before. For instance, new identified AML clusters comprised genetic lesions such as CEBPα mutations, or FLT3 ITD mutations, or 11q23 aberrations, indicating that these cytogenetic markers alone are not sufficient to determine the prognosis of an AML patient or the most optimal intervention strategy (drug treatment).

Whereas the well-defined AML subgroups AML1/ETO, PML/RARα and CBFβ/MYH11, could be identified based on measurement of the expression level of only one or two genes in a cell sample, many of the newly discovered AML classes were defined on the basis of differential expression of a plurality of genes. Genes that define an AML class are hereinafter also termed cluster-specific genes or signature genes. Prediction Analysis of Microarrays (PAM) was applied to determine the minimal gene sets that predict these prognostically important clusters with high accuracy. In one of the novel clusters half of the AML patients had unfavorable markers, such as elevated expression of EVI1 and/or loss of chromosome 7(q). Interestingly, more than 90 percent of patients in this cluster (cluster no. 10, see Example) responded poorly to therapy. The fact that a distinct gene expression signature defines this class of AML patients, suggests the existence of a currently unknown gene- or pathway defect that corresponds with poor treatment outcome.

The present invention thus provides a method of classifying AML. Using this method, a total of 286 AML samples analyzed on a DNA microarray consisting of 22283 probe sets, representing approximately 13,000 genes could be classified into at least 16 distinct clusters. These 16 distinct clusters of AML patients were assigned on the basis of strong correlation between their individual differential expression profiles for 2856 probe sets (Table 1; FIG. 1). The methods used to analyze the expression level values to identify differentially expressed genes were employed such that optimal results in clustering, i.e., unsupervised ordering, were obtained. This then resulting in the definition of the 16 clusters of reference profiles based on molecular signature. The genes that defined the position or clustering of these 16 individual clusters could be determined and the minimal sets of genes required to accurately predict the prognostically important AML classes corresponding to these clusters could be derived. It should be understood that the method for classifying AML according to the present invention may result in a distinct clustering pattern and therefore in a different classification scheme when other (numbers of) subjects are used as reference, or when other types of oligonucleotide microarrays for establishing gene expression profiles are used.

The present invention thus provides a comprehensive classification of AML covering various previously identified genetically defined classes. Further analysis of classes by prediction analysis of microarrays (PAM) to determine the minimum number of genes that defined or predicted these prognostically important classes resulted in the establishment of cluster-specific genes or signature genes. The presence of distinct gene expression profiles defining the novel classes suggests the presence of yet unknown common gene defects or pathway defects among AML cases in those classes. Several classes could be distinguished on the basis of the expression level of a single gene, whereas others could only be distinguished on the basis of 20 or more differentially expressed genes (Table 3).

The methods of the present invention comprise in some aspects the step of defining cluster-specific genes by selecting those genes of which the expression level characterizes the clustered position of the corresponding AML class among the various AML classes within a classification scheme of the present invention. Such cluster-specific genes are selected preferably on the basis of PAM analysis. This method of selection comprises the following.

PAM, or partition round medoids, is one of the k-medoids methods. Different from usual k-means approach, it also accepts a dissimilarity matrix, and it is more robust because it minimizes a sum of dissimilarities instead of a sum of squared Euclidean distances. The PAM-algorithm is based on the search for "k" representative objects or medoids among the observations of the dataset, which should represent the structure of the data. After finding a set of "k" medoids, "k" clusters are constructed by assigning each observation to the nearest medoid. The goal is to find "k" representative objects that minimize the sum of the dissimilarities of the observations to their closest representative object. The distance metric to be used for calculating dissimilarities between observations are "euclidean" and "manhattan." Euclidean distances are root sum-of-squares of differences, and manhattan distances are the sum of absolute differences. PAM calculates how many genes are necessary to identify all members (patients) belonging to a certain cluster.

The methods of the present invention comprise in some aspects the step of establishing whether the level of expression of cluster-specific genes in a subject shares sufficient similarity to the level of expression that is characteristic for an individual AML class. This step is necessary in determining the presence of that particular AML class in a subject under investigation, in which case the expression of that gene is used as a disease marker. Whether the level of expression of cluster-specific genes in a subject shares sufficient similarity to the level of expression of that particular gene in an individual AML class may, for instance, be determined by setting a threshold value.

The present invention also reveals genes with a high differential level of expression in specific AML classes compared the geometric mean of all reference subjects. These highly differentially expressed genes are selected from the genes shown in Table 2. These genes and their expression products are useful as markers to detect the presence of AML in a patient. Antibodies or other reagents or tools may be used to detect the presence of these markers of AML.

The present invention also reveals gene expression profiles comprising values representing the expression levels of genes in the various identified AML classes. In a preferred embodiment, these expression profiles comprise the values representing the differential expression levels. Thus, in one embodiment the expression profiles of the invention comprise one or more values representing the expression level of a gene having differential expression in a defined AML class. Each expression profile contains a sufficient number of values such that the profile can be used to distinguish one AML class from another. In some embodiments, the expression profiles comprise only one value. For example, it can be determined whether a subject affected by AML is in the AML class defined by cluster #9 (inv(16)) based only on the expression level of MYH11 201497_x_at (see Tables 2 and 31). Similarly, it can be determined whether a subject affected by AML is in the AML class defined by cluster #12 (t(15,17)) based only on the expression level of the cDNA of 2 genes FGF 13 205110_s_at and HGF 210997_at and 210998_s_at (see Tables 2 and 34). In this case, the expression profile comprises two values corresponding to two differentially expressed genes. In other embodiments, the expression profile comprises more than one or two values corresponding to a differentially expressed gene, for example, at least 3 values, at least 4 values, at least 5 values, at least 6 values, at least 7 values, at least 8 values, at least 9 values, at least 10 values, at least 11 values, at least 12 values, at least 13 values, at least 14 values, at least 15 values, at least 16 values, at least 17 values, at least 18 values, at least 19 values, at least 20 values, at least 22 values, at least 25 values, at least 27 values, at least 30 values, at least 35 values, at least 40 values, at least 45 values, at least 50 values, at least 75 values, at least 100 values, at least 125 values, at least 150 values, at least 175 values, at least 200 values, at least 250 values, at least 300 values, at least 400 values, at least 500 values, at least 600 values, at least 700 values, at least 800 values, at least 900 values, at least 1000 values, at least 1200 values, at least 1500 values, or at least 2000 or more values.

It is recognized that the diagnostic accuracy of assigning a subject to an AML class will vary based on the number of values contained in the expression profile. Generally, the number of values contained in the expression profile is selected such that the diagnostic accuracy is at least 85%, at least 87%, at least 90%, at least 91%, at least 92%, at least 93%, at least 94%, at least 95%, at least 96%, at least 97%, at least 98%, or at least 99%, as calculated using methods described elsewhere herein, with an obvious preference for higher percentages of diagnostic accuracy.

It is recognized that the diagnostic accuracy of assigning a subject to an AML class will vary based on the strength of the correlation between the expression levels of the differentially expressed genes within that specific AML class. When the values in the expression profiles represent the expression levels of genes whose expression is strongly correlated with that specific AML class, it may be possible to use fewer number of values (genes) in the expression profile and still obtain an acceptable level of diagnostic or prognostic accuracy.

The strength of the correlation between the expression level of a differentially expressed gene and a specific AML class may be determined by a statistical test of significance. For example, the chi square test used to select genes in some embodiments of the present invention assigns a chi square value to each differentially expressed gene, indicating the strength of the correlation of the expression of that gene to a specific AML class. Similarly, the T-statistics metric and the Wilkins' metric both provide a value or score indicative of the strength of the correlation between the expression of the gene and its specific AML class. These scores may be used to select the genes of which the expression levels have the greatest correlation with a particular AML class to increase the diagnostic or prognostic accuracy of the methods of the invention, or in order to reduce the number of values contained in the expression profile while maintaining the diagnostic or prognostic accuracy of the expression profile. Preferably, a database is kept wherein the expression profiles of reference subjects are collected and to which database new profiles can be added and clustered with the already existing profiles such as to provide the clustered position of the new profile among the already present reference profiles. Furthermore, the addition of new profiles to the database will improve the diagnostic and prognostic accuracy of the methods of the invention. Preferably, in a method of the present invention SAM or PAM analysis tools are used to determine the strength of such correlations.

The methods of the invention comprise the steps of providing an expression profile from a sample from a subject affected by AML and comparing this subject expression profile to one or more reference profiles that are associated with a particular AML class, a class with a known prognosis, or a class with a favorable response to therapy. By identifying the AML class reference profile that is most similar to the subject expression profile, e.g., when their clustered positions fall together, the subject can be assigned to an AML class. The AML class assigned is that with which the reference profile(s) are associated. Similarly, the prognosis of a subject affected by AML can be predicted by determining whether the expression profile from the subject is sufficiently similar to a reference profile associated with an established prognosis, such as a good prognosis or a bad prognosis. Whenever a subject's expression profile can be assigned to an established AML class, a preferred intervention strategy, or therapeutic treatment can then be proposed for the subject, and the subject can be treated according to the assigned strategy. As a result, treatment of a subject with AML can be optimized according to the specific class of AML with which the subject is affected. For instance, the AML class belonging to cluster #12, characterized by the presence of t(15,17), may be treated with retinoic acid. Within one class or cluster, further division may be made according to responders and non-responders to treatment or therapy. Such divisions may provide for further detailed characterization of AML subjects. In another embodiment, the subject expression profile is from a subject affected by AML who is undergoing a therapy to treat the AML. The subject expression profile is compared to one or more reference expression profiles to monitor the efficacy of the therapy.

In some embodiments, the assignment of a subject affected by AML to an AML class is used in a method of choosing a therapy for the subject affected by AML. A therapy, as used herein, refers to a course of treatment intended to reduce or eliminate the affects or symptoms of a disease, in this case AML. A therapy regime will typically comprise, but is not limited to, a prescribed dosage of one or more drugs or hematopoietic stem cell transplantation. Therapies, ideally, will be beneficial and reduce the disease state but in many instances, the effect of a therapy will have non-desirable effects as well.

In one aspect, the present invention provides a method of determining the prognosis for an AML-affected subject, the method comprising the steps of providing a classification scheme for AML by producing such a scheme according to a method of the invention and determining the prognosis for each AML class in the scheme based on clinical records for the AML subjects comprised in the class. In order to predict the progression of the disease in a subject, one has to rely on clinical records. The present invention provides for the assignment of the various clinical data recorded with reference subjects affected by AML to the various AML classes as defined herein. This assignment preferably occurs in a database. This has the advantage that once a new subject is identified as belonging to a particular AML class, either by performing a specific AML diagnostic method of the invention using the cluster-specific genes as disease markers or by performing a method of classifying an AML in an AML-affected subject according to the invention, then the prognosis that is assigned to that class may be assigned to that subject.

The present invention provides compositions that are useful in determining the gene expression profile for a subject affected by AML and selecting a reference profile that is similar to the subject expression profile. These compositions include arrays comprising a substrate having capture probes that can bind specifically to nucleic acid molecules that are differentially expressed in AML classes. Also provided is a computer-readable medium having digitally encoded reference profiles useful in the methods of the claimed invention.

The present invention provides arrays comprising capture probes for detection of polynucleotides (transcriptional state) or for detection of proteins (translational state) in order to detect differentially expressed genes of the invention. By "array" is intended a solid support or substrate with peptide or nucleic acid probes attached to the support or substrate. Arrays typically comprise a plurality of different nucleic acid or peptide capture probes that are coupled to a surface of a substrate in different, known locations. These arrays, also described as "microarrays" or colloquially "chips" have been generally described in the art, and reference is made U.S. Pat. Nos. 5,143,854, 5,445,934, 5,744,305, 5,677,195, 6,040,193, 5,424,186, 6,329,143, and 6,309,831 and Fodor et al. (1991) Science 251:767-77. These arrays may generally be produced using mechanical synthesis methods or light directed synthesis methods which incorporate a combination of photolithographic methods and solid phase synthesis methods. Typically, "oligonucleotide microarrays" will be used for determining the transcriptional state, whereas "peptide microarrays" will be used for determining the translational state of a cell.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

Particularly preferred are peptide nucleic acids (PNA) that include peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched basepairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be double-stranded or single-stranded, as specified, or contain portions of both double-stranded or single-stranded sequence. As will be appreciated by those in the art, the depiction of a single strand also defines the sequence of the complementary strand; thus the sequences described herein also provide the complement of the sequence. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

"Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g., the individual units of a peptide nucleic acid, each containing a base, are referred to herein as a nucleoside.

As used herein, a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not functionally interfere with hybridization. Thus, e.g., probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled such as with isotopes, chromophores, lumiphores, chromogens, or indirectly labeled such as with biotin to which a streptavidin complex may later bind or with enzymatic labels. By assaying for the hybridization of the probe to its target nucleic acid sequence, one can detect the presence or absence of the select sequence or subsequence. Diagnosis or prognosis may be based at the genomic level, or at the level of RNA or protein expression.

The skilled person is capable of designing oligonucleotide probes that can be used in diagnostic methods of the present invention. Preferably, such probes are immobilized on a solid surface as to form an oligonucleotide microarray of the invention. The oligonucleotide probes useful in methods of the present invention are capable of hybridizing under stringent conditions to AML-associated nucleic acids, such as to one or more of the genes selected from Table 1, preferably to one or more of the genes selected from Table 2, more preferably to one or more of the genes selected from Table 3.

Techniques for the synthesis of arrays using mechanical synthesis methods are described in, e.g., U.S. Pat. No. 5,384, 261, to which reference is made herein. Although a planar array surface is preferred, the array may be fabricated on a surface of virtually any shape or even a multiplicity of surfaces. Arrays may be peptides or nucleic acids on beads, gels, polymeric surfaces, fibers such as fiber optics, glass or any other appropriate substrate, for the purpose of which reference is made to U.S. Pat. Nos. 5,770,358, 5,789,162, 5,708, 153, 6,040,193 and 5,800,992. Arrays may be packaged in such a manner as to allow for diagnostics or other manipulation of an all-inclusive device. Reference is, for example, made to U.S. Pat. Nos. 5,856,174 and 5,922,591.

The arrays provided by the present invention comprise capture probes that can specifically bind a nucleic acid molecule that is differentially expressed in AML classes. These arrays can be used to measure the expression levels of nucleic acid molecules to thereby create an expression profile for use in methods of determining the diagnosis and prognosis for AML patients, and for monitoring the efficacy of a therapy in these patients as described elsewhere herein.

In some embodiments, each capture probe in the array detects a nucleic acid molecule selected from the nucleic acid molecules designated in Tables 1 and 2. The designated nucleic acid molecules include those differentially expressed in AML classes selected from cluster #1-cluster #16 as depicted in FIG. 1.

The arrays of the invention comprise a substrate having a plurality of addresses, where each address has a capture probe that can specifically bind a target nucleic acid molecule. The number of addresses on the substrate varies with the purpose for which the array is intended. The arrays may be low-density arrays or high-density arrays and may contain 4 or more, 8 or more, 12 or more, 16 or more, 20 or more, 24 or more, 32 or more, 48 or more, 64 or more, 72 or more 80 or more, 96, or more addresses, or 192 or more, 288 or more, 384 or more, 768 or more, 1536 or more, 3072 or more, 6144 or more, 9216 or more, 12288 or more, 15360 or more, or 18432 or more addresses. In some embodiments, the substrate has no more than 12, 24, 48, 96, or 192, or 384 addresses, no more than 500, 600, 700, 800, or 900 addresses, or no more than 1000, 1200, 1600, 2400, or 3600 addresses.

The invention also provides a computer-readable medium comprising one or more digitally encoded expression profiles, where each profile has one or more values representing the expression of a gene that is differentially expressed in an AML class. The preparation and use of such profiles is well within the reach of the skilled person (see, e.g., WO 03/083140). In some embodiments, the digitally encoded expression profiles are comprised in a database. See, for example, U.S. Pat. No. 6,308,170.

The present invention also provides kits useful for diagnosing, treating, and monitoring the disease state in subjects affected by AML. These kits comprise an array and a computer readable medium. The array comprises a substrate having addresses, where each address has a capture probe that can specifically bind a nucleic acid molecule (by using an oligonucleotide array) or a peptide (by using a peptide array) that is differentially expressed in at least one AML class. The results are converted into a computer-readable medium that has digitally encoded expression profiles containing values representing the expression level of a nucleic acid molecule detected by the array.

By using the array described above, the amounts of various kinds of nucleic acid molecules contained in a nucleic acid sample can be simultaneously determined. In addition, there is an advantage such that the determination can be carried out even with a small amount of the nucleic acid sample. For instance, mRNA in the sample is labeled, or labeled cDNA is prepared by using mRNA as a template, and the labeled mRNA or cDNA is subjected to hybridization with the array, so that mRNAs being expressed in the sample are simultaneously detected, whereby their expression levels can be determined.

Genes each of which expression is altered due to AML can be found by determining expression levels of various genes in the AML-affected cells and classified into certain types as described above and comparing the expression levels with the expression level in a control tissue.

The method for determining the expression levels of genes is not particularly limited, and any of techniques for confirming alterations of the gene expressions mentioned above can be suitably used. Among all, the method using the array is especially preferable because the expressions of a large number of genes can be simultaneously determined. Suitable arrays are commercially available, e.g., from Affymetrix.

For instance, mRNA is prepared from blast cells, and then reverse transcription is carried out with the resulting mRNA as a template. During this process, labeled cDNA can be obtained by using, for instance, any suitable labeled primers or labeled nucleotides.

As to the labeling substance used for labeling, there can be used substances such as radioisotopes, fluorescent substances, chemiluminescent substances and substances with fluophor, and the like. For instance, the fluorescent substance includes Cy2, Fluor X, Cy3, Cy3.5, Cy5, Cy5.5, Cy7, fluorescein isothiocyanate (FITC), Texas Red, Rhodamine and the like. In addition, it is desired that samples to be tested (cancer samples to be tested in the present selection method) and a sample to be used as a control are each labeled with different fluorescent substances, using two or more fluorescent substances, from the viewpoint of enabling simultaneous detection. Here, labeling of the samples is carried out by labeling mRNA in the samples, cDNA derived from the mRNA, or nucleic acids produced by transcription or amplification from cDNA.

Next, the hybridization is carried out between the above-mentioned labeled cDNA and the array to which a nucleic acid corresponding to a suitable gene or its fragment is immobilized. The hybridization may be performed according to any known processes under conditions that are appropriate for the array and the labeled cDNA to be used. For instance, the hybridization can be performed under the conditions described in Molecular Cloning, A laboratory manual, 2nd ed., 9.52-9.55 (1989).

The hybridization between the nucleic acids derived from the samples and the array is carried out, under the above-mentioned hybridization conditions. When much time is needed for the time period required for procedures from the collection of samples to the determination of expression levels of genes, the degradation of mRNA may take place due to actions of ribonuclease. In order to determine the difference in the gene expressions in the samples to be tested (i.e., cell or tissue samples of AML patients) and the gene expressions in a control sample, it is preferable that the mRNA levels in both of these samples are adjusted using a standard gene with relatively little alterations in expressions.

Thereafter, by comparing the hybridization results of the samples to be tested with those of the control sample, genes exhibiting differential expression levels in both samples can be detected. Concretely, a signal that is appropriate depending upon the method of labeling used, is detected for the array, which is subjected to hybridization with the nucleic acid sample labeled by the method as described above, whereby the expression levels in the samples to be tested can be compared with the expression level in the control sample for each of the genes on the array.

The genes thus obtained which have a significant difference in signal intensities are genes each of which expression is altered specifically for certain AML classes.

The present invention also provides a computer-readable medium comprising a plurality of digitally encoded expression profiles wherein each profile of the plurality has a plurality of values, each value representing the expression of a gene that is differentially expressed in at least one AML class. The invention also provides for the storage and retrieval of a collection of data relating to AML-specific gene expression data of the present invention, including sequences and expression levels in a computer data storage apparatus, which can include magnetic disks, optical disks, magneto-optical disks, DRAM, SRAM, SGRAM, SDRAM, RDRAM, DDR RAM, magnetic bubble memory devices, and other data storage devices, including CPU registers and on-CPU data storage arrays. Typically, the data records are stored as a bit pattern in an array of magnetic domains on a magnetizable medium or as an array of charge states or transistor gate states, such as an array of cells in a DRAM device (e.g., each cell comprised of a transistor and a charge storage area, which may be on the transistor).

For use in diagnostic, research, and therapeutic applications suggested above, kits are also provided by the invention. In the diagnostic and research applications such kits may include any or all of the following: assay reagents, buffers, AML class-specific nucleic acids or antibodies, hybridization probes and/or primers, antisense polynucleotides, ribozymes, dominant negative AML polypeptides or polynucleotides, small molecules inhibitors of AML-associated sequences, arrays, antibodies, Fab fragments, capture peptides etc. In addition, the kits may include instructional materials containing directions (i.e., protocols) for the practice of the methods of this invention. While the instructional materials typically comprise written or printed materials, they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials. One such internet site may provide a database of AML reference expression profiles useful for performing similarity clustering of a newly determine subject expression profiles with a large set of reference profiles of AML subjects comprised in the database. Preferably, the database includes clinically relevant data such as patient prognosis, successful methods of treatment and cytogenetic characteristics for the various AML classes in the database.

The invention encompasses, for instance, kits comprising an array of the invention and a computer-readable medium having digitally encoded reference profiles with values representing the expression of nucleic acid molecules detected by the arrays. These kits are useful for assigning a subject affected by AML to an AML class and for diagnosing AML in a subject.

The present invention also provides for kits for screening for modulators of AML-associated sequences. Such kits can be prepared from readily available materials and reagents. For example, such kits can comprise one or more of the following materials: an AML-associated polypeptide or polynucleotide, reaction tubes, and instructions for testing AML-associated activity. Optionally the kit may comprise an array for detecting AML-associated genes, specifically cluster-defining genes according to the invention. A wide variety of kits and components can be prepared according to the present invention, depending upon the intended user of the kit and the particular needs of the user.

Diagnosis would typically involve evaluation of a plurality of genes or products. The genes will be selected based on correlations with important parameters in disease that may be identified in historical or outcome data.

In a preferred embodiment, a kit-of-parts according to the invention comprises an oligonucleotide microarray according to the invention and means for comparing a gene expression profile determined by using the microarray with a database of AML reference expression profiles. The present invention also comprises kits of parts suitable for performing a method of the invention as well as the use of the various products of the invention, including databases, microarrays, oligonucleotide probes and classification schemes in diagnostic or prognostic methods of the invention.

The methods and compositions of the invention may be used to screen test compounds to identify therapeutic compounds useful for the treatment of AML. In one embodiment, the test compounds are screened in a sample comprising primary cells or a cell line representative of a particular AML class. After treatment with the test compound, the expression levels in the sample of one or more of the differentially expressed genes of the invention are measured using methods described elsewhere herein. Values representing the expression levels of the differentially expressed genes are used to generate a subject expression profile. This subject expression profile is then compared to a reference profile associated with the AML class represented by the sample to determine the similarity between the subject expression profile and the reference expression profile. Differences between the subject expression profile and the reference expression profile may be used to determine whether the test compound has anti-leukemogenic activity.

The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one compound" library method; and synthetic library methods using . . . affinity chromatography selection. The biological library approach is limited to polypeptide libraries, while the other four approaches are applicable to polypeptide, non-peptide oligomer or small molecule libraries of compounds (Lam (1997) Anticancer Drug Res. 12:145).

Examples of methods for the synthesis of molecular libraries can be found in the art, for example, in DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233. Libraries of compounds may be presented in solution (e.g., Houghten (1992) Biotechniques 13:412-421), or on beads (Lam (1991) Nature 354:82-84), chips (Fodor (1993) Nature 364:555-556), bacteria (U.S. Pat. No. 5,223,409), spores (U.S. Pat. No. 5,223,409), plasmids (Cull et al. (1992) Proc. Natl. Acad. Sci. USA 89:1865-1869) or on phage (Scott and Smith (1990) Science 249:386-390; Devlin (1990) Science 249:404-406; Cwirla et al. (1990) Proc. Natl. Acad. Sci. U.S.A. 97:6378-6382; Felici (1991) J. Mol. Biol. 222:301-310).

Candidate compounds include, for example, 1) peptides such as soluble peptides, including Ig-tailed fusion peptides and members of random peptide libraries (see, e.g., Lam et al. (1991) Nature 354:82-84; Houghten et al. (1991) Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) Cell 72:767-778); 3) antibodies (e.g., polyclonal, monoclonal, humanized, anti-idiotypic, chimeric, and single chain antibodies as well as Fab, F(ab')Z, Fab expression library fragments, and epitope-binding fragments of antibodies); 4) small organic and inorganic molecules (e.g., molecules obtained from combinatorial and natural product libraries; 5) zinc analogs; 6) leukotriene A4 and derivatives; 7) classical aminopeptidase inhibitors and derivatives of such inhibitors, such as bestatin and arphamenine A and B and derivatives; 8) and artificial peptide substrates and other substrates, such as those disclosed herein above and derivatives thereof.

The present invention discloses a number of genes that are differentially expressed in AML classes. These differentially expressed genes are shown in Tables 1 and 2. Because the expression of these genes is associated with AML risk factors, these genes may play a role in leukemogenesis. Accordingly, these genes and their gene products are potential therapeutic targets that are useful in methods of screening test compounds to identify therapeutic compounds for the treatment of AML. Genes that are common between a number of AML classes are preferred as targets for therapeutic treatment, since a broader working over the patient population can be expected. It is very likely that genes that are present in more than one AML class, as defined in the present invention, are involved in general processes underlying AML. Thus, the expression of these genes is likely to be associated with AML risk factors and thus play a role in leukemogenesis. Genes that are present in several classes or clusters may thus define superclusters, which superclusters may define the processes that play an important role in leukemogenesis in general, and AML in particular.

The differentially expressed genes of the invention may be used in cell-based screening assays involving recombinant host cells expressing the differentially expressed gene product. The recombinant host cells are then screened to identify compounds that can activate the product of the differentially expressed gene (i.e., agonists) or inactivate the product of the differentially expressed gene (i.e., antagonists).

Any of the leukemogenic functions mediated by the product of the differentially expressed gene may be used as an endpoint in the screening assay for identifying therapeutic compounds for the treatment of AML. Such endpoint assays include assays for cell proliferation, assays for modulation of the cell cycle, assays for the expression of markers indicative of AML, and assays for the expression level of genes differentially expressed in AML classes as described above. Modulators of the activity of a product of a differentially expressed gene identified according to these drug-screening assays provided above can be used to treat a subject with AML. These methods of treatment include the steps of administering the modulators of the activity of a product of a differentially expressed gene in a pharmaceutical composition as described herein, to a subject in need of such treatment.

The following examples are offered by way of illustration and not by way of limitation.

EXAMPLE 1

Methods Used

Patients and Cell Samples

Patients with a confirmed diagnosis of de novo AML were included in this study (Table 4). All patients were treated according to the HOVON (Dutch-Belgian Hematology-Oncology Co-operative group) protocols (WorldWideWeb.hovon.nl). The treatment protocols have been described previously Rombouts et al., 2001). Bone marrow or peripheral blood aspirations of AML patients at diagnosis (n=286) and healthy volunteers (n=5) were taken after informed consent. Blasts and mononuclear cells were purified by Ficoll-Hypaque (Nygaard, Oslo, Norway) centrifugation and cryopreserved. CD34-positive cells of healthy volunteers (n=3) were sorted using the fluorescent activated cell sorter (FACS).

According to cytological analysis, the AML samples contained 80-100% blast cells after thawing independent of the blast count at diagnosis.

RNA Isolation and Quality Control

After thawing, cells were washed once with Hanks balanced salt solution. High quality total RNA was extracted by lyses with guanidinium isothiocyanate followed by cesium chloride gradient purification (Chomczynski & Sacchi, 1987). RNA concentration, quality and purity were examined using the RNA 6000 Nano assay on the Agilent 2100 Bioanalyzer (Agilent, Amstelveen, The Netherlands). None of the samples showed RNA degradation (28S/18S rRNA ratio≧2) or DNA contamination.

Gene Profiling and Quality Control 286 newly diagnosed cases of AML (Table 3) were analyzed by gene profiling using the Affymetrix U133A GeneChip. The U133A GeneChips contain 22283 probe sets representing approximately 13000 distinct genes. Ten micrograms of total RNA was used for the production of antisense biotinylated RNA. Single-stranded cDNA and double-stranded cDNA were synthesized according to the manufactures protocol (Invitrogen Life Technologies, Breda, The Netherlands) using the T7-(dT)24-primer (Genset Corp, Paris France). In vitro transcription was performed with biotin-11-CTP and biotin-16-UTP (Perkin Elmer, Hoofddorp, The Netherlands) and the MEGAScript T7 labeling kit (Ambion, Cambridgeshire, UK). Double-stranded cDNA and cRNA were purified and fragmented with the GeneChip Sample Cleanup Module (Affymetrix, Santa Clara, Calif.). Biotinylated RNA was subsequently hybridized to the Affymetrix U133A GeneChip (45° C. for 16 hours). Staining, washing and scanning procedures were carried out as described in the GeneChip Expression Analysis Technical Manual (Affymetrix, Santa Clara, Calif.). All GeneChips were visually inspected for obvious irregularities. The global method of scaling/normalization was applied and the differences between the scaling/normalization factors of all GeneChips (n=294) were less than three-fold (0.70, SD 0.26). All additional quality metrics, i.e., percent genes present (50.6, SD 3.8), actin 3' to 5' ratio (1.24, SD 0.19) and GAPDH 3' to 5' ratio (1.05, SD 0.14) indicated high overall sample and assay quality.

Data Normalization, Analysis and Visualization

The mean intensity values of all probe sets were calculated by the global method of scaling/normalization using MAS5.0. As most genes with values below 30 are absent (83% of all absent calls), these values were classified as unreliable and set to 30. This process resulted also in the exclusion of possibly unreliable present calls (10% of all present calls). The ratios between measured intensity and geometric mean intensity were calculated for each probe set and log 2 transformed to be used for further data analyses with Omniviz©, SAM© and PAM©.

Omniviz© (Maynard, Mass. (version 3.6))—Different numbers of probe sets were selected by filtering for those genes that in one or more samples differed at least n-fold from the geometric mean expression level of all AML patients. By using various ratios different numbers of differentially expressed probe sets were selected for the correlation visualization tool (Table 2). For each number of selected probe sets the clustering of the AML patients in specific molecularly recognizable groups was investigated using the Correlation Visualization tool of Omniviz.

Table 5 (below) shows the evaluation of the Correlation View results on the basis of the clustering of AML patients with similar molecular abnormalities.). The few AML cases with abnormalities involving chromosome 5 were excluded.

Ratio: ratio between measured intensity and geometric mean intensity by which probe sets were selected.

SAM© (version 1.21) Trustees of Leland Stanford Junior University—All supervised analyses were performed using Significance Analysis of Microarrays (SAM) (Tusher et al., 2001). The criterion to identify the top40 genes for the assigned clusters was: at least a two-fold difference between selected cluster and the remaining AML samples and a q-value of less than 5%.

PAM© (version 1.12) Trustees of Leland Stanford Junior University—All supervised class prediction analyses were performed by applying Prediction Analysis of Microarrays (PAM) software in R (version 1.7.1) (Tibshirani et al., 2002).

RT-PCR and Sequence Analyses

Reverse trancriptase-polymerase chain reactions (RT-PCR) and sequence analyses for mutations in FLT3-ITD, FLT3-TKD, N-RAS, K-RAS and cEBPα, as well as real-time PCR for EVI1 were performed as described previously (van Waalwijk van Doorn-Khosrovani et al., 2003a; van Waalwijk van Doorn-Khosrovani et al., 2003b; Valk et al., 2004; Care et al., 2003).

Statistical Analyses of Survival

Statistical analyses were performed with Stata Statistical Software, Release 7.0 (Stata, College Station, Tex.). Actuarial probabilities of overall survival (OS, with failure death due to any cause) and event-free survival (EFS, with failure in case of no complete remission at day 1, at relapse or death in first CR) were estimated by the method of Kaplan and Meier.

Results

Correlation Visualization of De Novo AML by Gene Expression

The best unsupervised ordering by applying the visualization tool of Omniviz of the AML cases in relation to different molecular markers was reached using 2856 probe sets (representing 2008 annotated genes and 146 ESTs) (FIG. 1A and Table 5). Sixteen distinct groups of AML patients were assigned on the basis of strong correlation between adjacent AML patients, i.e., within one red square along the diagonal, as well as the correlation and anti-correlation between the different groups, i.e., between the red squares along the diagonal (FIG. 1A). The final Omniviz Correlation View generated with 2856 probe sets was adapted such that cytological, cytogenetic and molecular parameters could be plotted directly adjacent to the original diagonal. This resulted in a unique way of visualization of the groups of patients with high correlation and related parameters (FIG. 1B).

Distinct clusters of AML t(8;21), AML inv(16) and AML t(15;17) were apparent (FIG. 1B). Although these distinct clusters were readily identified with less probe sets using the correlation tool, clusters of AML patients with mutations in FLT3 or cEBPα, or with overexpression of EVI1 were only apparent with 2856 probe sets (Table 5 and FIGS. 4 to 10). When more genes were used for the correlation visualization this compact clustering vanished (Table 5).

Unique genes characteristic for each of the 16 identified clusters were obtained by supervised analysis using SAM. The expression profiles of the top40 genes are plotted in FIG. 1B alongside the Correlation View. The SAM analyses resulted in only 599 discriminating genes (Tables 23-39) since a distinct gene profile for cluster #14 could not be identified, suggesting tight overlap with genes in clusters #7 and #8.

AML and Recurrent Translocations

CBFβ/MYH11—All inv(16) AML patients clustered within cluster #9 (FIG. 1B). Of note, four patients who were previously not known to harbor an inv(16) were included within this cluster. Molecular analysis and Southern blotting revealed the presence of CBFβ/MYH11 fusion gene in those cases (FIG. 11). SAM analysis revealed that MYH11 was the most prominent discriminating gene for this cluster. Interestingly, CBFβ anti-correlated with this cluster, suggesting that the CBFβ/MYH11 fusion protein down modulates the expression of the CBF/3 allele.

PML/RARα—Cluster #12 contains all cases of acute promyelocytic leukemia (APL) with t(15;17) (FIG. 1B), including two patients previously recognized as APL with PML/RARα by RT-PCR only. SAM analyses revealed that genes encoding growth factors such as hepatocyte growth factor (HGF), macrophage-stimulating 1 (hepatocyte growth factor-like (MST1)) and fibroblast growth factor 13 (FGF13) were specific for this cluster. In addition, cluster #12 could be separated into two subgroups with either high or low white blood cell count (WBC). This subdivision corresponds with FLT3 ITD mutation status (FIG. 1B).

AML1/ETO—All patients with a t(8;21) grouped within cluster #13 (FIG. 1B), including one patient without a t(8;21) (2496). SAM identified ETO as the most discriminative gene for this cluster.

AML with 11q23 Abnormalities

AML patients with 11q23 abnormalities were intermingled within the 286 AML patients, although two subgroups were apparent, i.e., cluster #1 and cluster #16 (FIG. 1B). Cluster #16 contains four cases of t(9;11) and one case of t(11;19) (5/11 cases (45%)). SAM analyses identified a strong signature with a group of genes specifically up-regulated in the majority of cases in this cluster (FIG. 1B). Although seven of 14 (50%) cases within cluster #1 have chromosome 11 abnormalities as well, this subgroup appears quite heterogeneous with a less uniform signature (FIG. 1B).

AML and cEBPα Mutations

Interestingly, two separate clusters (#4 and #15) comprise AML patients with predominantly normal karyotypes and a high frequency of mutations in cEBPα (FIG. 1B (Clusters #4 (8/15 cases (53%)) and #15 (5/8 cases (62%))). In cluster #4a set of up- and down-regulated genes could be defined, which appeared to discriminate the AML cases in cluster #4 from cluster #15. The up-regulated genes represent certain T-cell genes, such as the CD7 antigen (CD7) and the T-cell receptor delta locus (TRD@), which are known to be expressed on immature subsets of AML as well (Lo Coco et al., 1989; Boeckx et al., 2002). All but one of the top40 genes of cluster #15 are down-regulated. Interestingly, these genes are similarly down-regulated in cluster #4 (FIG. 1B). The genes encoding alpha1-catenin (CTNNA1), tubulin beta-5 (TUBBS) and Nedd4 family interacting protein 1 (NDFIP1) were the only genes down-modulated and among the top40 in both cluster #4 and #15.

AML and EVI1 Overexpression

A separate cluster (#10) of AML was identified in which 44% (10/22 cases) showed increased expression of EVI1. Aberrant expression of EVI1 in cluster #10 correlated with chromosome 7 abnormalities (6/10 EVI1-positive cases). This complete group of patients could be discriminated based on a selection of genes, suggesting that all patients, even the EVI1-negative cases, carry abnormalities in a common pathway. Cluster #8 also contains a relatively high number of chromosome 7 aberrations (5/13 cases), but it displays a different molecular signature compared to cluster #10 (FIG. 1B). This suggests that high expression of EVI1 and/or EVI1-related proteins determines the molecular profile of cluster #10. Four out of 14 cases within the heterogeneous cluster #1 also demonstrated increased EVI1 expression. These patients may cluster outside cluster #10 since their molecular signatures are most likely the result of EVI1 overexpression and an 11q23 abnormality.

AML with FLT3 Mutations

Groups of patients with mutations in the FLT3 receptor gene were recognized within the Correlation View (FIG. 1B). In fact, clusters #2 and #6 merely consist of patients with a FLT3 ITD. Interestingly, almost all of these patients have a normal karyotype. In addition, the FLT3 ITD mutation status seems to divide several clusters into two groups, e.g., clusters #3, #5 and AML with t(15;17) (#12). Other individual cases of AML with FLT3 ITD were more dispersed over the whole group of AML patients. AML patients with mutations in the tyrosine kinase domain (TKD) of FLT3 did not cluster. Likewise patients with mutations in codons 12, 13 or 61 of the small GTPase RAS (N-RAS and K-RAS) do not have apparent signatures and do not aggregate in the Correlation View (FIG. 1B).

Other Unique AML Clusters

AML patients with normal karyotypes clustered in several subgroups within the assigned clusters (FIG. 1B). In fact, the majority of patients in cluster #11 have normal karyotypes without any consistent additional abnormality. Other unique clusters, i.e., cluster #3, #5, #7, #8 and #14, were identified which could not be annotated with any known cytogenetic or molecular abnormality. Cluster #5 mainly contains AML patients that belong to the French-American-British (FAB) classification M4 or M5 subtypes (FIG. 1B), suggesting that the morphology was the main determinant for classifying these cases within this subgroup. Clusters #3, #7, #8, #11 and #14 contain AML cases, that do not belong to one FAB subtype, but can be discriminated based on distinct gene expression profiles.

Class Prediction of Distinct Clusters in AML

All 286 AML cases were randomized and divided into a training- (n=190) and a validation set (n=96). PAM was applied on the dataset to determine the minimal number of genes to predict distinct abnormalities with prognostic value in AML[1], i.e., t(8;21), inv(16), t(15;17), 11q23 (cluster #16), EVI1/monosomy 7 (cluster #10), cEBPα (clusters #4 and #15) (Table 3). In addition, since FLT3 ITD mutations are frequent abnormalities in AML and associated with poor outcome[2], the minimal set of genes to predict FLT3 ITD mutations in AML were identified.

All patients with favorable cytogenetics within the validation set were predicted with 100% accuracy and with only few genes (Table 3). As expected from the SAM analyses, ETO for t(8;21), MYH11 for inv(16) and HGF for t(15;17) were among the most predictive genes. Interestingly, cluster #10 (EVI1/monosomy 7) was predicted with high accuracy, although with a higher ten-fold cross-validation error. Cluster #16 (11q23) was predicted with fairly high accuracy. Since cluster #15 (cEBPα) consists of few patients only, we combined both cEBPα clusters. These two clusters could subsequently be predicted within the validation set with fairly high accuracy. A highly predictive signature for the FLT3 ITD cluster could not be defined by means of expression profiling within the AML patient cohort investigated.

Table 3 (below) shows the class prediction using PAM (ten-fold CV error: ten-fold cross-validation prediction error on training set (n=190), Error validation set: prediction error on validation set (n=96), #Probe sets: Number of probe sets used for prediction, #Genes: number of genes represented by probe sets used for prediction. *After randomization none of the AML patients from cEBPα cluster #15 were included in the validation set.

Survival Analyses

Overall survival (OS), event free survival (EFS) and relapse rate (RR) of AML patients from clusters containing > 20 cases in the Correlation View, were determined, i.e., clusters #5 (M4/M5), #9 (inv(16)), #10 (EVI1/monosomy 7), #12 (t(15;17)) and #13 (t(8;21)). Patients with a complete clinical data set were included in the survival analyses (FIG. 2). The mean actuarial OS and DFS probabilities at 60 months of the patients with favorable cytogenetics were 62% (±8.7%) and 50% (±2.4%), respectively. AML patients included in cluster #5 had intermediate survival (OS 27% and EFS 32%), whereas patients from cluster #10 showed poor treatment response (OS 6% (P=0.001) and EFS 18% (P=0.004)) mainly as a result of increased relapse incidence (FIG. 2C).

Discussion

The results of the study presented here show profound diagnostic impact of expression profiling. Among AML with considerable genetic diversity, expression profiling provides an approach to distinguish these highly variable genetic subsets into clusters with distinct signatures. Patients with AML were classified in 16 groups based on their gene expression profiles by unsupervised Pearson's correlation coefficient analyses. The results show that each of the assigned clusters represents true AML subgroups with specific molecular signatures.

Firstly, all cases with t(8;21) (AML1/ETO), inv(16) (CBFβ/MYH11) or t(15;17) (PML/RARα), including patients that could not be recognized by karyotyping, could be clustered in three separate clusters with unique gene expression profiles. Unique correlations between gene expression profiles: and favorable cytogenetic aberrations have been shown in the prior (Debernardi et al., 2003; Schoch et al., 2002), however, here we demonstrate that these patients can even be recognized with high accuracy within a representative cohort of AML patients.

Secondly, Significance Analyses of Microarrays (SAM) and Prediction Analyses of Microarrays (PAM), showed a strong concordance between the specific genes identified for the different assigned clusters, demonstrating that we identified truly discriminative genes for all the clusters that we assigned. For instance, we identified two distinct clusters (#4 and #15) with overlapping signatures, which both included cases with normal karyotypes and mutations in cEBPα. Multiple genes appeared to be down-regulated in both subclasses but were unaffected in any other AML subgroup.

Thirdly, the discriminative genes identified by SAM and PAM may in addition reveal specific functional pathways critical for the pathophysiology of AML. This is suggested by the identification of several functionally important genes implicated in specific subtypes of AML, such as the IL5Rα in AML with t(8;21) (Touw et al., 1991) and the bona fide FLT3/STAT5 targets IL2Rα (Kim et al., 2001) and PIM1 (Lilly et al., 1992) in AML with FLT3 ITD mutations.

Five clusters (#5, #9, #10, #12 and #13) 20 or more cases were evaluated in relation to outcome of therapy. As expected, clusters #9 (CBFβ/MYH11), #12 (PML/RARα) and #13 (AML1/ETO), comprised cases with a favorable response to therapy. However, cases that belong to cluster #10 showed a distinct poor outcome. Patients in this cluster could be predicted with high accuracy in an independent validation set with a minimal set of genes. The high frequency of poor prognostic markers, e.g., −7(q), −5(q), t(9;22) or high EVI1 is in agreement with the observation that this cluster represents a bad-risk AML group. However, since the cluster contains AML cases with a variety of genetically defined poor risk markers and since a significant portion of the cases did not express any of these lesions, this suggests that a unique pathway represented by the molecular signature of this cluster of AML patients is associated with bad outcome.

This hypothesis is further strengthened by the fact that large numbers of cases with the same poor-risk markers were present in other clusters (#1, #2, #8 and #16). Analysis of the genes up- or down-regulated in AML cases from cluster #10 may predict the pathway(s) involved the pathophysiology of this subgroup of AML patients. This might also shed light on the findings that the other cases with distinct poor-prognostic markers are grouped in different clusters. Unfortunately, these latter groups were too small for an accurate analysis of treatment outcome.

The 44 AML patients in cluster #5 showed an intermediate survival estimate. Since these cases belong to AML FAB-M4 or -M5 subtype, it is possible that monocyte/macrophage related genes mainly drove clustering of these cases. Unsupervised clustering of larger numbers of only AML FAB-M4 or -M5 cases with a normal karyotype may result in the identification of specific subgroups with unique gene expression profiles and perhaps variable prognosis.

Three clusters mainly consisting of patients with normal karyotype were identified. The majority of patients in two of those clusters (#2 and #6) were also characterized by FLT3 ITD mutations, whereas patients in cluster #11, with a discriminative molecular signature, did not contain any consistent abnormality.

Two clusters (#1 and #16) were recognized, which harbored 11q23 abnormalities, representing defects involving the mixed-lineage leukemia gene. The reason for the separation of these two subgroups is most likely caused by different additional genetic defects in the cases of the distinct clusters, causing different gene expression profiles. In cluster #1 this abnormality may be the frequently observed high expression of EVI1, which is not apparent in AML cases from cluster #16. A similar explanation may hold for AML cases in clusters #4 and #15, both comprising cEBPα mutant cases, AML patients in clusters #1 and #10 (high EVI1 expression), or patients in clusters #8 and #10 with frequent monosomy 7. Given the fact that each of these clusters expressed such a distinct molecular signature most probably means that in the cases without the characteristic genetic lesion, other currently unidentified mutations affecting the same pathways are responsible for the genetic profiles.

Internal tandem duplications (ITD) in the FLT3 gene adversely affect clinical outcome (Levis & Small, 2003). The molecular signature induced by the constitutively activated the FLT3 receptor appears not strong enough to distinguish FLT3 ITD carrying AML patients from the other cases. However, the clustering of FLT3 ITD-positive patients within assigned clusters, as is the case in the APL subgroup (cluster #12), demonstrates that the presence of FLT3 ITD results in different biological entities within one type of disease.

To this end, our study demonstrates that cytogenetically known as well as new clusters of AML with characteristic gene expression signatures can be identified with one single assay. The quality of genome-wide analysis will further advance with the availability of novel whole genome arrays, improved sequence annotation and the development of more sophisticated protocols and software, allowing analysis of subtle differences in gene expression and comprehensive pathway prediction. These studies, while augmenting our understanding of the pathways involved in pathophysiology of AML, will result in improved diagnostics and possibly lead the way to the development anti-cancer drugs that interfere with disease related pathways.

EXAMPLE 2

Analyses of Novel AML Patients

Patients and Cell Samples

Eligible patients have a diagnosis of primary AML, confirmed by cytological examination of blood and bone marrow. Blasts and mononuclear cells should be purified by Ficoll-Hypaque (Nygaard, Oslo, Norway) centrifugation. Add 1:1 diluted peripheral blood or bone marrow 1:4 diluted both in PBS up to 20-25 ml on to 15 ml Ficoll-Hypaque. Spin 15 minutes at 1880 rpm. Collect interphase with mononuclear cells and wash twice with PBS (total volume 50 ml, 8 minutes 2000 rpm). The pellet contains the mononuclear cells, including the blast cells. As a result, the AML samples should contain 80-100 percent blast cells, regardless of the blast count at diagnosis. $30 \times 10^6$ cells/ml should be frozen in 1 vol PBS/1 vol heat inactivated FCS/0.5 vol DMSO stored in liquid nitrogen.

RNA Isolation and Quality Control

After thawing, cells were washed once with Hanks balanced salt solution. High quality total RNA should extracted by lysis with guanidinium isothiocyanate followed by cesium chloride gradient purification. RNA concentration, quality and purity should be examined using the RNA 6000 Nano assay on the Agilent 2100 Bioanalyzer (Agilent, Amstelveen, The Netherlands). None of the samples should show RNA degradation (28S/18S rRNA ratio$\geq$2) or contamination by DNA.

Gene Profiling and Quality Control

Ten µg of total RNA should be used to prepare antisense biotinylated RNA. Single-stranded cDNA and double-stranded cDNA should be synthesized according to the manufacturer's protocol (Invitrogen Life Technologies, Breda, The Netherlands) using the $T7-(dT)_{24}$-primer (Genset Corp, Paris, France). In vitro transcription should be performed with biotin-11-CTP and biotin-16-UTP (Perkin Elmer, Hoofddorp, The Netherlands) and the MEGAScript T7 labeling kit (Ambion, Cambridgeshire, UK). Double-stranded cDNA and cRNA should be purified and fragmented with the GeneChip® Sample Cleanup Module (Affymetrix, Santa Clara, Calif.). Biotinylated RNA should be hybridized to the Affymetrix U133A GeneChip® (45° C. for 16 hours). Samples should be analyzed using Affymetrix U133A or U133 Plus2.0 GeneChips®. The U133A GeneChip® contains 22283 probe sets, representing approximately 13000 genes. These probe sets can also be selected from the U133 Plus2.0 GeneChip®. Staining, washing and scanning procedures should be carried out as described in the GeneChip® Expression Analysis Technical Manual (Affymetrix, Santa Clara, Calif.). All GeneChips® should be visually inspected for irregularities. The global method of scaling/normalization should be applied and the differences between the scaling/normalization factors of all GeneChips® up to the Target Gene Intensity of 100 (reference value n=285: scaling factor=0.70, SD 0.26). All additional measures of quality—percent genes present (reference value n=285: 50.6±3.8), actin 3' to 5' ratio (reference value n=285: 1.24±0.19) and GAPDH 3' to 5' ratio (reference value n=285: 1.05±0.14)—should indicate high overall sample and assay quality.

Reference Data Set

A reference data set (gene expression data and detailed clinical and molecular data) of 285 AML patients should be downloaded from the Gene Expression Omnibus (WorldWideWeb.ncbi.nlm.nih.gov/geo, accession number GSE1159).

Data Normalization, Analysis and Visualization

All intensity values (reference set (n=285) and new AML patients to be included) should be scaled to an average value of 100 per GeneChip® according to the method of global scaling/normalization, available in the Affymetrix Microarray Suite (MAS5.0). All other setting should be default according to the manufacturer.

As our methods reliably identify samples with an average intensity value >30 but do not reliably discriminate values from 0-<30, these values should be set to 30.

For each probe set, the geometric mean of the hybridization intensities of all patient samples should calculated. The level of expression of each probe set in every sample was determined relative to this geometric mean and transformed to $\log_2$ to ascribe equal weight to gene-expression levels with similar relative distances to the geometric mean. The transformed expression data should be subsequently imported into Omniviz.

Pearson's Correlation Visualization tool of Omniviz (Maynard, Mass. (version 3.6))—The Omniviz package should be used to perform and visualize unsupervised cluster analysis. The clustering of molecularly recognizable specific groups of patients should be investigated with the 2856 probe sets (Table 1) taking the reference set (n=285) and new patients to be analyzed into account.

REFERENCES

Alizadeh A. A., M. B. Eisen, and R. E. Davis, et al. Distinct types of diffuse large B-cell lymphoma identified by gene expression profiling. Nature 2000; 403:503-11.

Armstrong S. A., J. E. Staunton, and L. B. Silverman, et al. MLL translocations specify a distinct gene expression profile that distinguishes a unique leukemia. Nat. Genet. 2002; 30:41-7.

Boeckx N., M. J. Willemse, and T. Szczepanski, et al. Fusion gene transcripts and Ig/TCR gene rearrangements are complementary but infrequent targets for PCR-based detection of minimal residual disease in acute myeloid leukemia. Leukemia 2002; 16:368-75.

Care R. S., P. J. Valk, and A. C. Goodeve, et al. Incidence and prognosis of c-KIT and FLT3 mutations in core binding factor (CBF) acute myeloid leukaemias. Br. J. Haematol. 2003; 121:775-7.

Chomczynski P., and N. Sacchi. Single-step method of RNA isolation by acid guanidinium thiocyanate-phenol-chloroform extraction. Anal. Biochem. 1987; 162:156-9.

Debernardi S., D. M. Lillington, and T. Chaplin, et al. Genome-wide analysis of acute myeloid leukemia with normal karyotype reveals a unique pattern of homeobox gene expression distinct from those with translocation-mediated fusion events. Genes Chromosomes Cancer 2003; 37:149-58.

Eisen M. B., M. B. Spellman, P. O. Brown, and D. Botstein. Cluster analysis and display of genome-wide expression patterns. Proc. Natl. Acad. Sci. U.S.A. 1998; 95:14863-8.

Golub T. R., D. K. Slonim, and P. Tamayo, et al. Molecular classification of cancer: class discovery and class prediction by gene expression monitoring. Science 1999; 286:53: 1-7.

Kim H. P., J. Kelly, and W. J. Leonard. The basis for IL-2-induced IL-2 receptor alpha chain gene regulation: importance of two widely separated IL-2 response elements. Immunity 2001; 15:159-72.

Levis M., and D. Small. FLT3: ITDoes matter in leukemia. Leukemia 2003; 17:1738-52.

Lilly M, T. Le, P. Holland, and S. L. Hendrickson. Sustained expression of the pim-1 kinase is specifically induced in myeloid cells by cytokines whose receptors are structurally related. Oncogene 1992; 7:727-32.

Lo Coco F., G. De Rossi, and D. Pasqualetti, et al. CD7-positive acute myeloid leukaemia: a subtype associated with cell immaturity. Br. J. Haematol. 1989; 73:480-5.

Löwenberg B., J. R. Downing, and A. Burnett. Acute myeloid leukemia. N. Engl. J. Med. 1999; 341:1051-62.

Preudhomme C., C. Sagot, and N. Boissel, et al. Favorable prognostic significance of CEBPA mutations in patients with de novo acute myeloid leukemia: a study from the Acute Leukemia French Association (ALFA). Blood 2002; 100:2717-23.

Rombouts W. J., B. Löwenberg, W. L. van Putten, and R. E. Ploemacher. Improved prognostic significance of cytokine-induced proliferation in vitro in patients with de novo acute myeloid leukemia of intermediate risk: impact of internal tandem duplications in the Flt3 gene. Leukemia 2001; 15:1046-53.

Ross M. E., X. Zhou, and G. Song, et al. Classification of pediatric acute lymphoblastic leukemia by gene expression profiling. Blood 2003; 1:1.

Schoch C., A. Kohlmann, and S. Schnittger, et al. Acute myeloid leukemias with reciprocal rearrangements can be distinguished by specific gene expression profiles. Proc. Natl. Acad. Sci. U.S.A. 2002; 99:10008-13.

Tibshirani R., T. Hastie, B. Narasimhan, and G. Chu. Diagnosis of multiple cancer types by shrunken centroids of gene expression. Proc. Natl. Acad. Sci. U.S.A. 2002; 99:6567-72.

Touw I., J. Donath, and K. Pouwels, et al. Acute myeloid leukemias with chromosomal abnormalities involving the 21q22 region are identified by their in vitro responsiveness to interleukin-5. Leukemia 1991; 5:687-92.

Tusher V. G., R. Tibshirani, and G. Chu. Significance analysis of microarrays applied to the ionizing radiation response. Proc. Natl. Acad. Sci. U.S.A. 2001; 98:5116-21.

Valk P. J. M. B. D., M. E. Frew, A. C. Goodeve, B. Löwenberg, and J. T. W. Reilly. "Second hit" mutations in the RTK/RAS signaling pathway in acute myeloid leukaemia and inv(16). Haematologica 2004; 89:In press.

Van Waalwijk van Doorn-Khosrovani S. B., C. Erpelinck, and J. Meijer, et al. Biallelic mutations in the CEBPA gene and low CEBPA expression levels as prognostic markers in intermediate-risk AML. Hematol. J. 2003; 4:31-40.

Van Waalwijk van Doorn-Khosrovani S. B., C. Erpelinck, and W. L. van Putten, et al. High EVI1 expression predicts poor survival in acute myeloid leukemia: a study of 319 de novo AML patients. Blood 2003; 101:837-45.

Yeoh E. J., M. E. Ross, and S. A. Shurtleff, et al. Classification, subtype discovery, and prediction of outcome in pediatric acute lymphoblastic leukemia by gene expression profiling. Cancer Cell 2002; 1:133-43.

TABLE 1

About 2856 genes used for classifying AML of 286 patients into defined clusters as identified in Correlation View

| Affymetrix probe set id | gene symbol | unigene ID |
| --- | --- | --- |
| 117_at | HSPA6 | Hs.3268 |
| 1405_i_at | CCL5 | Hs.241392 |
| 1598_g_at | GAS6 | Hs.437710 |
| 200067_x_at | SNX3 | Hs.12102 |
| 200075_s_at | GUK1 | Hs.376933 |
| 200099_s_at | — | — // — |
| 200602_at | APP | Hs.177486 |
| 200606_at | DSP | Hs.349499 |
| 200612_s_at | AP2B1 | Hs.370123 |

TABLE 1-continued

About 2856 genes used for classifying AML of 286 patients into defined clusters as identified in Correlation View

| Affymetrix probe set id | gene symbol | unigene ID |
| --- | --- | --- |
| 200616_s_at | KIAA0152 | Hs.181418 |
| 200628_s_at | WARS | Hs.82030 |
| 200629_at | WARS | Hs.82030 |
| 200632_s_at | NDRG1 | Hs.318567 |
| 200644_at | MLP | Hs.75061 |
| 200648_s_at | GLUL | Hs.442669 |
| 200660_at | S100A11 | Hs.417004 |
| 200661_at | PPGB | Hs.118126 |
| 200665_s_at | SPARC | Hs.111779 |
| 200671_s_at | SPTBN1 | Hs.205401 |
| 200672_x_at | SPTBN1 | Hs.205401 |
| 200675_at | CD81 | Hs.54457 |
| 200678_x_at | GRN | Hs.180577 |
| 200696_s_at | GSN | Hs.446537 |
| 200697_at | HK1 | Hs.118625 |
| 200703_at | DNCL1 | Hs.5120 |
| 200704_at | LITAF | Hs.76507 |
| 200706_s_at | LITAF | Hs.76507 |
| 200736_s_at | GPX1 | Hs.76686 |
| 200762_at | DPYSL2 | Hs.173381 |
| 200765_x_at | CTNNA1 | Hs.254321 |
| 200766_at | CTSD | Hs.343475 |
| 200771_at | LAMC1 | Hs.432855 |
| 200780_x_at | GNAS | Hs.157307 |
| 200782_at | ANXA5 | Hs.145741 |
| 200784_s_at | LRP1 | Hs.162757 |
| 200785_s_at | LRP1 | Hs.162757 |
| 200791_s_at | IQGAP1 | Hs.1742 |
| 200795_at | SPARCL1 | Hs.75445 |
| 200796_s_at | MCL1 | Hs.86386 |
| 200799_at | HSPA1A | Hs.75452 |
| 200800_s_at | HSPA1A | Hs.75452 |
| 200808_s_at | ZYX | Hs.75873 |
| 200832_s_at | SCD | Hs.119597 |
| 200838_at | CTSB | Hs.135226 |
| 200839_s_at | CTSB | Hs.135226 |
| 200853_at | H2AFZ | Hs.119192 |
| 200871_s_at | PSAP | Hs.406455 |
| 200872_at | S100A10 | Hs.143873 |
| 200878_at | EPAS1 | Hs.8136 |
| 200895_s_at | FKBP4 | Hs.848 |
| 200897_s_at | KIAA0992 | Hs.194431 |
| 200907_s_at | KIAA0992 | Hs.194431 |
| 200921_s_at | BTG1 | Hs.255935 |
| 200923_at | LGALS3BP | Hs.79339 |
| 200931_s_at | VCL | Hs.75350 |
| 200952_s_at | CCND2 | Hs.376071 |
| 200953_s_at | CCND2 | Hs.376071 |
| 200962_at | RPL31 | Hs.375921 |
| 200965_s_at | ABLIM1 | Hs.442540 |
| 200981_x_at | GNAS | Hs.157307 |
| 200982_s_at | ANXA6 | Hs.412117 |
| 200983_x_at | CD59 | Hs.278573 |
| 200985_s_at | CD59 | Hs.278573 |
| 200986_at | SERPING1 | Hs.384598 |
| 200989_at | HIF1A | Hs.412416 |
| 200991_s_at | SNX17 | Hs.278569 |
| 200998_s_at | CKAP4 | Hs.74368 |
| 200999_s_at | CKAP4 | Hs.74368 |
| 201005_at | CD9 | Ns.387579 |
| 201008_s_at | TXNIP | Ns.179526 |
| 201012_at | ANXA1 | Hs.287558 |
| 201013_s_at | PAICS | Hs.444439 |
| 201015_s_at | JUP | Hs.2340 |
| 201024_x_at | IF2 | Hs.158688 |
| 201034_at | ADD3 | Hs.324470 |
| 201037_at | PFKP | Hs.26010 |
| 201041_s_at | DUSP1 | Hs.171695 |
| 201043_s_at | ANP32A | Hs.124977 |
| 201044_x_at | DUSP1 | Hs.171695 |
| 201047_x_at | RAB6A | Hs.5636 |
| 201050_at | PLD3 | Hs.74573 |
| 201052_s_at | PSMF1 | Hs.437495 |
| 201058_s_at | MYL9 | Hs.433814 |
| 201060_x_at | STOM | Hs.439776 |

TABLE 1-continued

About 2856 genes used for classifying AML of 286 patients into defined clusters as identified in Correlation View

| Affymetrix probe set id | gene symbol | unigene ID |
| --- | --- | --- |
| 201061_s_at | STOM | Hs.439776 |
| 201069_at | MMP2 | Hs.367877 |
| 201105_at | LGALS1 | Hs.407909 |
| 201107_s_at | THBS1 | Hs.164226 |
| 201108_s_at | THBS1 | Hs.164226 |
| 201109_s_at | THBS1 | Hs.164226 |
| 201110_s_at | THBS1 | Hs.164226 |
| 201123_s_at | EIF5A | Hs.310621 |
| 201125_s_at | ITGB5 | Hs.149846 |
| 201131_s_at | CDH1 | Hs.194657 |
| 201136_at | PLP2 | Hs.77422 |
| 201137_s_at | HLA-DPB1 | Hs.368409 |
| 201141_at | GPNMB | Hs.389964 |
| 201160_s_at | CSDA | Hs.221889 |
| 201161_s_at | CSDA | Hs.221889 |
| 201162_at | IGFBP7 | Hs.435795 |
| 201163_s_at | IGFBP7 | Hs.435795 |
| 201169_s_at | BHLHB2 | Hs.171825 |
| 201170_s_at | BHLHB2 | Hs.171825 |
| 201174_s_at | TERF2IP | Hs.274428 |
| 201178_at | FBXO7 | Hs.5912 |
| 201189_s_at | ITPR3 | Hs.77515 |
| 201193_at | IDH1 | Hs.11223 |
| 201195_s_at | SLC7A5 | Hs.184601 |
| 201201_at | CSTB | Hs.695 |
| 201218_at | CTBP2 | Hs.171391 |
| 201220_x_at | CTBP2 | Hs.171391 |
| 201222_s_at | RAD23B | Hs.159087 |
| 201223_s_at | RAD23B | Hs.159087 |
| 201234_at | ILK | Hs.6196 |
| 201242_s_at | ATP1B1 | Hs.78629 |
| 201249_at | SLC2A1 | Hs.169902 |
| 201250_s_at | SLC2A1 | Hs.169902 |
| 201251_at | PKM2 | Hs.198281 |
| 201272_at | AKR1B1 | Hs.75313 |
| 201285_at | MKRN1 | Hs.7838 |
| 201291_s_at | TOP2A | Hs.156346 |
| 201294_s_at | WSB1 | Hs.315379 |
| 201295_s_at | WSB1 | Hs.315379 |
| 201300_s_at | PRNP | Hs.438582 |
| 201301_s_at | ANXA4 | Hs.422986 |
| 201302_at | ANXA4 | Hs.422986 |
| 201307_at | FLJ10849 | Hs.386784 |
| 201309_x_at | C5orf13 | Hs.508742 |
| 201313_at | ENO2 | Hs.146580 |
| 201324_at | EMP1 | Hs.306692 |
| 201325_s_at | EMP1 | Hs.306692 |
| 201328_at | ETS2 | Hs.292477 |
| 201329_s_at | ETS2 | Hs.292477 |
| 201333_s_at | ARHGEF12 | Hs.413112 |
| 201334_s_at | ARHGEF12 | Hs.413112 |
| 201348_at | GPX3 | Hs.386793 |
| 201360_at | CST3 | Hs.304682 |
| 201373_at | PLEC1 | Hs.79706 |
| 201389_at | ITGA5 | Hs.149609 |
| 201392_s_at | IGF2R | Hs.76473 |
| 201393_s_at | IGF2R | Hs.76473 |
| 201412_at | LRP10 | Hs.28368 |
| 201416_at | SOX4 | Hs.357901 |
| 201417_at | SOX4 | Hs.357901 |
| 201418_s_at | SOX4 | Hs.357901 |
| 201422_at | IFI30 | Hs.14623 |
| 201425_at | ALDH2 | Hs.436437 |
| 201426_s_at | VIM | Hs.435800 |
| 201427_s_at | SEPP1 | Hs.275775 |
| 201431_s_at | DPYSL3 | Hs.150358 |
| 201445_at | CNN3 | Hs.194662 |
| 201459_at | RUVBL2 | Hs.6455 |
| 201462_at | KIAA0193 | Hs.75137 |
| 201464_x_at | JUN | Hs.78465 |
| 201465_s_at | JUN | Hs.78465 |
| 201466_s_at | JUN | Hs.78465 |
| 201473_at | JUNB | Hs.400124 |
| 201487_at | CTSC | Hs.128065 |
| 201497_x_at | MYH11 | Hs.78344 |
| 201506_at | TGFBI | Hs.421496 |
| 201508_at | IGFBP4 | Hs.1516 |
| 201518_at | CBX1 | Hs.77254 |
| 201522_x_at | SNRPN | Hs.48375 |
| 201531_at | ZFP36 | Hs.343586 |
| 201536_at | na | Hs.181046 |
| 201539_s_at | FHL1 | Hs.421383 |
| 201540_at | FHL1 | Hs.421383 |
| 201548_s_at | PLU-1 | Hs.143323 |
| 201549_x_at | PLU-1 | Hs.143323 |
| 201550_x_at | ACTG1 | Hs.14376 |
| 201563_at | SORD | Hs.878 |
| 201564_s_at | FSCN1 | Hs.118400 |
| 201565_s_at | ID2 | Hs.180919 |
| 201566_x_at | ID2 | Hs.180919 |
| 201579_at | FAT | Hs.166994 |
| 201590_x_at | ANXA2 | Hs.437110 |
| 201596_x_at | KRT18 | Hs.406013 |
| 201599_at | OAT | Hs.75485 |
| 201601_x_at | IFITM1 | Hs.458414 |
| 201631_s_at | IER3 | Hs.76095 |
| 201644_at | TSTA3 | Hs.404119 |
| 201655_s_at | HSPG2 | Hs.211573 |
| 201656_at | ITGA6 | Hs.212296 |
| 201666_at | TIMP1 | Hs.446641 |
| 201667_at | GJA1 | Hs.74471 |
| 201668_x_at | MARCKS | Hs.318603 |
| 201669_s_at | MARCKS | Hs.318603 |
| 201670_s_at | MARCKS | Hs.318603 |
| 201688_s_at | TPD52 | Hs.162089 |
| 201689_s_at | TPD52 | Hs.162089 |
| 201690_s_at | TPD52 | Hs.162089 |
| 201693_s_at | EGR1 | Hs.326035 |
| 201694_s_at | EGR1 | Hs.326035 |
| 201695_s_at | NP | Hs.75514 |
| 201700_at | CCND3 | Hs.83173 |
| 201711_x_at | RANBP2 | Hs.199179 |
| 201714_at | TUBG1 | Hs.21635 |
| 201720_s_at | LAPTM5 | Hs.436200 |
| 201734_at | CLCN3 | Hs.372528 |
| 201735_s_at | CLCN3 | Hs.372528 |
| 201739_at | SGK | Hs.296323 |
| 201743_at | CD14 | Hs.75627 |
| 201746_at | TP53 | Hs.426890 |
| 201752_s_at | ADD3 | Hs.324470 |
| 201753_s_at | ADD3 | Hs.324470 |
| 201790_s_at | DHCR7 | Hs.11806 |
| 201791_s_at | DHCR7 | Hs.11806 |
| 201792_at | AEBP1 | Hs.439463 |
| 201795_at | LBR | Hs.435166 |
| 201798_s_at | FER1L3 | Hs.362731 |
| 201809_s_at | ENG | Hs.76753 |
| 201810_s_at | SH3BP5 | Hs.109150 |
| 201811_x_at | SH3BP5 | Hs.109150 |
| 201824_at | RNF14 | Hs.170926 |
| 201831_s_at | VDP | Hs.325948 |
| 201839_s_at | TACSTD1 | Hs.692 |
| 201841_s_at | HSPB1 | Hs.76067 |
| 201842_s_at | EFEMP1 | Hs.76224 |
| 201850_at | CAPG | Hs.82422 |
| 201852_x_at | COL3A1 | Hs.443625 |
| 201858_s_at | PRG1 | Hs.1908 |
| 201859_at | PRG1 | Hs.1908 |
| 201860_s_at | PLAT | Hs.274404 |
| 201883_s_at | B4GALT1 | Hs.396798 |
| 201887_at | IL13RA1 | Hs.285115 |
| 201888_s_at | IL13RA1 | Hs.285115 |
| 201890_at | RRM2 | Hs.226390 |
| 201893_x_at | DCN | Hs.156316 |
| 201909_at | RPS4Y | Hs.180911 |
| 201912_s_at | GSPT1 | Hs.2707 |
| 201923_at | PRDX4 | Hs.83383 |
| 201938_at | CDK2AP1 | Hs.433201 |
| 201944_at | HEXB | Hs.69293 |
| 201952_at | ALCAM | Hs.10247 |

TABLE 1-continued

About 2856 genes used for classifying AML of 286 patients into defined clusters as identified in Correlation View

| Affymetrix probe set id | gene symbol | unigene ID |
|---|---|---|
| 201963_at | FACL2 | Hs.406678 |
| 201968_s_at | PGM1 | Hs.1869 |
| 201995_at | EXT1 | Hs.184161 |
| 202007_at | NID | Hs.356624 |
| 202014_at | PPP1R15A | Hs.76556 |
| 202016_at | MEST | Hs.416498 |
| 202017_at | EPHX1 | Hs.89649 |
| 202018_s_at | LTF | Hs.437457 |
| 202059_s_at | KPNA1 | Hs.161008 |
| 202068_s_at | LDLR | Hs.213289 |
| 202071_at | SDC4 | Hs.252189 |
| 202073_at | OPTN | Hs.390162 |
| 202074_s_at | OPTN | Hs.390162 |
| 202083_s_at | SEC14L1 | Hs.75232 |
| 202085_at | TJP2 | Hs.75608 |
| 202086_at | MX1 | Hs.436836 |
| 202087_s_at | CTSL | Hs.418123 |
| 202088_at | LIV-1 | Hs.79136 |
| 202096_s_at | BZRP | Hs.202 |
| 202107_s_at | MCM2 | Hs.57101 |
| 202112_at | VWF | Hs.440848 |
| 202119_s_at | CPNE3 | Hs.14158 |
| 202124_s_at | ALS2CR3 | Hs.154248 |
| 202125_s_at | ALS2CR3 | Hs.154248 |
| 202129_s_at | RIOK3 | Hs.209061 |
| 202130_at | RIOK3 | Hs.209061 |
| 202131_s_at | RIOK3 | Hs.209061 |
| 202145_at | LY6E | Hs.77667 |
| 202153_s_at | NUP62 | Hs.437023 |
| 202177_at | GAS6 | Hs.437710 |
| 202191_s_at | GAS7 | Hs.226133 |
| 202192_s_at | GAS7 | Hs.226133 |
| 202193_at | LIMK2 | Hs.278027 |
| 202201_at | BLVRB | Hs.76289 |
| 202203_s_at | AMFR | Hs.295137 |
| 202204_s_at | AMFR | Hs.295137 |
| 202206_at | ARL7 | Hs.111554 |
| 202207_at | ARL7 | Hs.111554 |
| 202208_s_at | ARL7 | Hs.111554 |
| 202219_at | SLC6A8 | Hs.388375 |
| 202234_s_at | SLC16A1 | Hs.75231 |
| 202236_s_at | SLC16A1 | Hs.75231 |
| 202237_at | NNMT | Hs.364345 |
| 202238_s_at | NNMT | Hs.364345 |
| 202241_at | C8FW | Hs.444947 |
| 202242_at | TM4SF2 | Hs.439586 |
| 202252_at | RAB13 | Hs.151536 |
| 202265_at | BMI1 | Hs.380403 |
| 202269_x_at | GBP1 | Hs.62661 |
| 202270_at | GBP1 | Hs.62661 |
| 202283_at | SERPINF1 | Hs.173594 |
| 202284_s_at | CDKN1A | Hs.370771 |
| 202286_s_at | TACSTD2 | Hs.23582 |
| 202291_s_at | MGP | Hs.365706 |
| 202295_s_at | CTSH | Hs.114931 |
| 202310_s_at | COL1A1 | Hs.172928 |
| 202336_s_at | PAM | Hs.352733 |
| 202340_x_at | NR4A1 | Hs.1119 |
| 202345_s_at | FABP5 | Hs.408061 |
| 202364_at | MXI1 | Hs.118630 |
| 202379_s_at | NKTR | Hs.369815 |
| 202388_at | RGS2 | Hs.78944 |
| 202391_at | BASP1 | Hs.79516 |
| 202395_at | NSF | Hs.431279 |
| 202403_s_at | COL1A2 | Hs.232115 |
| 202409_at | na | Hs.251664 |
| 202411_at | IFI27 | Hs.278613 |
| 202425_x_at | PPP3CA | Hs.272458 |
| 202426_s_at | RXRA | Hs.20084 |
| 202429_s_at | PPP3CA | Hs.272458 |
| 202431_s_at | MYC | Hs.202453 |
| 202435_s_at | CYP1B1 | Hs.154654 |
| 202436_s_at | CYP1B1 | Hs.154654 |
| 202437_s_at | CYP1B1 | Hs.154654 |
| 202443_x_at | NOTCH2 | Hs.8121 |
| 202452_at | ZYG | Hs.29285 |
| 202456_s_at | ZYG | Hs.29285 |
| 202457_s_at | PPP3CA | Hs.272458 |
| 202459_s_at | LPIN2 | Hs.437425 |
| 202460_s_at | LPIN2 | Hs.437425 |
| 202464_s_at | PFKFB3 | Hs.195471 |
| 202478_at | TRB2 | Hs.155418 |
| 202479_s_at | TRB2 | Hs.155418 |
| 202481_at | SDR1 | Hs.17144 |
| 202492_at | FLJ22169 | Hs.323363 |
| 202497_x_at | SLC2A3 | Hs.419240 |
| 202498_s_at | SLC2A3 | Hs.419240 |
| 202499_s_at | SLC2A3 | Hs.419240 |
| 202500_at | DNAJB2 | Hs.77768 |
| 202503_s_at | KIAA0101 | Hs.81892 |
| 202510_s_at | TNFAIP2 | Hs.101382 |
| 202523_s_at | SPOCK2 | Hs.436193 |
| 202524_s_at | SPOCK2 | Hs.436193 |
| 202545_at | PRKCD | Hs.155342 |
| 202546_at | VAMP8 | Hs.172684 |
| 202548_s_at | ARHGEF7 | Hs.172813 |
| 202551_s_at | CRIM1 | Hs.170752 |
| 202554_s_at | GSTM3 | Hs.2006 |
| 202555_s_at | MYLK | Hs.386078 |
| 202565_s_at | SVIL | Hs.163111 |
| 202566_s_at | SVIL | Hs.163111 |
| 202581_at | HSPA1A | Hs.274402 |
| 202587_s_at | AK1 | Hs.76240 |
| 202589_at | TYMS | Hs.87491 |
| 202599_s_at | NRIP1 | Hs.155017 |
| 202600_s_at | NRIP1 | Hs.155017 |
| 202609_at | EPS8 | Hs.2132 |
| 202614_at | C4orf1 | Hs.364615 |
| 202624_s_at | CABIN1 | Hs.435798 |
| 202626_s_at | LYN | Hs.80887 |
| 202627_s_at | SERPINE1 | Hs.414795 |
| 202628_s_at | SERPINE1 | Hs.414795 |
| 202637_s_at | ICAM1 | Hs.168383 |
| 202638_s_at | ICAM1 | Hs.168383 |
| 202643_s_at | TNFAIP3 | Hs.211600 |
| 202644_s_at | TNFAIP3 | Hs.211600 |
| 202660_at | — | Hs.406751 |
| 202671_s_at | MGC15873 | Hs.284491 |
| 202672_s_at | ATF3 | Hs.460 |
| 202686_s_at | AXL | Hs.83341 |
| 202687_s_at | TNFSF10 | Hs.387871 |
| 202688_at | TNFSF10 | Hs.387871 |
| 202704_at | TOB1 | Hs.178137 |
| 202708_s_at | HIST2H2BE | Hs.2178 |
| 202718_at | IGFBP2 | Hs.433326 |
| 202720_at | TES | Ha.129129 |
| 202724_s_at | FOXO1A | Hs.170133 |
| 202728_s_at | LTBP1 | Hs.241257 |
| 202729_s_at | LTBP1 | Hs.241257 |
| 202741_at | PRKACB | Hs.156324 |
| 202742_s_at | PRKACB | Hs.156324 |
| 202746_at | ITM2A | Hs.17109 |
| 202747_s_at | ITM2A | Hs.17109 |
| 202748_at | GBP2 | Hs.386567 |
| 202759_s_at | AKAP2 | Hs.42322 |
| 202760_s_at | AKAP2 | Hs.42322 |
| 202761_s_at | SYNE2 | Hs.444069 |
| 202763_at | CASP3 | Hs.141125 |
| 202768_at | FOSB | Hs.75678 |
| 202800_at | SLC1A3 | Hs.371369 |
| 202803_s_at | ITGB2 | Hs.375957 |
| 202804_at | ABCC1 | Hs.391464 |
| 202813_at | TARBP1 | Hs.151518 |
| 202820_at | AHR | Hs.170087 |
| 202833_s_at | SERPINA1 | Hs.297681 |
| 202838_at | FUCA1 | Hs.576 |
| 202845_s_at | RALBP1 | Hs.75447 |
| 202850_at | ABCD3 | Hs.76781 |
| 202855_s_at | SLC16A3 | Hs.386678 |
| 202859_x_at | IL8 | Hs.624 |

TABLE 1-continued

About 2856 genes used for classifying AML of 286 patients into defined clusters as identified in Correlation View

| Affymetrix probe set id | gene symbol | unigene ID |
|---|---|---|
| 202861_at | PER1 | Hs.445534 |
| 202869_at | OAS1 | Hs.442936 |
| 202871_at | TRAF4 | Hs.8375 |
| 202877_s_at | C1QR1 | Hs.97199 |
| 202878_s_at | C1QR1 | Hs.97199 |
| 202887_s_at | RTP801 | Hs.111244 |
| 202888_s_at | ANPEP | Hs.1239 |
| 202901_x_at | CTSS | Hs.181301 |
| 202902_s_at | CTSS | Hs.181301 |
| 202906_s_at | NBS1 | Hs.25812 |
| 202908_at | WFS1 | Hs.26077 |
| 202912_at | ADM | Hs.441047 |
| 202917_s_at | S100A8 | Hs.416073 |
| 202923_s_at | GCLC | Hs.414985 |
| 202926_at | NAG | Hs.413771 |
| 202944_at | NAGA | Hs.75372 |
| 202947_s_at | GYPC | Hs.81994 |
| 202948_at | IL1R1 | Hs.82112 |
| 202949_s_at | FHL2 | Hs.8302 |
| 202953_at | C1QB | Hs.8986 |
| 202974_at | MPP1 | Hs.422215 |
| 202988_s_at | RGS1 | Hs.75256 |
| 202990_at | PYGL | Hs.771 |
| 203021_at | SLPI | Hs.251754 |
| 203037_s_at | MTSS1 | Hs.77694 |
| 203038_at | PTPRK | Hs.354262 |
| 203040_s_at | HMBS | Hs.82609 |
| 203045_at | NINJ1 | Hs.11342 |
| 203052_at | C2 | Hs.2253 |
| 203056_s_at | PRDM2 | Hs.413375 |
| 203057_s_at | PRDM2 | Hs.413375 |
| 203060_s_at | PAPSS2 | Hs.274230 |
| 203063_at | PPM1F | Hs.278441 |
| 203065_s_at | CAV1 | Hs.74034 |
| 203066_at | GALNAC4S-6ST | Hs.6079 |
| 203069_at | SV2A | Hs.7979 |
| 203074_at | ANXA8 | Hs.87268 |
| 203088_at | FBLN5 | Hs.11494 |
| 203097_s_at | PDZGEF1 | Hs.373588 |
| 203104_at | CSF1R | Hs.174142 |
| 203115_at | FECH | Hs.443610 |
| 203116_s_at | FECH | Hs.443610 |
| 203126_at | IMPA2 | Hs.5753 |
| 203130_s_at | KIF5C | Hs.6641 |
| 203139_at | DAPK1 | Hs.244318 |
| 203140_at | BCL6 | Hs.155024 |
| 203146_s_at | GABBR1 | Hs.167017 |
| 203151_at | MAP1A | Hs.194301 |
| 203153_at | IFIT1 | Hs.20315 |
| 203180_at | ALDH1A3 | Hs.75746 |
| 203184_at | FBN2 | Hs.79432 |
| 203186_s_at | S100A4 | Hs.81256 |
| 203192_at | ABCB6 | Hs.107911 |
| 203196_at | ABCC4 | Hs.307915 |
| 203213_at | CDC2 | Hs.334562 |
| 203215_s_at | MYO6 | Hs.118483 |
| 203216_s_at | MYO6 | Hs.118483 |
| 203221_at | TLE1 | Hs.406491 |
| 203234_at | UP | Hs.314828 |
| 203236_s_at | LGALS9 | Hs.81337 |
| 203276_at | LMNB1 | Hs.89497 |
| 203289_s_at | C16orf35 | Hs.19699 |
| 203290_at | HLA-DQA1 | Hs.387679 |
| 203299_s_at | AP1S2 | Hs.40368 |
| 203300_x_at | AP1S2 | Hs.40368 |
| 203304_at | NMA | Hs.348802 |
| 203305_at | F13A1 | Hs.80424 |
| 203308_x_at | HPS1 | Hs.404568 |
| 203309_s_at | HPS1 | Hs.404568 |
| 203323_at | CAV2 | Hs.139851 |
| 203324_s_at | CAV2 | Hs.139851 |
| 203325_s_at | COL5A1 | Hs.433695 |
| 203333_at | KIFAP3 | Hs.433442 |
| 203349_s_at | ETV5 | Hs.43697 |
| 203372_s_at | SOCS2 | Hs.405946 |
| 203373_at | SOCS2 | Hs.405946 |
| 203381_s_at | APOE | Hs.169401 |
| 203382_s_at | APOE | Hs.169401 |
| 203387_s_at | TBC1D4 | Hs.173802 |
| 203388_at | ARRB2 | Hs.435811 |
| 203397_s_at | GALNT3 | Hs.278611 |
| 203402_at | KCNAB2 | Hs.440497 |
| 203407_at | PPL | Hs.192233 |
| 203408_s_at | SATB1 | Hs.416026 |
| 203411_s_at | LMNA | Hs.436441 |
| 203413_at | NELL2 | Hs.79389 |
| 203430_at | HEBP2 | Hs.439081 |
| 203434_s_at | MME | Hs.307734 |
| 203435_s_at | MME | Hs.307734 |
| 203440_at | CDH2 | Hs.334131 |
| 203456_at | JM4 | Hs.29595 |
| 203470_s_at | PLEK | Hs.77436 |
| 203471_s_at | PLEK | Hs.77436 |
| 203476_at | TPBG | Hs.82128 |
| 203485_at | RTN1 | Hs.99947 |
| 203502_at | BPGM | Hs.198365 |
| 203504_s_at | ABCA1 | Hs.147259 |
| 203505_at | ABCA1 | Hs.147259 |
| 203508_at | TNFRSF1B | Hs.256278 |
| 203509_at | SORL1 | Hs.438159 |
| 203513_at | FLJ21439 | Hs.431338 |
| 203518_at | CHS1 | Hs.130188 |
| 203523_at | LSP1 | Hs.56729 |
| 203524_s_at | MPST | Hs.248267 |
| 203535_at | S100A9 | Hs.112405 |
| 203542_s_at | BTEB1 | Hs.150557 |
| 203543_s_at | BTEB1 | Hs.150557 |
| 203544_s_at | STAM | Hs.441498 |
| 203547_at | CD4 | Hs.17483 |
| 203548_s_at | LPL | Hs.180878 |
| 203549_s_at | LPL | Hs.180878 |
| 203555_at | PTPN18 | Hs.210913 |
| 203556_at | ZHX2 | Hs.30209 |
| 203559_s_at | ABP1 | Hs.437420 |
| 203561_at | FCGR2A | Hs.352642 |
| 203562_at | FEZ1 | Hs.79226 |
| 203570_at | LOXL1 | Hs.65436 |
| 203574_at | NFIL3 | Hs.79334 |
| 203585_at | ZNF185 | Hs.16622 |
| 203591_s_at | CSF3R | Hs.381027 |
| 203627_at | IGF1R | Hs.239176 |
| 203628_at | IGF1R | Hs.239176 |
| 203638_s_at | FGFR2 | Hs.404081 |
| 203641_s_at | KIAA0977 | Hs.300855 |
| 203642_s_at | KIAA0977 | Hs.300855 |
| 203645_s_at | CD163 | Hs.74076 |
| 203661_s_at | TMOD1 | Hs.374849 |
| 203662_s_at | TMOD1 | Hs.374849 |
| 203665_at | HMOX1 | Hs.202833 |
| 203666_at | CXCL12 | Hs.436042 |
| 203675_at | NUCB2 | Hs.423095 |
| 203676_at | GNS | Hs.334534 |
| 203680_at | PRKAR2B | Hs.77439 |
| 203690_at | TUBGCP3 | Hs.9884 |
| 203691_at | PI3 | Hs.112341 |
| 203695_s_at | DFNA5 | Hs.304365 |
| 203708_at | PDE4B | Hs.188 |
| 203710_at | ITPR1 | Hs.149900 |
| 203716_s_at | DPP4 | Hs.44926 |
| 203717_at | DPP4 | Hs.44926 |
| 203725_at | GADD45A | Hs.80409 |
| 203726_s_at | LAMA3 | Hs.83450 |
| 203753_at | TCF4 | Hs.359289 |
| 203757_s_at | CEACAM6 | Hs.436718 |
| 203758_at | CTSO | Hs.75262 |
| 203760_s_at | SLA | Hs.75367 |
| 203761_at | SLA | Hs.75367 |
| 203764_at | DLG7 | Hs.77695 |
| 203767_s_at | STS | Hs.79876 |
| 203768_s_at | STS | Hs.79876 |

TABLE 1-continued

About 2856 genes used for classifying AML of 286 patients into defined clusters as identified in Correlation View

| Affymetrix probe set id | gene symbol | unigene ID |
|---|---|---|
| 203795_s_at | BCL7A | Hs.371758 |
| 203796_s_at | BCL7A | Hs.371758 |
| 203799_at | DCL-1 | Hs.2441 |
| 203802_x_at | WBSCR20A | Hs.272820 |
| 203819_s_at | IMP-3 | Hs.79440 |
| 203820_s_at | IMP-3 | Hs.79440 |
| 203821_at | DTR | Hs.799 |
| 203828_s_at | NK4 | Hs.943 |
| 203836_s_at | MAP3K5 | Hs.151988 |
| 203845_at | PCAF | Hs.203475 |
| 203853_s_at | GAB2 | Hs.30687 |
| 203859_s_at | PALM | Hs.78482 |
| 203860_at | PCCA | Hs.80741 |
| 203868_s_at | VCAM1 | Hs.109225 |
| 203878_s_at | MMP11 | Hs.143751 |
| 203887_s_at | THBD | Hs.2030 |
| 203888_at | THBD | Hs.2030 |
| 203895_at | PLCB4 | Hs.151408 |
| 203911_at | RAP1GA1 | Hs.433797 |
| 203913_s_at | HPGD | Hs.77348 |
| 203914_x_at | HPGD | Hs.77348 |
| 203915_at | CXCL9 | Hs.77367 |
| 203921_at | CHST2 | Hs.8786 |
| 203922_s_at | CYBB | Hs.88974 |
| 203923_s_at | CYBB | Hs.88974 |
| 203925_at | GCLM | Hs.315562 |
| 203932_at | HLA-DMB | Hs.1162 |
| 203933_at | Rab11-FIP3 | Hs.119004 |
| 203936_s_at | MMP9 | Hs.151738 |
| 203939_at | NT5E | Hs.153952 |
| 203946_s_at | ARG2 | Hs.172851 |
| 203948_s_at | MPO | Hs.458272 |
| 203949_at | MPO | Hs.458272 |
| 203966_s_at | PPM1A | Hs.130036 |
| 203973_s_at | KIAA0146 | Hs.381058 |
| 203979_at | CYP27A1 | Hs.82568 |
| 203980_at | FABP4 | Hs.391561 |
| 203987_at | FZD6 | Hs.114218 |
| 203989_x_at | F2R | Hs.128087 |
| 204004_at | — | Hs.503576 // est |
| 204006_s_at | FCGR3A | Hs.372679 |
| 204007_at | FCGR3A | Hs.372679 |
| 204011_at | SPRY2 | Hs.18676 |
| 204018_x_at | HBA1 | Hs.449630 |
| 204030_s_at | SCHIP1 | Hs.61490 |
| 204035_at | SCG2 | Hs.436577 |
| 204039_at | CEBPA | Hs.76171 |
| 204044_at | QPRT | Hs.8935 |
| 204051_s_at | SFRP4 | Hs.105700 |
| 204057_at | ICSBP1 | Hs.14453 |
| 204059_s_at | ME1 | Hs.14732 |
| 204069_at | MEIS1 | Hs.170177 |
| 204070_at | RARRES3 | Hs.17466 |
| 204073_s_at | C11orf9 | Hs.184640 |
| 204081_at | NRGN | Hs.232004 |
| 204082_at | PBX3 | Hs.294101 |
| 204083_s_at | TPM2 | Hs.300772 |
| 204086_at | PRAME | Hs.30743 |
| 204099_at | SMARCD3 | Hs.444445 |
| 204103_at | CCL4 | Hs.75703 |
| 204112_s_at | HNMT | Hs.42151 |
| 204116_at | IL2RG | Hs.84 |
| 204118_at | CD48 | Hs.901 |
| 204122_at | TYROBP | Hs.9963 |
| 204131_s_at | FOXO3A | Hs.423523 |
| 204132_s_at | FOXO3A | Hs.423523 |
| 204134_at | PDE2A | Hs.154437 |
| 204141_at | TUBB | Hs.300701 |
| 204147_s_at | TFDP1 | Hs.79353 |
| 204150_at | STAB1 | Hs.301989 |
| 204151_x_at | AKR1C1 | Hs.295131 |
| 204153_s_at | MFNG | Hs.371768 |
| 204158_s_at | TCIRG1 | Hs.46465 |
| 204159_at | CDKN2C | Hs.4854 |
| 204160_s_at | ENPP4 | Hs.54037 |
| 204165_at | WASF1 | Hs.75850 |
| 204170_s_at | CKS2 | Hs.83758 |
| 204172_at | CPO | Hs.89866 |
| 204174_at | ALOX5AP | Hs.100194 |
| 204182_s_at | ZNF297B | Hs.355581 |
| 204187_at | GMPR | Hs.1435 |
| 204192_at | CD37 | Hs.153053 |
| 204197_s_at | RUNX3 | Hs.170019 |
| 204198_s_at | RUNX3 | Hs.170019 |
| 204203_at | CEBPG | Hs.2227 |
| 204214_s_at | RAB32 | Hs.32217 |
| 204222_s_at | GLIPR1 | Hs.401813 |
| 204224_s_at | GCH1 | Hs.86724 |
| 204232_at | FCER1G | Hs.433300 |
| 204235_s_at | CED-6 | Hs.107056 |
| 204237_at | CED-6 | Hs.107056 |
| 204254_s_at | VDR | Hs.2062 |
| 204257_at | FADS3 | Hs.21765 |
| 204259_at | MMP7 | Hs.2256 |
| 204270_at | SKI | Hs.2969 |
| 204285_s_at | PMAIP1 | Hs.96 |
| 204286_s_at | PMAIP1 | Hs.96 |
| 204298_s_at | LOX | Hs.102267 |
| 204301_at | KIAA0711 | Hs.5333 |
| 204304_s_at | PROM1 | Hs.370052 |
| 204319_s_at | RGS10 | Hs.82280 |
| 204321_at | NEO1 | Hs.388613 |
| 204326_x_at | MT1X | Hs.374950 |
| 204341_at | TRIM16 | Hs.241305 |
| 204351_at | S100P | Hs.2962 |
| 204362_at | SCAP2 | Hs.410745 |
| 204363_at | F3 | Hs.62192 |
| 204379_s_at | FGFR3 | Hs.1420 |
| 204381_at | LRP3 | Hs.143641 |
| 204385_at | KYNU | Hs.444471 |
| 204388_s_at | MAOA | Hs.183109 |
| 204392_at | CAMK1 | Hs.434875 |
| 204396_s_at | GPRK5 | Hs.211569 |
| 204403_x_at | KIAA0738 | Hs.406492 |
| 204409_s_at | EIF1AY | Hs.205080 |
| 204410_at | EIF1AY | Hs.205080 |
| 204415_at | G1P3 | Hs.287721 |
| 204416_x_at | APOC1 | Hs.268571 |
| 204419_x_at | HBG2 | Hs.302145 |
| 204420_at | FOSL1 | Hs.283565 |
| 204429_s_at | SLC2A5 | Hs.33084 |
| 204430_s_at | SLC2A5 | Hs.33084 |
| 204438_at | MRC1 | Hs.75182 |
| 204439_at | C1orf29 | Hs.389724 |
| 204440_at | CD83 | Hs.79197 |
| 204445_s_at | ALOX5 | Hs.89499 |
| 204446_s_at | ALOX5 | Hs.89499 |
| 204447_at | ProSAPiP1 | Hs.90232 |
| 204451_at | FZD1 | Hs.94234 |
| 204457_s_at | GAS1 | Hs.65029 |
| 204466_s_at | SNCA | Hs.76930 |
| 204467_s_at | SNCA | Hs.76930 |
| 204468_s_at | TIE | Hs.78824 |
| 204470_at | CXCL1 | Hs.789 |
| 204490_s_at | CD44 | Hs.306278 |
| 204494_s_at | LOC56905 | Hs.306331 |
| 204497_at | ADCY9 | Hs.20196 |
| 204498_s_at | ADCY9 | Hs.20196 |
| 204501_at | NOV | Hs.235935 |
| 204502_at | SAMHD1 | Hs.371264 |
| 204505_s_at | EPB49 | Hs.274122 |
| 204517_at | PPIC | Hs.110364 |
| 204526_s_at | TBC1D8 | Hs.442657 |
| 204529_s_at | TOX | Hs.439767 |
| 204533_at | CXCL10 | Hs.413924 |
| 204537_s_at | GABRE | Hs.22785 |
| 204540_at | EEF1A2 | Hs.433839 |
| 204547_at | RAB40B | Hs.302498 |
| 204548_at | STAR | Hs.440760 |
| 204560_at | FKBP5 | Hs.7557 |

TABLE 1-continued

About 2856 genes used for classifying AML of 286 patients into defined clusters as identified in Correlation View

| Affymetrix probe set id | gene symbol | unigene ID |
|---|---|---|
| 204561_x_at | APOC2 | Hs.75615 |
| 204562_at | IRF4 | Hs.127686 |
| 204563_at | SELL | Hs.82848 |
| 204581_at | CD22 | Hs.262150 |
| 204588_s_at | SLC7A7 | Hs.194693 |
| 204604_at | PFTK1 | Hs.57856 |
| 204611_s_at | PPP2R5B | Hs.75199 |
| 204614_at | SERPINB2 | Hs.75716 |
| 204619_s_at | CSPG2 | Hs.434488 |
| 204620_s_at | CSPG2 | Hs.434488 |
| 204621_s_at | NR4A2 | Hs.82120 |
| 204622_x_at | NR4A2 | Hs.82120 |
| 204623_at | TFF3 | Hs.82961 |
| 204625_s_at | ITGB3 | Hs.87149 |
| 204626_s_at | ITGB3 | Hs.87149 |
| 204627_s_at | ITGB3 | Hs.87149 |
| 204628_s_at | ITGB3 | Hs.87149 |
| 204638_at | ACP5 | Hs.1211 |
| 204639_at | ADA | Hs.407135 |
| 204647_at | HOMER3 | Hs.410683 |
| 204655_at | CCL5 | Hs.241392 |
| 204661_at | CDW52 | Hs.276770 |
| 204670_x_at | HLA-DRB4 | Hs.449633 |
| 204671_s_at | ANKRD6 | Hs.30991 |
| 204677_at | CDH5 | Hs.76206 |
| 204679_at | KCNK1 | Hs.376874 |
| 204682_at | LTBP2 | Hs.83337 |
| 204684_at | NPTX1 | Hs.84154 |
| 204698_at | ISG20 | Hs.105434 |
| 204713_s_at | F5 | Hs.30054 |
| 204714_s_at | F5 | Hs.30054 |
| 204720_s_at | DNAJC6 | Hs.44896 |
| 204729_s_at | STX1A | Hs.75671 |
| 204736_s_at | CSPG4 | Hs.436301 |
| 204745_x_at | MT1G | Hs.433391 |
| 204747_at | IFIT4 | Hs.181874 |
| 204748_at | PTGS2 | Hs.196384 |
| 204749_at | NAP1L3 | Hs.21365 |
| 204750_s_at | DSC2 | Hs.95612 |
| 204751_x_at | DSC2 | Hs.95612 |
| 204753_s_at | HLF | Hs.250692 |
| 204755_x_at | HLF | Hs.250692 |
| 204774_at | EVI2A | Hs.70499 |
| 204777_s_at | MAL | Hs.80395 |
| 204787_at | Z39IG | Hs.8904 |
| 204788_s_at | PPOX | Hs.376314 |
| 204789_at | FMNL | Hs.100217 |
| 204790_at | MADH7 | Hs.370849 |
| 204793_at | GASP | Hs.113082 |
| 204794_at | DUSP2 | Hs.1183 |
| 204798_at | MYB | Hs.407830 |
| 204806_x_at | HLA-F | Hs.411958 |
| 204808_s_at | TMEM5 | Hs.112986 |
| 204811_s_at | CACNA2D2 | Hs.389415 |
| 204820_s_at | BTN3A3 | Hs.167741 |
| 204823_at | NAV3 | Hs.306322 |
| 204829_s_at | FOLR2 | Hs.433159 |
| 204834_at | FGL2 | Hs.351808 |
| 204848_x_at | HBG1 | Hs.449631 |
| 204858_s_at | ECGF1 | Hs.435067 |
| 204872_at | BCE-1 | Hs.99824 |
| 204881_s_at | UGCG | Hs.432605 |
| 204885_s_at | MSLN | Hs.408488 |
| 204890_s_at | LCK | Hs.1765 |
| 204891_s_at | LCK | Hs.1765 |
| 204896_s_at | PTGER4 | Hs.199248 |
| 204897_at | PTGER4 | Hs.199248 |
| 204899_s_at | SAP30 | Hs.413835 |
| 204900_x_at | SAP30 | Hs.413835 |
| 204908_s_at | BCL3 | Hs.31210 |
| 204912_at | IL10RA | Hs.327 |
| 204914_s_at | SOX11 | Hs.432638 |
| 204916_at | RAMP1 | Hs.32989 |
| 204917_s_at | MLLT3 | Hs.404 |
| 204923_at | CXorf9 | Hs.61469 |
| 204924_at | TLR2 | Hs.439608 |
| 204949_at | ICAM3 | Hs.353214 |
| 204951_at | ARHH | Hs.109918 |
| 204959_at | MNDA | Hs.153837 |
| 204961_s_at | NCF1 | Hs.1583 |
| 204971_at | CSTA | Hs.412999 |
| 204972_at | OAS2 | Hs.414332 |
| 204976_s_at | LOC286505 | Hs.433256 // — |
| 204984_at | GPC4 | Hs.58367 |
| 204990_s_at | ITGB4 | Hs.85266 |
| 204992_s_at | PFN2 | Hs.91747 |
| 204998_s_at | ATF5 | Hs.9754 |
| 205000_at | DDX3Y | Hs.99120 |
| 205001_s_at | DDX3Y | Hs.99120 |
| 205012_s_at | HAGH | Hs.155482 |
| 205019_s_at | VIPR1 | Hs.348500 |
| 205020_s_at | ARL4 | Hs.245540 |
| 205027_s_at | MAP3K8 | Hs.432453 |
| 205033_s_at | DEFA1 | Hs.274463 |
| 205035_at | CTDP1 | Hs.4076 |
| 205041_s_at | ORM1 | Hs.572 |
| 205047_s_at | ASNS | Hs.446546 |
| 205049_s_at | CD79A | Hs.79630 |
| 205051_s_at | KIT | Hs.81665 |
| 205055_at | ITGAE | Hs.389133 |
| 205067_at | IL1B | Hs.126256 |
| 205076_s_at | CRA | Hs.425144 |
| 205081_at | CRIP1 | Hs.423190 |
| 205098_at | CCR1 | Hs.301921 |
| 205099_s_at | CCR1 | Hs.301921 |
| 205110_s_at | FGF13 | Hs.6540 |
| 205114_s_at | CCL3 | Hs.73817 |
| 205118_at | FPR1 | Hs.753 |
| 205119_s_at | FPR1 | Hs.753 |
| 205130_at | RAGE | Hs.104119 |
| 205131_x_at | SCGF | Hs.105927 |
| 205157_s_at | KRT17 | Hs.2785 |
| 205159_at | CSF2RB | Hs.285401 |
| 205174_s_at | QPCT | Hs.79033 |
| 205179_s_at | ADAM8 | Hs.86947 |
| 205193_at | MAFF | Hs.51305 |
| 205200_at | TNA | Hs.65424 |
| 205205_at | RELB | Hs.307905 |
| 205207_at | IL6 | Hs.130210 |
| 205213_at | CENTB1 | Hs.337242 |
| 205214_at | STK17B | Hs.88297 |
| 205220_at | HM74 | Hs.458425 |
| 205227_at | IL1RAP | Hs.143527 |
| 205229_s_at | COCH | Hs.21016 |
| 205230_at | RPH3A | Hs.21239 |
| 205237_at | FCN1 | Hs.440898 |
| 205239_at | AREG | Hs.270833 |
| 205240_at | LGN | Hs.278328 |
| 205241_at | SCO2 | Hs.410944 |
| 205249_at | EGR2 | Hs.1395 |
| 205254_x_at | TCF7 | Hs.169294 |
| 205255_x_at | TCF7 | Hs.169294 |
| 205262_at | KCNH2 | Hs.188021 |
| 205266_at | LIF | Hs.2250 |
| 205267_at | POU2AF1 | Hs.2407 |
| 205268_s_at | ADD2 | Hs.113614 |
| 205270_s_at | LCP2 | Hs.2488 |
| 205278_at | GAD1 | Hs.420036 |
| 205281_s_at | PIGA | Hs.51 |
| 205289_at | BMP2 | Hs.73853 |
| 205297_s_at | CD79B | Hs.89575 |
| 205312_at | SPI1 | Hs.157441 |
| 205321_at | EIF2S3 | Hs.433518 |
| 205328_at | CLDN10 | Hs.26126 |
| 205330_at | MN1 | Hs.268515 |
| 205348_s_at | DNCI1 | Hs.65248 |
| 205349_at | GNA15 | Hs.73797 |
| 205353_s_at | PBP | Hs.433863 |
| 205361_s_at | PFDN4 | Hs.91161 |
| 205366_s_at | HOXB6 | Hs.98428 |

TABLE 1-continued

About 2856 genes used for classifying AML of 286 patients into defined clusters as identified in Correlation View

| Affymetrix probe set id | gene symbol | unigene ID |
|---|---|---|
| 205382_s_at | DF | Hs.155597 |
| 205389_s_at | ANK1 | Hs.443711 |
| 205390_s_at | ANK1 | Hs.443711 |
| 205391_x_at | ANK1 | Hs.443711 |
| 205392_s_at | CCL15 | Hs.272493 |
| 205400_at | WAS | Hs.2157 |
| 205402_x_at | PRSS2 | Hs.367767 |
| 205403_at | IL1R2 | Hs.25333 |
| 205409_at | FOSL2 | Hs.301612 |
| 205414_s_at | KIAA0672 | Hs.6336 |
| 205419_at | EBI2 | Hs.784 |
| 205445_at | PRL | Hs.1905 |
| 205453_at | HOXB2 | Hs.290432 |
| 205456_at | CD3E | Hs.3003 |
| 205463_s_at | PDGFA | Hs.376032 |
| 205466_s_at | HS3ST1 | Hs.40968 |
| 205469_s_at | IRF5 | Hs.334450 |
| 205471_s_at | DACH | Hs.63931 |
| 205472_s_at | DACH | Hs.63931 |
| 205476_at | CCL20 | Hs.75498 |
| 205479_s_at | PLAU | Hs.77274 |
| 205483_s_at | G1P2 | Hs.458485 |
| 205484_at | SIT | Hs.88012 |
| 205488_at | GZMA | Hs.90708 |
| 205495_s_at | GNLY | Hs.105806 |
| 205513_at | TCN1 | Hs.2012 |
| 205528_s_at | CBFA2T1 | Hs.90858 |
| 205529_s_at | CBFA2T1 | Hs.90858 |
| 205544_s_at | CR2 | Hs.73792 |
| 205547_s_at | TAGLN | Hs.433401 |
| 205550_s_at | BRE | Hs.80426 |
| 205552_s_at | OAS1 | Hs.442936 |
| 205557_at | BPI | Hs.303523 |
| 205568_at | AQP9 | Hs.104624 |
| 205570_at | PIP5K2A | Hs.108966 |
| 205572_at | ANGPT2 | Hs.115181 |
| 205582_s_at | GGTLA1 | Hs.437156 |
| 205590_at | RASGRP1 | Hs.189527 |
| 205592_at | SLC4A1 | Hs.443948 |
| 205593_s_at | PDE9A | Hs.389777 |
| 205599_at | TRAF1 | Hs.438253 |
| 205608_s_at | ANGPT1 | Hs.2463 |
| 205609_at | ANGPT1 | Hs.2463 |
| 205612_at | MMRN | Hs.268107 |
| 205614_x_at | MST1 | Hs.349110 |
| 205624_at | CPA3 | Hs.646 |
| 205627_at | CDA | Hs.72924 |
| 205632_s_at | PIP5K1B | Hs.297604 |
| 205633_s_at | ALAS1 | Hs.78712 |
| 205653_at | CTSG | Hs.421724 |
| 205660_at | OASL | Hs.118633 |
| 205668_at | LY75 | Hs.153563 |
| 205681_at | BCL2A1 | Hs.227817 |
| 205683_x_at | TPSB2 | Hs.405479 |
| 205707_at | IL17R | Hs.129751 |
| 205712_at | PTPRD | Hs.323079 |
| 205715_at | BST1 | Hs.169998 |
| 205717_x_at | PCDHGC3 | Hs.283794 |
| 205718_at | ITGB7 | Hs.1741 |
| 205721_at | — | Hs.441202 // est |
| 205739_x_at | ZFD25 | Hs.50216 |
| 205743_at | STAC | Hs.56045 |
| 205758_at | CD8A | Hs.85258 |
| 205767_at | EREG | Hs.115263 |
| 205769_at | SLC27A2 | Hs.11729 |
| 205780_at | BIK | Hs.155419 |
| 205786_s_at | ITGAM | Hs.172631 |
| 205789_at | CD1D | Hs.1799 |
| 205790_at | SCAP1 | Hs.411942 |
| 205798_at | IL7R | Hs.362807 |
| 205801_s_at | RASGRP3 | Hs.24024 |
| 205819_at | MARCO | Hs.67726 |
| 205821_at | D12S2489E | Hs.387787 |
| 205826_at | MYOM2 | Hs.443683 |
| 205831_at | CD2 | Hs.89476 |
| 205837_s_at | GYPA | Hs.34287 |
| 205838_at | GYPA | Hs.34287 |
| 205839_s_at | BZRAP1 | Hs.112499 |
| 205844_at | VNN1 | Hs.12114 |
| 205848_at | GAS2 | Hs.135665 |
| 205856_at | SLC14A1 | Hs.101307 |
| 205857_at | SLC18A2 | Hs.50458 |
| 205859_at | LY86 | Hs.184018 |
| 205861_at | SPIB | Hs.437905 |
| 205863_at | S100A12 | Hs.19413 |
| 205879_x_at | RET | Hs.350321 |
| 205882_x_at | ADD3 | Hs.324470 |
| 205884_at | ITGA4 | Hs.145140 |
| 205891_at | ADORA2B | Hs.45743 |
| 205896_at | SLC22A4 | Hs.441130 |
| 205898_at | CX3CR1 | Hs.78913 |
| 205899_at | CCNA1 | Hs.417050 |
| 205900_at | KRT1 | Hs.80828 |
| 205901_at | PNOC | Hs.371809 |
| 205919_at | HBE1 | Hs.117848 |
| 205922_at | VNN2 | Hs.293130 |
| 205927_s_at | CTSE | Hs.1355 |
| 205929_at | GPA33 | Hs.437229 |
| 205933_at | SETBP1 | Hs.201369 |
| 205935_at | FOXF1 | Hs.155591 |
| 205936_s_at | HK3 | Hs.411695 |
| 205942_s_at | SAH | Hs.409501 |
| 205944_s_at | CLTCL1 | Hs.184916 |
| 205950_s_at | CA1 | Hs.23118 |
| 205960_at | PDK4 | Hs.8364 |
| 205983_at | DPEP1 | Hs.109 |
| 205984_at | CRHBP | Hs.115617 |
| 205987_at | CD1C | Hs.1311 |
| 206001_at | NPY | Hs.1832 |
| 206011_at | CASP1 | Hs.2490 |
| 206025_s_at | TNFAIP6 | Hs.407546 |
| 206026_s_at | TNFAIP6 | Hs.407546 |
| 206034_at | SERPINB8 | Hs.368077 |
| 206039_at | RAB33A | Hs.56294 |
| 206042_x_at | SNRPN | Hs.48375 |
| 206046_at | ADAM23 | Hs.432317 |
| 206049_at | SELP | Hs.73800 |
| 206059_at | ZNF91 | Hs.8597 |
| 206067_s_at | WT1 | Hs.1145 |
| 206070_s_at | EPHA3 | Hs.123642 |
| 206074_s_at | HMGA1 | Hs.57301 |
| 206077_at | KEL | Hs.420322 |
| 206093_x_at | TNXB | Hs.411644 |
| 206106_at | MAPK12 | Hs.432642 |
| 206108_s_at | SFRS6 | Hs.6891 |
| 206110_at | HIST1H3H | Hs.70937 |
| 206111_at | RNASE2 | Hs.728 |
| 206115_at | EGR3 | Hs.74088 |
| 206118_at | STAT4 | Hs.80642 |
| 206130_s_at | ASGR2 | Hs.1259 |
| 206134_at | ADAMDEC1 | Hs.145296 |
| 206135_at | ST18 | Hs.151449 |
| 206145_at | RHAG | Hs.368178 |
| 206146_s_at | RHAG | Hs.368178 |
| 206148_at | IL3RA | Hs.389251 |
| 206150_at | TNFRSF7 | Hs.355307 |
| 206157_at | PTX3 | Hs.2050 |
| 206159_at | GDF10 | Hs.2171 |
| 206167_s_at | ARHGAP6 | Hs.250830 |
| 206169_x_at | RoXaN | Hs.25347 |
| 206177_s_at | ARG1 | Hs.440934 |
| 206187_at | PTGIR | Hs.393 |
| 206196_s_at | RPIP8 | Hs.6755 |
| 206206_at | LY64 | Hs.87205 |
| 206207_at | CLC | Hs.889 |
| 206222_at | TNFRSF10C | Hs.119684 |
| 206232_s_at | B4GALT6 | Hs.369994 |
| 206233_at | B4GALT6 | Hs.369994 |
| 206235_at | LIG4 | Hs.166091 |
| 206244_at | CR1 | Hs.334019 |

TABLE 1-continued

About 2856 genes used for classifying AML of 286 patients into defined clusters as identified in Correlation View

| Affymetrix probe set id | gene symbol | unigene ID |
| --- | --- | --- |
| 206245_s_at | IVNS1ABP | Hs.197298 |
| 206255_at | BLK | Hs.389900 |
| 206277_at | P2RY2 | Hs.339 |
| 206279_at | PRKY | Hs.183165 |
| 206281_at | ADCYAP1 | Hs.68137 |
| 206283_s_at | TAL1 | Hs.498079 |
| 206298_at | RhoGAP2 | Hs.87241 |
| 206302_s_at | NUDT4 | Hs.355399 |
| 206303_s_at | NUDT4 | Hs.355399 |
| 206304_at | MYBPH | Hs.927 |
| 206310_at | SPINK2 | Hs.98243 |
| 206331_at | CALCRL | Hs.152175 |
| 206332_s_at | IFI16 | Hs.370873 |
| 206337_at | CCR7 | Hs.1652 |
| 206341_at | IL2RA | Hs.130058 |
| 206342_x_at | IDS | Hs.352304 |
| 206343_s_at | NRG1 | Hs.172816 |
| 206359_at | SOCS3 | Hs.436943 |
| 206360_s_at | SOCS3 | Hs.436943 |
| 206361_at | GPR44 | Hs.299567 |
| 206363_at | MAF | Hs.134859 |
| 206366_x_at | XCL1 | Hs.174228 |
| 206367_at | REN | Hs.3210 |
| 206371_at | FOLR3 | Hs.352 |
| 206372_at | MYF6 | Hs.35937 |
| 206374_at | DUSP8 | Hs.41688 |
| 206377_at | FOXF2 | Hs.44481 |
| 206380_s_at | PFC | Hs.53155 |
| 206381_at | SCN2A2 | Hs.435796 |
| 206390_x_at | PF4 | Hs.81564 |
| 206398_s_at | CD19 | Hs.96023 |
| 206404_at | FGF9 | Hs.111 |
| 206420_at | IGSF6 | Hs.135194 |
| 206433_s_at | SPOCK3 | Hs.159425 |
| 206453_s_at | NDRG2 | Hs.243960 |
| 206461_x_at | MT1H | Hs.438462 |
| 206464_at | BMX | Hs.27372 |
| 206471_s_at | PLXNC1 | Hs.286229 |
| 206472_s_at | TLE3 | Hs.287362 |
| 206478_at | KIAA0125 | Hs.38365 |
| 206485_at | CD5 | Hs.58685 |
| 206488_s_at | CD36 | Hs.443120 |
| 206491_s_at | NAPA | Hs.75932 |
| 206493_at | ITGA2B | Hs.411312 |
| 206494_s_at | ITGA2B | Hs.411312 |
| 206508_at | TNFSF7 | Hs.99899 |
| 206513_at | AIM2 | Hs.105115 |
| 206515_at | CYP4F3 | Hs.106242 |
| 206519_x_at | SIGLEC6 | Hs.397255 |
| 206520_x_at | SIGLEC6 | Hs.397255 |
| 206522_at | MGAM | Hs.122785 |
| 206545_at | CD28 | Hs.1987 |
| 206546_at | SYCP2 | Hs.202676 |
| 206574_s_at | PTP4A3 | Hs.43666 |
| 206580_s_at | EFEMP2 | Hs.381870 |
| 206582_s_at | GPR56 | Hs.6527 |
| 206584_at | LY96 | Hs.69328 |
| 206589_at | GFI1 | Hs.73172 |
| 206591_at | RAG1 | Hs.73958 |
| 206618_at | IL18R1 | Hs.159301 |
| 206622_at | TRH | Hs.182231 |
| 206624_at | USP9Y | Hs.371255 |
| 206631_at | PTGER2 | Hs.2090 |
| 206632_s_at | APOBEC3B | Hs.226307 |
| 206634_at | SIX3 | Hs.227277 |
| 206637_at | GPR105 | Hs.2465 |
| 206643_at | HAL | Hs.190783 |
| 206647_at | HBZ | Hs.272003 |
| 206655_s_at | PNUTL1 | Hs.283743 |
| 206660_at | IGLL1 | Hs.348935 |
| 206662_at | GLRX | Hs.28988 |
| 206665_s_at | BCL2L1 | Hs.305890 |
| 206666_at | GZMK | Hs.277937 |
| 206674_at | FLT3 | Hs.385 |
| 206676_at | CEACAM8 | Hs.41 |
| 206682_at | CLECSF13 | Hs.54403 |
| 206697_s_at | HP | Hs.403931 |
| 206698_at | XK | Hs.78919 |
| 206700_s_at | SMCY | Hs.80358 |
| 206707_x_at | C6orf32 | Hs.389488 |
| 206710_s_at | EPB41L3 | Hs.103839 |
| 206724_at | CBX4 | Hs.5637 |
| 206726_at | PGDS | Hs.128433 |
| 206752_s_at | DFFB | Hs.133089 |
| 206759_at | FCER2 | Hs.1416 |
| 206760_s_at | FCER2 | Hs.1416 |
| 206761_at | TACTILE | Hs.142023 |
| 206762_at | KCNA5 | Hs.150208 |
| 206765_at | KCNJ2 | Hs.1547 |
| 206788_s_at | CBFB | Hs.179881 |
| 206793_at | PNMT | Hs.1892 |
| 206804_at | CD3G | Hs.2259 |
| 206834_at | HBD | Hs.36977 |
| 206851_at | RNASE3 | Hs.73839 |
| 206857_s_at | FKBP1B | Hs.306834 |
| 206858_s_at | HOXC6 | Hs.820 |
| 206871_at | ELA2 | Hs.99863 |
| 206877_at | MAD | Hs.379930 |
| 206881_s_at | LILRA3 | Hs.113277 |
| 206918_s_at | RBM12 | Hs.166887 |
| 206924_at | IL11 | Hs.1721 |
| 206932_at | CH25H | Hs.47357 |
| 206934_at | SIRPB1 | Hs.194784 |
| 206937_at | SPTA1 | Hs.418378 |
| 206940_s_at | POU4F1 | Hs.458303 |
| 206950_at | SCN9A | Hs.2319 |
| 206951_at | HIST1H4E | Hs.240135 |
| 206953_s_at | LPHN2 | Hs.24212 |
| 206978_at | CCR2 | Hs.395 |
| 206991_s_at | CCR5 | Hs.54443 |
| 206999_at | IL12RB2 | Hs.413608 |
| 207001_x_at | DSIPI | Hs.420569 |
| 207008_at | IL8RB | Hs.846 |
| 207030_s_at | CSRP2 | Hs.10526 |
| 207031_at | BAPX1 | Hs.105941 |
| 207034_s_at | GLI2 | Hs.111867 |
| 207038_at | SLC16A6 | Hs.42645 |
| 207043_s_at | SLC6A9 | Hs.442590 |
| 207067_s_at | HDC | Hs.1481 |
| 207072_at | IL18RAP | Hs.158315 |
| 207075_at | CIAS1 | Hs.159483 |
| 207076_s_at | ASS | Hs.160786 |
| 207085_x_at | CSF2RA | Hs.227835 |
| 207087_x_at | ANK1 | Hs.443711 |
| 207090_x_at | ZFP30 | Hs.276763 |
| 207094_at | IL8RA | Hs.194778 |
| 207104_x_at | LILRB1 | Hs.149924 |
| 207111_at | EMR1 | Hs.2375 |
| 207113_s_at | TNF | Hs.241570 |
| 207117_at | H-plk | Hs.250693 |
| 207134_x_at | TPSB2 | Hs.405479 |
| 207161_at | KIAA0087 | Hs.69749 |
| 207172_s_at | CDH11 | Hs.443435 |
| 207173_x_at | CDH11 | Hs.443435 |
| 207206_s_at | ALOX12 | Hs.1200 |
| 207216_at | TNFSF8 | Hs.177136 |
| 207224_s_at | SIGLEC7 | Hs.274470 |
| 207237_at | KCNA3 | Hs.169948 |
| 207269_at | DEFA4 | Hs.2582 |
| 207275_s_at | FACL2 | Hs.406678 |
| 207292_s_at | MAPK7 | Hs.150136 |
| 207316_at | HAS1 | Hs.57697 |
| 207329_at | MMP8 | Hs.390002 |
| 207332_s_at | TFRC | Hs.185726 |
| 207339_s_at | LTB | Hs.376208 |
| 207341_at | PRTN3 | Hs.928 |
| 207357_s_at | GALNT10 | Hs.13785 |
| 207358_x_at | MACF1 | Hs.372463 |
| 207376_at | VENTX2 | Hs.125231 |
| 207384_at | PGLYRP | Hs.137583 |

TABLE 1-continued

About 2856 genes used for classifying AML of 286 patients into defined clusters as identified in Correlation View

| Affymetrix probe set id | gene symbol | unigene ID |
|---|---|---|
| 207387_s_at | GK | Hs.1466 |
| 207389_at | GP1BA | Hs.1472 |
| 207419_s_at | RAC2 | Hs.301175 |
| 207425_s_at | MSF | Hs.288094 |
| 207433_at | IL10 | Hs.193717 |
| 207435_s_at | SRRM2 | Hs.433343 |
| 207459_x_at | GYPB | Hs.438658 |
| 207467_x_at | CAST | Hs.440961 |
| 207496_at | MS4A2 | Hs.386748 |
| 207509_s_at | LAIR2 | Hs.43803 |
| 207511_s_at | CGI-57 | Hs.4973 |
| 207522_s_at | ATP2A3 | Hs.5541 |
| 207526_s_at | IL1RL1 | Hs.66 |
| 207533_at | CCL1 | Hs.72918 |
| 207535_s_at | NFKB2 | Hs.73090 |
| 207540_s_at | SYK | Hs.192182 |
| 207542_s_at | AQP1 | Hs.76152 |
| 207550_at | MPL | Hs.84171 |
| 207571_x_at | C1orf38 | Hs.10649 |
| 207574_s_at | GADD45B | Hs.110571 |
| 207605_x_at | H-plk | Hs.250693 |
| 207610_s_at | EMR2 | Hs.137354 |
| 207651_at | H963 | Hs.159545 |
| 207655_s_at | BLNK | Hs.167746 |
| 207667_s_at | MAP2K3 | Hs.180533 |
| 207674_at | FCAR | Hs.193122 |
| 207675_x_at | ARTN | Hs.194689 |
| 207677_s_at | NCF4 | Hs.196352 |
| 207691_x_at | ENTPD1 | Hs.205353 |
| 207695_s_at | IGSF1 | Hs.22111 |
| 207697_x_at | LILRB3 | Hs.306230 |
| 207705_s_at | KIAA0980 | Hs.227743 |
| 207741_x_at | TPSB2 | Hs.405479 |
| 207793_s_at | EPB41 | Hs.37427 |
| 207794_at | CCR2 | Hs.395 |
| 207795_s_at | KLRD1 | Hs.41682 |
| 207801_s_at | RNF10 | Hs.387944 |
| 207802_at | SGP28 | Hs.404466 |
| 207826_s_at | ID3 | Hs.76884 |
| 207827_x_at | SNCA | Hs.76930 |
| 207836_s_at | RBPMS | Hs.195825 |
| 207838_x_at | PBXIP1 | Hs.8068 |
| 207850_at | CXCL3 | Hs.89690 |
| 207854_at | GYPE | Hs.395535 |
| 207857_at | LILRB1 | Hs.149924 |
| 207872_s_at | LILRB1 | Hs.149924 |
| 207890_s_at | MMP25 | Hs.290222 |
| 207911_s_at | TGM5 | Hs.129719 |
| 207938_at | PI15 | Hs.129732 |
| 207978_s_at | NR4A3 | Hs.279522 |
| 207979_s_at | CD8B1 | Hs.405667 |
| 207983_s_at | STAG2 | Hs.8217 |
| 208018_s_at | HCK | Hs.89555 |
| 208029_s_at | LAPTM4B | Hs.296398 |
| 208034_s_at | PROZ | Hs.1011 |
| 208056_s_at | CBFA2T3 | Hs.110099 |
| 208067_x_at | UTY | Hs.115277 |
| 208071_s_at | LAIR1 | Hs.407964 |
| 208078_s_at | TCF8 | Hs.232068 |
| 208091_s_at | DKFZP564K0822 | Hs.4750 |
| 208112_x_at | EHD1 | Hs.155119 |
| 208116_s_at | MAN1A1 | Hs.255149 |
| 208120_x_at | — | — // — |
| 208130_s_at | TBXAS1 | Hs.444510 |
| 208131_s_at | PTGIS | Hs.302085 |
| 208132_x_at | BAT2 | Hs.436093 |
| 208146_s_at | CPVL | Hs.95594 |
| 208151_x_at | DDX17 | Hs.349121 |
| 208161_s_at | ABCC3 | Hs.90786 |
| 208187_s_at | — | — // — |
| 208248_x_at | APLP2 | Hs.279518 |
| 208255_s_at | FKBP8 | Hs.173464 |
| 208296_x_at | GG2-1 | Hs.17839 |
| 208304_at | CCR3 | Hs.506190 |
| 208306_x_at | HLA-DRB4 | Hs.449633 |
| 208335_s_at | FY | Hs.183 |
| 208352_x_at | ANK1 | Hs.443711 |
| 208353_x_at | ANK1 | Hs.443711 |
| 208370_s_at | DSCR1 | Hs.282326 |
| 208416_s_at | SPTB | Hs.438514 |
| 208436_s_at | IRF7 | Hs.166120 |
| 208438_s_at | FGR | Hs.1422 |
| 208443_x_at | SHOX2 | Hs.55967 |
| 208450_at | LGALS2 | Hs.113987 |
| 208451_s_at | C4A | Hs.150833 |
| 208459_s_at | XPO7 | Hs.172685 |
| 208470_s_at | HP | Hs.403931 |
| 208476_s_at | FLJ10210 | Hs.171532 |
| 208488_s_at | CR1 | Hs.334019 |
| 208490_x_at | HIST1H2BF | Hs.182137 |
| 208498_s_at | AMY1A | Hs.274376 |
| 208501_at | GFI1B | Hs.118539 |
| 208502_s_at | PITX1 | Hs.84136 |
| 208523_x_at | HIST1H2BI | Hs.182140 |
| 208527_x_at | HIST1H2BE | Hs.182138 |
| 208534_s_at | POLR2J2 | Hs.433879 |
| 208540_x_at | — | — // — |
| 208546_x_at | HIST1H4G | Hs.247815 |
| 208553_at | HIST1H1E | Hs.248133 |
| 208579_x_at | H2BFS | Hs.473961 |
| 208581_x_at | MT1X | Hs.374950 |
| 208592_s_at | CD1E | Hs.249217 |
| 208594_x_at | LILRB3 | Hs.306230 |
| 208601_s_at | TUBB1 | Hs.303023 |
| 208602_x_at | CD6 | Hs.436949 |
| 208605_s_at | NTRK1 | Hs.406293 |
| 208609_s_at | TNXB | Hs.411644 |
| 208613_s_at | FLNB | Hs.81008 |
| 208614_s_at | FLNB | Hs.81008 |
| 208621_s_at | VIL2 | Hs.403997 |
| 208622_s_at | VIL2 | Hs.403997 |
| 208623_s_at | VIL2 | Hs.403997 |
| 208631_s_at | HADHA | Hs.75860 |
| 208632_at | RNF10 | Hs.387944 |
| 208633_s_at | MACF1 | Hs.372463 |
| 208634_s_at | MACF1 | Hs.372463 |
| 208636_at | na | Hs.447510 // — |
| 208646_at | RPS14 | Hs.381126 |
| 208650_s_at | CD24 | Hs.375108 |
| 208651_x_at | CD24 | Hs.375108 |
| 208653_s_at | CD164 | Hs.43910 |
| 208657_s_at | MSF | Hs.288094 |
| 208677_s_at | BSG | Hs.371654 |
| 208683_at | CAPN2 | Hs.350899 |
| 208690_s_at | PDLIM1 | Hs.75807 |
| 208691_at | TFRC | Hs.185726 |
| 208702_x_at | APLP2 | Hs.279518 |
| 208703_s_at | APLP2 | Hs.279518 |
| 208704_x_at | APLP2 | Hs.279518 |
| 208711_s_at | CCND1 | Hs.371468 |
| 208712_at | CCND1 | Hs.371468 |
| 208719_s_at | DDX17 | Hs.349121 |
| 208729_x_at | HLA-B | Hs.77961 |
| 208744_x_at | HSPH1 | Hs.36927 |
| 208747_s_at | C1S | Hs.458355 |
| 208751_at | NAPA | Hs.75932 |
| 208767_s_at | LAPTM4B | Hs.296398 |
| 208771_s_at | LTA4H | Hs.81118 |
| 208782_at | FSTL1 | Hs.433622 |
| 208789_at | PTRF | Hs.437191 |
| 208791_at | CLU | Hs.436657 |
| 208792_s_at | CLU | Hs.436657 |
| 208797_s_at | GOLGIN-67 | Hs.182982 |
| 208798_x_at | GOLGIN-67 | Hs.182982 |
| 208812_x_at | HLA-C | Hs.274485 |
| 208820_at | PTK2 | Hs.434281 |
| 208827_at | PSMB6 | Hs.77060 |
| 208854_s_at | STK24 | Hs.168913 |
| 208855_s_at | STK24 | Hs.168913 |
| 208869_s_at | GABARAPL1 | Hs.336429 |

TABLE 1-continued

About 2856 genes used for classifying AML of 286 patients into defined clusters as identified in Correlation View

| Affymetrix probe set id | gene symbol | unigene ID |
|---|---|---|
| 208886_at | H1F0 | Hs.226117 |
| 208890_s_at | PLXNB2 | Hs.3989 |
| 208891_at | DUSP6 | Hs.298654 |
| 208892_s_at | DUSP6 | Hs.298654 |
| 208893_s_at | DUSP6 | Hs.298654 |
| 208894_at | HLA-DRA | Hs.409805 |
| 208906_at | BSCL2 | Hs.438912 |
| 208914_at | GGA2 | Hs.133340 |
| 208924_at | RNF11 | Hs.96334 |
| 208928_at | POR | Hs.354056 |
| 208937_s_at | ID1 | Hs.410900 |
| 208949_s_at | LGALS3 | Hs.411701 |
| 208953_at | KIAA0217 | Hs.192881 |
| 208960_s_at | COPEB | Hs.285313 |
| 208961_s_at | COPEB | Hs.285313 |
| 208962_s_at | FADS1 | Hs.132898 |
| 208965_s_at | IFI16 | Hs.370873 |
| 208966_x_at | IFI16 | Hs.370873 |
| 208970_s_at | UROD | Hs.78601 |
| 208971_at | UROD | Hs.78601 |
| 208978_at | CRIP2 | Hs.70327 |
| 208981_at | PECAM1 | Hs.78146 |
| 208982_at | PECAM1 | Hs.78146 |
| 208983_s_at | PECAM1 | Hs.78146 |
| 208997_s_at | UCP2 | Hs.80658 |
| 209007_s_at | DJ465N24.2.1 | Hs.259412 |
| 209018_s_at | PINK1 | Hs.439600 |
| 209022_at | STAG2 | Hs.8217 |
| 209023_s_at | STAG2 | Hs.8217 |
| 209030_s_at | IGSF4 | Hs.156682 |
| 209031_at | IGSF4 | Hs.156682 |
| 209032_s_at | IGSF4 | Hs.156682 |
| 209035_at | MDK | Hs.82045 |
| 209037_s_at | EHD1 | Hs.155119 |
| 209039_x_at | EHD1 | Hs.155119 |
| 209040_s_at | PSMB8 | Hs.180062 |
| 209046_s_at | GABARAPL2 | Hs.6518 |
| 209047_at | AQP1 | Hs.76152 |
| 209079_x_at | PCDHGC3 | Hs.283794 |
| 209081_s_at | COL18A1 | Hs.413175 |
| 209083_at | CORO1A | Hs.415067 |
| 209086_x_at | MCAM | Hs.211579 |
| 209087_x_at | MCAM | Hs.211579 |
| 209094_at | DDAH1 | Hs.380870 |
| 209098_s_at | JAG1 | Hs.409202 |
| 209099_x_at | JAG1 | Hs.409202 |
| 209101_at | CTGF | Hs.410037 |
| 209116_x_at | HBB | Hs.155376 |
| 209117_at | WBP2 | Hs.231840 |
| 209118_s_at | TUBA3 | Hs.433394 |
| 209122_at | ADFP | Hs.3416 |
| 209129_at | TRIP6 | Hs.380230 |
| 209138_x_at | — | Hs.505407 |
| 209140_x_at | HLA-B | Hs.77961 |
| 209152_s_at | TCF3 | Hs.371282 |
| 209153_s_at | TCF3 | Hs.371282 |
| 209156_s_at | COL6A2 | Hs.420269 |
| 209160_at | AKR1C3 | Hs.78183 |
| 209167_at | GPM6B | Hs.5422 |
| 209168_at | GPM6B | Hs.5422 |
| 209170_s_at | GPM6B | Hs.5422 |
| 209173_at | AGR2 | Hs.226391 |
| 209182_s_at | DEPP | Hs.93675 |
| 209183_s_at | DEPP | Hs.93675 |
| 209184_s_at | IRS2 | Hs.143648 |
| 209185_s_at | IRS2 | Hs.143648 |
| 209189_at | FOS | Hs.25647 |
| 209191_at | TUBB-5 | Hs.274398 |
| 209193_at | PIM1 | Hs.81170 |
| 209199_s_at | MEF2C | Hs.368950 |
| 209200_at | MEF2C | Hs.368950 |
| 209201_x_at | CXCR4 | Hs.421986 |
| 209205_s_at | LMO4 | Hs.3844 |
| 209208_at | MPDU1 | Hs.6710 |
| 209216_at | JM5 | Hs.21753 |
| 209217_s_at | JM5 | Hs.21753 |
| 209239_at | NFKB1 | Hs.160557 |
| 209250_at | DEGS | Hs.299878 |
| 209264_s_at | TM4SF7 | Hs.26518 |
| 209267_s_at | BIGM103 | Hs.284205 |
| 209273_s_at | MGC4276 | Hs.270013 |
| 209274_s_at | MGC4276 | Hs.270013 |
| 209276_s_at | GLRX | Hs.28988 |
| 209281_s_at | ATP2B1 | Hs.20952 |
| 209282_at | PRKD2 | Hs.205431 |
| 209285_s_at | RAP140 | Hs.23440 |
| 209286_at | CDC42EP3 | Hs.352554 |
| 209287_s_at | CDC42EP3 | Hs.352554 |
| 209288_s_at | CDC42EP3 | Hs.352554 |
| 209297_at | ITSN1 | Hs.66392 |
| 209301_at | CA2 | Hs.155097 |
| 209304_x_at | GADD45B | Hs.110571 |
| 209305_s_at | GADD45B | Hs.110571 |
| 209312_x_at | HLA-DRB3 | Hs.308026 |
| 209318_x_at | PLAGL1 | Hs.132911 |
| 209325_s_at | RGS16 | Hs.413297 |
| 209339_at | SIAH2 | Hs.20191 |
| 209340_at | UAP1 | Hs.21293 |
| 209344_at | TPM4 | Hs.250641 |
| 209348_s_at | MAF | Hs.134859 |
| 209357_at | CITED2 | Hs.82071 |
| 209360_s_at | RUNX1 | Hs.410774 |
| 209367_at | STXBP2 | Hs.379204 |
| 209369_at | ANXA3 | Hs.442733 |
| 209374_s_at | IGHM | Hs.153261 |
| 209377_s_at | HMGN3 | Hs.77558 |
| 209383_at | DDIT3 | Hs.392171 |
| 209386_at | TM4SF1 | Hs.351316 |
| 209387_s_at | TM4SF1 | Hs.351316 |
| 209392_at | ENPP2 | Hs.23719 |
| 209394_at | ASMTL | Hs.458420 |
| 209395_at | CHI3L1 | Hs.382202 |
| 209396_s_at | CHI3L1 | Hs.382202 |
| 209398_at | HIST1H1C | Hs.7644 |
| 209436_at | SPON1 | Hs.5378 |
| 209437_s_at | SPON1 | Hs.5378 |
| 209452_s_at | VTI1B | Hs.419995 |
| 209457_at | DUSP5 | Hs.2128 |
| 209458_x_at | HBA1 | Hs.449630 |
| 209473_at | ENTPD1 | Hs.205353 |
| 209474_s_at | ENTPD1 | Hs.205353 |
| 209480_at | HLA-DQB1 | Hs.409934 |
| 209487_at | RBPMS | Hs.195825 |
| 209488_s_at | RBPMS | Hs.195825 |
| 209498_at | CEACAM1 | Hs.434918 |
| 209499_x_at | TNFSF13 | Hs.54673 |
| 209500_x_at | TNFSF13 | Hs.54673 |
| 209514_s_at | RAB27A | Hs.298530 |
| 209515_s_at | RAB27A | Hs.298530 |
| 209524_at | HDGFRP3 | Hs.127842 |
| 209526_s_at | HDGFRP3 | Hs.127842 |
| 209536_s_at | EHD4 | Hs.55058 |
| 209540_at | IGF1 | Hs.308053 |
| 209541_at | IGF1 | Hs.308053 |
| 209542_x_at | IGF1 | Hs.308053 |
| 209543_s_at | CD34 | Hs.374990 |
| 209545_s_at | RIPK2 | Hs.103755 |
| 209555_s_at | CD36 | Hs.443120 |
| 209560_s_at | DLK1 | Hs.169228 |
| 209561_at | THBS3 | Hs.169875 |
| 209568_s_at | RGL | Hs.79219 |
| 209576_at | GNAI1 | Hs.203862 |
| 209581_at | HRASLS3 | Hs.417630 |
| 209582_s_at | MOX2 | Hs.79015 |
| 209583_s_at | MOX2 | Hs.79015 |
| 209585_s_at | MINPP1 | Hs.95907 |
| 209587_at | PITX1 | Hs.84136 |
| 209598_at | PNMA2 | Hs.7782 |
| 209604_s_at | GATA3 | Hs.169946 |
| 209606_at | PSCDBP | Hs.270 |

TABLE 1-continued

About 2856 genes used for classifying AML of 286 patients into defined clusters as identified in Correlation View

| Affymetrix probe set id | gene symbol | unigene ID |
|---|---|---|
| 209615_s_at | PAK1 | Hs.64056 |
| 209616_s_at | CES1 | Hs.278997 |
| 209619_at | CD74 | Hs.446471 |
| 209627_s_at | OSBPL3 | Hs.197955 |
| 209628_at | NXT2 | Hs.25010 |
| 209629_s_at | NXT2 | Hs.25010 |
| 209636_at | NFKB2 | Hs.73090 |
| 209651_at | TGFB1I1 | Hs.25511 |
| 209652_s_at | PGF | Hs.252820 |
| 209670_at | TRA@ | Hs.74647 |
| 209671_x_at | TRA@ | Hs.74647 |
| 209676_at | TFPI | Hs.102301 |
| 209679_s_at | LOC57228 | Hs.206501 |
| 209686_at | S100B | Hs.422181 |
| 209687_at | CXCL12 | Hs.436042 |
| 209695_at | PTP4A3 | Hs.43666 |
| 209696_at | FBP1 | Hs.360509 |
| 209699_x_at | AKR1C2 | Hs.201967 |
| 209702_at | FTO | Hs.284741 |
| 209706_at | NKX3-1 | Hs.55999 |
| 209710_at | GATA2 | Hs.367725 |
| 209716_at | CSF1 | Hs.173894 |
| 209717_at | — | Hs.387251 |
| 209727_at | GM2A | Hs.387156 |
| 209728_at | HLA-DRB4 | Hs.449633 |
| 209732_at | CLECSF2 | Hs.85201 |
| 209735_at | ABCG2 | Hs.194720 |
| 209757_s_at | MYCN | Hs.25960 |
| 209763_at | NRLN1 | Hs.440324 |
| 209771_x_at | — | Hs.376280 // — |
| 209772_s_at | CD24 | Hs.375108 |
| 209773_s_at | RRM2 | Hs.226390 |
| 209774_x_at | CXCL2 | Hs.75765 |
| 209790_s_at | CASP6 | Hs.3280 |
| 209791_at | PADI2 | Hs.33455 |
| 209795_at | CD69 | Hs.82401 |
| 209803_s_at | TSSC3 | Hs.154036 |
| 209806_at | HIST1H2BK | Hs.247817 |
| 209813_x_at | — | Hs.407442 |
| 209815_at | na | Hs.454253 // — |
| 209822_s_at | VLDLR | Hs.370422 |
| 209823_x_at | HLA-DQB1 | Hs.409934 |
| 209829_at | C6orf32 | Hs.389488 |
| 209835_x_at | CD44 | Hs.306278 |
| 209845_at | MKRN1 | Hs.7838 |
| 209863_s_at | TP73L | Hs.137569 |
| 209870_s_at | APBA2 | Hs.26468 |
| 209875_s_at | SPP1 | Hs.313 |
| 209879_at | SELPLG | Hs.423077 |
| 209881_s_at | LAT | Hs.437775 |
| 209884_s_at | SLC4A7 | Hs.250072 |
| 209890_at | TM4SF9 | Hs.8037 |
| 209892_at | FUT4 | Hs.390420 |
| 209893_s_at | FUT4 | Hs.390420 |
| 209894_at | LEPR | Hs.23581 |
| 209900_s_at | SLC16A1 | Hs.75231 |
| 209901_x_at | AIF1 | Hs.76364 |
| 209905_at | HOXA9 | Hs.127428 |
| 209906_at | C3AR1 | Hs.155935 |
| 209911_x_at | HTST1H2BD | Hs.180779 |
| 209921_at | SLC7A11 | Hs.6682 |
| 209930_s_at | NFE2 | Hs.75643 |
| 209949_at | NCF2 | Hs.949 |
| 209950_s_at | VILL | Hs.103665 |
| 209959_at | NR4A3 | Hs.279522 |
| 209960_at | HGF | Hs.396530 |
| 209961_s_at | HGF | Hs.396530 |
| 209962_at | EPOR | Hs.127826 |
| 209963_s_at | EPOR | Hs.127826 |
| 209967_s_at | CREM | Hs.231975 |
| 209968_s_at | NCAM1 | Hs.78792 |
| 209969_s_at | STAT1 | Hs.21486 |
| 209982_s_at | NRXN2 | Hs.124085 |
| 209993_at | ABCB1 | Hs.21330 |
| 209994_s_at | ABCB1 | Hs.21330 |
| 209995_s_at | TCL1A | Hs.2484 |
| 210001_s_at | SOCS1 | Hs.50640 |
| 210004_at | OLR1 | Hs.445299 |
| 210016_at | MYT1L | Hs.434418 |
| 210024_s_at | UBE2E3 | Hs.4890 |
| 210031_at | CD3Z | Hs.97087 |
| 210032_s_at | SPAG6 | Hs.158213 |
| 210033_s_at | SPAG6 | Hs.158213 |
| 210036_s_at | KCNH2 | Hs.188021 |
| 210038_at | PRKCQ | Hs.408049 |
| 210042_s_at | CTSZ | Hs.252549 |
| 210074_at | CTSL2 | Hs.87417 |
| 210075_at | LOC51257 | Hs.331308 |
| 210084_x_at | TPSB2 | Hs.405479 |
| 210088_x_at | MYL4 | Hs.356717 |
| 210095_s_at | IGFBP3 | Hs.440409 |
| 210102_at | LOH11CR2A | Hs.152944 |
| 210105_s_at | FYN | Hs.390567 |
| 210107_at | CLCA1 | Hs.194659 |
| 210113_s_at | DEFCAP | Hs.104305 |
| 210116_at | SH2D1A | Hs.151544 |
| 210118_s_at | IL1A | Hs.1722 |
| 210123_s_at | CHRNA7 | Hs.2540 |
| 210134_x_at | SHOX2 | Hs.55967 |
| 210135_s_at | SHOX2 | Hs.55967 |
| 210139_s_at | PMP22 | Hs.372031 |
| 210140_at | CST7 | Hs.143212 |
| 210142_x_at | FLOT1 | Hs.179986 |
| 210146_x_at | LILRB3 | Hs.306230 |
| 210151_s_at | DYRK3 | Hs.164267 |
| 210152_at | LILRB4 | Hs.67846 |
| 210164_at | GZMB | Hs.1051 |
| 210166_at | TLR5 | Hs.114408 |
| 210172_at | SF1 | Hs.440835 |
| 210190_at | STX11 | Hs.118958 |
| 210215_at | TFR2 | Hs.63758 |
| 210222_s_at | RTN1 | Hs.99947 |
| 210225_x_at | LILRB3 | Hs.306230 |
| 210230_at | — | — // — |
| 210237_at | ARTN | Hs.194689 |
| 210239_at | IRX5 | Hs.25351 |
| 210244_at | CAMP | Hs.51120 |
| 210247_at | SYN2 | Hs.445503 |
| 210254_at | MS4A3 | Hs.99960 |
| 210260_s_at | GG2-1 | Hs.17839 |
| 210262_at | TPX1 | Hs.2042 |
| 210264_at | GPR35 | Hs.239891 |
| 210269_s_at | DXYS155E | Hs.21595 |
| 210279_at | GPR18 | Hs.88269 |
| 210298_x_at | FHL1 | Hs.421383 |
| 210299_s_at | FHL1 | Hs.421383 |
| 210313_at | LIR9 | Hs.406708 |
| 210314_x_at | TNFSF13 | Hs.54673 |
| 210321_at | GZMH | Hs.348264 |
| 210340_s_at | CSF2RA | Hs.227835 |
| 210356_x_at | MS4A1 | Hs.438040 |
| 210357_s_at | C20orf16 | Hs.433337 |
| 210368_at | PCDHGC3 | Hs.283794 |
| 210387_at | HIST1H2BG | Hs.352109 |
| 210395_x_at | MYL4 | Hs.356717 |
| 210397_at | DEFB1 | Hs.32949 |
| 210422_x_at | SLC11A1 | Hs.135163 |
| 210423_s_at | SLC11A1 | Hs.135163 |
| 210425_x_at | GOLGIN-67 | Hs.356225 |
| 210426_x_at | RORA | Hs.388617 |
| 210427_x_at | ANXA2 | Hs.437110 |
| 210429_at | RHD | Hs.458333 |
| 210430_x_at | RHD | Hs.283822 |
| 210432_s_at | SCN3A | Hs.300717 |
| 210446_at | GATA1 | Hs.765 |
| 210448_s_at | P2RX5 | Hs.408615 |
| 210461_s_at | ABLIM1 | Hs.442540 |
| 210473_s_at | GPR125 | Hs.356876 |
| 210479_s_at | RORA | Hs.388617 |
| 210487_at | DNTT | Hs.397294 |

TABLE 1-continued

About 2856 genes used for classifying AML of 286 patients into defined clusters as identified in Correlation View

| Affymetrix probe set id | gene symbol | unigene ID |
|---|---|---|
| 210495_x_at | FN1 | Hs.418138 |
| 210504_at | KLF1 | Hs.37860 |
| 210508_s_at | KCNQ2 | Hs.4975 |
| 210512_s_at | VEGF | Hs.73793 |
| 210514_x_at | HLA-A | Hs.181244 |
| 210517_s_at | AKAP12 | Hs.197081 |
| 210524_x_at | MT1F | Hs.438737 |
| 210538_s_at | BIRC3 | Hs.127799 |
| 210546_x_at | CTAG1 | Hs.167379 |
| 210548_at | CCL23 | Hs.169191 |
| 210549_s_at | CCL23 | Hs.169191 |
| 210554_s_at | CTBP2 | Hs.171391 |
| 210561_s_at | WSB1 | Hs.315379 |
| 210582_s_at | LIMK2 | Hs.278027 |
| 210586_x_at | RHD | Hs.458333 |
| 210605_s_at | MFGE8 | Hs.3745 |
| 210606_x_at | KLRD1 | Hs.41682 |
| 210612_s_at | SYNJ2 | Hs.434494 |
| 210638_s_at | FBXO9 | Hs.388387 |
| 210640_s_at | GPR30 | Hs.113207 |
| 210649_s_at | SMARCF1 | Hs.170333 |
| 210655_s_at | FOXO3A | Hs.14845 |
| 210660_at | LILRB1 | Hs.149924 |
| 210663_s_at | KYNU | Hs.444471 |
| 210664_s_at | TFPI | Hs.102301 |
| 210665_at | TFPI | Hs.102301 |
| 210666_at | IDS | Hs.352304 |
| 210681_s_at | USP15 | Hs.339425 |
| 210693_at | SPPL2B | Hs.284161 |
| 210724_at | EMR3 | Hs.438468 |
| 210744_s_at | IL5RA | Hs.68876 |
| 210746_s_at | EPB42 | Hs.368642 |
| 210755_at | HGF | Hs.396530 |
| 210756_s_at | NOTCH2 | Hs.8121 |
| 210762_s_at | DLC1 | Hs.8700 |
| 210772_at | FPRL1 | Hs.99855 |
| 210773_s_at | FPRL1 | Hs.99855 |
| 210783_x_at | SCGF | Hs.105927 |
| 210784_x_at | LILRB3 | Hs.306230 |
| 210785_s_at | C1orf38 | Hs.10649 |
| 210786_s_at | FLI1 | Hs.257049 |
| 210794_s_at | MEG3 | Hs.418271 |
| 210796_x_at | SIGLEC6 | Hs.397255 |
| 210815_s_at | CALCRL | Hs.152175 |
| 210825_s_at | STOM | Hs.439776 |
| 210835_s_at | CTBP2 | Hs.171391 |
| 210839_s_at | ENPP2 | Hs.23719 |
| 210840_s_at | IQGAP1 | Hs.1742 |
| 210844_x_at | CTNNA1 | Hs.254321 |
| 210845_s_at | PLAUR | Hs.179657 |
| 210854_x_at | SLC6A8 | Hs.388375 |
| 210869_s_at | MCAM | Hs.211579 |
| 210873_x_at | APOBEC3A | Hs.348983 |
| 210889_s_at | FCGR2B | Hs.126384 |
| 210895_s_at | CD86 | Hs.27954 |
| 210904_s_at | IL13RA1 | Hs.285115 |
| 210915_x_at | TRB@ | Hs.419777 |
| 210916_s_at | CD44 | Hs.306278 |
| 210948_s_at | LEF1 | Hs.44865 |
| 210951_x_at | RAB27A | Hs.298530 |
| 210972_x_at | TRA@ | Hs.74647 |
| 210973_s_at | FGFR1 | Hs.748 |
| 210976_s_at | PFKM | Hs.75160 |
| 210982_s_at | HLA-DRA | Hs.409805 |
| 210986_s_at | TPM1 | Hs.133892 |
| 210987_x_at | — | — // — |
| 210992_x_at | FCGR2B | Hs.126384 |
| 210993_s_at | MADH1 | Hs.388294 |
| 210997_at | HGF | Hs.396530 |
| 210998_s_at | HGF | Hs.396530 |
| 210999_s_at | GRB10 | Hs.81875 |
| 211005_at | LAT | Hs.437775 |
| 211024_s_at | TITF1 | Hs.197764 |
| 211025_x_at | COX5B | Hs.1342 |
| 211031_s_at | CYLN2 | Hs.104717 |
| 211052_s_at | TBCD | Hs.12570 |
| 211066_x_at | PCDHGC3 | Hs.283794 |
| 211071_s_at | AF1Q | Hs.75823 |
| 211100_x_at | LILRB1 | Hs.149924 |
| 211101_x_at | LILRB1 | Hs.149924 |
| 211102_s_at | LILRB1 | Hs.149924 |
| 211126_s_at | CSRP2 | Hs.10526 |
| 211133_x_at | LILRB3 | Hs.306230 |
| 211135_x_at | LILRB3 | Hs.306230 |
| 211143_x_at | NR4A1 | Hs.1119 |
| 211144_x_at | TRGC2 | Hs.385086 |
| 211148_s_at | ANGPT2 | Hs.115181 |
| 211163_s_at | TNFRSF10C | Hs.119684 |
| 211202_s_at | PLU-1 | Hs.143323 |
| 211207_s_at | FACL6 | Hs.14945 |
| 211210_x_at | SH2D1A | Hs.151544 |
| 211254_x_at | RHAG | Hs.368178 |
| 211269_s_at | IL2RA | Hs.130058 |
| 211284_s_at | GRN | Hs.180577 |
| 211286_x_at | CSF2RA | Hs.227835 |
| 211302_s_at | PDE4B | Hs.188 |
| 211307_s_at | FCAR | Hs.193122 |
| 211336_x_at | LILRB1 | Hs.149924 |
| 211339_s_at | ITK | Hs.211576 |
| 211340_s_at | MCAM | Hs.211579 |
| 211341_at | POU4F1 | Hs.458303 |
| 211354_s_at | LEPR | Hs.23581 |
| 211355_x_at | LEPR | Hs.23581 |
| 211356_x_at | LEPR | Hs.23581 |
| 211367_s_at | CASP1 | Hs.2490 |
| 211368_s_at | CASP1 | Hs.2490 |
| 211372_s_at | IL1R2 | Hs.25333 |
| 211395_x_at | FCGR2B | Hs.126384 |
| 211404_s_at | APLP2 | Hs.279518 |
| 211413_s_at | PADI4 | Hs.397050 |
| 211421_s_at | RET | Hs.350321 |
| 211423_s_at | SC5DL | Hs.434074 |
| 211429_s_at | SERPINA1 | Hs.297681 |
| 211430_s_at | IGHG3 | Hs.413826 |
| 211434_s_at | CCRL2 | Hs.302043 |
| 211450_s_at | MSH6 | Hs.445052 |
| 211456_x_at | na | Hs.456549 |
| 211458_s_at | GABARAPL3 | Hs.334497 |
| 211464_x_at | CASP6 | Hs.3280 |
| 211478_s_at | SERPINB6 | Hs.41072 |
| 211474_s_at | DPP4 | Hs.44926 |
| 211495_x_at | TNFSF13 | Hs.54673 |
| 211506_s_at | — | — // — |
| 211517_s_at | IL5RA | Hs.68876 |
| 211521_s_at | PSCD4 | Hs.7189 |
| 211527_x_at | VEGF | Hs.73793 |
| 211529_x_at | HLA-A | Hs.181244 |
| 211535_s_at | FGFR1 | Hs.748 |
| 211546_x_at | SNCA | Hs.76930 |
| 211548_s_at | HPGD | Hs.77348 |
| 211560_s_at | ALAS2 | Hs.440455 |
| 211566_x_at | BRE | Hs.80426 |
| 211571_s_at | CSPG2 | Hs.434488 |
| 211597_s_at | HOP | Hs.13775 |
| 211633_x_at | — | Hs.406615 |
| 211634_x_at | — | Hs.449011 |
| 211635_x_at | — | Hs.449011 |
| 211637_x_at | — | Hs.383169 |
| 211639_x_at | — | Hs.383438 |
| 211641_x_at | — | Hs.64568 // — |
| 211643_x_at | na | Hs.377975 |
| 211644_x_at | na | Hs.377975 |
| 211645_x_at | na | Hs.377975 |
| 211649_x_at | — | Hs.449057 |
| 211650_x_at | — | Hs.448957 |
| 211653_x_at | AKR1C2 | Hs.201967 |
| 211654_x_at | HLA-DQB1 | Hs.409934 |
| 211656_x_at | HLA-DQB1 | Hs.409934 |
| 211657_at | CEACAM6 | Hs.436718 |
| 211658_at | PRDX2 | Hs.432121 |

TABLE 1-continued

About 2856 genes used for classifying AML of 286 patients into defined clusters as identified in Correlation View

| Affymetrix probe set id | gene symbol | unigene ID |
|---|---|---|
| 211661_x_at | — | — // — |
| 211663_x_at | PTGDS | Hs.446429 |
| 211668_s_at | PLAU | Hs.77274 |
| 211674_x_at | CTAG1 | Hs.167379 |
| 211675_s_at | HIC | Hs.132739 |
| 211682_x_at | UGT2B28 | Hs.137585 |
| 211696_x_at | HBB | Hs.155376 |
| 211699_x_at | HBA1 | Hs.449630 |
| 211709_s_at | SCGF | Hs.105927 |
| 211719_x_at | FN1 | Hs.418138 |
| 211726_s_at | FMO2 | Hs.361155 |
| 211732_x_at | HNMT | Hs.42151 |
| 211734_s_at | FCER1A | Hs.897 |
| 211742_s_at | EVI2B | Hs.5509 |
| 211743_s_at | PRG2 | Hs.99962 |
| 211745_x_at | HBA1 | Hs.449630 |
| 211748_x_at | PTGDS | Hs.446429 |
| 211764_s_at | UBE2D1 | Hs.129683 |
| 211776_s_at | EPB41L3 | Hs.103839 |
| 211781_x_at | — | — // — |
| 211796_s_at | — | — // — |
| 211798_x_at | IGLJ3 | Hs.102950 |
| 211799_x_at | HLA-C | Hs.274485 |
| 211813_x_at | DCN | Hs.156316 |
| 211816_x_at | FCAR | Hs.193122 |
| 211820_x_at | GYPA | Hs.34287 |
| 211821_x_at | GYPA | Hs.34287 |
| 211858_x_at | GNAS | Hs.157307 |
| 211864_s_at | FER1L3 | Hs.362731 |
| 211868_x_at | — | — // — |
| 211876_x_at | PCDHGC3 | Hs.283794 |
| 211881_x_at | IGLJ3 | Hs.102950 |
| 211883_x_at | CEACAM1 | Hs.434918 |
| 211893_x_at | CD6 | Hs.436949 |
| 211896_s_at | DCN | Hs.156316 |
| 211900_x_at | CD6 | Hs.436949 |
| 211902_x_at | TRA@ | Hs.74647 |
| 211911_x_at | HLA-B | Hs.77961 |
| 211919_s_at | CXCR4 | Hs.421986 |
| 211922_s_at | CAT | Hs.395771 |
| 211924_s_at | PLAUR | Hs.179657 |
| 211941_s_at | PBP | Hs.433863 |
| 211959_at | IGFBP5 | Hs.380833 |
| 211962_s_at | ZFP36L1 | Hs.85155 |
| 211964_at | COL4A2 | Hs.407912 |
| 211965_at | ZFP36L1 | Hs.85155 |
| 211966_at | COL4A2 | Hs.407912 |
| 211970_x_at | ACTG1 | Hs.14376 |
| 211983_x_at | ACTG1 | Hs.14376 |
| 211986_at | MGC5395 | Hs.378738 |
| 211990_at | HLA-DPA1 | Hs.914 |
| 211991_s_at | HLA-DPA1 | Hs.914 |
| 211992_at | PRKWNK1 | Hs.43129 |
| 211993_at | PRKWNK1 | Hs.43129 |
| 211994_at | PRKWNK1 | Hs.43129 |
| 211995_x_at | ACTG1 | Hs.14376 |
| 211996_s_at | na | Hs.406494 // — |
| 212012_at | D2S448 | Hs.118893 // — |
| 212013_at | D2S448 | Hs.118893 // — |
| 212014_x_at | CD44 | Hs.306278 |
| 212046_x_at | MAPK3 | Hs.861 |
| 212055_at | DKFZP586M1523 | Hs.22981 |
| 212056_at | KIAA0182 | Hs.222171 |
| 212057_at | KIAA0182 | Hs.222171 |
| 212062_at | ATP9A | Hs.406434 // — |
| 212067_s_at | C1R | Hs.376414 // — |
| 212069_s_at | MGC10526 | Hs.389588 |
| 212070_at | GPR56 | Hs.6527 |
| 212077_at | CALD1 | Hs.443811 |
| 212086_x_at | LMNA | Hs.436441 |
| 212089_at | LMNA | Hs.436441 |
| 212090_at | GRINA | Hs.339697 |
| 212091_s_at | COL6A1 | Hs.415997 |
| 212097_at | CAV1 | Hs.74034 |
| 212099_at | ARHB | Hs.406064 |
| 212143_s_at | — | Hs.450230 // — |
| 212148_at | PBX1 | Hs.408222 |
| 212151_at | PBX1 | Hs.408222 |
| 212154_at | SDC2 | Hs.1501 |
| 212157_at | SDC2 | Hs.1501 |
| 212158_at | SDC2 | Hs.1501 |
| 212166_at | XPO7 | Hs.172685 |
| 212172_at | AK2 | Hs.294008 |
| 212173_at | AK2 | Hs.294008 |
| 212181_s_at | NUDT4 | Hs.355399 |
| 212183_at | NUDT4 | Hs.355399 |
| 212185_x_at | MT2A | Hs.118786 |
| 212187_x_at | PTGDS | Hs.446429 |
| 212188_at | LOC115207 | Hs.109438 |
| 212190_at | SERPINE2 | Hs.21858 |
| 212192_at | LOC115207 | Hs.109438 |
| 212203_x_at | IFITM3 | Hs.374650 |
| 212221_x_at | na | Hs.303154 // — |
| 212223_at | na | Hs.303154 // — |
| 212224_at | ALDH1A1 | Hs.76392 |
| 212225_at | SUI1 | Hs.150580 |
| 212236_x_at | KRT17 | Hs.2785 |
| 212242_at | TUBA1 | Hs.75318 |
| 212254_s_at | BPAG1 | Hs.443518 |
| 212263_at | QKI | Hs.22248 |
| 212265_at | QKI | Hs.22248 |
| 212273_x_at | GNAS | Hs.157307 |
| 212285_s_at | AGRN | Hs.273330 // — |
| 212311_at | KIAA0746 | Hs.49500 // — |
| 212312_at | BCL2L1 | Hs.305890 |
| 212314_at | KIAA0746 | Hs.49500 // — |
| 212330_at | TFDP1 | Hs.79353 |
| 212334_at | GNS | Hs.334534 |
| 212340_at | MGC21416 | Hs.82719 |
| 212341_at | MGC21416 | Hs.82719 |
| 212355_at | KIAA0323 | Hs.7911 |
| 212358_at | CLIPR-59 | Hs.7357 |
| 212363_x_at | ACTG1 | Hs.14376 |
| 212372_at | MYH10 | Hs.280311 // — |
| 212377_s_at | NOTCH2 | Hs.8121 |
| 212382_at | TCF4 | Hs.359289 |
| 212385_at | TCF4 | Hs.359289 |
| 212386_at | TCF4 | Hs.359289 |
| 212387_at | TCF4 | Hs.359289 |
| 212390_at | PDE4DIP | Hs.265848 |
| 212414_s_at | 38961 | Hs.90998 |
| 212428_at | KIAA0368 | Hs.445255 |
| 212430_at | RNPC1 | Hs.236361 |
| 212464_s_at | FN1 | Hs.418138 |
| 212467_at | KIAA0678 | Hs.12707 // — |
| 212472_at | MICAL2 | Hs.309674 |
| 212473_s_at | MICAL2 | Hs.309674 |
| 212479_s_at | FLJ13910 | Hs.75277 |
| 212488_at | COL5A1 | Hs.433695 |
| 212489_at | COL5A1 | Hs.433695 |
| 212492_s_at | KIAA0876 | Hs.301011 // — |
| 212501_at | CEBPB | Hs.99029 |
| 212509_s_at | — | Hs.356623 // est |
| 212512_s_at | CARM1 | Hs.371416 // — |
| 212526_at | SPG20 | Hs.205088 |
| 212531_at | LCN2 | Hs.204238 |
| 212535_at | MEF2A | Hs.415033 |
| 212540_at | CDC34 | Hs.423615 |
| 212543_at | AIM1 | Hs.422550 // — |
| 212558_at | GDAP1L1 | Hs.20977 |
| 212560_at | SORL1 | Hs.438159 |
| 212570_at | KIAA0830 | Hs.167115 |
| 212586_at | CAST | Hs.440961 |
| 212589_at | RRAS2 | Hs.206097 |
| 212592_at | IGJ | Hs.381568 |
| 212599_at | AUTS2 | Hs.296720 |
| 212602_at | WDFY3 | Hs.105340 |
| 212611_at | MPEG1 | Hs.62264 // — |
| 212614_at | MRF2 | Hs.12702 // — |
| 212624_s_at | CHN1 | Hs.380138 |

TABLE 1-continued

About 2856 genes used for classifying AML of 286 patients into defined clusters as identified in Correlation View

| Affymetrix probe set id | gene symbol | unigene ID |
|---|---|---|
| 212636_at | QKI | Hs.22248 |
| 212645_x_at | BRE | Hs.80426 |
| 212646_at | RAFTLIN | Hs.436432 // — |
| 212647_at | RRAS | Hs.9651 |
| 212657_s_at | IL1RN | Hs.81134 |
| 212659_s_at | IL1RN | Hs.81134 |
| 212670_at | ELN | Hs.252418 |
| 212671_s_at | HLA-DQA1 | Hs.387679 |
| 212680_x_at | PPP1R14B | Hs.120197 |
| 212681_at | EPB41L3 | Hs.103839 |
| 212686_at | KIAA1157 | Hs.21894 // — |
| 212692_s_at | LRBA | Hs.209846 |
| 212699_at | SCAMP5 | Hs.7934 |
| 212713_at | MFAP4 | Hs.296049 |
| 212719_at | PLEKHE1 | Hs.38176 // — |
| 212724_at | ARHE | Hs.6838 |
| 212732_at | MEG3 | Hs.418271 |
| 212741_at | MAOA | Hs.183109 |
| 212750_at | PPP1R16B | Hs.45719 |
| 212758_s_at | TCF8 | Hs.232068 |
| 212761_at | TCF7L2 | Hs.214039 |
| 212762_s_at | TCF7L2 | Hs.214039 |
| 212764_at | TCF8 | Hs.232068 |
| 212768_s_at | GW112 | Hs.273321 |
| 212769_at | TLE3 | Hs.287362 |
| 212771_at | LOC221061 | Hs.66762 // — |
| 212776_s_at | KIAA0657 | Hs.6654 // — |
| 212812_at | na | Hs.288232 // — |
| 212820_at | RC3 | Hs.200828 |
| 212827_at | IGHM | Hs.153261 |
| 212828_at | SYNJ2 | Hs.434494 |
| 212829_at | — | Hs.57079 // — |
| 212830_at | EGFL5 | Hs.5599 // — |
| 212831_at | EGFL5 | Hs.5599 // — |
| 212842_x_at | — | Hs.452310 // est |
| 212843_at | NCAM1 | Hs.78792 |
| 212859_x_at | MT1E | Hs.418241 |
| 212865_s_at | COL14A1 | Hs.403836 |
| 212873_at | na | Hs.165728 // — |
| 212884_x_at | APOC4 | Hs.110675 |
| 212895_s_at | ABR | Hs.434004 |
| 212906_at | na | Hs.347534 // — |
| 212907_at | SLC30A1 | Hs.55610 |
| 212912_at | RPS6KA2 | Hs.301664 |
| 212915_at | SEMACAP3 | Hs.177635 |
| 212930_at | ATP2B1 | Hs.20952 |
| 212937_s_at | COL6A1 | Hs.415997 |
| 212942_s_at | KIAA1199 | Hs.212584 |
| 212956_at | KIAA0882 | Hs.411317 // — |
| 212958_x_at | PAM | Hs.352733 |
| 212973_at | RPIA | Hs.79886 |
| 212977_at | RDC1 | Hs.231853 |
| 212987_at | FBXO9 | Hs.388387 |
| 212988_x_at | ACTG1 | Hs.14376 |
| 212989_at | MOB | Hs.153716 |
| 212993_at | na | Hs.349356 // — |
| 212998_x_at | HLA-DQB2 | Hs.375115 |
| 212999_x_at | HLA-DQB1 | Hs.409934 |
| 213002_at | MARCKS | Hs.318603 |
| 213005_s_at | KANK | Hs.77546 |
| 213006_at | KIAA0146 | Hs.381058 |
| 213015_at | na | Hs.171553 // — |
| 213035_at | KIAA0379 | Hs.273104 // — |
| 213036_x_at | ATP2A3 | Hs.5541 |
| 213038_at | FLJ90005 | Hs.128366 |
| 213060_s_at | CHI3L2 | Hs.154138 |
| 213061_s_at | LOC123803 | Hs.351573 |
| 213075_at | LOC169611 | Hs.357004 |
| 213089_at | na | Hs.166361 // — |
| 213094_at | GPR126 | Hs.419170 |
| 213095_x_at | AIF1 | Hs.76364 |
| 213096_at | HUCEP11 | Hs.6360 |
| 213110_s_at | COL4A5 | Hs.169825 |
| 213122_at | KIAA1750 | Hs.173094 |
| 213125_at | DKFZP586L151 | Hs.43658 |
| 213135_at | TIAM1 | Hs.115176 |
| 213146_at | KIAA0346 | Hs.103915 // — |
| 213147_at | HOXA10 | Hs.110637 |
| 213150_at | HOXA10 | Hs.110637 |
| 213182_x_at | CDKN1C | Hs.106070 |
| 213193_x_at | TRB@ | Hs.419777 |
| 213194_at | ROBO1 | Hs.301198 |
| 213201_s_at | TNNT1 | Hs.73980 |
| 213212_x_at | — | Hs.459128 // est |
| 213214_x_at | ACTG1 | Hs.14376 |
| 213217_at | ADCY2 | Hs.414591 |
| 213236_at | SASH1 | Hs.166311 |
| 213241_at | PLXNC1 | Hs.286229 |
| 213258_at | TFPI | Hs.102301 |
| 213260_at | FOXC1 | Hs.348883 |
| 213274_s_at | CTSB | Hs.135226 |
| 213275_x_at | CTSB | Hs.135226 |
| 213288_at | LOC129642 | Hs.90797 |
| 213309_at | PLCL2 | Hs.54886 |
| 213317_at | na | Hs.21103 |
| 213338_at | RIS1 | Hs.35861 |
| 213348_at | CDKN1C | Hs.106070 |
| 213350_at | RPS11 | Hs.433529 |
| 213361_at | PCTAIRE2BP | Hs.416543 |
| 213362_at | PTPRD | Hs.323079 |
| 213375_s_at | CG018 | Hs.277888 |
| 213394_at | MAPKBP1 | Hs.376657 // — |
| 213395_at | MLC1 | Hs.74518 |
| 213413_at | SBLF | Hs.54961 |
| 213415_at | CLIC2 | Hs.54570 |
| 213418_at | HSPA6 | Hs.3268 |
| 213428_s_at | COL6A1 | Hs.415997 |
| 213435_at | SATB2 | Hs.412327 // — |
| 213437_at | RIPX | Hs.7972 |
| 213439_x_at | — | Hs.500197 // est |
| 213446_s_at | IQGAP1 | Hs.1742 |
| 213451_x_at | TNXB | Hs.411644 |
| 213478_at | KIAA1026 | Hs.368823 |
| 213479_at | NPTX2 | Hs.3281 |
| 213482_at | DOCK3 | Hs.7022 |
| 213484_at | na | Hs.66187 // — |
| 213488_at | FLJ00133 | Hs.7949 |
| 213492_at | COL2A1 | Hs.408182 |
| 213502_x_at | LOC91316 | Hs.435211 // — |
| 213503_x_at | ANXA2 | Hs.437110 |
| 213506_at | F2RL1 | Hs.154299 |
| 213515_x_at | HBG2 | Hs.302145 |
| 213521_at | PTPN18 | Hs.210913 |
| 213524_s_at | G0S2 | Hs.432132 |
| 213537_at | HLA-DPA1 | Hs.914 |
| 213539_at | CD3D | Hs.95327 |
| 213541_s_at | ERG | Hs.45514 |
| 213545_x_at | SNX3 | Hs.12102 |
| 213549_at | SLC18A2 | Hs.50458 |
| 213553_x_at | APOC1 | Hs.268571 |
| 213566_at | RNASE6 | Hs.23262 |
| 213572_s_at | SERPINB1 | Hs.381167 |
| 213605_s_at | na | Hs.166361 // — |
| 213608_s_at | TFIP11 | Hs.20225 |
| 213618_at | CENTD1 | Hs.427719 |
| 213624_at | ASM3A | Hs.277962 |
| 213629_x_at | MT1F | Hs.438737 |
| 213666_at | 38961 | Hs.90998 |
| 213668_s_at | SOX4 | Hs.357901 |
| 213674_x_at | — | Hs.439852 |
| 213716_s_at | SECTM1 | Hs.95655 |
| 213737_x_at | — | Hs.50787 // est |
| 213757_at | EIF5A | Hs.310621 |
| 213791_at | PENK | Hs.339831 |
| 213797_at | cig5 | Hs.17518 |
| 213808_at | na | Hs.12514 // — |
| 213817_at | na | Hs.170056 // — |
| 213823_at | HOXA11 | Hs.249171 |
| 213825_at | OLIG2 | Hs.176977 |
| 213830_at | TRD@ | Hs.2014 |

TABLE 1-continued

About 2856 genes used for classifying AML of 286 patients into defined clusters as identified in Correlation View

| Affymetrix probe set id | gene symbol | unigene ID |
|---|---|---|
| 213831_at | HLA-DQA1 | Hs.387679 |
| 213841_at | na | Hs.301281 // — |
| 213842_x_at | WBSCR20C | Hs.436034 |
| 213843_x_at | SLC6A8 | Hs.388375 |
| 213844_at | HOXA5 | Hs.37034 |
| 213848_at | DUSP7 | Hs.3843 |
| 213857_s_at | CD47 | Hs.446414 |
| 213888_at | DJ434O14.3 | Hs.147434 |
| 213891_s_at | TCF4 | Hs.359289 |
| 213894_at | LOC221981 | Hs.23799 // — |
| 213906_at | MYBL1 | Hs.300592 // — |
| 213908_at | LOC339005 | Hs.212670 // — |
| 213915_at | NKG7 | Hs.10306 |
| 213931_at | — | Hs.502810 // est |
| 213943_at | TWIST1 | Hs.66744 |
| 213958_at | CD6 | Hs.436949 |
| 213960_at | na | Hs.185701 // — |
| 213975_s_at | LYZ | Hs.234734 |
| 213988_s_at | SAT | Hs.28491 |
| 213994_s_at | SPON1 | Hs.5378 |
| 214016_s_at | SFPQ | Hs.180610 |
| 214020_x_at | ITGB5 | Hs.149846 |
| 214022_s_at | IFITM1 | Hs.458414 |
| 214032_at | ZAP70 | Hs.234569 |
| 214039_s_at | LAPTM4B | Hs.296398 |
| 214040_s_at | GSN | Hs.446537 |
| 214041_x_at | RPL37A | Hs.433701 |
| 214043_at | PTPRD | Hs.323079 |
| 214049_x_at | CD7 | Hs.36972 |
| 214054_at | DOK2 | Hs.71215 |
| 214058_at | MYCL1 | Hs.437922 |
| 214059_at | IFI44 | Hs.82316 |
| 214061_at | MGC21654 | Hs.95631 |
| 214063_s_at | TF | Hs.433923 |
| 214084_x_at | na | Hs.448231 // — |
| 214085_x_at | HRB2 | Hs.269857 |
| 214093_s_at | FUBP1 | Hs.118962 |
| 214100_x_at | WBSCR20C | Hs.436034 |
| 214121_x_at | ENIGMA | Hs.436339 |
| 214131_at | CYorf15B | Hs.145010 |
| 214146_s_at | PPBP | Hs.2164 |
| 214153_at | ELOVL5 | Hs.343667 |
| 214183_s_at | TKTL1 | Hs.102866 |
| 214203_s_at | PRODH | Hs.343874 |
| 214211_at | FTH1 | Hs.418650 |
| 214218_s_at | LOC139202 | Hs.83623 // — |
| 214228_x_at | TNFRSF4 | Hs.129780 |
| 214230_at | CDC42 | Hs.355832 |
| 214235_at | CYP3A5 | Hs.150276 |
| 214255_at | ATP10A | Hs.125595 |
| 214273_x_at | C16orf35 | Hs.19699 |
| 214290_s_at | HIST2H2AA | Hs.417332 |
| 214295_at | KIAA0485 | Hs.89121 // — |
| 214297_at | CSPG4 | Hs.436301 |
| 214321_at | NOV | Hs.285935 |
| 214329_x_at | TNFSF10 | Hs.387871 |
| 214349_at | — | Hs.464403 // est |
| 214366_s_at | ALOX5 | Hs.89499 |
| 214370_at | S100A8 | Hs.416073 |
| 214407_x_at | GYPB | Hs.438658 |
| 214414_x_at | HBA1 | Hs.449630 |
| 214421_x_at | CYP2C9 | Hs.418127 |
| 214428_x_at | C4A | Hs.150833 |
| 214433_s_at | SELENBP1 | Hs.334841 |
| 214446_at | ELL2 | Hs.192221 |
| 214450_at | CTSW | Hs.416848 |
| 214453_s_at | IFI44 | Hs.82316 |
| 214455_at | HIST1H2BC | Hs.356901 |
| 214459_x_at | HLA-C | Hs.274485 |
| 214464_at | CDC42BPA | Hs.18586 |
| 214467_at | GPR65 | Hs.131924 |
| 214469_at | HIST1H2AE | Hs.121017 |
| 214470_at | KLRB1 | Hs.169824 |
| 214472_at | HIST1H3D | Hs.239458 |
| 214481_at | HIST1H2AM | Hs.134999 |
| 214500_at | H2AFY | Hs.75258 |
| 214505_s_at | FHL1 | Hs.421383 |
| 214511_x_at | FCGR1A | Hs.77424 |
| 214522_x_at | HIST1H3D | Hs.239458 |
| 214523_at | CEBPE | Hs.426867 |
| 214530_x_at | EPB41 | Hs.37427 |
| 214535_s_at | ADAMTS2 | Hs.120330 |
| 214539_at | SERPINB10 | Hs.158339 |
| 214548_x_at | GNAS | Hs.157307 |
| 214551_s_at | CD7 | Hs.36972 |
| 214564_s_at | PCDHGC3 | Hs.283794 |
| 214574_x_at | LST1 | Hs.410065 |
| 214575_s_at | AZU1 | Hs.72885 |
| 214581_x_at | TNFRSF21 | Hs.159651 |
| 214590_s_at | UBE2D1 | Hs.129683 |
| 214614_at | HLXB9 | Hs.37035 |
| 214617_at | PRF1 | Hs.2200 |
| 214620_x_at | PAM | Hs.352733 |
| 214627_at | EPX | Hs.46295 |
| 214637_at | OSM | Hs.248156 |
| 214651_s_at | HOXA9 | Hs.127428 |
| 214657_s_at | TncRNA | Hs.433324 // — |
| 214667_s_at | TP53I11 | Hs.433813 // — |
| 214669_x_at | na | Hs.377975 |
| 214677_x_at | IGLJ3 | Hs.449601 |
| 214682_at | PKD1 | Hs.75813 |
| 214696_at | MGC14376 | Hs.417157 |
| 214721_x_at | CDC42EP4 | Hs.3903 |
| 214722_at | FLJ21272 | Hs.218329 |
| 214743_at | CUTL1 | Hs.438974 |
| 214761_at | OAZ | Hs.158593 |
| 214768_x_at | na | Hs.377975 |
| 214770_at | MSR1 | Hs.436887 |
| 214777_at | na | Hs.377975 |
| 214789_x_at | SRP46 | Hs.155160 |
| 214790_at | SUSP1 | Hs.435628 |
| 214805_at | EIF4A1 | Hs.129673 |
| 214836_x_at | na | Hs.377975 |
| 214867_at | NDST2 | Hs.225129 |
| 214870_x_at | — | — // — |
| 214875_x_at | APLP2 | Hs.279518 |
| 214903_at | na | Hs.25422 // — |
| 214909_s_at | DDAH2 | Hs.247362 |
| 214916_x_at | — | Hs.448957 |
| 214920_at | LOC221981 | Hs.23799 // — |
| 214950_at | — | Hs.459588 // est |
| 214953_s_at | APP | Hs.177486 |
| 214973_x_at | — | Hs.448982 // — |
| 214983_at | na | Hs.433656 // — |
| 214989_x_at | PEPP2 | Hs.242537 |
| 215012_at | ZNF451 | Hs.188662 |
| 215016_x_at | BPAG1 | Hs.443518 |
| 215032_at | — | Hs.300934 // — |
| 215034_s_at | TM4SF1 | Hs.351316 |
| 215037_s_at | BCL2L1 | Hs.305890 |
| 215047_at | BIA2 | Hs.323858 |
| 215049_x_at | CD163 | Hs.74076 |
| 215051_x_at | AIF1 | Hs.76364 |
| 215054_at | EPOR | Hs.127826 |
| 215071_s_at | — | Hs.28777 // — |
| 215076_s_at | COL3A1 | Hs.443625 |
| 215078_at | SOD2 | Hs.384944 |
| 215089_s_at | RBM10 | Hs.348276 |
| 215111_s_at | TSC22 | Hs.114360 |
| 215116_s_at | DNM1 | Hs.436132 |
| 215118_s_at | MGC27165 | Hs.366 |
| 215121_x_at | — | Hs.356861 |
| 215123_at | — | Hs.375005 // — |
| 215137_at | — | Hs.467531 // est |
| 215143_at | FLJ36166 | Hs.351178 // — |
| 215146_s_at | KIAA1043 | Hs.387856 |
| 215150_at | DKFZp451J1719 | Hs.391944 // — |
| 215163_at | — | Hs.203349 // — |
| 215176_x_at | — | Hs.503443 // — |
| 215177_s_at | ITGA6 | Hs.212296 |

TABLE 1-continued

About 2856 genes used for classifying AML of 286 patients into defined clusters as identified in Correlation View

| Affymetrix probe set id | gene symbol | unigene ID |
| --- | --- | --- |
| 215193_x_at | HLA-DRB1 | Hs.411726 |
| 215200_x_at | na | Hs.456817 // — |
| 215204_at | — | Hs.288575 // — |
| 215214_at | — | Hs.449579 // — |
| 215222_x_at | MACF1 | Hs.372463 |
| 215223_s_at | SOD2 | Hs.384944 |
| 215224_at | RPL23 | Hs.406300 |
| 215242_at | PIGC | Hs.386487 |
| 215248_at | GRB10 | Hs.81875 |
| 215284_at | — | Hs.12432 // — |
| 215288_at | TRPC2 | Hs.131910 // — |
| 215306_at | — | Hs.161283 // — |
| 215311_at | na | Hs.185701 // — |
| 215320_at | DKFZP434M131 | Hs.189296 // — |
| 215338_s_at | NKTR | Hs.369815 |
| 215342_s_at | KIAA0471 | Hs.242271 |
| 215375_x_at | — | Hs.438377 // — |
| 215379_x_at | IGLJ3 | Hs.449601 |
| 215382_x_at | TPSB2 | Hs.405479 |
| 215388_s_at | HFL1 | Hs.296941 |
| 215401_at | — | Hs.507633 // — |
| 215411_s_at | C6orf4 | Hs.437508 |
| 215415_s_at | CHS1 | Hs.130188 |
| 215438_x_at | GSPT1 | Hs.2707 |
| 215446_s_at | — | — // — |
| 215447_at | TFPI | Hs.102301 |
| 215449_at | na | Hs.357392 // — |
| 215485_s_at | ICAM1 | Hs.168383 |
| 215489_x_at | HOMER3 | Hs.410683 |
| 215498_s_at | MAP2K3 | Hs.180533 |
| 215499_at | MAP2K3 | Hs.180533 |
| 215501_s_at | DUSP10 | Hs.177534 |
| 215504_x_at | — | Hs.337534 // — |
| 215537_x_at | DDAH2 | Hs.247362 |
| 215571_at | — | Hs.287415 // — |
| 215592_at | — | Hs.464205 // — |
| 215594_at | na | Hs.296832 // — |
| 215599_at | SMA3 | Hs.440958 |
| 215602_at | FGD2 | Hs.376059 |
| 215621_s_at | — | Hs.448957 |
| 215623_x_at | SMC4L1 | Hs.50758 |
| 215630_at | — | Hs.475611 // — |
| 215640_at | KIAA1055 | Hs.438702 |
| 215646_s_at | CSPG2 | Hs.434488 |
| 215663_at | MBNL1 | Hs.28578 |
| 215666_at | HLA-DRB4 | Hs.449633 |
| 215684_s_at | FLJ21588 | Hs.436407 |
| 215692_s_at | C11orf8 | Hs.432000 |
| 215716_s_at | ATP2B1 | Hs.20952 |
| 215733_x_at | CTAG2 | Hs.87225 |
| 215761_at | RC3 | Hs.200828 |
| 215771_x_at | RET | Hs.350321 |
| 215775_at | THBS1 | Hs.164226 |
| 215777_at | IGLV@ | Hs.381262 |
| 215779_s_at | HIST1H2BG | Hs.352109 |
| 215783_s_at | ALPL | Hs.250769 |
| 215784_at | CD1E | Hs.249217 |
| 215806_x_at | TRGC2 | Hs.385086 |
| 215807_s_at | PLXNB1 | Hs.278311 |
| 215811_at | — | Hs.275706 // — |
| 215812_s_at | — | Hs.499113 // est |
| 215819_s_at | RHCE | Hs.278994 |
| 215836_s_at | PCDHGC3 | Hs.283794 |
| 215838_at | LIR9 | Hs.406708 |
| 215851_at | EVI1 | Hs.436019 |
| 215853_at | — | Hs.287427 // — |
| 215874_at | — | Hs.287730 // — |
| 215891_s_at | GM2A | Hs.387156 |
| 215913_s_at | CED-6 | Hs.107056 |
| 215925_s_at | CD72 | Hs.116481 |
| 215933_s_at | HHEX | Hs.118651 |
| 215946_x_at | LOC91316 | Hs.435211 // — |
| 215949_x_at | — | — // — |
| 215967_s_at | LY9 | Hs.403857 |
| 215990_s_at | BCL6 | Hs.155024 |
| 216012_at | — | Hs.159901 // — |
| 216015_s_at | CIAS1 | Hs.159483 |
| 216016_at | CIAS1 | Hs.159483 |
| 216022_at | — | Hs.16074 // — |
| 216025_x_at | CYP2C9 | Hs.418127 |
| 216033_s_at | FYN | Hs.390567 |
| 216036_x_at | KIAA1037 | Hs.172825 |
| 216041_x_at | GRN | Hs.180577 |
| 216052_x_at | ARTN | Hs.194689 |
| 216054_x_at | MYL4 | Hs.356717 |
| 216056_at | CD44 | Hs.306278 |
| 216063_at | — | Hs.470084 // est |
| 216080_s_at | FADS3 | Hs.21765 |
| 216109_at | KIAA1025 | Hs.435249 // — |
| 216129_at | ATP9A | Hs.406434 // — |
| 216147_at | — | Hs.306504 // — |
| 216180_s_at | SYNJ2 | Hs.434494 |
| 216191_s_at | TRD@ | Hs.2014 |
| 216197_at | — | Hs.434491 // — |
| 216207_x_at | IGKV1D-13 | Hs.390427 |
| 216218_s_at | PLCL2 | Hs.54886 |
| 216236_s_at | SLC2A14 | Hs.401274 |
| 216243_s_at | IL1RN | Hs.81134 |
| 216248_s_at | NR4A2 | Hs.82120 |
| 216268_s_at | JAG1 | Hs.409202 |
| 216286_at | — | Hs.306324 // — |
| 216317_x_at | RHCE | Hs.278994 |
| 216320_x_at | MST1 | Hs.349110 |
| 216331_at | ITGA7 | Hs.74369 |
| 216333_x_at | TNXB | Hs.411644 |
| 216336_x_at | — | — // — |
| 216356_x_at | BAIAP3 | Hs.458427 |
| 216370_x_at | TKTL1 | Hs.102866 |
| 216379_x_at | — | — // — |
| 216380_x_at | — | — // — |
| 216401_x_at | — | — // — |
| 216417_x_at | HOXB9 | Hs.321142 |
| 216442_x_at | na | Hs.287820 // — |
| 216449_x_at | TRA1 | Hs.192374 |
| 216474_x_at | TPSB2 | Hs.405479 |
| 216491_x_at | — | — // — |
| 216510_x_at | — | — // — |
| 216511_s_at | — | — // — |
| 216522_at | — | — // — |
| 216526_x_at | HLA-C | Hs.274485 |
| 216541_x_at | — | — // — |
| 216557_x_at | — | — // — |
| 216560_x_at | — | — // — |
| 216565_x_at | — | — // — |
| 216576_x_at | na | Hs.377975 |
| 216598_s_at | CCL2 | Hs.303649 |
| 216602_s_at | FARSL | Hs.23111 |
| 216614_at | — | — // — |
| 216620_s_at | ARHGEF10 | Hs.436196 |
| 216667_at | — | — // — |
| 216693_x_at | HDGFRP3 | Hs.127842 |
| 216705_s_at | ADA | Hs.407135 |
| 216733_s_at | GATM | Hs.75335 |
| 216766_at | — | — // — |
| 216813_at | — | — // — |
| 216832_at | CBFA2T1 | Hs.90858 |
| 216833_x_at | GYPE | Hs.395535 |
| 216834_at | RGS1 | Hs.75256 |
| 216841_s_at | SOD2 | Hs.384944 |
| 216858_x_at | — | — // — |
| 216860_s_at | GDF11 | Hs.432439 |
| 216894_x_at | CDKN1C | Hs.106070 |
| 216913_s_at | KIAA0690 | Hs.434251 |
| 216920_s_at | TRGC2 | Hs.385086 |
| 216925_s_at | TAL1 | Hs.73828 |
| 216950_s_at | FCGR1A | Hs.77424 |
| 216956_s_at | ITGA2B | Hs.411312 |
| 216984_x_at | — | Hs.449592 // — |
| 217022_s_at | MGC27165 | Hs.366 |
| 217023_x_at | — | — // — |

TABLE 1-continued

About 2856 genes used for classifying AML of 286 patients into
defined clusters as identified in Correlation View

| Affymetrix probe set id | gene symbol | unigene ID |
|---|---|---|
| 217025_s_at | DBN1 | Hs.89434 |
| 217028_at | CXCR4 | Hs.421986 |
| 217118_s_at | KIAA0930 | Hs.13255 |
| 217143_at | TRD@ | Hs.2014 |
| 217147_s_at | TRIM | Hs.138701 |
| 217148_x_at | — | Hs.449592 // — |
| 217157_x_at | — | Hs.449620 // — |
| 217165_x_at | MT1F | Hs.438737 |
| 217179_x_at | — | Hs.440830 |
| 217192_s_at | PRDM1 | Hs.381140 |
| 217227_x_at | — | Hs.449598 // — |
| 217232_x_at | — | — // — |
| 217234_s_at | VIL2 | Hs.403997 |
| 217235_x_at | — | Hs.449593 // — |
| 217258_x_at | — | Hs.449599 // — |
| 217274_x_at | — | — // — |
| 217276_x_at | dJ222E13.1 | Hs.301947 |
| 217281_x_at | — | Hs.448987 // — |
| 217284_x_at | dJ222E13.1 | Hs.301947 |
| 217286_s_at | NDRG3 | Hs.437338 |
| 217354_s_at | — | — |
| 217378_x_at | — | — // — |
| 217388_s_at | KYNU | Hs.444471 |
| 217404_s_at | COL2A1 | Hs.408182 |
| 217414_x_at | — | — // — |
| 217418_x_at | MS4A1 | Hs.438040 |
| 217419_x_at | AGRN | Hs.273330 // — |
| 217422_s_at | CD22 | Hs.262150 |
| 217478_s_at | HLA-DMA | Hs.351279 |
| 217480_x_at | — | — // — |
| 217502_at | IFIT2 | Hs.169274 |
| 217507_at | SLC11A1 | Hs.135163 |
| 217520_x_at | na | Hs.374397 // — |
| 217521_at | HAL | Hs.190783 |
| 217523_at | CD44 | Hs.306278 |
| 217526_at | — | Hs.502482 // est |
| 217552_x_at | CR1 | Hs.334019 |
| 217572_at | — | — // — |
| 217591_at | SKIL | Hs.272108 |
| 217593_at | SNX11 | Hs.15827 |
| 217610_at | — | Hs.506223 // est |
| 217649_at | ZNF216 | Hs.406096 |
| 217653_x_at | — | Hs.499531 // est |
| 217655_at | — | Hs.407053 // — |
| 217671_at | — | Hs.279706 // est |
| 217673_x_at | GNAS | Hs.157307 |
| 217678_at | — | Hs.499751 // est |
| 217712_at | — | Hs.369545 // est |
| 217715_x_at | — | Hs.417310 // est |
| 217728_at | S100A6 | Hs.275243 |
| 217729_s_at | AES | Hs.446610 |
| 217735_s_at | HRI | Hs.434986 |
| 217736_s_at | HRI | Hs.434986 |
| 217738_at | PBEF | Hs.293464 |
| 217739_s_at | PBEF | Hs.293464 |
| 217748_at | ADIPOR1 | Hs.5298 |
| 217752_s_at | CN2 | Hs.149185 |
| 217757_at | A2M | Hs.74561 |
| 217762_s_at | RAB31 | Hs.223025 |
| 217763_s_at | RAB31 | Hs.223025 |
| 217764_s_at | RAB31 | Hs.223025 |
| 217771_at | GOLPH2 | Hs.352662 |
| 217799_x_at | UBE2H | Hs.372758 |
| 217800_s_at | NDFIP1 | Hs.9788 |
| 217817_at | ARPC4 | Hs.323342 |
| 217818_s_at | ARPC4 | Hs.323342 |
| 217838_s_at | EVL | Hs.241471 |
| 217848_s_at | PP | Hs.380830 |
| 217867_x_at | BACE2 | Hs.436490 |
| 217868_s_at | DREV1 | Hs.279583 |
| 217901_at | DSG2 | Hs.412597 |
| 217911_s_at | BAG3 | Hs.15259 |
| 217941_s_at | ERBB2IP | Hs.8117 |
| 217963_s_at | NGFRAP1 | Hs.448588 |
| 217966_s_at | C1orf24 | Hs.48778 |
| 217967_s_at | C1orf24 | Hs.48778 |
| 217977_at | SEPX1 | Hs.279623 |
| 217979_at | TM4SF13 | Hs.364544 |
| 217983_s_at | RNASE6PL | Hs.388130 |
| 217985_s_at | BAZ1A | Hs.436488 |
| 217986_s_at | BAZ1A | Hs.436488 |
| 217988_at | HEI10 | Hs.107003 |
| 217995_at | SQRDL | Hs.435468 |
| 217996_at | PHLDA1 | Hs.82101 |
| 217997_at | PHLDA1 | Hs.82101 |
| 217999_s_at | PHLDA1 | Hs.82101 |
| 218000_s_at | PHLDA1 | Hs.82101 |
| 218012_at | SE20-4 | Hs.136164 |
| 218034_at | TTC11 | Hs.423968 |
| 218035_s_at | FLJ20273 | Hs.95549 |
| 218039_at | ANKT | Hs.279905 |
| 218051_s_at | FLJ12442 | Hs.84753 |
| 218066_at | SLC12A7 | Hs.172613 |
| 218084_x_at | FXYD5 | Hs.333418 |
| 218086_at | NPDC1 | Hs.105547 |
| 218091_at | HRB | Hs.371589 |
| 218094_s_at | C20orf35 | Hs.256086 |
| 218113_at | TMEM2 | Hs.160417 |
| 218116_at | LOC51759 | Hs.278429 |
| 218136_s_at | MSCP | Hs.283716 |
| 218141_at | E2-230K | Hs.16130 |
| 218145_at | C20orf97 | Hs.344378 |
| 218205_s_at | MKNK2 | Hs.75056 |
| 218211_s_at | MLPH | Hs.297405 |
| 218217_at | RISC | Hs.431107 |
| 218224_at | PNMA1 | Hs.194709 |
| 218231_at | NAGK | Hs.7036 |
| 218232_at | C1QA | Hs.9641 |
| 218237_s_at | SLC38A1 | Hs.132246 |
| 218243_at | RUFY1 | Hs.306769 |
| 218273_s_at | PPM2C | Hs.22265 |
| 218280_x_at | HIST2H2AA | Hs.417332 |
| 218284_at | DKFZP586N0721 | Hs.99843 |
| 218298_s_at | FLJ20950 | Hs.285673 |
| 218319_at | PELI1 | Hs.7886 |
| 218332_at | BEX1 | Hs.334370 |
| 218345_at | HCA112 | Hs.12126 |
| 218346_s_at | PA26 | Hs.14125 |
| 218352_at | RCBTB1 | Hs.58452 |
| 218376_s_at | NICAL | Hs.33476 |
| 218394_at | FLJ22386 | Hs.22795 |
| 218400_at | OAS3 | Hs.56009 |
| 218404_at | SNX10 | Hs.418132 |
| 218417_s_at | FLJ20489 | Hs.438867 |
| 218418_s_at | KIAA1518 | Hs.284208 |
| 218454_at | FLJ22662 | Hs.178470 |
| 218456_at | C1QDC1 | Hs.234355 |
| 218468_s_at | CKTSF1B1 | Hs.40098 |
| 218469_at | CKTSF1B1 | Hs.40098 |
| 218487_at | ALAD | Hs.1227 |
| 218523_at | LHPP | Hs.20950 |
| 218532_at | FLJ20152 | Hs.82273 |
| 218559_s_at | MAFB | Hs.169487 |
| 218589_at | P2RY5 | Hs.123464 |
| 218596_at | FLJ10743 | Hs.3376 |
| 218608_at | HSA9947 | Hs.128866 |
| 218614_at | FLJ20696 | Hs.236844 |
| 218618_s_at | FAD104 | Hs.299883 |
| 218625_at | NRN1 | Hs.103291 |
| 218644_at | PLEK2 | Hs.170473 |
| 218660_at | DYSF | Hs.408679 |
| 218676_s_at | PCTP | Hs.285218 |
| 218686_s_at | RHBDF1 | Hs.57988 |
| 218710_at | FLJ20272 | Hs.26090 |
| 218711_s_at | SDPR | Hs.26530 |
| 218718_at | PDGFC | Hs.43080 |
| 218723_s_at | RGC32 | Hs.76640 |
| 218729_at | LXN | Hs.124491 |
| 218742_at | HPRN | Hs.22158 |
| 218781_at | SMC6L1 | Hs.424559 |

TABLE 1-continued

About 2856 genes used for classifying AML of 286 patients into defined clusters as identified in Correlation View

| Affymetrix probe set id | gene symbol | unigene ID |
|---|---|---|
| 218786_at | — | Hs.374350 |
| 218788_s_at | SMYD3 | Hs.8109 |
| 218793_s_at | SCML1 | Hs.109655 |
| 218803_at | CHFR | Hs.23794 |
| 218805_at | IAN4L1 | Hs.412331 |
| 218810_at | FLJ23231 | Hs.288300 |
| 218824_at | FLJ10781 | Hs.8395 |
| 218825_at | EGFL7 | Hs.91481 |
| 218828_at | PLSCR3 | Hs.433154 |
| 218831_s_at | FCGRT | Hs.111903 |
| 218847_at | IMP-2 | Hs.30299 |
| 218853_s_at | DJ473B4 | Hs.57549 |
| 218854_at | SART2 | Hs.388014 |
| 218856_at | TNFRSF21 | Hs.159651 |
| 218858_at | FLJ12428 | Hs.87729 |
| 218864_at | TNS | Hs.439442 |
| 218865_at | FLJ22390 | Hs.195345 |
| 218872_at | TSC | Hs.345908 |
| 218876_at | CGI-38 | Hs.412685 |
| 218880_at | FOSL2 | Hs.301612 |
| 218881_s_at | FLJ23306 | Hs.5890 |
| 218899_s_at | BAALC | Hs.169395 |
| 218902_at | NOTCH1 | Hs.311559 |
| 218927_s_at | CHST12 | Hs.25204 |
| 218935_at | EHD3 | Hs.368808 |
| 218952_at | PCSK1N | Hs.429437 |
| 218963_s_at | KRT23 | Hs.9029 |
| 218964_at | DRIL2 | Hs.10431 |
| 218974_at | FLJ10159 | Hs.346203 |
| 218978_s_at | MSCP | Hs.283716 |
| 218986_s_at | FLJ20035 | Hs.109309 |
| 218988_at | SLC35E3 | Hs.445043 |
| 219019_at | LRDD | Hs.438986 |
| 219032_x_at | OPN3 | Hs.170129 |
| 219033_at | FLJ21308 | Hs.310185 |
| 219036_at | BITE | Hs.127217 |
| 219049_at | ChGn | Hs.341073 |
| 219054_at | FLJ14054 | Hs.13528 |
| 219059_s_at | XLKD1 | Hs.17917 |
| 219090_at | SLC24A3 | Hs.439909 |
| 219093_at | FLJ20701 | Hs.424598 |
| 219123_at | ZNF232 | Hs.279914 |
| 219183_s_at | PSCD4 | Hs.7189 |
| 219191_s_at | BIN2 | Hs.14770 |
| 219218_at | FLJ23058 | Hs.415799 |
| 219228_at | ZNF463 | Hs.147644 |
| 219243_at | HIMAP4 | Hs.30822 |
| 219247_s_at | ZDHHC14 | Hs.292541 |
| 219255_x_at | IL17RB | Hs.5470 |
| 219256_s_at | FLJ20356 | Hs.61053 |
| 219259_at | FLJ12287 | Hs.408846 |
| 219277_s_at | FLJ10851 | Hs.17860 |
| 219288_at | HT021 | Hs.47166 |
| 219295_s_at | PCOLCE2 | Hs.8944 |
| 219304_s_at | SCDGF-B | Hs.112885 |
| 219308_s_at | AK5 | Hs.18268 |
| 219316_s_at | C14orf58 | Hs.267566 |
| 219332_at | FLJ23471 | Hs.376617 |
| 219339_s_at | Eu-HMTase1 | Hs.416692 |
| 219358_s_at | CENTA2 | Hs.415471 |
| 219359_at | FLJ22635 | Hs.353181 |
| 219360_s_at | TRPM4 | Hs.31608 |
| 219371_s_at | KLF2 | Hs.107740 |
| 219373_at | DPM3 | Hs.110477 |
| 219383_at | FLJ14213 | Hs.183506 |
| 219396_s_at | NEIL1 | Hs.197423 |
| 219403_s_at | HPSE | Hs.44227 |
| 219414_at | CLSTN2 | Hs.12079 |
| 219434_at | TREM1 | Hs.283022 |
| 219443_at | C20orf13 | Hs.88367 |
| 219457_s_at | RIN3 | Hs.413374 |
| 219463_at | C20orf103 | Hs.22920 |
| 219471_at | C13orf18 | Hs.413071 |
| 219478_at | WFDC1 | Hs.36688 |
| 219480_at | SNAI1 | Hs.48029 |
| 219489_s_at | RHBDL2 | Hs.133999 |
| 219497_s_at | BCL11A | Hs.314623 |
| 219505_at | CECR1 | Hs.170310 |
| 219506_at | FLJ23221 | Hs.91283 |
| 219511_s_at | SNCAIP | Hs.24948 |
| 219519_s_at | SN | Hs.31869 |
| 219520_s_at | KIAA1280 | Hs.12913 |
| 219528_s_at | BCL11B | Hs.57987 |
| 219534_x_at | CDKN1C | Hs.106070 |
| 219541_at | FLJ20406 | Hs.149227 |
| 219546_at | BMP2K | Hs.20137 |
| 219559_at | C20orf59 | Hs.353013 |
| 219563_at | C14orf139 | Hs.41502 |
| 219569_s_at | MGC3295 | Hs.101257 |
| 219593_at | PHT2 | Hs.237856 |
| 219602_s_at | FLJ23403 | Hs.293907 |
| 219607_s_at | MS4A4A | Hs.325960 |
| 219622_at | RAB20 | Hs.179791 |
| 219628_at | WIG1 | Hs.252406 |
| 219629_at | FLJ20635 | Hs.265018 |
| 219630_at | MAP17 | Hs.431099 |
| 219654_at | PTPLA | Hs.114062 |
| 219666_at | MS4A6A | Hs.371612 |
| 219667_s_at | BANK | Hs.193736 |
| 219669_at | PRV1 | Hs.232165 |
| 219672_at | ERAF | Hs.274309 |
| 219681_s_at | RCP | Hs.96125 |
| 219686_at | HSA250839 | Hs.58241 |
| 219695_at | FLJ10640 | Hs.91753 |
| 219714_s_at | CACNA2D3 | Hs.435112 |
| 219737_s_at | — | Hs.458282 // est |
| 219738_s_at | PCDH9 | Hs.404723 |
| 219740_at | FLJ12505 | Hs.96885 |
| 219747_at | FLJ23191 | Hs.16026 |
| 219753_at | STAG3 | Hs.323634 |
| 219759_at | LRAP | Hs.374490 |
| 219777_at | hIAN2 | Hs.105468 |
| 219788_at | PILRA | Hs.122591 |
| 219789_at | NPR3 | Hs.237028 |
| 219790_s_at | NPR3 | Hs.237028 |
| 219799_s_at | RDHL | Hs.179608 |
| 219806_s_at | FN5 | Hs.416456 |
| 219812_at | STAG3 | Hs.323634 |
| 219814_at | MBNL3 | Hs.105134 |
| 219837_s_at | C17 | Hs.13872 |
| 219859_at | CLECSF9 | Hs.236516 |
| 219870_at | ATF7IP2 | Hs.189813 |
| 219871_at | FLJ13197 | Hs.29725 |
| 219872_at | DKFZp434L142 | Hs.323583 |
| 219884_at | LHX6 | Hs.103137 |
| 219890_at | CLECSF5 | Hs.126355 |
| 219892_at | TM6SF1 | Hs.151155 |
| 219895_at | FLJ20716 | Hs.437563 |
| 219905_at | ERMAP | Hs.427672 |
| 219918_s_at | ASPM | Hs.121028 |
| 219919_s_at | SSH-3 | Hs.29173 |
| 219922_s_at | LTBP3 | Hs.289019 |
| 219932_at | VLCS-H1 | Hs.49765 |
| 219947_at | CLECSF6 | Hs.115515 |
| 219952_s_at | MCOLN1 | Hs.372029 |
| 219978_s_at | ANKT | Hs.279905 |
| 219992_at | TAC3 | Hs.9730 |
| 220001_at | PADI4 | Hs.397050 |
| 220005_at | GPR86 | Hs.13040 |
| 220006_at | FLJ12057 | Hs.134807 |
| 220010_at | KCNE1L | Hs.146372 |
| 220014_at | LOC51334 | Hs.157461 |
| 220017_x_at | CYP2C9 | Hs.418127 |
| 220037_s_at | XLKD1 | Hs.17917 |
| 220051_at | PRSS21 | Hs.72026 |
| 220057_at | GAGED2 | Hs.112208 |
| 220059_at | BRDG1 | Hs.121128 |
| 220066_at | CARD15 | Hs.135201 |
| 220068_at | VPREB3 | Hs.136713 |
| 220088_at | C5R1 | Hs.2161 |

TABLE 1-continued

About 2856 genes used for classifying AML of 286 patients into defined clusters as identified in Correlation View

| Affymetrix probe set id | gene symbol | unigene ID |
|---|---|---|
| 220091_at | SLC2A6 | Hs.244378 |
| 220110_s_at | NXF3 | Hs.60386 |
| 220122_at | FLJ22344 | Hs.107716 |
| 220173_at | C14orf45 | Hs.260555 |
| 220179_at | LOC64180 | Hs.302028 |
| 220220_at | FLJ10120 | Hs.378860 |
| 220266_s_at | KLF4 | Hs.376206 |
| 220306_at | FLJ20202 | Hs.356216 |
| 220319_s_at | MIR | Hs.443793 |
| 220330_s_at | SAMSN1 | Hs.221851 |
| 220335_x_at | FLJ21736 | Hs.268700 |
| 220359_s_at | ARPP-21 | Hs.412268 |
| 220370_s_at | KIAA1453 | Hs.11387 |
| 220377_at | C14orf110 | Hs.395486 |
| 220404_at | GPR97 | Hs.383403 |
| 220416_at | ATP8B4 | Hs.313841 |
| 220448_at | KCNK12 | Hs.252617 |
| 220485_s_at | SIRPB2 | Hs.50716 |
| 220496_at | CLEC2 | Hs.409794 |
| 220507_s_at | UPB1 | Hs.285512 |
| 220532_s_at | LR8 | Hs.190161 |
| 220560_at | C11orf21 | Hs.272100 |
| 220570_at | RETN | Hs.283091 |
| 220591_s_at | FLJ22843 | Hs.301143 |
| 220595_at | DKFZp434B0417 | Hs.380044 |
| 220617_s_at | FLJ10697 | Hs.368756 |
| 220646_s_at | KLRF1 | Hs.183125 |
| 220668_s_at | DNMT3B | Hs.251673 |
| 220684_at | TBX21 | Hs.272409 |
| 220704_at | ZNFN1A1 | Hs.435949 |
| 220720_x_at | FLJ14346 | Hs.287640 |
| 220727_at | KCNK10 | Hs.365690 |
| 220751_s_at | C5orf4 | Hs.10235 |
| 220757_s_at | UBXD1 | Hs.435255 |
| 220793_at | SAGE | Hs.195292 |
| 220807_at | HBQ1 | Hs.247921 |
| 220811_at | PRG3 | Hs.251386 |
| 220832_at | TLR8 | Hs.272410 |
| 220864_s_at | GRIM19 | Hs.279574 |
| 220898_at | — | — // — |
| 220911_s_at | KIAA1305 | Hs.496280 |
| 220918_at | RUNX1 | Hs.410774 |
| 220937_s_at | SIAT7D | Hs.3972 |
| 220940_at | KIAA1641 | Hs.503503 |
| 220941_s_at | C21orf91 | Hs.293811 |
| 220945_x_at | FLJ10298 | Hs.5999 |
| 220954_s_at | PILRB | Hs.349256 |
| 221004_s_at | ITM2C | Hs.111577 |
| 221011_s_at | LBH | Hs.57209 |
| 221012_s_at | TRIM8 | Hs.54580 |
| 221019_s_at | COLEC12 | Hs.29423 |
| 221059_s_at | CHST6 | Hs.157439 |
| 221060_s_at | TLR4 | Hs.174312 |
| 221063_x_at | RNF123 | Hs.406364 |
| 221075_s_at | NCR2 | Hs.194721 |
| 221140_s_at | G2A | Hs.441131 |
| 221205_at | — | — // — |
| 221210_s_at | C1orf13 | Hs.64896 |
| 221223_x_at | CISH | Hs.8257 |
| 221234_s_at | BACH2 | Hs.88414 |
| 221237_s_at | OSBP2 | Hs.7740 |
| 221245_s_at | DKFZP434E2135 | Hs.17631 |
| 221246_x_at | TNS | Hs.439442 |
| 221261_x_at | MAGED4 | Hs.376347 |
| 221269_s_at | SH3BGRL3 | Hs.109051 |
| 221286_s_at | PACAP | Hs.409563 |
| 221345_at | GPR43 | Hs.248056 |
| 221349_at | VPREB1 | Hs.247979 |
| 221363_x_at | GPR25 | Hs.248123 |
| 221425_s_at | MGC4276 | Hs.270013 |
| 221477_s_at | SOD2 | Hs.384944 |
| 221478_at | BNIP3L | Hs.132955 |
| 221479_s_at | BNIP3L | Hs.132955 |
| 221484_at | B4GALT5 | Hs.107526 |
| 221491_x_at | HLA-DRB3 | Hs.308026 |
| 221520_s_at | CDCA8 | Hs.48855 |
| 221529_s_at | PLVAP | Hs.107125 |
| 221530_s_at | BHLHB3 | Hs.437282 |
| 221541_at | DKFZP434B044 | Hs.262958 |
| 221551_x_at | SIAT7D | Hs.3972 |
| 221558_s_at | LEF1 | Hs.44865 |
| 221563_at | DUSP10 | Hs.177534 |
| 221577_x_at | PLAB | Hs.296638 |
| 221578_at | RASSF4 | Hs.319124 |
| 221581_s_at | WBSCR5 | Hs.56607 |
| 221584_s_at | KCNMA1 | Hs.354740 |
| 221601_s_at | TOSO | Hs.58831 |
| 221602_s_at | TOSO | Hs.58831 |
| 221607_x_at | ACTG1 | Hs.14376 |
| 221627_at | TRIM10 | Hs.274295 |
| 221646_s_at | ZDHHC11 | Hs.50754 |
| 221651_x_at | na | Hs.377975 |
| 221658_s_at | IL21R | Hs.210546 |
| 221666_s_at | ASC | Hs.197875 |
| 221671_x_at | na | Hs.377975 |
| 221675_s_at | CHPT1 | Hs.225567 |
| 221690_s_at | NALP2 | Hs.369279 |
| 221698_s_at | CLECSF12 | Hs.161786 |
| 221704_s_at | FLJ12750 | Hs.77870 |
| 221724_s_at | CLECSF6 | Hs.115515 |
| 221728_x_at | LOC139202 | Hs.83623 // — |
| 221731_x_at | CSPG2 | Hs.434488 |
| 221747_at | TNS | Hs.439442 |
| 221748_s_at | TNS | Hs.439442 |
| 221756_at | MGC17330 | Hs.26670 |
| 221757_at | MGC17330 | Hs.26670 |
| 221760_at | MAN1A1 | Hs.255149 |
| 221764_at | MGC16353 | Hs.388956 |
| 221765_at | UGCG | Hs.432605 |
| 221766_s_at | C6orf37 | Hs.10784 |
| 221768_at | SFPQ | Hs.180610 |
| 221779_at | MIRAB13 | Hs.8535 |
| 221802_s_at | KIAA1598 | Hs.98002 |
| 221807_s_at | PP2447 | Hs.33026 |
| 221809_at | KIAA1464 | Hs.441888 // — |
| 221814_at | GPR124 | Hs.17270 |
| 221824_s_at | c-MIR | Hs.288156 |
| 221840_at | PTPRE | Hs.437980 |
| 221841_s_at | KLF4 | Hs.376206 |
| 221861_at | — | Hs.12853 // — |
| 221870_at | EHD2 | Hs.325650 |
| 221875_x_at | HLA-F | Hs.411958 |
| 221884_at | EVI1 | Hs.436019 |
| 221902_at | na | Hs.7967 // — |
| 221920_s_at | MSCP | Hs.283716 |
| 221932_s_at | C14orf87 | Hs.294083 |
| 221942_s_at | GUCY1A3 | Hs.433488 |
| 221950_at | EMX2 | Hs.202095 |
| 221962_s_at | UBE2H | Hs.372758 |
| 221969_at | — | Hs.22030 // est |
| 221978_at | HLA-F | Hs.411958 |
| 221983_at | MGC3035 | Hs.22412 |
| 222001_x_at | — | Hs.503585 // est |
| 222040_at | HNRPA1 | Hs.356721 |
| 222067_x_at | HIST1H2BD | Hs.180779 |
| 222068_s_at | LOC123872 | Hs.310164 |
| 222074_at | UROD | Hs.78601 |
| 222087_at | — | Hs.32458 // est |
| 222088_s_at | SLC2A14 | Hs.401274 |
| 222108_at | AMIGO2 | Hs.121520 |
| 222125_s_at | PH-4 | Hs.271224 |
| 222142_at | CYLD | Hs.386952 |
| 222144_at | KIF17 | Hs.130411 // — |
| 222145_at | na | Hs.406494 // — |
| 222146_s_at | TCF4 | Hs.359289 |
| 222154_s_at | DKFZP564A2416 | Hs.230767 |
| 222162_s_at | ADAMTS1 | Hs.8230 |
| 222186_at | — | Hs.306329 // — |
| 222218_s_at | PILRA | Hs.122591 |
| 222221_x_at | EHD1 | Hs.155119 |

TABLE 1-continued

About 2856 genes used for classifying AML of 286 patients into defined clusters as identified in Correlation View

| Affymetrix probe set id | gene symbol | unigene ID |
|---|---|---|
| 222222_s_at | — | — // — |
| 222258_s_at | SH3BP4 | Hs.17667 |
| 222281_s_at | — | Hs.370494 // est |
| 222284_at | — | Hs.373565 // est |
| 222288_at | — | Hs.130526 // est |
| 222294_s_at | RAB27A | Hs.298530 |
| 222303_at | ETS2 | Hs.292477 |
| 222313_at | — | Hs.293334 // est |
| 222315_at | — | Hs.292853 // est |
| 222316_at | — | Hs.292689 // est |
| 222326_at | — | Hs.432534 // est |
| 222330_at | — | Hs.445711 // est |
| 222363_at | — | Hs.132670 // est |
| 222375_at | — | Hs.372146 // est |
| 266_s_at | CD24 | Hs.375108 |
| 31874_at | GAS2L1 | Hs.322852 |
| 33304_at | ISG20 | Hs.105434 |
| 336_at | — | — // — |
| 33646_g_at | GM2A | Hs.387156 |
| 34210_at | CDW52 | Hs.276770 |
| 35626_at | SGSH | Hs.31074 |
| 35666_at | SEMA3F | Hs.32981 |
| 35820_at | GM2A | Hs.387156 |
| 36553_at | — | Hs.461056 // est |
| 36554_at | ASMTL | Hs.458420 |
| 36564_at | FLJ90005 | Hs.128366 |
| 36711_at | MAFF | Hs.51305 |
| 37028_at | PPP1R15A | Hs.76556 |
| 37145_at | GNLY | Hs.105806 |
| 37986_at | EPOR | Hs.127826 |
| 38037_at | DTR | Hs.799 |
| 38487_at | STAB1 | Hs.301989 |
| 38521_at | CD22 | Hs.262150 |
| 39248_at | AQP3 | Hs.234642 |
| 39318_at | TCL1A | Hs.2484 |
| 39402_at | IL1B | Hs.126256 |
| 396_f_at | EPOR | Hs.127826 |
| 39729_at | PRDX2 | Hs.432121 |
| 40020_at | CELSR3 | Hs.55173 |
| 40093_at | LU | Hs.155048 |
| 40850_at | FKBP8 | Hs.173464 |
| 41386_i_at | KIAA0346 | Hs.103915 // — |
| 41469_at | PI3 | Hs.112341 |
| 41577_at | PPP1R16B | Hs.45719 |
| 41644_at | SASH1 | Hs.166311 |
| 44673_at | SN | Hs.31869 |
| 45297_at | EHD2 | Hs.325650 |
| 46665_at | SEMA4C | Hs.7188 |
| 48031_r_at | C5orf4 | Hs.10235 |
| 48106_at | FLJ20489 | Hs.438867 |
| 48808_at | DHFR | Hs.83765 |
| 49306_at | RASSF4 | Hs.319124 |
| 51158_at | — | Hs.27373 // — |
| 53987_at | na | Hs.6343 // — |
| 54037_at | HPS4 | Hs.441481 |
| 55081_at | MIRAB13 | Hs.8535 |
| 55705_at | — | Hs.498224 // est |
| 57540_at | RBSK | Hs.11916 |
| 57588_at | SLC24A3 | Hs.439909 |
| 64064_at | IAN4L1 | Hs.412331 |
| 64942_at | na | Hs.7967 // — |
| AFFX-HUMISGF3A/ M97935_5_at | — | — // — |
| AFFX-HUMRGE/ M10098_3_at | — | — // — |
| AFFX-HUMRGE/ M10098_5_at | — | — // — |
| AFFX-HUMRGE/ M10098_M_at | — | — // — |
| AFFX-M27830_5_at | — | — // — |
| AFFX-M27830_M_at | — | — // — |
| AFFX-r2-Hs18SrRNA-3_s_at | — | — // — |
| AFFX-r2-Hs18SrRNA-5_at | — | — // — |
| AFFX-r2-Hs18SrRNA-M_x_at | — | — // — |
| AFFX-r2-Hs28SrRNA-3_at | — | — // — |
| AFFX-r2-Hs28SrRNA-M_at | — | — // — |

TABLE 2

About 599 genes defining assigned clusters of AML as identified by SAM.

| Affymetrix probe set id | Gene symbol | Cluster defined | Unigene ID |
|---|---|---|---|
| 202672_s_at | ATF3 | cluster1 | Hs.460 |
| 201464_x_at | JUN | cluster1 | Hs.78465 |
| 202497_x_at | SLC2A3 | cluster1 | Hs.419240 |
| 204622_x_at | NR4A2 | cluster1 | Hs.82120 |
| 216236_s_at | SLC2A14 | cluster1 | Hs.401274 |
| 216248_s_at | NR4A2 | cluster1 | Hs.82120 |
| 204621_s_at | NR4A2 | cluster1 | Hs.82120 |
| 222088_s_at | SLC2A14 | cluster1 | Hs.401274 |
| 220014_at | LOC51334 | cluster1 | Hs.157461 |
| 206762_at | KCNA5 | cluster1 | Hs.150208 |
| 213094_at | GPR126 | cluster1 | Hs.419170 |
| 218502_s_at | TRPS1 | cluster1 | Hs.26102 |
| 221530_s_at | BHLHB3 | cluster1 | Hs.437282 |
| 221884_at | EVI1 | cluster1 | Hs.436019 |
| 203642_s_at | KIAA0977 | cluster1 | Hs.300855 |
| 212827_at | IGHM | cluster1 | Hs.153261 |
| 205612_at | MMRN | cluster1 | Hs.268107 |
| 209200_at | MEF2C | cluster1 | Hs.368950 |
| 214255_at | ATP10A | cluster1 | Hs.125595 |
| 201539_s_at | FHL1 | cluster1 | Hs.421383 |
| 205717_x_at | PCDHGC3 | cluster1 | Hs.283794 |
| 222144_at | KIF17 | cluster1 | Hs.130411 // — |
| 219922_s_at | LTBP3 | cluster1 | Hs.289019 |
| 215836_s_at | PCDHGC3 | cluster1 | Hs.283794 |
| 205861_at | SPIB | cluster1 | Hs.437905 |
| 203372_s_at | SOCS2 | cluster1 | Hs.405946 |
| 209079_x_at | PCDHGC3 | cluster1 | Hs.283794 |
| 215811_at | — | cluster1 | Hs.275706 // — |
| 209199_s_at | MEF2C | cluster1 | Hs.368950 |
| 207655_s_at | BLNK | cluster1 | Hs.167746 |
| 203716_s_at | DPP4 | cluster1 | Hs.44926 |
| 219737_s_at | — | cluster1 | Hs.458282 // est |
| 204304_s_at | PROM1 | cluster1 | Hs.370052 |
| 203373_at | SOCS2 | cluster1 | Hs.405946 |
| 218237_s_at | SLC38A1 | cluster1 | Hs.132246 |
| 202265_at | BMI1 | cluster1 | Hs.380403 |
| 210298_x_at | FHL1 | cluster1 | Hs.421383 |
| 208436_s_at | IRF7 | cluster1 | Hs.166120 |
| 210032_s_at | SPAG6 | cluster1 | Hs.158213 |
| 206571_s_at | MAP4K4 | cluster2 | Hs.3628 |
| 213152_at | — | cluster2 | Hs.476680 // est |
| 214582_at | PDE3B | cluster2 | Hs.337616 |
| 209458_x_at | HBA1 | cluster2 | Hs.449630 |
| 208623_s_at | VIL2 | cluster2 | Hs.403997 |
| 204018_x_at | HBA1 | cluster2 | Hs.449630 |
| 211745_x_at | HBA1 | cluster2 | Hs.449630 |
| 211696_x_at | HBB | cluster2 | Hs.155376 |
| 214414_x_at | HBA1 | cluster2 | Hs.449630 |
| 209116_x_at | HBB | cluster2 | Hs.155376 |
| 217232_x_at | — | cluster2 | — // — |
| 211699_x_at | HBA1 | cluster2 | Hs.449630 |
| 217414_x_at | — | cluster2 | — // — |
| 208792_s_at | CLU | cluster2 | Hs.436657 |
| 216268_s_at | JAG1 | cluster2 | Hs.409202 |
| 208798_x_at | GOLGIN-67 | cluster2 | Hs.182982 |
| 213844_at | HOXA5 | cluster2 | Hs.37034 |
| 204030_s_at | SCHIP1 | cluster2 | Hs.61490 |
| 209193_at | PIM1 | cluster2 | Hs.81170 |
| 221942_s_at | GUCY1A3 | cluster2 | Hs.433488 |
| 208767_s_at | LAPTM4B | cluster2 | Hs.296398 |
| 210425_x_at | GOLGIN-67 | cluster2 | Hs.356225 |
| 209409_at | GRB10 | cluster2 | Hs.81875 |

TABLE 2-continued

About 599 genes defining assigned clusters of AML as identified by SAM.

| Affymetrix probe set id | Gene symbol | Cluster defined | Unigene ID |
|---|---|---|---|
| 212070_at | GPR56 | cluster2 | Hs.6527 |
| 205453_at | HOXB2 | cluster2 | Hs.290432 |
| 208797_s_at | GOLGIN-67 | cluster2 | Hs.182982 |
| 206582_s_at | GPR56 | cluster2 | Hs.6527 |
| 207533_at | CCL1 | cluster2 | Hs.72918 |
| 206298_at | RhoGAP2 | cluster2 | Hs.87241 |
| 212276_at | LPIN1 | cluster2 | Hs.81412 |
| 219615_s_at | KCNK5 | cluster2 | Hs.444448 |
| 203187_at | DOCK1 | cluster2 | Hs.437620 |
| 206574_s_at | PTP4A3 | cluster2 | Hs.43666 |
| 204341_at | TRIM16 | cluster2 | Hs.241305 |
| 210145_at | PLA2G4A | cluster2 | Hs.211587 |
| 205190_at | PLS1 | cluster2 | Hs.203637 |
| 215288_at | TRPC2 | cluster2 | Hs.131910 // — |
| 211269_s_at | IL2RA | cluster2 | Hs.130058 |
| 206341_at | IL2RA | cluster2 | Hs.130058 |
| 207034_s_at | GLI2 | cluster2 | Hs.111867 |
| 212543_at | AIM1 | cluster3 | Hs.422550 // — |
| 204500_s_at | AGTPBP1 | cluster3 | Hs.21542 |
| 211729_x_at | BLVRA | cluster3 | Hs.435726 |
| 218831_s_at | FCGRT | cluster3 | Hs.111903 |
| 221830_at | RAP2A | cluster3 | Hs.48554 |
| 203773_x_at | BLVRA | cluster3 | Hs.435726 |
| 206034_at | SERPINB8 | cluster3 | Hs.368077 |
| 212195_at | IL6ST | cluster3 | Hs.71968 |
| 205707_at | IL17R | cluster3 | Hs.129751 |
| 203973_s_at | KIAA0146 | cluster3 | Hs.381058 |
| 220377_at | C14orf110 | cluster3 | Hs.395486 |
| 201829_at | NET1 | cluster3 | Hs.25155 |
| 207838_x_at | PBXIP1 | cluster3 | Hs.8068 |
| 201427_s_at | SEPP1 | cluster3 | Hs.275775 |
| 214228_x_at | TNFRSF4 | cluster3 | Hs.129780 |
| 201663_s_at | SMC4L1 | cluster3 | Hs.50758 |
| 215388_s_at | HFL1 | cluster3 | Hs.296941 |
| 203187_at | DOCK1 | cluster3 | Hs.437620 |
| 219304_s_at | SCDGF-B | cluster3 | Hs.112885 |
| 219602_s_at | FLJ23403 | cluster3 | Hs.293907 |
| 215471_s_at | MAP7 | cluster3 | Hs.254605 |
| 202890_at | MAP7 | cluster3 | Hs.254605 |
| 206582_s_at | GPR56 | cluster3 | Hs.6527 |
| 214039_s_at | LAPTM4B | cluster3 | Hs.296398 |
| 204341_at | TRIM16 | cluster3 | Hs.241305 |
| 204160_s_at | ENPP4 | cluster3 | Hs.54037 |
| 213217_at | ADCY2 | cluster3 | Hs.414591 |
| 210116_at | SH2D1A | cluster3 | Hs.151544 |
| 201664_at | SMC4L1 | cluster3 | Hs.50758 |
| 217975_at | LOC51186 | cluster3 | Hs.15984 |
| 202889_x_at | ANPEP | cluster3 | Hs.254605 |
| 204044_at | QPRT | cluster3 | Hs.8935 |
| 208029_s_at | LAPTM4B | cluster3 | Hs.296398 |
| 206298_at | RhoGAP2 | cluster3 | Hs.87241 |
| 208767_s_at | LAPTM4B | cluster3 | Hs.296398 |
| 213110_s_at | COL4A5 | cluster3 | Hs.169825 |
| 205190_at | PLS1 | cluster3 | Hs.203637 |
| 207533_at | CCL1 | cluster3 | Hs.72918 |
| 205848_at | GAS2 | cluster3 | Hs.135665 |
| 206950_at | SCN9A | cluster3 | Hs.2319 |
| 210844_x_at | CTNNA1 | cluster4 | Hs.254321 |
| 200764_s_at | CTNNA1 | cluster4 | Hs.254321 |
| 200765_x_at | CTNNA1 | cluster4 | Hs.254321 |
| 209191_at | TUBB-5 | cluster4 | Hs.274308 |
| 202241_at | C8FW | cluster4 | Hs.444947 |
| 217800_s_at | NDFIP1 | cluster4 | Hs.9788 |
| 202252_at | RAB13 | cluster4 | Hs.151536 |
| 201412_at | LRP10 | cluster4 | Hs.28368 |
| 201160_s_at | CSDA | cluster4 | Hs.221889 |
| 208683_at | CAPN2 | cluster4 | Hs.350899 |
| 205382_s_at | DF | cluster4 | Hs.155597 |
| 203233_at | IL4R | cluster4 | Hs.75545 |
| 219371_s_at | KLF2 | cluster4 | Hs.107740 |
| 208923_at | CYFIP1 | cluster4 | Hs.26704 |
| 218627_at | FLJ11259 | cluster4 | Hs.416393 |
| 213416_at | ITGA4 | cluster4 | Hs.145140 |
| 205884_at | ITGA4 | cluster4 | Hs.145140 |
| 214757_at | — | cluster4 | Hs.488749 // est |
| 203987_at | FZD6 | cluster4 | Hs.114218 |
| 202242_at | TM4SF2 | cluster4 | Hs.439586 |
| 206726_at | PGDS | cluster4 | Hs.128433 |
| 54037_at | HPS4 | cluster4 | Hs.441481 |
| 216525_x_at | PMS2L9 | cluster4 | Hs.278467 |
| 210448_s_at | P2RX5 | cluster4 | Hs.408615 |
| 209993_at | ABCB1 | cluster4 | Hs.21330 |
| 217147_s_at | TRIM | cluster4 | Hs.138701 |
| 206233_at | B4GALT6 | cluster4 | Hs.369994 |
| 209994_s_at | ABCB1 | cluster4 | Hs.21330 |
| 220567_at | ZNFN1A2 | cluster4 | Hs.278963 |
| 207996_s_at | C18orf1 | cluster4 | Hs.285091 |
| 213910_at | IGFBP7 | cluster4 | Hs.435795 |
| 214049_x_at | CD7 | cluster4 | Hs.36972 |
| 214551_s_at | CD7 | cluster4 | Hs.36972 |
| 217143_s_at | TRD@ | cluster4 | Hs.2014 |
| 219383_at | FLJ14213 | cluster4 | Hs.183506 |
| 211682_x_at | UGT2B28 | cluster4 | Hs.137585 |
| 213830_at | TRD@ | cluster4 | Hs.2014 |
| 206232_s_at | B4GALT6 | cluster4 | Hs.369994 |
| 216191_s_at | TRD@ | cluster4 | Hs.2014 |
| 216286_at | — | cluster4 | Hs.306324 // — |
| 50221_at | TFEB | cluster5 | Hs.23391 |
| 202895_s_at | EPHB4 | cluster5 | Hs.156114 |
| 205099_s_at | CCR1 | cluster5 | Hs.301921 |
| 200866_s_at | PSAP | cluster5 | Hs.406455 |
| 208594_s_at | LILRB3 | cluster5 | Hs.306230 |
| 211135_x_at | LILRB3 | cluster5 | Hs.306230 |
| 213624_at | ASM3A | cluster5 | Hs.277962 |
| 218559_s_at | MAFB | cluster5 | Hs.169487 |
| 221578_at | RASSF4 | cluster5 | Hs.319124 |
| 212334_at | GNS | cluster5 | Hs.334534 |
| 203769_s_at | STS | cluster5 | Hs.79876 |
| 205686_s_at | CD86 | cluster5 | Hs.27954 |
| 205685_at | CD86 | cluster5 | Hs.27954 |
| 207104_x_at | LILRB1 | cluster5 | Hs.149924 |
| 220066_at | CARD15 | cluster5 | Hs.135201 |
| 201642_at | IFNGR2 | cluster5 | Hs.409200 |
| 204487_s_at | KCNQ1 | cluster5 | Hs.367809 |
| 217992_s_at | MGC4342 | cluster5 | Hs.301342 |
| 211732_x_at | HNMT | cluster5 | Hs.42151 |
| 210660_at | LILRB1 | cluster5 | Hs.149924 |
| 204858_s_at | ECGF1 | cluster5 | Hs.435067 |
| 203768_s_at | STS | cluster5 | Hs.79876 |
| 222218_s_at | PILRA | cluster5 | Hs.122591 |
| 210146_x_at | LILRB3 | cluster5 | Hs.306230 |
| 220832_at | TLR8 | cluster5 | Hs.272410 |
| 219593_at | PHT2 | cluster5 | Hs.237856 |
| 204619_s_at | CSPG2 | cluster5 | Hs.434488 |
| 206278_at | PTAFR | cluster5 | Hs.46 |
| 207224_s_at | SIGLEC7 | cluster5 | Hs.274470 |
| 203767_s_at | STS | cluster5 | Hs.79876 |
| 204254_s_at | VDR | cluster5 | Hs.2062 |
| 214590_s_at | UBE2D1 | cluster5 | Hs.129683 |
| 212681_at | EPB41L3 | cluster5 | Hs.103839 |
| 219872_at | DKFZp434L142 | cluster5 | Hs.323583 |
| 204392_at | CAMK1 | cluster5 | Hs.434875 |
| 219788_at | PILRA | cluster5 | Hs.122591 |
| 206934_at | SIRPB1 | cluster5 | Hs.194784 |
| 211776_s_at | EPB41L3 | cluster5 | Hs.103839 |
| 207872_s_at | LILRB1 | cluster5 | Hs.149924 |
| 206710_s_at | EPB41L3 | cluster5 | Hs.103839 |
| 209083_at | CORO1A | cluster6 | Hs.415067 |
| 204319_s_at | RGS10 | cluster6 | Hs.82280 |
| 217845_x_at | HIG1 | cluster6 | Hs.7917 |
| 205672_at | XPA | cluster6 | Hs.288867 |
| 217118_s_at | KIAA0930 | cluster6 | Hs.13255 |
| 211990_at | HLA-DPA1 | cluster6 | Hs.914 |
| 210982_s_at | HLA-DRA | cluster6 | Hs.409805 |
| 208982_at | PECAM1 | cluster6 | Hs.78146 |
| 209619_at | CD74 | cluster6 | Hs.446471 |
| 215193_x_at | HLA-DRB1 | cluster6 | Hs.411726 |
| 201641_at | BST2 | cluster6 | Hs.118110 |

TABLE 2-continued

About 599 genes defining assigned clusters of AML as identified by SAM.

| Affymetrix probe set id | Gene symbol | Cluster defined | Unigene ID |
|---|---|---|---|
| 213266_at | — | cluster6 | Hs.497941 // est |
| 202729_s_at | LTBP1 | cluster6 | Hs.241257 |
| 204751_x_at | DSC2 | cluster6 | Hs.95612 |
| 215573_at | CAT | cluster6 | Hs.395771 |
| 220898_at | — | cluster6 | — // — |
| 215388_s_at | HFL1 | cluster6 | Hs.296941 |
| 219036_at | BITE | cluster6 | Hs.127217 |
| 204750_s_at | DSC2 | cluster6 | Hs.95612 |
| 218786_at | — | cluster6 | Hs.374350 |
| 208414_s_at | HOXB4 | cluster6 | Hs.147465 |
| 201431_s_at | DPYSL3 | cluster6 | Hs.150358 |
| 215623_x_at | SMC4L1 | cluster6 | Hs.50758 |
| 213260_at | FOXC1 | cluster6 | Hs.348883 |
| 219932_at | VLCS-H1 | cluster6 | Hs.49765 |
| 206377_at | FOXF2 | cluster6 | Hs.44481 |
| 202728_s_at | LTBP1 | cluster6 | Hs.241257 |
| 219651_at | FLJ10713 | cluster6 | Hs.317659 |
| 213217_at | ADCY2 | cluster6 | Hs.414591 |
| 218710_at | FLJ20272 | cluster6 | Hs.26090 |
| 219602_s_at | FLJ23403 | cluster6 | Hs.293907 |
| 215807_s_at | PLXNB1 | cluster6 | Hs.278311 |
| 212019_at | DKFZP564M182 | cluster6 | Hs.158995 |
| 204983_s_at | GPC4 | cluster6 | Hs.58367 |
| 204984_at | GPC4 | cluster6 | Hs.58367 |
| 221959_at | MGC39325 | cluster6 | Hs.34054 |
| 209702_at | FTO | cluster6 | Hs.284741 |
| 219511_s_at | SNCAIP | cluster6 | Hs.24948 |
| 51158_at | — | cluster6 | Hs.27373 // — |
| 221880_s_at | — | cluster6 | Hs.27373 // — |
| 201733_at | CLCN3 | cluster7 | Hs.372528 |
| 218978_s_at | MSCP | cluster7 | Hs.283716 |
| 214433_s_at | SELENBP1 | cluster7 | Hs.334841 |
| 201249_at | SLC2A1 | cluster7 | Hs.169902 |
| 205389_s_at | ANK1 | cluster7 | Hs.443711 |
| 207793_s_at | EPB41 | cluster7 | Hs.37427 |
| 212804_s_at | DKFZP434C212 | cluster7 | Hs.287266 |
| 221237_s_at | OSBP2 | cluster7 | Hs.7740 |
| 216925_s_at | TAL1 | cluster7 | Hs.73828 |
| 206077_at | KEL | cluster7 | Hs.420322 |
| 213843_x_at | SLC6A8 | cluster7 | Hs.388375 |
| 206145_at | RHAG | cluster7 | Hs.368178 |
| 217274_x_at | — | cluster7 | — // — |
| 216063_at | — | cluster7 | Hs.470084 // est |
| 220751_s_at | C5orf4 | cluster7 | Hs.10235 |
| 210854_x_at | SLC6A8 | cluster7 | Hs.388375 |
| 210586_x_at | RHD | cluster7 | Hs.458333 |
| 210395_x_at | MYL4 | cluster7 | Hs.356717 |
| 205262_at | KCNH2 | cluster7 | Hs.188021 |
| 208353_x_at | ANK1 | cluster7 | Hs.443711 |
| 208416_s_at | SPTB | cluster7 | Hs.438514 |
| 219630_at | MAP17 | cluster7 | Hs.431099 |
| 208352_x_at | ANK1 | cluster7 | Hs.443711 |
| 207087_x_at | ANK1 | cluster7 | Hs.443711 |
| 211254_x_at | RHAG | cluster7 | Hs.368178 |
| 206647_at | HBZ | cluster7 | Hs.272003 |
| 214530_x_at | EPB41 | cluster7 | Hs.37427 |
| 203911_at | RAP1GA1 | cluster7 | Hs.433797 |
| 218864_at | TNS | cluster7 | Hs.439442 |
| 207043_s_at | SLC6A9 | cluster7 | Hs.442590 |
| 205391_x_at | ANK1 | cluster7 | Hs.443711 |
| 210088_x_at | MYL4 | cluster7 | Hs.356717 |
| 216054_x_at | MYL4 | cluster7 | Hs.356717 |
| 206146_at | RHAG | cluster7 | Hs.368178 |
| 204720_s_at | DNAJC6 | cluster7 | Hs.44896 |
| 205390_s_at | ANK1 | cluster7 | Hs.443711 |
| 56748_at | TRIM10 | cluster7 | Hs.274295 |
| 221577_x_at | PLAB | cluster7 | Hs.296638 |
| 207854_at | GYPE | cluster7 | Hs.395535 |
| 206116_s_at | TPM1 | cluster7 | Hs.133892 |
| 203115_at | FECH | cluster8 | Hs.443610 |
| 208352_x_at | ANK1 | cluster8 | Hs.443711 |
| 48031_r_at | C5orf4 | cluster8 | Hs.10235 |
| 214433_s_at | SELENBP1 | cluster8 | Hs.334841 |
| 218853_s_at | DJ473B4 | cluster8 | Hs.57549 |
| 209890_at | TM4SF9 | cluster8 | Hs.8037 |
| 210586_x_at | RHD | cluster8 | Hs.458333 |
| 213843_x_at | SLC6A8 | cluster8 | Hs.388375 |
| 207087_x_at | ANK1 | cluster8 | Hs.443711 |
| 204467_s_at | SNCA | cluster8 | Hs.76930 |
| 216317_x_at | RHCE | cluster8 | Hs.278994 |
| 202124_s_at | ALS2CR3 | cluster8 | Hs.154248 |
| 216833_x_at | GYPE | cluster8 | Hs.395535 |
| 201886_at | WDR23 | cluster8 | Hs.283976 |
| 202074_s_at | OPTN | cluster8 | Hs.390162 |
| 215812_s_at | — | cluster8 | Hs.499113 // est |
| 218864_at | TNS | cluster8 | Hs.439442 |
| 211820_x_at | GYPA | cluster8 | Hs.34287 |
| 203794_at | CDC42BPA | cluster8 | Hs.18586 |
| 216925_s_at | TAL1 | cluster8 | Hs.73828 |
| 202219_at | SLC6A8 | cluster8 | Hs.388375 |
| 205838_at | GYPA | cluster8 | Hs.34287 |
| 211649_x_at | — | cluster8 | Hs.449057 |
| 217572_at | — | cluster8 | — // — |
| 202125_s_at | ALS2CR3 | cluster8 | Hs.154248 |
| 208353_x_at | ANK1 | cluster8 | Hs.443711 |
| 205837_s_at | GYPA | cluster8 | Hs.34287 |
| 202364_at | MXI1 | cluster8 | Hs.118630 |
| 220751_s_at | C5orf4 | cluster8 | Hs.10235 |
| 214464_at | CDC42BPA | cluster8 | Hs.18586 |
| 221237_s_at | OSBP2 | cluster8 | Hs.7740 |
| 205391_x_at | ANK1 | cluster8 | Hs.443711 |
| 210430_x_at | RHD | cluster8 | Hs.283822 |
| 201333_s_at | ARHGEF12 | cluster8 | Hs.413112 |
| 212151_at | PBX1 | cluster8 | Hs.408222 |
| 40093_at | LU | cluster8 | Hs.155048 |
| 202073_at | OPTN | cluster8 | Hs.390162 |
| 209735_at | ABCG2 | cluster8 | Hs.194720 |
| 201131_s_at | CDH1 | cluster8 | Hs.194657 |
| 213338_at | RIS1 | cluster8 | Hs.35861 |
| 200675_at | CD81 | cluster9 | Hs.54457 |
| 202370_s_at | CBFB | cluster9 | Hs.179881 |
| 211031_s_at | CYLN2 | cluster9 | Hs.104717 |
| 218927_s_at | CHST12 | cluster9 | Hs.25204 |
| 206788_s_at | CBFB | cluster9 | Hs.179881 |
| 219218_at | FLJ23058 | cluster9 | Hs.415799 |
| 211026_s_at | MGLL | cluster9 | Hs.409826 |
| 204198_s_at | RUNX3 | cluster9 | Hs.170019 |
| 213779_at | EMU1 | cluster9 | Hs.289106 |
| 218414_at | NDE1 | cluster9 | Hs.263925 |
| 200984_s_at | CD59 | cluster9 | Hs.278573 |
| 204197_s_at | RUNX3 | cluster9 | Hs.170019 |
| 203329_at | PTPRM | cluster9 | Hs.154151 |
| 218876_at | CGI-38 | cluster9 | Hs.412685 |
| 210889_s_at | FCGR2B | cluster9 | Hs.126384 |
| 212771_at | LOC221061 | cluster9 | Hs.66762 // — |
| 202481_at | SDR1 | cluster9 | Hs.17144 |
| 205330_at | MN1 | cluster9 | Hs.268515 |
| 203939_at | NT5E | cluster9 | Hs.153952 |
| 212912_at | RPS6KA2 | cluster9 | Hs.301664 |
| 201506_at | TGFBI | cluster9 | Hs.421496 |
| 200665_s_at | SPARC | cluster9 | Hs.111779 |
| 204787_at | Z39IG | cluster9 | Hs.8904 |
| 207194_s_at | ICAM4 | cluster9 | Hs.435625 |
| 219308_s_at | AK5 | cluster9 | Hs.18268 |
| 209395_at | CHI3L1 | cluster9 | Hs.382202 |
| 205076_s_at | CRA | cluster9 | Hs.425144 |
| 219694_at | FLJ11127 | cluster9 | Hs.91165 |
| 209396_s_at | CHI3L1 | cluster9 | Hs.382202 |
| 204885_s_at | MSLN | cluster9 | Hs.408488 |
| 221019_s_at | COLEC12 | cluster9 | Hs.29423 |
| 205987_at | CD1C | cluster9 | Hs.1311 |
| 203058_s_at | PAPSS2 | cluster9 | Hs.274230 |
| 203060_s_at | PAPSS2 | cluster9 | Hs.274230 |
| 206682_at | CLECSF13 | cluster9 | Hs.54403 |
| 212298_at | NRP1 | cluster9 | Hs.173548 |
| 206135_at | ST18 | cluster9 | Hs.151449 |
| 212358_at | CLIPR-59 | cluster9 | Hs.7357 |
| 207961_x_at | MYH11 | cluster9 | Hs.78344 |

TABLE 2-continued

About 599 genes defining assigned clusters of AML as identified by SAM.

| Affymetrix probe set id | Gene symbol | Cluster defined | Unigene ID |
|---|---|---|---|
| 201497_x_at | MYH11 | cluster9 | Hs.78344 |
| 214575_s_at | AZU1 | cluster10 | Hs.72865 |
| 205382_s_at | DF | cluster10 | Hs.155597 |
| 209906_at | C3AR1 | cluster10 | Hs.155935 |
| 206111_at | RNASE2 | cluster10 | Hs.728 |
| 212071_s_at | SPTBN1 | cluster10 | Hs.205401 |
| 203796_s_at | BCL7A | cluster10 | Hs.371758 |
| 218899_s_at | BAALC | cluster10 | Hs.169395 |
| 209488_s_at | RBPMS | cluster10 | Hs.195825 |
| 218086_at | NPDC1 | cluster10 | Hs.105547 |
| 204581_at | CD22 | cluster10 | Hs.262150 |
| 208614_s_at | FLNB | cluster10 | Hs.81008 |
| 204540_at | EEF1A2 | cluster10 | Hs.433839 |
| 204917_s_at | MLLT3 | cluster10 | Hs.404 |
| 209437_s_at | SPON1 | cluster10 | Hs.5378 |
| 212827_at | IGHM | cluster10 | Hs.153261 |
| 200672_x_at | SPTBN1 | cluster10 | Hs.205401 |
| 203756_at | P164RHOGEF | cluster10 | Hs.45180 |
| 220377_at | C14orf110 | cluster10 | Hs.395486 |
| 209576_at | GNAI1 | cluster10 | Hs.203862 |
| 205330_at | MN1 | cluster10 | Hs.268515 |
| 212750_at | PPP1R16B | cluster10 | Hs.45719 |
| 204484_at | PIK3C2B | cluster10 | Hs.343329 |
| 209436_at | SPON1 | cluster10 | Hs.5378 |
| 209282_at | PRKD2 | cluster10 | Hs.205431 |
| 207836_s_at | RBPMS | cluster10 | Hs.195825 |
| 209487_at | RBPMS | cluster10 | Hs.195825 |
| 204083_s_at | TPM2 | cluster10 | Hs.300772 |
| 207788_s_at | SCAM-1 | cluster10 | Hs.301302 |
| 212558_at | GDAP1L1 | cluster10 | Hs.20977 |
| 209679_s_at | LOC57228 | cluster10 | Hs.206501 |
| 41577_at | PPP1R16B | cluster10 | Hs.45719 |
| 213506_at | F2RL1 | cluster10 | Hs.154299 |
| 205933_at | SETBP1 | cluster10 | Hs.201369 |
| 204004_at | — | cluster10 | Hs.503576 // est |
| 213488_at | FLJ00133 | cluster10 | Hs.7949 |
| 200671_s_at | SPTBN1 | cluster10 | Hs.205401 |
| 209763_at | NRLN1 | cluster10 | Hs.440324 |
| 47560_at | FLJ11939 | cluster10 | Hs.94229 |
| 202551_s_at | CRIM1 | cluster10 | Hs.170752 |
| 219145_at | FLJ11939 | cluster10 | Hs.94229 |
| 201560_at | CLIC4 | cluster11 | Hs.25035 |
| 204401_at | KCNN4 | cluster11 | Hs.10082 |
| 212658_at | LHFPL2 | cluster11 | Hs.79299 |
| 221223_x_at | CISH | cluster11 | Hs.8257 |
| 201559_at | CLIC4 | cluster11 | Hs.25035 |
| 201425_at | ALDH2 | cluster11 | Hs.436437 |
| 209543_s_at | CD34 | cluster11 | Hs.374990 |
| 203217_s_at | SIAT9 | cluster11 | Hs.415117 |
| 215116_s_at | DNM1 | cluster11 | Hs.436132 |
| 213848_at | DUSP7 | cluster11 | Hs.3843 |
| 200665_s_at | SPARC | cluster11 | Hs.111779 |
| 211675_s_at | HIC | cluster11 | Hs.132739 |
| 208873_s_at | DP1 | cluster11 | Hs.173119 |
| 205101_at | MHC2TA | cluster11 | Hs.126714 |
| 209723_at | SERPINB9 | cluster11 | Hs.104879 |
| 200762_at | DPYSL2 | cluster11 | Hs.173381 |
| 201279_s_at | DAB2 | cluster11 | Hs.81988 |
| 217838_s_at | EVL | cluster11 | Hs.241471 |
| 218589_at | P2RY5 | cluster11 | Hs.123464 |
| 216033_s_at | FYN | cluster11 | Hs.390567 |
| 218966_at | MYO5C | cluster11 | Hs.111782 |
| 31874_at | GAS2L1 | cluster11 | Hs.322852 |
| 203139_at | DAPK1 | cluster11 | Hs.244318 |
| 208886_at | H1F0 | cluster11 | Hs.226117 |
| 201656_at | ITGA6 | cluster11 | Hs.212296 |
| 219777_at | hIAN2 | cluster11 | Hs.105468 |
| 218237_s_at | SLC38A1 | cluster11 | Hs.132246 |
| 212171_x_at | VEGF | cluster11 | Hs.73793 |
| 203542_s_at | BTEB1 | cluster11 | Hs.150557 |
| 203859_s_at | PALM | cluster11 | Hs.78482 |
| 214953_s_at | APP | cluster11 | Hs.177486 |
| 218805_at | IAN4L1 | cluster11 | Hs.412331 |
| 204385_at | KYNU | cluster11 | Hs.444471 |
| 209583_s_at | MOX2 | cluster11 | Hs.79015 |
| 206042_x_at | SNRPN | cluster11 | Hs.48375 |
| 201601_x_at | IFITM1 | cluster11 | Hs.458414 |
| 201522_x_at | SNRPN | cluster11 | Hs.48375 |
| 218825_at | EGFL7 | cluster11 | Hs.91481 |
| 207076_s_at | ASS | cluster11 | Hs.160786 |
| 209079_x_at | PCDHGC3 | cluster11 | Hs.283794 |
| 204425_at | ARHGAP4 | cluster12 | Hs.3109 |
| 203236_s_at | LGALS9 | cluster12 | Hs.81337 |
| 204152_s_at | MFNG | cluster12 | Hs.371768 |
| 202600_s_at | NRIP1 | cluster12 | Hs.155017 |
| 204362_at | SCAP2 | cluster12 | Hs.410745 |
| 200931_s_at | VCL | cluster12 | Hs.75350 |
| 202599_s_at | NRIP1 | cluster12 | Hs.155017 |
| 204153_s_at | MFNG | cluster12 | Hs.371768 |
| 200935_at | CALR | cluster12 | Hs.353170 |
| 210140_at | CST7 | cluster12 | Hs.143212 |
| 200656_s_at | P4HB | cluster12 | Hs.410578 |
| 200654_at | P4HB | cluster12 | Hs.410578 |
| 214203_s_at | PRODH | cluster12 | Hs.343874 |
| 206105_at | FMR2 | cluster12 | Hs.54472 |
| 211663_x_at | PTGDS | cluster12 | Hs.446429 |
| 207031_at | BAPX1 | cluster12 | Hs.105941 |
| 212204_at | DKFZP564G2022 | cluster12 | Hs.200692 |
| 200770_s_at | LAMC1 | cluster12 | Hs.432855 |
| 209960_at | HGF | cluster12 | Hs.396530 |
| 207650_x_at | PTGER1 | cluster12 | Hs.159360 |
| 212509_s_at | — | cluster12 | Hs.356623 // est |
| 201276_at | RAB5B | cluster12 | Hs.77690 |
| 209815_at | na | cluster12 | Hs.454253 // — |
| 209961_s_at | HGF | cluster12 | Hs.396530 |
| 218043_s_at | AZ2 | cluster12 | Hs.437336 |
| 207895_at | NAALADASEL | cluster12 | Hs.13967 |
| 212732_at | MEG3 | cluster12 | Hs.418271 |
| 203397_s_at | GALNT3 | cluster12 | Hs.278611 |
| 210755_at | HGF | cluster12 | Hs.396530 |
| 206634_at | SIX3 | cluster12 | Hs.227277 |
| 203074_at | ANXA8 | cluster12 | Hs.87268 |
| 216320_x_at | MST1 | cluster12 | Hs.349110 |
| 202260_s_at | STXBP1 | cluster12 | Hs.325862 |
| 205663_at | PCBP3 | cluster12 | Hs.121241 |
| 205614_x_at | MST1 | cluster12 | Hs.349110 |
| 204537_s_at | GABRE | cluster12 | Hs.22785 |
| 210794_s_at | MEG3 | cluster12 | Hs.418271 |
| 205110_s_at | FGF13 | cluster12 | Hs.6540 |
| 210998_s_at | HGF | cluster12 | Hs.396530 |
| 210997_at | HGF | cluster12 | Hs.396530 |
| 221581_s_at | WBSCR5 | cluster13 | Hs.56607 |
| 220560_at | C11orf21 | cluster13 | Hs.272100 |
| 208091_s_at | DKFZP564K0822 | cluster13 | Hs.4750 |
| 204494_s_at | LOC56905 | cluster13 | Hs.306331 |
| 208885_at | LCP1 | cluster13 | Hs.381099 |
| 203741_s_at | ADCY7 | cluster13 | Hs.172199 |
| 210010_s_at | SLC25A1 | cluster13 | Hs.111024 |
| 214946_x_at | FLJ10824 | cluster13 | Hs.375174 // — |
| 211685_s_at | NCALD | cluster13 | Hs.90063 |
| 206793_at | PNMT | cluster13 | Hs.1892 |
| 209822_s_at | VLDLR | cluster13 | Hs.370422 |
| 204073_s_at | C11orf9 | cluster13 | Hs.184640 |
| 219686_at | HSA250839 | cluster13 | Hs.58241 |
| 214920_at | LOC221981 | cluster13 | Hs.23799 // — |
| 218742_at | HPRN | cluster13 | Hs.22158 |
| 201655_s_at | HSPG2 | cluster13 | Hs.211573 |
| 204396_s_at | GPRK5 | cluster13 | Hs.211569 |
| 203088_at | FBLN5 | cluster13 | Hs.11494 |
| 213894_at | LOC221981 | cluster13 | Hs.23799 // — |
| 201621_at | NBL1 | cluster13 | Hs.439671 |
| 216356_x_at | BAIAP3 | cluster13 | Hs.458427 |
| 206622_at | TRH | cluster13 | Hs.182231 |
| 218613_at | DKFZp761K1423 | cluster13 | Hs.236438 |
| 212492_s_at | KIAA0876 | cluster13 | Hs.301011 // — |
| 212496_s_at | KIAA0876 | cluster13 | Hs.301011 // — |
| 203065_s_at | CAV1 | cluster13 | Hs.74034 |
| 204874_x_at | BAIAP3 | cluster13 | Hs.458427 |

TABLE 2-continued

About 599 genes defining assigned clusters of AML as identified by SAM.

| Affymetrix probe set id | Gene symbol | Cluster defined | Unigene ID |
|---|---|---|---|
| 206128_at | ADRA2C | cluster13 | Hs.123022 |
| 216832_at | CBFA2T1 | cluster13 | Hs.90858 |
| 212097_at | CAV1 | cluster13 | Hs.74034 |
| 204990_s_at | ITGB4 | cluster13 | Hs.85266 |
| 211341_at | POU4F1 | cluster13 | Hs.458303 |
| 211517_s_at | IL5RA | cluster13 | Hs.68876 |
| 210744_s_at | IL5RA | cluster13 | Hs.68876 |
| 206940_s_at | POU4F1 | cluster13 | Hs.458303 |
| 204811_s_at | CACNA2D2 | cluster13 | Hs.389415 |
| 213194_at | ROBO1 | cluster13 | Hs.301198 |
| 216831_at | CBFA2T1 | cluster13 | Hs.90858 |
| 205528_s_at | CBFA2T1 | cluster13 | Hs.90858 |
| 205529_s_at | CBFA2T1 | cluster13 | Hs.90858 |
| 221737_at | GNA12 | cluster15 | Hs.182874 |
| 40489_at | DRPLA | cluster15 | Hs.169488 |
| 218501_at | ARHGEF3 | cluster15 | Hs.25951 |
| 217853_at | TEM6 | cluster15 | Hs.12210 |
| 220974_x_at | BA108L7.2 | cluster15 | Hs.283844 |
| 209191_at | TUBB-5 | cluster15 | Hs.274398 |
| 212459_x_at | SUCLG2 | cluster15 | Hs.446476 |
| 212311_at | KIAA0746 | cluster15 | Hs.49500 // — |
| 218847_at | IMP-2 | cluster15 | Hs.30299 |
| 215772_x_at | SUCLG2 | cluster15 | Hs.247309 // — |
| 212314_at | KIAA0746 | cluster15 | Hs.49500 // — |
| 202236_s_at | SLC16A1 | cluster15 | Hs.75231 |
| 201841_s_at | HSPB1 | cluster15 | Hs.76067 |
| 217800_s_at | NDFIP1 | cluster15 | Hs.9788 |
| 217226_s_at | PMX1 | cluster15 | Hs.443452 |
| 202391_at | BASP1 | cluster15 | Hs.79516 |
| 200765_x_at | CTNNA1 | cluster15 | Hs.254321 |
| 213400_at | TBL1X | cluster15 | Hs.76536 |
| 213147_at | HOXA10 | cluster15 | Hs.110637 |
| 212906_at | na | cluster15 | Hs.347534 // — |
| 218552_at | FLJ10948 | cluster15 | Hs.170915 |
| 214651_s_at | HOXA9 | cluster15 | Hs.127428 |
| 210365_at | RUNX1 | cluster15 | Hs.410774 |
| 209374_s_at | IGHM | cluster15 | Hs.153261 |
| 213150_at | HOXA10 | cluster15 | Hs.110637 |
| 201719_s_at | EPB41L2 | cluster15 | Hs.440387 |
| 218627_at | FLJ11259 | cluster15 | Hs.416393 |
| 219256_s_at | FLJ20356 | cluster15 | Hs.61053 |
| 205453_at | HOXB2 | cluster15 | Hs.290432 |
| 208962_s_at | FADS1 | cluster15 | Hs.132898 |
| 205600_x_at | HOXB5 | cluster15 | Hs.149548 |
| 204069_at | MEIS1 | cluster15 | Hs.170177 |
| 201867_s_at | TBL1X | cluster15 | Hs.76536 |
| 209905_at | HOXA9 | cluster15 | Hs.127428 |
| 214835_s_at | SUCLG2 | cluster15 | Hs.446476 |
| 203542_s_at | BTEB1 | cluster15 | Hs.150557 |
| 212827_at | IGHM | cluster15 | Hs.153261 |
| 211182_x_at | RUNX1 | cluster15 | Hs.410774 |
| 204661_at | CDW52 | cluster15 | Hs.276770 |
| 206676_at | CEACAM8 | cluster15 | Hs.41 |
| 220057_at | GAGED2 | cluster16 | Hs.112208 |
| 219360_s_at | TRPM4 | cluster16 | Hs.31608 |
| 219414_at | CLSTN2 | cluster16 | Hs.12079 |
| 220116_at | KCNN2 | cluster16 | Hs.98280 |
| 216370_s_at | TKTL1 | cluster16 | Hs.102866 |
| 205550_s_at | BRE | cluster16 | Hs.80426 |
| 211566_x_at | BRE | cluster16 | Hs.80426 |
| 214183_s_at | TKTL1 | cluster16 | Hs.102866 |
| 209031_at | IGSF4 | cluster16 | Hs.156682 |
| 212645_x_at | BRE | cluster16 | Hs.80426 |
| 209030_s_at | IGSF4 | cluster16 | Hs.156682 |
| 213791_at | PENK | cluster16 | Hs.339831 |
| 206508_at | TNFSF7 | cluster16 | Hs.99899 |
| 219506_at | FLJ23221 | cluster16 | Hs.91283 |
| 211421_s_at | RET | cluster16 | Hs.350321 |
| 203241_at | UVRAG | cluster16 | Hs.13137 |
| 213908_at | LOC339005 | cluster16 | Hs.212670 // — |
| 207911_s_at | TGM5 | cluster16 | Hs.129719 |
| 214190_x_at | GGA2 | cluster16 | Hs.133340 |
| 204561_x_at | APOC2 | cluster16 | Hs.75615 |
| 209663_s_at | ITGA7 | cluster16 | Hs.74369 |
| 214259_s_at | AKR7A2 | cluster16 | Hs.6980 |
| 205472_s_at | DACH | cluster16 | Hs.63931 |
| 216331_at | ITGA7 | cluster16 | Hs.74369 |
| 220010_at | KCNE1L | cluster16 | Hs.146372 |
| 213484_at | na | cluster16 | Hs.66187 // — |
| 204497_at | ADCY9 | cluster16 | Hs.20196 |
| 215771_x_at | RET | cluster16 | Hs.350321 |
| 209032_s_at | IGSF4 | cluster16 | Hs.156682 |
| 219714_s_at | CACNA2D3 | cluster16 | Hs.435112 |
| 219463_at | C20orf103 | cluster16 | Hs.22920 |
| 202139_at | AKR7A2 | cluster16 | Hs.6980 |
| 219143_s_at | FLJ20374 | cluster16 | Hs.8562 |
| 205996_s_at | AK2 | cluster16 | Hs.294008 |
| 219288_at | HT021 | cluster16 | Hs.47166 |
| 215663_at | MBNL1 | cluster16 | Hs.28578 |
| 213361_at | PCTAIRE2BP | cluster16 | Hs.416543 |
| 210658_s_at | GGA2 | cluster16 | Hs.133340 |
| 213772_s_at | GGA2 | cluster16 | Hs.133340 |
| 212174_at | AK2 | cluster16 | Hs.294008 |

TABLE 3

| Abnormality | 10-fold CV error | Error validation set | #Probe sets | #Genes |
|---|---|---|---|---|
| t(8; 21) - AML1/ETO | 0/190 | 0/96 | 3 | 2 |
| t(15; 17) - PML/RARα | 1/190 | 0/96 | 3 | 2 |
| inv(16) - CBFβ/MYH11 | 0/190 | 0/96 | 1 | 1 |
| 11q23 (cluster #16) | 3/190 | 3/96 | 31 | 25 |
| EVI1 (cluster #10) | 16/190 | 0/96 | 28 | 25 |
| cEBPα (cluster #4) | 8/190 | 2/96 | 13 | 8 |
| cEBPα (cluster #15) | 17/190 | 6/96* | 36 | 32 |
| cEBPα (cluster #4 and #15) | 5/190 | 2/96 | 9 | 5 |
| FLT3 ITD | 27/190 | 21/96 | 56 | 41 |

TABLE 4

Clinical and molecular characteristics of the 286 patients with de novo AML.

| | # | % |
|---|---|---|
| Gender | | |
| Male | 138 | 49 |
| Female | 148 | 51 |
| Age groups | | |
| Younger than 35 | 77 | 27 |
| 35-60 | 177 | 62 |
| 60 and older | 32 | 11 |
| Age (median (range)) | 45.1 (15.2-77.6) | |
| White blood cell (WBC) count ($10^9$/l, median (range)) | 75.5 (0.3-263) | |
| Blast count (%, median (range)) | 70 (0-98) | |
| Platelet count ($10^9$/l, median (range)) | 57 (3-931) | |
| FAB | | |
| M0 | 6 | 2 |
| M1 | 64 | 22 |
| M2 | 66 | 23 |
| M3 | 19 | 7 |
| M4 | 53 | 18 |
| M5 | 65 | 23 |
| M6 | 3 | 1 |
| Mixed | 8 | 3 |
| Unclassified | 2 | 1 |

TABLE 4-continued

Clinical and molecular characteristics of the 286 patients with de novo AML.

|  | # | % |
|---|---|---|
| Cytogenetic risk groups |  |  |
| Favourable | 58 | 20 |
| t(8; 21) | 22 | 8 |
| inv(16) | 19 | 7 |
| t(15; 17) | 17 | 6 |
| Unfavourable | 39 | 14 |
| 11q23 abnormalities | 17 | 6 |
| −5/7(q) abnormalities | 22 | 8 |
| Normal Cytogenetics | 118 | 41 |
| Molecular abnormalities |  |  |
| Mutation |  |  |
| FLT3 ITD | 78 | 27 |
| FLT3 TKD | 33 | 12 |
| N-RAS | 26 | 9 |
| K-RAS | 9 | 3 |
| cEBPα | 17 | 6 |
| Overexpression |  |  |
| EVI1 | 24 | 8 |

TABLE 5

| #Probe sets: | 147 | 293 | 569 | 984 | 1692 | 2856 | 5071 |
|---|---|---|---|---|---|---|---|
| Ratio: | >32 | >22.6 | >16 | >11.3 | >8 | >5.6 | >4 |
| chromosomal abnormalities |  |  |  |  |  |  |  |
| t(8; 21) | +/− | + | + | + | ++ | ++ | + |
| inv(16) | +/− | +/− | +/− | + | ++ | ++ | ++ |
| t(15; 17) | +/− | + | ++ | ++ | ++ | ++ | + |
| 11q23 | +/− | +/− | +/− | +/− | + | + | +/− |
| −7(q) | +/− | +/− | +/− | +/− | +/− | + | +/− |
| mutation |  |  |  |  |  |  |  |
| FLT3 ITD | +/− | +/− | +/− | +/− | +/− | +/− | +/− |
| FLT3 TKD | − | − | − | − | − | − | − |
| N-RAS | − | − | − | − | − | − | − |
| K-RAS | − | − | − | − | − | − | − |
| cEBPα | − | +/− | +/− | + | + | + | + |
| overexpression |  |  |  |  |  |  |  |
| EVI1 | − | − | − | − | +/− | + | +/− |

(++: 100% clustering, +: clustering in ≦2 recognizable clusters, +/−: clustering in ≧2 recognizable clusters, −: no clustering)

TABLE 6

Characteristics of cluster #1 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 1595 | #1 | M1 | NN | + | − | − | − | − | − |
| 2187 | #1 | M1 | NN | − | − | − | − | − | − |
| 3488 | #1 | M1 | Complex | − | − | − | − | − | − |
| 1401 | #1 | M1 | NN | − | − | − | − | − | − |
| 2255 | #1 | M1 | 11q23 (t(4; 11)) | − | − | − | + | − | − |
| 2302 | #1 | M1 | +11/11q23(sMLL) | − | − | − | − | − | − |
| 2765 | #1 | M1 | +11/+11/Other | − | − | − | − | − | − |
| 2280 | #1 | M2 | NN | − | − | − | − | − | − |
| 3304 | #1 | M5 | NN | + | − | − | − | − | − |
| 3328 | #1 | M5 | 11q23 (t(11; 19)) | − | − | − | − | + | − |
| 2682 | #1 | M4 | Other/11q23 (t(2; 9; 11)) | − | − | − | − | + | − |
| 2207 | #1 | M1 | 11q23 (t(6; 11)) | − | − | − | − | + | − |
| 2772 | #1 | M5 | 11q23 (t(6; 11)) | − | − | − | − | + | − |
| 2196 | #1 | M5 | NN | − | − | − | − | + | − |

TABLE 7

Characteristics of cluster #2 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 3330 | #2 | M4 | +8 | − | − | − | − | − | − |
| 2681 | #2 | M1 | NN | + | − | − | − | − | − |
| 2688 | #2 | ND | NN | + | − | − | − | − | − |
| 2685 | #2 | M4 | −9q | − | + | − | − | − | − |
| 2689 | #2 | M4 | NN | − | − | − | − | − | − |

TABLE 7-continued

Characteristics of cluster #2 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 2498 | #2 | M4 | t(6; 9) | + | − | − | − | − | − |
| 2183 | #2 | M4 | NN | + | − | − | − | − | − |
| 2214 | #2 | M5 | NN | + | + | − | − | − | − |
| 2201 | #2 | M5 | NN | + | − | − | − | − | − |
| 3100 | #2 | M1 | NN | + | − | − | − | − | − |
| 2672 | #2 | M5 | NN | + | + | − | − | − | − |
| 2195 | #2 | M4 | NN | + | − | − | − | − | − |
| 1747 | #2 | M2 | NN | + | − | − | − | − | − |
| 2774 | #2 | M4 | NN | + | − | − | − | − | ND |
| 1551 | #2 | M1 | NN | + | − | − | − | − | − |
| 2194 | #2 | M4 | NN | + | − | − | − | − | + |
| 2182 | #2 | M5 | +8 | + | − | − | − | − | − |

TABLE 8

Characteristics of cluster #3 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 2480 | #3 | M1 | NN | + | − | − | − | − | − |
| 3099 | #3 | M2 | NN | + | − | − | − | − | − |
| 2236 | #3 | M1 | NN | + | − | − | − | − | − |
| 3331 | #3 | M2 | NN | + | − | − | − | − | − |
| 2177 | #3 | M2 | NN | + | − | − | − | − | − |
| 2306 | #3 | M1 | NN | − | − | − | − | − | − |
| 2286 | #3 | M1 | NN | + | − | − | − | − | − |
| 2754 | #3 | M1 | NN | + | − | − | − | − | − |
| 3320 | #3 | M1 | NN | + | − | − | − | − | − |
| 2326 | #3 | M2 | t(9; 22) | − | − | − | − | + | − |
| 2270 | #3 | M1 | +8/Other | − | + | − | − | − | − |
| 2241 | #3 | M4 | NN | − | ND | − | − | − | − |
| 2288 | #3 | M4 | −7/11q23 | − | − | − | − | + | − |
| 2205 | #3 | M2 | t(6; 9)/Other | − | − | − | − | − | − |
| 2665 | #3 | M5 | t(6; 9) | + | − | − | − | − | − |
| 2257 | #3 | M1 | NN | − | − | − | − | − | − |
| 2271 | #3 | M2 | NN | − | + | − | − | − | − |
| 2299 | #3 | M2 | +21 | − | + | − | − | − | − |
| 2676 | #3 | M2 | ND | + | − | − | − | − | − |

TABLE 9

Characteristics of cluster #4 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 3327 | #4 | M1 | NN | − | − | − | − | − | − |
| 2242 | #4 | M1 | −9q | − | − | − | − | − | + |

TABLE 9-continued

Characteristics of cluster #4 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 2668 | #4 | M0 | Complex | − | − | − | − | − | − |
| 2238 | #4 | M1 | NN | − | − | − | − | − | − |
| 3314 | #4 | ND | Complex(+8, +11) | − | − | − | − | − | − |
| 2686 | #4 | M1 | NN | − | − | − | − | − | + |
| 3483 | #4 | M1 | Other | − | − | − | − | − | − |
| 3491 | #4 | M1 | NN | − | − | − | − | − | − |
| 2218 | #4 | M1 | NN/11q23 (sMLL) | − | − | − | − | − | + |
| 1316 | #4 | M1 | NN | + | − | − | − | − | + |
| 2273 | #4 | M1 | NN | − | − | − | − | − | + |
| 2545 | #4 | M1 | NN | − | − | − | − | − | − |
| 2169 | #4 | M1 | NN | − | − | + | − | − | + |
| 2753 | #4 | M1 | −9q | − | − | − | − | − | + |
| 2192 | #4 | M1 | NN | − | − | − | − | − | + |

TABLE 10

Characteristics of cluster #5 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 3301 | #5 | M5 | −5/7(q) | − | + | + | − | + | − |
| 2228 | #5 | M4 | NN | − | − | + | − | + | − |
| 2272 | #5 | M5 | +8/Other | + | − | − | − | − | − |
| 2525 | #5 | M5 | NN | − | − | ND | ND | − | − |
| 2655 | #5 | M4 | ND | − | − | − | + | − | − |
| 2278 | #5 | M5 | NN | − | − | − | − | − | − |
| 2283 | #5 | M4 | +8/Other | − | − | − | − | − | − |
| 2279 | #5 | M4 | NN | − | − | − | − | − | − |
| 2259 | #5 | M4 | Complex | − | − | − | − | − | − |
| 2220 | #5 | M5 | +11 | − | − | − | − | − | − |
| 3490 | #5 | M5 | Other | − | − | − | − | − | − |
| 2217 | #5 | M5 | +8/Other | − | + | − | − | − | + |
| 3486 | #5 | M4 | NN | − | − | − | − | − | − |
| 3097 | #5 | M4 | +8/Other | − | − | − | − | − | − |
| 2687 | #5 | M5 | NN | − | − | − | − | − | − |
| 3325 | #5 | M4 | NN | − | − | − | − | − | − |
| 2467 | #5 | M5 | ND | − | − | − | − | − | − |
| 2244 | #5 | M5 | +8/3q/Other | − | − | − | + | − | − |
| 2282 | #5 | M4 | NN | − | − | − | − | − | − |
| 2771 | #5 | M5 | NN | − | + | − | − | − | − |
| 2185 | #5 | M5 | NN | + | − | − | − | − | − |
| 3484 | #5 | M4 | NN | − | − | − | − | − | − |
| 2191 | #5 | ND | NN | − | − | − | + | − | − |
| 3321 | #5 | M5 | +8 | + | − | − | − | − | − |
| 3493 | #5 | M5 | Other | − | − | − | − | − | − |
| 2296 | #5 | M5 | NN | + | − | − | − | − | − |
| 2231 | #5 | M4 | NN | + | − | − | − | − | − |
| 2227 | #5 | M5 | NN/11q23 (sMLL) | − | + | − | − | − | − |
| 2275 | #5 | M5 | NN | + | − | − | − | − | − |
| 2692 | #5 | M5 | NN | + | − | − | − | − | − |
| 2174 | #5 | M5 | NN | − | − | + | − | − | − |
| 2669 | #5 | M5 | NN | + | − | − | − | − | − |
| 2175 | #5 | M5 | NN | − | − | − | − | − | − |
| 2291 | #5 | M5 | +8 | − | + | − | − | − | − |
| 2670 | #5 | M5 | t(6; 9) | + | − | − | − | − | − |
| 2289 | #5 | M5 | NN | + | + | − | − | − | − |
| 2181 | #5 | M5 | NN | + | − | − | − | − | − |

TABLE 10-continued

Characteristics of cluster #5 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 2198 | #5 | M5 | NN | − | − | − | − | − | − |
| 3482 | #5 | M5 | NN | + | − | − | − | − | − |
| 1482 | #5 | M4 | NN | − | − | + | + | − | − |
| 2176 | #5 | M4 | NN | + | − | − | − | − | − |
| 2305 | #5 | M5 | NN | + | − | − | − | − | − |
| 2534 | #5 | M2 | Complex | − | − | − | − | − | − |
| 1197 | #5 | M0 | Complex | − | − | − | − | − | − |

TABLE 11

Characteristics of cluster #6 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 2683 | #6 | M2 | NN | + | − | − | − | − | − |
| 1063 | #6 | M1 | NN | + | − | − | + | − | − |
| 3333 | #6 | M2 | NN | + | − | − | + | − | − |
| 2248 | #6 | M1 | NN | + | − | − | − | − | − |
| 2203 | #6 | M1 | NN | + | − | − | − | − | − |
| 2679 | #6 | M2 | NN | + | − | − | − | − | − |
| 2644 | #6 | M1 | NN | + | − | − | − | − | − |
| 2173 | #6 | M1 | ND | + | + | − | − | − | − |

TABLE 12

Characteristics of cluster #7 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 3310 | #7 | M2 | NN | − | − | − | − | − | − |
| 3098 | #7 | M3 | NN | − | − | − | − | − | − |
| 2199 | #7 | M1 | NN | + | − | − | − | − | − |
| 2769 | #7 | M1 | NN | − | − | − | − | − | − |
| 2268 | #7 | M1 | NN | + | − | − | − | − | − |
| 2507 | #7 | M2 | NN | + | − | − | − | − | − |
| 3489 | #7 | M2 | Other | − | − | − | − | − | − |
| 2284 | #7 | M6 | NN | − | − | − | − | − | − |
| 2246 | #7 | M1 | NN | − | − | − | − | − | − |
| 2224 | #7 | M6 | Other | − | − | − | − | − | − |
| 2490 | #7 | M6 | NN | + | − | − | − | − | − |
| 3319 | #7 | M5 | NN | − | − | − | − | − | − |
| 3334 | #7 | ND | Other | − | − | − | − | − | − |
| 2544 | #7 | M2 | +8/Other | − | − | − | − | − | − |
| 2251 | #7 | M2 | Complex(3q/+8) | − | − | − | − | − | − |
| 2222 | #7 | M1 | NN | − | − | − | − | + | − |

TABLE 12-continued

Characteristics of cluster #7 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 2252 | #7 | M2 | NN | − | − | − | − | − | − |
| 3293 | #7 | M3 | ND | − | − | − | − | + | − |

TABLE 13

Characteristics of cluster #8 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 2223 | #8 | M2 | +21 | − | − | − | − | − | − |
| 2514 | #8 | M5 | Complex (−7(q)/+8) | − | − | − | − | − | − |
| 3318 | #8 | M2 | Complex (11q23 (t(8; 11)), −5, 3q) | − | − | − | − | − | − |
| 3481 | #8 | ND | +11/Other | − | − | − | − | − | − |
| 3485 | #8 | M2 | NN | − | − | − | − | − | − |
| 3315 | #8 | ND | +8, −7(q) | − | − | + | − | − | − |
| 2256 | #8 | M2 | NN | − | − | − | − | − | − |
| 3326 | #8 | M2 | inv7(q)/other | − | − | − | − | − | − |
| 2656 | #8 | M2 | −7 | − | − | − | − | − | − |
| 2543 | #8 | M2 | NN | − | − | − | − | − | − |
| 2290 | #8 | M2 | Other | − | − | − | − | − | − |
| 2304 | #8 | M0 | Other | − | − | − | − | − | − |
| 2756 | #8 | M2 | NN | − | − | − | − | − | − |

TABLE 14

Characteristics of cluster #9 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, BP: inv(16) breakpoint, RT: real-time PCR for CBF β-MYH11 (Primer CBFβ 5'-AAGACTGGATGGTATGGGCTGT-3' (sense), Primer 126REV 5'-CAGGGCCCGCTTGGA-3' (antisense), Probe CBFβ 6-FAM 5'-TGGAGTTTGATGAGGAGCGAGCCC-3' TAMRA); FLT3 ITD: internal tandem duplication in FLT3; FLT3 TKD: tyrosine kinase domain mutation in FLT3; N- or K-RAS: mutation in codon 12, 13 or 61 of N- or K-RAS; EVI1: EVI1 overexpression; CEPBA: mutation in CEBPA, ND: not determined).

| Patient | Cluster | FAB | Karyotype | BP | RT | FLT3 ITD | FLT3 TKD | N-RAS | K-RAS | EVI1 | CEBPA |
|---|---|---|---|---|---|---|---|---|---|---|---|
| 3277 | #9 | M1 | idt(16) | A | + | − | − | − | − | − | − |
| 3286 | #9 | M4 | idt(16) | A | + | − | − | + | − | − | − |
| 3309 | #9 | M4 | idt(16)/−7(q) | A | + | − | + | + | − | − | − |
| 3115 | #9 | M5 | idt(16) | A | + | − | − | − | − | − | − |
| 2235 | #9 | M4 | idt(16) | A | + | − | − | − | − | − | − |
| 2293 | #9 | M4 | idt(16) | A | + | − | − | − | − | − | − |
| 2696 | #9 | M4 | NN | A | + | − | − | + | − | − | − |
| 3324 | #9 | M5 | idt(16) | A | + | − | − | − | − | − | − |
| 2647 | #9 | M4 | idt(16) | A | + | − | + | − | − | − | − |
| 2172 | #9 | M4 | NN | A | + | − | + | + | − | − | − |
| 2254 | #9 | M4 | idt(16) | A | + | − | − | − | − | − | − |
| 2287 | #9 | M4 | idt(16) | D | + | − | + | − | − | − | − |
| 2189 | #9 | M4 | idt(16) | A | + | − | − | + | − | − | − |

TABLE 14-continued

Characteristics of cluster #9 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, BP: inv(16) breakpoint, RT: real-time PCR for CBF β-MYH11 (Primer CBFβ 5'-AAGACTGGATGGTATGGGCTGT-3' (sense), Primer 126REV 5'-CAGGGCCCGCTTGGA-3' (antisense), Probe CBFβ 6-FAM 5'-TGGAGTTTGATGAGGAGCGAGCCC-3' TAMRA); FLT3 ITD: internal tandem duplication in FLT3; FLT3 TKD: tyrosine kinase domain mutation in FLT3; N- or K-RAS: mutation in codon 12, 13 or 61 of N- or K-RAS; EVI1: EVI1 overexpression; CEPBA: mutation in CEBPA, ND: not determined).

| Patient | Cluster | FAB | Karyotype | BP | RT | FLT3 ITD | FLT3 TKD | N-RAS | K-RAS | EVI1 | CEBPA |
|---|---|---|---|---|---|---|---|---|---|---|---|
| 2766 | #9 | M4 | idt(16) | A | + | − | + | − | − | − | − |
| 2249 | #9 | M5 | −7(q) | A | + | − | + | − | − | − | − |
| 2215 | #9 | M4 | idt(16)/+8 | A | + | − | − | + | − | − | − |
| 2678 | #9 | M4 | idt(16) | A | + | − | − | − | ND | − | − |
| 2202 | #9 | M4 | idt(16) | A | + | − | − | + | − | − | − |
| 3487 | #9 | ND | idt(16) | A | + | − | − | − | + | − | − |
| 3329 | #9 | M4 | idt(16) | A | + | − | − | − | − | − | − |
| 2274 | #9 | M4 | NN | A | + | − | − | − | − | − | − |
| 2750 | #9 | M2 | idt(16)/+8 | A | + | − | − | − | − | − | − |
| 3285 | #9 | M4 | idt(16) | A | + | − | − | + | − | − | − |

TABLE 15

Characteristics of cluster #10 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 2661 | #10 | M4 | ND | − | − | − | − | + | − |
| 3102 | #10 | M2 | −7 | − | − | − | − | + | − |
| 2747 | #10 | M5 | −7/3q | − | − | − | − | + | − |
| 2327 | #10 | M2 | −7(q) | + | − | − | − | + | − |
| 2551 | #10 | M5 | Other | − | − | − | − | + | − |
| 2276 | #10 | M0 | Other | − | − | − | − | + | − |
| 2226 | #10 | M1 | +11 | − | − | + | − | − | − |
| 3308 | #10 | M1 | t(9; 22) | − | + | − | − | − | − |
| 2546 | #10 | M1 | +8 | − | − | − | − | − | − |
| 2757 | #10 | M5 | −5 | − | − | − | − | − | − |
| 3313 | #10 | M0 | Other | − | − | − | − | − | − |
| 2664 | #10 | M0 | −7/3q | − | − | + | − | + | − |
| 2666 | #10 | M5 | ND | − | − | − | − | + | − |
| 1188 | #10 | M1 | −7(q) | − | − | − | − | − | − |
| 2550 | #10 | M1 | Other | − | − | − | − | − | + |
| 2539 | #10 | ND | ND | − | − | − | − | − | − |
| 2250 | #10 | M1 | −7 | − | − | − | − | + | − |
| 2773 | #10 | M2 | NN | + | − | + | − | − | − |
| 2186 | #10 | M5 | −7 | − | − | − | − | + | − |
| 2301 | #10 | M1 | NN | + | − | − | − | − | − |
| 2497 | #10 | M1 | Other | + | − | − | − | − | − |
| 2247 | #10 | M1 | Other | − | − | − | − | − | − |

TABLE 16

Characteristics of cluster #11 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 2209 | #11 | M4 | Other | − | − | − | − | − | − |
| 3096 | #11 | M4 | NN | − | + | − | − | − | − |
| 2239 | #11 | M5 | Other | − | + | − | − | − | − |
| 2261 | #11 | M5 | NN | − | + | − | − | − | − |
| 1299 | #11 | M2 | NN | + | − | − | − | − | − |
| 1432 | #11 | M1 | NN | − | − | − | − | − | − |
| 3311 | #11 | M5 | NN | − | − | − | − | − | − |
| 1766 | #11 | ND | NN | − | − | + | − | − | − |
| 2206 | #11 | M5 | NN | − | − | + | − | − | − |

TABLE 17

Characteristics of cluster #12 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR for PML-RARα (Primer PML3-for 5'-CCCCAGGAGCCCCGT-3' (sense), Primer PML-kbr 5'-CCTGCAGGACCTCAGCTCTT-3'(sense), Primer RAR4-rev 5'-AAAGCAAGGCTTGTAGATGCG-3'(antisense), Probe RARA 6-FAM 5'-AGTGCCCAGCCCTCCCTCGC-3' TAMRA); FLT3 ITD: internal tandem duplication in FLT3; FLT3 TKD: tyrosine kinase domain mutation in FLT3; N- or K-RAS: mutation in codon 12, 13 or 61 of N- or K-RAS; EVI1: EVI1 overexpression; CEPBA: mutation in CEBPA, ND: not determined).

| Patient | Cluster | FAB | Karyotype | RT | FLT3 ITD | FLT3 TKD | N-RAS | K-RAS | EVI1 | CEBPA |
|---|---|---|---|---|---|---|---|---|---|---|
| 2466 | #12 | M3 | t(15; 17) | + | − | − | − | − | − | − |
| 2509 | #12 | M3 | t(15; 17) | + | − | − | − | − | − | − |
| 2219 | #12 | M3 | t(15; 17) | + | − | + | − | − | − | − |
| 2263 | #12 | M3 | t(15; 17) | + | − | − | − | − | − | − |
| 2307 | #12 | M3 | t(15; 17) | + | − | − | − | − | − | − |
| 2510 | #12 | M3 | t(15; 17) | + | − | + | − | − | − | − |
| 2297 | #12 | M3 | t(15; 17) | + | − | + | − | − | − | − |
| 2265 | #12 | M3 | t(15; 17)/Other | + | − | − | − | − | − | − |
| 2266 | #12 | M3 | t(15; 17)/Other | + | − | − | − | − | − | − |
| 3279 | #12 | M3 | t(15; 17) | + | − | − | − | − | − | − |
| 2170 | #12 | M3 | t(15; 17)/Other | + | − | + | − | − | − | − |
| 2680 | #12 | M2 | t(15; 17) | + | + | − | − | − | − | − |
| 2671 | #12 | M3 | t(15; 17) | + | + | − | − | − | − | − |
| 2516 | #12 | M3 | t(15; 17) | + | − | + | − | − | − | − |
| 2468 | #12 | M3 | t(15; 17) | + | + | − | − | − | − | − |
| 3278 | #12 | M3 | t(15; 17) | + | − | − | − | − | − | − |
| 322 | #12 | M3 | Other* | + | + | − | − | − | − | − |
| 2179 | #12 | M4 | t(15; 17)/Other | + | + | − | − | − | − | − |
| 1448 | #12 | M3 | t(15; 17)/+8 | + | + | − | − | − | − | − |

*Full karyotype of patient 322: 46, XX, add(12)(p1?3).

TABLE 18

Characteristics of cluster #13 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR for AML1-ETO (Primer 821 For 5'-TCACTCTGACCATCACTGTCTTCA-3' (sense), Primer 821 Rev 5'-ATTGTGGAGTGCTTCTCAGTACGAT-3'(antisense), Probe ETO 6-FAM 5'-ACCCACCGCAAGTCGCCACCT-3' TAMRA); FLT3 ITD: internal tandem duplication in FLT3; FLT3 TKD: tyrosine kinase domain mutation in FLT3; N- or K-RAS: mutation in codon 12, 13 or 61 of N- or K-RAS; EVI1: EVI1 overexpression; CEPBA: mutation in CEBPA, ND: not determined).

| Patient | Cluster | FAB | Karyotype | RT | FLT3 ITD | FLT3 TKD | N-RAS | K-RAS | EVI1 | CEBPA |
|---|---|---|---|---|---|---|---|---|---|---|
| 2243 | #13 | M2 | t(+8; 21)/Other | + | − | − | − | − | − | + |
| 2658 | #13 | M4 | t(+8; 21) | + | − | − | − | − | − | − |
| 2752 | #13 | M2 | t(+8; 21) | + | − | − | − | − | − | − |
| 2197 | #13 | M2 | t(+8; 21)/Other | + | + | − | − | − | − | − |
| 2245 | #13 | M2 | t(+8; 21)/Other | + | − | + | − | − | − | − |
| 3332 | #13 | M2 | t(+8; 21) | + | − | − | − | − | − | − |
| 2262 | #13 | M2 | t(+8; 21)/Other | + | − | − | − | − | − | − |
| 2178 | #13 | M2 | t(+8; 21)/Other | + | − | − | − | − | − | − |
| 2511 | #13 | M2 | t(+8; 21)/+8/Other | + | − | − | − | − | − | − |
| 2200 | #13 | M2 | t(+8; 21)/Other | + | − | − | − | − | − | − |
| 2208 | #13 | M2 | t(+8; 21) | + | − | − | − | − | − | − |
| 3295 | #13 | M2 | t(+8; 21) | + | − | − | − | − | − | − |
| 2204 | #13 | M2 | t(+8; 21)/Other | + | − | − | + | − | − | − |
| 3292 | #13 | M2 | t(+8; 21) | + | − | − | − | − | − | − |
| 2549 | #13 | M2 | t(+8; 21)/Other | + | − | − | − | − | − | − |
| 2267 | #13 | M2 | t(+8; 21)/Other | + | − | − | − | − | − | − |
| 2695 | #13 | M1 | t(+8; 21) | + | − | − | − | − | − | − |
| 2751 | #13 | M2 | t(+8; 21)/Other | + | − | − | − | + | − | − |
| 2211 | #13 | M2 | t(+8; 21)/Other | + | − | − | − | − | − | − |
| 2764 | #13 | M2 | t(+8; 21)/Other | + | − | − | − | − | − | − |
| 2210 | #13 | M2 | t(+8; 21)/Other | + | − | − | + | − | − | − |
| 2762 | #13 | M2 | t(+8; 21)/Other | + | − | − | + | − | − | − |

TABLE 19

Characteristics of cluster #14 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 2536 | #14 | ND | ND | − | − | − | − | − | − |
| 2704 | #14 | M2 | ND | + | − | − | − | − | − |
| 2690 | #14 | M2 | +8/Other | − | − | + | − | − | − |
| 3289 | #14 | M2 | 11q23 (ND) | + | − | − | − | − | − |
| 2212 | #14 | M2 | −5(q) | − | − | − | − | − | − |
| 2233 | #14 | M1 | Complex(−5/−7/+8) | − | − | − | − | − | − |
| 1201 | #14 | M4 | Complex | − | + | − | − | − | − |
| 2188 | #14 | M2 | +8 | − | − | − | − | − | − |
| 3492 | #14 | M2 | NN | + | + | − | − | − | − |
| 2260 | #14 | M5 | NN | − | − | − | − | − | − |

TABLE 20

Characteristics of cluster #15 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 2767 | #15 | M1 | ND | − | + | − | − | − | − |
| 2748 | #15 | M4 | NN | − | − | − | − | − | + |
| 2240 | #15 | M1 | NN | − | − | − | − | − | + |
| 3101 | #15 | M2 | NN | + | − | + | − | − | + |
| 2234 | #15 | M2 | Other | − | − | − | − | − | + |
| 2230 | #15 | M2 | NN | + | − | − | − | − | − |
| 2253 | #15 | M2 | NN | − | − | − | − | − | + |
| 2237 | #15 | M1 | −7/Other | − | − | − | − | − | − |

TABLE 21

Characteristics of cluster #16 (Patient: patient number, Cluster: cluster number (2856 probe sets); FAB: FAB subtype of AML; Karyotype: t(15; 17), t(8; 21), inv(16)/t(16; 16), +8, +11, +21, −5(q), −7(q), t(9; 22), 3q abnormalities, 11q23 abnormalities (translocation/self fusion (sMLL)), complex(abnormalities involved) (>3 abnormalities) and normal karyotype (NN) are indicated, RT: real-time PCR; FLT3 ITD: internal tandem duplication in FLT3; FLT3 TKD: tyrosine kinase domain mutation in FLT3; N- or K-RAS: mutation in codon 12, 13 or 61 of N- or KRAS; EVI1: EVI1 overexpression; CEPBA: mutation in CEBPA, ND: not determined).

| Patient | Cluster | FAB | Karyotype | FLT3 ITD | FLT3 TKD | N-RAS | K-RAS | EVI1 | CEBPA |
|---|---|---|---|---|---|---|---|---|---|
| 2225 | #16 | M4 | NN | − | − | − | − | − | − |
| 2184 | #16 | M5 | Other | − | − | − | − | − | − |
| 2535 | #16 | M5 | Other | − | − | − | − | − | − |
| 3322 | #16 | M5 | +8/11q23 (t(11; 19)) | − | − | − | − | − | − |
| 2285 | #16 | M5 | 11q23 (t(9; 11)) | − | + | − | − | − | − |
| 3316 | #16 | M5 | Other/11q23 (t(9; 11)) | − | − | − | − | − | − |
| 2694 | #16 | M5 | 11q23 (t(9; 11)) | − | − | − | − | − | − |
| 3317 | #16 | M5 | Other | − | − | − | − | − | − |
| 2749 | #16 | M5 | NN | − | − | − | − | − | − |
| 2281 | #16 | M1 | NN | − | − | − | − | − | − |
| 2541 | #16 | M5 | 11q23 (t(9; 11))/−7 | − | − | − | − | − | − |

TABLE 22

Frequency and percentage of cytogenetic and molecular abnormalities of all AML patients within each of the assigned clusters. All patients with a specific abnormality were considered, irrespective of the presence of additional abnormalities (NC: patients not assigned to any of the 16 clusters).

| | Cluster | | | | | | | | |
|---|---|---|---|---|---|---|---|---|---|
| | #1 | #2 | #3 | #4 | #5 | #6 | #7 | #8 | #9 |
| | | | | | Patients in cluster | | | | |
| | 14 | 17 | 19 | 15 | 44 | 8 | 18 | 13 | 23 |
| Cytogenetics | | | | | | | | | |
| t(15; 17) | | | | | | | | | |
| t(8; 21) | | | | | | | | | |
| inv(16)/t(16; 16) | | | | | | | | | 19 (83) |
| +8 | | 2 (12) | 1 (5) | 1 (7) | 7 (16) | | 2 (11) | 2 (15) | 2 (9) |
| +11 | 2 (14) | | | 1 (7) | 1 (2) | | | 1 (8) | |
| +21 | | | 1 (5) | | | | | 1 (8) | |
| −5 | | | | | | | | 1 (8) | |
| −5(q) | | | | | | | | | |
| −7 | | | 1 (5) | | 1 (2) | | | 1 (8) | |
| −7(q) | | | | | | | | 3 (23) | 2 (9) |
| 3q | | | | | 1 (2) | | 1 (6) | 1 (8) | |
| t(6; 9) | | 1 (6) | 2 (11) | | 1 (2) | | | | |

TABLE 22-continued

Frequency and percentage of cytogenetic and molecular abnormalities of all AML patients within each of the assigned clusters. All patients with a specific abnormality were considered, irrespective of the presence of additional abnormalities (NC: patients not assigned to any of the 16 clusters).

|  | #1 | #2 | #3 | #4 | #5 | #6 | #7 | #8 | #9 |
|---|---|---|---|---|---|---|---|---|---|
| t(9; 22) |  |  | 1 (5) |  |  |  |  |  |  |
| t(11q23) | 6 (43) |  | 1 (5) | 2 (13) | 1 (2) |  |  | 1 (8) |  |
| complex (>3 abn.) | 1 (7) |  |  | 2 (13) | 3 (7) |  | 1 (6) | 2 (15) |  |
| other non-complex | 2 (14) | 1 (6) | 2 (11) | 3 (20) | 7 (16) |  | 4 (22) | 4 (31) |  |
| normal | 6 (43) | 13 (76) | 13 (68) | 10 (67) | 27 (61) | 7 (88) | 12 (67) | 4 (31) | 3 (13) |
| ND |  |  |  |  | 2 (5) | 1 (13) | 1 (6) |  |  |
| Molecular markers |  |  |  |  |  |  |  |  |  |
| FLT3-ITD | 2 (14) | 14 (82) | 10 (53) | 1 (7) | 14 (32) | 8 (100) | 4 (22) |  |  |
| FLT3-TKD |  | 3 (18) | 3 (16) |  | 6 (14) | 1 (13) |  |  | 6 (26) |
| N-RAS |  |  |  | 1 (7) | 4 (9) |  |  | 1 (8) | 8 (35) |
| K-RAS | 1 (7) |  |  |  | 4 (9) | 2 (25) |  |  | 1 (4) |
| EVI1 | 5 (36) |  | 2 (11) |  | 2 (5) |  | 2 (11) |  |  |
| CEBPA |  | 1 (6) |  | 8 (53) | 1 (2) |  |  |  |  |

| | Cluster | | | | | | | |
|---|---|---|---|---|---|---|---|---|
|  | #10 | #11 | #12 | #13 | #14 | #15 | #16 | NC | total |
| Patients in cluster | 22 | 9 | 19 | 22 | 10 | 8 | 11 | 13 | 285 |
| Cytogenetics |  |  |  |  |  |  |  |  |  |
| t(15; 17) |  |  | 18 (95) |  |  |  |  |  | 18 (6) |
| t(8; 21) |  |  |  | 22 (100) |  |  |  |  | 22 (8) |
| inv(16)/t(16; 16) |  |  |  |  |  |  |  |  | 19 (7) |
| +8 | 1 (5) |  | 1 (5) | 1 (5) | 3 (30) |  | 1 (9) | 2 (15) | 26 (9) |
| +11 | 1 (5) |  |  |  |  |  |  | 1 (8) | 7 (2) |
| +21 |  |  |  |  |  |  |  |  | 2 (1) |
| −5 | 1 (5) |  |  |  | 1 (10) |  |  |  | 3 (1) |
| −5(q) |  |  |  |  | 1 (10) |  |  |  | 1 (<1) |
| −7 | 5 (23) |  |  |  | 1 (10) | 1 (13) | 1 (9) | 2 (15) | 13 (5) |
| −7(q) | 2 (9) |  |  |  |  |  |  |  | 7 (2) |
| 3q |  |  |  |  |  |  |  | 1 (8) | 4 (1) |
| t(6; 9) |  |  |  |  |  |  |  |  | 4 (1) |
| t(9; 22) |  | 1 (5) |  |  |  |  |  |  | 2 (1) |
| t(11q23) |  |  |  |  | 1 (10) |  | 5 (45) | 2 (15) | 19 (7) |
| complex (>3 abn.) |  |  |  |  | 2 (20) |  |  |  | 11 (4) |
| other non-complex | 6 (27) | 2 (22) | 4 (21) | 15 (68) | 1 (10) | 2 (25) | 4 (36) | 3 (23) | 60 (21) |
| normal | 2 (9) | 7 (78) |  |  | 2 (20) | 5 (63) | 3 (27) | 5 (38) | 119 (42) |
| ND | 3 (14) |  |  |  | 2 (20) | 1 (13) |  |  | 10 (4) |
| Molecular markers |  |  |  |  |  |  |  |  |  |
| FLT3-ITD | 4 (18) | 1 (11) | 6 (32) | 1 (5) | 3 (30) | 2 (25) |  | 8 (62) | 78 (27) |
| FLT3-TKD | 1 (5) | 3 (33) | 5 (26) | 1 (5) | 2 (20) | 1 (13) | 1 (9) |  | 33 (12) |
| N-RAS | 3 (14) | 2 (22) |  | 3 (14) | 1 (10) | 1 (13) |  | 2 (15) | 26 (9) |
| K-RAS |  |  |  | 1 (5) |  |  |  |  | 9 (3) |
| EVI1 | 10 (45) |  |  |  |  |  |  | 2 (15) | 23 (8) |
| CEBPA | 1 (5) |  |  | 1 (5) |  | 5 (63) |  |  | 17 (6) |

TABLE 23

Top 40 genes of cluster #1

| Probe Set ID | Gene symbol | Locus Link number | Accession number | Score SAM | q-value SAM (%) |
|---|---|---|---|---|---|
| 220014_at | LOC51334 | 51334 | NM_016644.1 | 7.09 | 1.96 |
| 206762_at | KCNA5 | 3741 | NM_002234.1 | 6.68 | 1.96 |
| 213094_at | GPR126 | 57211 | AL033377 | 6.18 | 1.96 |
| 218502_s_at | TRPS1 | 7227 | NM_014112.1 | 5.95 | 1.96 |
| 221530_s_at | BHLHB3 | 79365 | AB044088.1 | 5.63 | 1.96 |
| 221884_at | EVI1 | 2122 | BE466525 | 5.40 | 1.96 |
| 203642_s_at | KIAA0977 | 22837 | NM_014900.1 | 4.96 | 1.96 |
| 212827_at | IGHM | 3507 | X17115.1 | 4.85 | 1.96 |
| 205612_at | MMRN | 22915 | NM_007351.1 | 4.72 | 1.96 |
| 209200_at | MEF2C | 4208 | N22468 | 4.59 | 1.96 |
| 214255_at | ATP10A | 57194 | AB011138.1 | 4.41 | 1.96 |
| 201539_s_at | FHL1 | 2273 | U29538.1 | 4.37 | 1.96 |
| 205717_x_at | PCDHGC3 | 5098 | NM_002588.1 | 4.29 | 1.96 |
| 222144_at | KIF17 | 57576 | AA909345 | 4.25 | 1.96 |
| 219922_s_at | LTBP3 | 4054 | NM_021070.1 | 4.21 | 1.96 |
| 215836_s_at | PCDHGC3 | 5098 | AK026188.1 | 4.20 | 1.96 |
| 205861_at | SPIB | 6689 | NM_003121.1 | 4.15 | 1.96 |
| 203372_s_at | SOCS2 | 8835 | AB004903.1 | 4.12 | 1.96 |
| 209079_x_at | PCDHGC3 | 5098 | AF152318.1 | 4.11 | 1.96 |
| 215811_at | — | — | AF238870.1 | 4.09 | 1.96 |
| 209199_s_at | MEF2C | 4208 | N22468 | 4.08 | 1.96 |
| 207655_s_at | BLNK | 29760 | NM_013314.1 | 4.05 | 1.96 |
| 203716_s_at | DPP4 | 1803 | M80536.1 | 4.03 | 1.96 |
| 219737_s_at | — | — | AI524125 | 4.01 | 1.96 |
| 204304_s_at | PROM1 | 8842 | NM_006017.1 | 3.97 | 1.96 |
| 203373_at | SOCS2 | 8835 | NM_003877.1 | 3.95 | 1.96 |

TABLE 23-continued

Top 40 genes of cluster #1

| Probe Set ID | Gene symbol | Locus Link number | Accession number | Score SAM | q-value SAM (%) |
|---|---|---|---|---|---|
| 218237_s_at | SLC38A1 | 81539 | NM_030674.1 | 3.87 | 1.96 |
| 202265_at | BMI1 | 648 | NM_005180.1 | 3.86 | 1.96 |
| 210298_x_at | FHL1 | 2273 | AF098518.1 | 3.83 | 1.96 |
| 208436_s_at | IRF7 | 3665 | NM_004030.1 | 3.77 | 1.96 |
| 210032_s_at | SPAG6 | 9576 | AI651156 | 3.77 | 1.96 |
| 222088_s_at | SLC2A14 | 144195 | AA778684 | −3.76 | 1.96 |
| 204621_s_at | NR4A2 | 4929 | AI935096 | −3.80 | 1.96 |
| 216248_s_at | NR4A2 | 4929 | S77154.1 | −3.84 | 1.96 |
| 216236_s_at | SLC2A14 | 144195 | AL110298.1 | −3.85 | 1.96 |
| 204622_x_at | NR4A2 | 4929 | NM_006186.1 | −3.85 | 1.96 |
| 202497_x_at | SLC2A3 | 6515 | NM_006931.1 | −3.91 | 1.96 |
| 201464_x_at | JUN | 3725 | BG491844 | −3.92 | 1.96 |
| 202672_s_at | ATF3 | 467 | NM_001674.1 | −4.11 | 1.96 |

TABLE 24

Top 40 genes of cluster #2

| Probe Set ID | Gene symbol | Locus Link number | Accession number | Score SAM | q-value SAM (%) |
|---|---|---|---|---|---|
| 207034_s_at | GLI2 | 2736 | NM_030379.1 | 10.30 | 1.04 |
| 206341_at | IL2RA | 3559 | NM_000417.1 | 9.15 | 1.04 |
| 211269_s_at | IL2RA | 3559 | K03122.1 | 8.24 | 1.04 |
| 215288_at | TRPC2 | 7221 | AI769824 | 7.44 | 1.04 |
| 205190_at | PLS1 | 5357 | NM_002670.1 | 7.34 | 1.04 |
| 210145_at | PLA2G4A | 5321 | M68874.1 | 7.31 | 1.04 |
| 204341_at | TRIM16 | 10626 | NM_006470.1 | 7.23 | 1.04 |
| 206574_s_at | PTP4A3 | 11156 | NM_007079.1 | 7.01 | 1.04 |
| 203187_at | DOCK1 | 1793 | NM_001380.1 | 6.48 | 1.04 |
| 219615_s_at | KCNK5 | 8645 | NM_003740.1 | 6.29 | 1.04 |
| 212276_at | LPIN1 | 23175 | D80010.1 | 6.05 | 1.04 |
| 206298_at | RhoGAP2 | 58504 | NM_021226.1 | 5.82 | 1.04 |
| 207533_at | CCL1 | 6346 | NM_002981.1 | 5.69 | 1.04 |
| 206582_s_at | GPR56 | 9289 | NM_005682.1 | 5.41 | 1.04 |
| 208797_s_at | GOLGIN-67 | 23015 | AI829170 | 5.37 | 1.04 |
| 205453_at | HOXB2 | 3212 | NM_002145.1 | 5.12 | 1.04 |
| 212070_at | GPR56 | 9289 | AL554008 | 5.01 | 1.04 |
| 209409_at | GRB10 | 2887 | D86962.1 | 4.99 | 1.04 |
| 210425_x_at | GOLGIN-67 | 23015 | AF164622.1 | 4.97 | 1.04 |
| 208767_s_at | LAPTM4B | 55353 | AW149681 | 4.95 | 1.04 |
| 221942_s_at | GUCY1A3 | 2982 | AI719730 | 4.95 | 1.04 |
| 209193_at | PIM1 | 5292 | M24779.1 | 4.94 | 1.04 |
| 204030_s_at | SCHIP1 | 29970 | NM_014575.1 | 4.89 | 1.04 |
| 213844_at | HOXA5 | 3202 | NM_019102.1 | 4.74 | 1.04 |
| 208798_x_at | GOLGIN-67 | 23015 | AF204231.1 | 4.70 | 1.04 |
| 216268_s_at | JAG1 | 182 | U77914.1 | 4.68 | 1.04 |
| 208792_s_at | CLU | 1191 | M25915.1 | 4.60 | 1.04 |
| 217414_x_at | — | — | V00489 | −4.62 | 1.04 |
| 211699_x_at | HBA1 | 3039 | AF349571.1 | −4.67 | 1.04 |
| 217232_x_at | — | — | AF059180 | −4.71 | 1.04 |
| 209116_x_at | HBB | 3043 | M25079.1 | −4.71 | 1.04 |
| 214414_x_at | HBA1 | 3039 | T50399 | −4.72 | 1.04 |
| 211696_x_at | HBB | 3043 | AF349114.1 | −4.72 | 1.04 |
| 211745_x_at | HBA1 | 3039 | BC005931.1 | −4.75 | 1.04 |
| 204018_x_at | HBA1 | 3039 | NM_000558.2 | −4.83 | 1.04 |
| 208623_s_at | VIL2 | 7430 | J05021.1 | −4.91 | 1.04 |
| 209458_x_at | HBA1 | 3039 | AF105974.1 | −4.96 | 1.04 |
| 214582_at | PDE3B | 5140 | NM_000753.1 | −5.29 | 1.04 |
| 213152_s_at | — | — | AI343248 | −5.39 | 1.04 |
| 206571_s_at | MAP4K4 | 9448 | NM_004834.1 | −6.87 | 1.04 |

TABLE 25

Top 40 genes of cluster #3

| Probe Set ID | Gene symbol | Locus Link number | Accession number | Score SAM | q-value SAM (%) |
|---|---|---|---|---|---|
| 206950_at | SCN9A | 6335 | NM_002977.1 | 10.09 | 0.21 |
| 205848_at | GAS2 | 2620 | NM_005256.1 | 8.63 | 0.21 |
| 207533_at | CCL1 | 6346 | NM_002981.1 | 8.56 | 0.21 |
| 205190_at | PLS1 | 5357 | NM_002670.1 | 7.94 | 0.21 |
| 213110_s_at | COL4A5 | 1287 | AW052179 | 7.51 | 0.21 |
| 208767_s_at | LAPTM4B | 55353 | AW149681 | 7.09 | 0.21 |
| 206298_at | RhoGAP2 | 58504 | NM_021226.1 | 7.07 | 0.21 |
| 208029_s_at | LAPTM4B | 55353 | NM_018407.1 | 7.05 | 0.21 |
| 204044_at | QPRT | 23475 | NM_014298.2 | 7.04 | 0.21 |
| 202889_x_at | ANPEP | 9053 | T62571 | 6.84 | 0.21 |
| 217975_at | LOC51186 | 51186 | NM_016303.1 | 6.81 | 0.21 |
| 201664_at | SMC4L1 | 10051 | AL136877.1 | 6.81 | 0.21 |
| 210116_at | SH2D1A | 4068 | AF072930.1 | 6.74 | 0.21 |
| 213217_at | ADCY2 | 108 | AU149572 | 6.53 | 0.21 |
| 204160_s_at | ENPP4 | 22875 | AW194947 | 6.48 | 0.21 |
| 204341_at | TRIM16 | 10626 | NM_006470.1 | 6.42 | 0.21 |
| 214039_s_at | LAPTM4B | 55353 | T15777 | 6.41 | 0.21 |
| 206582_s_at | GPR56 | 9289 | NM_005682.1 | 6.28 | 0.21 |
| 202890_at | MAP7 | 9053 | T62571 | 6.28 | 0.21 |
| 215471_s_at | MAP7 | 9053 | AJ242502.1 | 6.23 | 0.21 |
| 219602_s_at | FLJ23403 | 63895 | NM_022068.1 | 6.20 | 0.21 |
| 219304_s_at | SCDGF-B | 80310 | NM_025208.1 | 6.05 | 0.21 |
| 203187_at | DOCK1 | 1793 | NM_001380.1 | 6.03 | 0.21 |
| 215388_s_at | HFL1 | 3078 | X56210.1 | 6.00 | 0.21 |
| 201663_s_at | SMC4L1 | 10051 | NM_005496.1 | 6.00 | 0.21 |
| 214228_x_at | TNFRSF4 | 7293 | AJ277151 | 5.96 | 0.21 |
| 201427_s_at | SEPP1 | 6414 | NM_005410.1 | 5.94 | 0.21 |
| 207838_x_at | PBXIP1 | 57326 | NM_020524.1 | 5.92 | 0.21 |
| 201829_at | NET1 | 10276 | AW263232 | 5.85 | 0.21 |
| 220377_at | C14orf110 | 29064 | NM_014151.1 | 5.85 | 0.21 |
| 203973_s_at | KIAA0146 | 23514 | NM_005195.1 | −5.88 | 0.21 |
| 205707_at | IL17R | 23765 | NM_014339.1 | −5.95 | 0.21 |
| 212195_at | IL6ST | 3572 | AL049265.1 | −6.03 | 0.21 |
| 206034_at | SERPINB8 | 5271 | NM_002640.1 | −6.11 | 0.21 |
| 203773_x_at | BLVRA | 644 | NM_000712.1 | −6.71 | 0.21 |
| 221830_at | RAP2A | 5911 | AI302106 | −6.94 | 0.21 |
| 218831_s_at | FCGRT | 2217 | NM_004107.1 | −7.10 | 0.21 |
| 211729_x_at | BLVRA | 644 | BC005902.1 | −7.18 | 0.21 |
| 204500_s_at | AGTPBP1 | 23287 | NM_015239.1 | −8.15 | 0.21 |
| 212543_at | AIM1 | 202 | U83115.1 | −8.19 | 0.21 |

TABLE 26

Top 40 genes of cluster #4

| Probe Set ID | Gene symbol | Locus Link number | Accession number | Score SAM | q-value SAM (%) |
|---|---|---|---|---|---|
| 216286_at | — | — | AV760769 | 13.34 | 0.11 |
| 216191_s_at | TRD@ | 6964 | X72501.1 | 13.01 | 0.11 |
| 206232_s_at | B4GALT6 | 9331 | NM_004775.1 | 12.59 | 0.11 |
| 213830_at | TRD@ | 6964 | AW007751 | 11.85 | 0.11 |
| 211682_x_at | UGT2B28 | 54490 | AF177272.1 | 11.60 | 0.11 |
| 219383_at | FLJ14213 | 79899 | NM_024841.1 | 11.57 | 0.11 |
| 217143_s_at | TRD@ | 6964 | X06557.1 | 11.55 | 0.11 |
| 214551_s_at | CD7 | 924 | NM_006137.2 | 11.22 | 0.11 |
| 214049_x_at | CD7 | 924 | AI829961 | 11.04 | 0.11 |
| 213910_at | IGFBP7 | 3490 | AW770896 | 10.85 | 0.11 |
| 207996_s_at | C18orf1 | 753 | NM_004338.1 | 10.65 | 0.11 |
| 220567_at | ZNFN1A2 | 22807 | NM_016260.1 | 10.27 | 0.11 |
| 209994_s_at | ABCB1 | 5243 | AF016535.1 | 9.90 | 0.11 |
| 206233_at | B4GALT6 | 9331 | AF097159.1 | 9.66 | 0.11 |
| 217147_s_at | TRIM | 50852 | AJ240085.1 | 9.44 | 0.11 |
| 209993_at | ABCB1 | 5243 | AF016535.1 | 9.40 | 0.11 |
| 210448_s_at | P2RX5 | 5026 | U49396.1 | 9.36 | 0.11 |
| 216525_x_at | PMS2L9 | 5387 | D38437.1 | 9.20 | 0.11 |
| 54037_at | HPS4 | 89781 | AL041451 | 9.16 | 0.11 |
| 206726_at | PGDS | 27306 | NM_014485.1 | 8.79 | 0.11 |
| 202242_at | TM4SF2 | 7102 | NM_004615.1 | 8.79 | 0.11 |
| 203987_at | FZD6 | 8323 | NM_003506.1 | 8.63 | 0.11 |

TABLE 26-continued

Top 40 genes of cluster #4

| Probe Set ID | Gene symbol | Locus Link number | Accession number | Score SAM | q-value SAM (%) |
|---|---|---|---|---|---|
| 214757_at | — | — | BG178274 | 8.50 | 0.11 |
| 205884_at | ITGA4 | 3676 | NM_000885.2 | 8.49 | 0.11 |
| 213416_at | ITGA4 | 3676 | BG532690 | 8.37 | 0.11 |
| 218627_at | FLJ11259 | 55332 | NM_018370.1 | −8.51 | 0.11 |
| 208923_at | CYFIP1 | 23191 | BC005097.1 | −8.75 | 0.11 |
| 219371_s_at | KLF2 | 10365 | NM_016270.1 | −8.95 | 0.11 |
| 203233_at | IL4R | 3566 | NM_000418.1 | −8.96 | 0.11 |
| 205382_s_at | DF | 1675 | NM_001928.1 | −8.98 | 0.11 |
| 208683_at | CAPN2 | 824 | M23254.1 | −9.08 | 0.11 |
| 201160_s_at | CSDA | 8531 | AL556190 | −9.13 | 0.11 |
| 201412_at | LRP10 | 26020 | NM_014045.1 | −9.19 | 0.11 |
| 202252_at | RAB13 | 5872 | NM_002870.1 | −9.25 | 0.11 |
| 217800_s_at | NDFIP1 | 80762 | NM_030571.1 | −9.98 | 0.11 |
| 202241_at | C8FW | 10221 | NM_025195.1 | −10.41 | 0.11 |
| 209191_at | TUBB-5 | 84617 | BC002654.1 | −10.60 | 0.11 |
| 200765_x_at | CTNNA1 | 1495 | NM_001903.1 | −14.35 | 0.11 |
| 200764_s_at | CTNNA1 | 1495 | AI826881 | −15.70 | 0.11 |
| 210844_x_at | CTNNA1 | 1495 | D14705.1 | −15.91 | 0.11 |

TABLE 27

Top 40 genes of cluster #5

| Probe Set ID | Gene symbol | Locus Link number | Accession number | Score SAM | q-value SAM (%) |
|---|---|---|---|---|---|
| 206710_s_at | EPB41L3 | 23136 | NM_012307.1 | 21.03 | 0.05 |
| 207872_s_at | LILRB1 | 10859 | NM_006863.1 | 19.91 | 0.05 |
| 211776_s_at | EPB41L3 | 23136 | BC006141.1 | 19.65 | 0.05 |
| 206934_at | SIRPB1 | 10326 | NM_006065.1 | 19.55 | 0.05 |
| 219788_at | PILRA | 29992 | NM_013439.1 | 17.93 | 0.05 |
| 204392_at | CAMK1 | 8536 | NM_003656.2 | 17.41 | 0.05 |
| 219872_at | DKFZp434L142 | 51313 | NM_016613.1 | 17.11 | 0.05 |
| 212681_at | EPB41L3 | 23136 | AI770004 | 17.04 | 0.05 |
| 214590_s_at | UBE2D1 | 7321 | AL545760 | 15.87 | 0.05 |
| 204254_s_at | VDR | 7421 | NM_000376.1 | 15.69 | 0.05 |
| 203767_s_at | STS | 412 | AU138166 | 15.64 | 0.05 |
| 207224_s_at | SIGLEC7 | 27036 | NM_016543.1 | 15.61 | 0.05 |
| 206278_at | PTAFR | 5724 | D10202.1 | 15.55 | 0.05 |
| 204619_s_at | CSPG2 | 1462 | BF590263 | 15.07 | 0.05 |
| 219593_at | PHT2 | 51296 | NM_016582.1 | 15.04 | 0.05 |
| 220832_at | TLR8 | 51311 | NM_016610.1 | 14.94 | 0.05 |
| 210146_x_at | LILRB3 | 11025 | AF004231.1 | 14.91 | 0.05 |
| 222218_s_at | PILRA | 29992 | AJ400843.1 | 14.71 | 0.05 |
| 203768_s_at | STS | 412 | AU138166 | 14.70 | 0.05 |
| 204858_s_at | ECGF1 | 1890 | NM_001953.2 | 14.70 | 0.05 |
| 210660_at | LILRB1 | 10859 | AF025529.1 | 14.70 | 0.05 |
| 211732_x_at | HNMT | 3176 | BC005907.1 | 14.69 | 0.05 |
| 217992_s_at | MGC4342 | 79180 | NM_024329.1 | 14.67 | 0.05 |
| 204487_s_at | KCNQ1 | 3784 | NM_000218.1 | 14.66 | 0.05 |
| 201642_at | IFNGR2 | 3460 | NM_005534.1 | 14.58 | 0.05 |
| 220066_at | CARD15 | 64127 | NM_022162.1 | 14.53 | 0.05 |
| 207104_x_at | LILRB1 | 10859 | NM_006669.1 | 14.46 | 0.05 |
| 205685_at | CD86 | 942 | BG236280 | 14.21 | 0.05 |
| 205686_s_at | CD86 | 942 | NM_006889.1 | 14.15 | 0.05 |
| 203769_s_at | STS | 412 | NM_000351.2 | 14.05 | 0.05 |
| 212334_at | GNS | 2799 | AW167793 | 14.03 | 0.05 |
| 221578_at | RASSF4 | 83937 | AF260335.1 | 14.00 | 0.05 |
| 218559_s_at | MAFB | 9935 | NM_005461.1 | 13.99 | 0.05 |
| 213624_at | ASM3A | 10924 | AA873600 | 13.96 | 0.05 |
| 211135_x_at | LILRB3 | 11025 | AF009644.1 | 13.91 | 0.05 |
| 208594_x_at | LILRB3 | 11025 | NM_024318.1 | 13.90 | 0.05 |
| 200866_s_at | PSAP | 5660 | M32221.1 | 13.89 | 0.05 |
| 205099_s_at | CCR1 | 1230 | NM_001295.1 | 13.87 | 0.05 |
| 202895_s_at | EPHB4 | 140885 | D86043.1 | 13.85 | 0.05 |
| 50221_at | TFEB | 7942 | AI524138 | 13.81 | 0.05 |

TABLE 28

Top 40 genes of cluster #6

| Probe Set ID | Gene symbol | Locus Link number | Accession number | Score SAM | q-value SAM (%) |
|---|---|---|---|---|---|
| 221880_s_at | — | — | AI279819 | 12.39 | 0.85 |
| 51158_at | — | — | AI801973 | 10.99 | 0.85 |
| 219511_s_at | SNCAIP | 9627 | NM_005460.1 | 8.81 | 0.85 |
| 209702_at | FTO | 79068 | U79260.1 | 8.51 | 0.85 |
| 221959_at | MGC39325 | 90362 | AK026141.1 | 8.40 | 0.85 |
| 204984_at | GPC4 | 2239 | NM_001448.1 | 8.34 | 0.85 |
| 204983_s_at | GPC4 | 2239 | AF064826.1 | 8.25 | 0.85 |
| 212019_at | DKFZP564M182 | 26156 | AK025446.1 | 7.56 | 0.85 |
| 215807_s_at | PLXNB1 | 5364 | AV693216 | 7.42 | 0.85 |
| 219602_s_at | FLJ23403 | 63895 | NM_022068.1 | 6.93 | 0.85 |
| 218710_at | FLJ20272 | 55622 | NM_017735.1 | 6.80 | 0.85 |
| 213217_at | ADCY2 | 108 | AU149572 | 6.78 | 0.85 |
| 219651_at | FLJ10713 | 55211 | NM_018189.1 | 6.78 | 0.85 |
| 202728_s_at | LTBP1 | 4052 | AI986120 | 6.64 | 0.85 |
| 206377_at | FOXF2 | 2295 | NM_001452.1 | 6.60 | 0.85 |
| 219932_at | VLCS-H1 | 28965 | NM_014031.1 | 6.31 | 0.85 |
| 213260_at | FOXC1 | 2296 | AU145890 | 6.23 | 0.85 |
| 215623_x_at | SMC4L1 | 10051 | AK002200.1 | 6.19 | 0.85 |
| 201431_s_at | DPYSL3 | 1809 | NM_001387.1 | 6.18 | 0.85 |
| 208414_s_at | HOXB4 | 3214 | NM_002146.1 | 6.17 | 0.85 |
| 218786_at | — | — | NM_016575.1 | 6.16 | 0.85 |
| 204750_s_at | DSC2 | 1824 | BF196457 | 6.16 | 0.85 |
| 219036_at | BITE | 80321 | NM_024491.1 | 6.13 | 0.85 |
| 215388_s_at | HFL1 | 3078 | X56210.1 | 6.12 | 0.85 |
| 220898_at | — | — | NM_024972.1 | 6.08 | 0.85 |
| 215573_at | CAT | 847 | AU147084 | 6.04 | 0.85 |
| 204751_x_at | DSC2 | 1824 | NM_004949.1 | 6.01 | 0.85 |
| 202729_s_at | LTBP1 | 4052 | NM_000627.1 | 5.97 | 0.85 |
| 213266_at | — | — | BF592982 | 5.61 | 0.85 |
| 201641_at | BST2 | 684 | NM_004335.2 | −5.55 | 0.85 |
| 215193_x_at | HLA-DRB1 | 3123 | AJ297586.1 | −5.56 | 0.85 |
| 209619_at | CD74 | 972 | K01144.1 | −5.58 | 0.85 |
| 208982_at | PECAM1 | 5175 | AW574504 | −5.62 | 0.85 |
| 210982_s_at | HLA-DRA | 3122 | M60333.1 | −5.68 | 0.85 |
| 211990_at | HLA-DPA1 | 3113 | M27487.1 | −5.84 | 0.85 |
| 217118_s_at | KIAA0930 | 23313 | AK025608.1 | −5.87 | 0.85 |
| 205672_at | XPA | 7507 | NM_000380.1 | −6.10 | 0.85 |
| 217845_x_at | HIG1 | 25994 | NM_014056.1 | −6.41 | 0.85 |
| 204319_s_at | RGS10 | 6001 | NM_002925.2 | −6.69 | 0.85 |
| 209083_at | CORO1A | 11151 | U34690.1 | −6.97 | 0.85 |

TABLE 29

Top 40 genes of cluster #7

| Probe Set ID | Gene symbol | Locus Link number | Accession number | Score SAM | q-value SAM (%) |
|---|---|---|---|---|---|
| 206116_s_at | TPM1 | 7168 | NM_000366.1 | 15.29 | 0.11 |
| 207854_at | GYPE | 2996 | NM_002102.1 | 13.28 | 0.11 |
| 221577_x_at | PLAB | 9518 | AF003934.1 | 12.76 | 0.11 |
| 56748_at | TRIM10 | 10107 | X90539 | 12.56 | 0.11 |
| 205390_s_at | ANK1 | 286 | NM_000037.2 | 11.78 | 0.11 |
| 204720_s_at | DNAJC6 | 9829 | AV729634 | 11.68 | 0.11 |
| 206146_s_at | RHAG | 6005 | AF178841.1 | 11.40 | 0.11 |
| 216054_x_at | MYL4 | 4635 | X58851 | 11.18 | 0.11 |
| 210088_x_at | MYL4 | 4635 | M36172.1 | 11.16 | 0.11 |
| 205391_x_at | ANK1 | 286 | M28880.1 | 11.09 | 0.11 |
| 207043_s_at | SLC6A9 | 6536 | NM_006934.1 | 11.08 | 0.11 |
| 218864_at | TNS | 7145 | AF116610.1 | 10.98 | 0.11 |
| 203911_at | RAP1GA1 | 5909 | NM_002885.1 | 10.94 | 0.11 |
| 214530_x_at | EPB41 | 2035 | AF156225.1 | 10.93 | 0.11 |
| 206647_at | HBZ | 3050 | NM_005332.2 | 10.90 | 0.11 |
| 211254_x_at | RHAG | 6005 | AF031549.1 | 10.88 | 0.11 |
| 207087_x_at | ANK1 | 286 | NM_020478.1 | 10.84 | 0.11 |
| 208352_x_at | ANK1 | 286 | NM_020479.1 | 10.83 | 0.11 |
| 219630_at | MAP17 | 10158 | NM_005764.1 | 10.71 | 0.11 |
| 208416_s_at | SPTB | 6710 | NM_000347.2 | 10.70 | 0.11 |
| 208353_x_at | ANK1 | 286 | NM_020480.1 | 10.70 | 0.11 |
| 205262_at | KCNH2 | 3757 | NM_000238.1 | 10.67 | 0.11 |
| 210395_x_at | MYL4 | 4635 | AF116676.1 | 10.65 | 0.11 |
| 210586_x_at | RHD | 6007 | AF312679.1 | 10.64 | 0.11 |

TABLE 29-continued

Top 40 genes of cluster #7

| Probe Set ID | Gene symbol | Locus Link number | Accession number | Score SAM | q-value SAM (%) |
|---|---|---|---|---|---|
| 210854_x_at | SLC6A8 | 6535 | U17986.1 | 10.61 | 0.11 |
| 220751_s_at | C5orf4 | 10826 | NM_016348.1 | 10.60 | 0.11 |
| 216063_at | — | — | N55205 | 10.60 | 0.11 |
| 217274_x_at | — | — | X52005.1 | 10.53 | 0.11 |
| 206145_at | RHAG | 6005 | NM_000324.1 | 10.51 | 0.11 |
| 213843_x_at | SLC6A8 | 6535 | AW276522 | 10.48 | 0.11 |
| 206077_at | KEL | 3792 | NM_000420.1 | 10.47 | 0.11 |
| 216925_s_at | TAL1 | 6886 | X51990.1 | 10.42 | 0.11 |
| 221237_s_at | OSBP2 | 23762 | NM_030758.1 | 10.37 | 0.11 |
| 212804_s_at | DKFZP434C212 | 26130 | AK023841.1 | 10.27 | 0.11 |
| 207793_s_at | EPB41 | 2035 | NM_004437.1 | 10.24 | 0.11 |
| 205389_s_at | ANK1 | 286 | AI659683 | 10.21 | 0.11 |
| 201249_at | SLC2A1 | 6513 | NM_006516.1 | 10.20 | 0.11 |
| 214433_s_at | SELENBP1 | 8991 | NM_003944.1 | 10.18 | 0.11 |
| 218978_s_at | MSCP | 51312 | NM_018586.1 | 10.13 | 0.11 |
| 201733_at | CLCN3 | 1182 | NM_001829.1 | 10.12 | 0.11 |

TABLE 30

Top 40 genes of cluster #8

| Probe Set ID | Gene symbol | Locus Link number | Accession number | Score SAM | q-value SAM (%) |
|---|---|---|---|---|---|
| 213338_at | RIS1 | 25907 | BF062629 | 12.86 | 0.17 |
| 201131_s_at | CDH1 | 999 | NM_004360.1 | 12.12 | 0.17 |
| 209735_at | ABCG2 | 9429 | AF098951.2 | 11.01 | 0.17 |
| 202073_at | OPTN | 10133 | AV757675 | 10.88 | 0.17 |
| 40093_at | LU | 4059 | X83425 | 10.45 | 0.17 |
| 212151_at | PBX1 | 5087 | BF967998 | 10.14 | 0.17 |
| 201333_s_at | ARHGEF12 | 23365 | NM_015313.1 | 9.95 | 0.17 |
| 210430_x_at | RHD | 6007 | L08429.1 | 9.72 | 0.17 |
| 205391_x_at | ANK1 | 286 | M28880.1 | 9.53 | 0.17 |
| 221237_s_at | OSBP2 | 23762 | NM_030758.1 | 9.53 | 0.17 |
| 214464_at | CDC42BPA | 8476 | NM_003607.1 | 9.44 | 0.17 |
| 220751_s_at | C5orf4 | 10826 | NM_016348.1 | 9.42 | 0.17 |
| 202364_at | MXI1 | 4601 | NM_005962.1 | 9.29 | 0.17 |
| 205837_s_at | GYPA | 2993 | BC005319.1 | 9.22 | 0.17 |
| 208353_x_at | ANK1 | 286 | NM_020480.1 | 9.20 | 0.17 |
| 202125_s_at | ALS2CR3 | 66008 | NM_015049.1 | 9.10 | 0.17 |
| 217572_at | — | — | AA654586 | 9.06 | 0.17 |
| 211649_x_at | — | — | L14456.1 | 9.04 | 0.17 |
| 205838_at | GYPA | 2993 | NM_002099.2 | 9.04 | 0.17 |
| 202219_at | SLC6A8 | 6535 | NM_005629.1 | 9.03 | 0.17 |
| 216925_s_at | TAL1 | 6886 | X51990.1 | 8.98 | 0.17 |
| 203794_at | CDC42BPA | 8476 | NM_014826.1 | 8.96 | 0.17 |
| 211820_x_at | GYPA | 2993 | U00179.1 | 8.95 | 0.17 |
| 218864_at | TNS | 7145 | AF116610.1 | 8.94 | 0.17 |
| 215812_s_at | — | — | U41163 | 8.90 | 0.17 |
| 202074_s_at | OPTN | 10133 | NM_021980.1 | 8.89 | 0.17 |
| 201886_at | WDR23 | 80344 | NM_025230.1 | 8.86 | 0.17 |
| 216833_x_at | GYPE | 2996 | U05255.1 | 8.84 | 0.17 |
| 202124_s_at | ALS2CR3 | 66008 | AV705253 | 8.84 | 0.17 |
| 216317_x_at | RHCE | 6006 | X63095.1 | 8.81 | 0.17 |
| 204467_s_at | SNCA | 6622 | NM_000345.2 | 8.80 | 0.17 |
| 207087_x_at | ANK1 | 286 | NM_020478.1 | 8.78 | 0.17 |
| 213843_x_at | SLC6A8 | 6535 | AW276522 | 8.78 | 0.17 |
| 210586_x_at | RHD | 6007 | AF312679.1 | 8.77 | 0.17 |
| 209890_at | TM4SF9 | 10098 | AF065389.1 | 8.75 | 0.17 |
| 218853_at | DJ473B4 | 56180 | NM_019556.1 | 8.74 | 0.17 |
| 214433_s_at | SELENBP1 | 8991 | NM_003944.1 | 8.70 | 0.17 |
| 48031_r_at | C5orf4 | 10826 | H93077 | 8.70 | 0.17 |
| 208352_x_at | ANK1 | 286 | NM_020479.1 | 8.69 | 0.17 |
| 203115_at | FECH | 2235 | AU152635 | 8.66 | 0.17 |

TABLE 31

Top 40 genes of cluster #9

| Probe Set ID | Gene symbol | Locus Link number | Accession number | Score SAM | q-value SAM (%) |
|---|---|---|---|---|---|
| 201497_x_at | MYH11 | 4629 | NM_022844.1 | 89.02 | 0.18 |
| 207961_x_at | MYH11 | 4629 | NM_022870.1 | 26.72 | 0.18 |
| 212358_at | CLIPR-59 | 25999 | AL117468.1 | 20.92 | 0.18 |
| 206135_at | ST18 | 9705 | NM_014682.1 | 19.69 | 0.18 |
| 212298_at | NRP1 | 8829 | BE620457 | 18.71 | 0.18 |
| 206682_at | CLECSF13 | 10462 | NM_006344.1 | 15.32 | 0.18 |
| 203060_s_at | PAPSS2 | 9060 | AF074331.1 | 15.04 | 0.18 |
| 203058_s_at | PAPSS2 | 9060 | AW299958 | 14.73 | 0.18 |
| 205987_at | CD1C | 911 | NM_001765.1 | 12.82 | 0.18 |
| 221019_s_at | COLEC12 | 81035 | NM_030781.1 | 12.69 | 0.18 |
| 204885_s_at | MSLN | 10232 | NM_005823.2 | 12.36 | 0.18 |
| 209396_s_at | CHI3L1 | 1116 | M80927.1 | 12.06 | 0.18 |
| 219694_at | FLJ11127 | 54491 | NM_019018.1 | 11.59 | 0.18 |
| 205076_s_at | CRA | 10903 | NM_006697.1 | 11.49 | 0.18 |
| 209395_at | CHI3L1 | 1116 | M80927.1 | 11.07 | 0.18 |
| 219308_s_at | AK5 | 26289 | NM_012093.1 | 10.88 | 0.18 |
| 207194_s_at | ICAM4 | 3386 | NM_001544.2 | 10.76 | 0.18 |
| 204787_at | Z39IG | 11326 | NM_007268.1 | 10.23 | 0.18 |
| 200665_s_at | SPARC | 6678 | NM_003118.1 | 10.18 | 0.18 |
| 201506_at | TGFBI | 7045 | NM_000358.1 | 9.99 | 0.18 |
| 212912_at | RPS6KA2 | 6196 | AI992251 | 9.82 | 0.18 |
| 203939_at | NT5E | 4907 | NM_002526.1 | 9.67 | 0.18 |
| 205330_at | MN1 | 4330 | NM_002430.1 | 9.24 | 0.18 |
| 202481_at | SDR1 | 9249 | NM_004753.1 | 8.92 | 0.18 |
| 212771_at | LOC221061 | 221061 | AU150943 | 8.85 | 0.18 |
| 210889_s_at | FCGR2B | 2213 | M31933.1 | 8.82 | 0.18 |
| 218876_at | CGI-38 | 51673 | NM_016140.1 | 8.45 | 0.18 |
| 203329_at | PTPRM | 5797 | NM_002845.1 | 8.25 | 0.18 |
| 204197_s_at | RUNX3 | 864 | NM_004350.1 | −8.25 | 0.18 |
| 200984_s_at | CD59 | 966 | NM_000611.1 | −8.33 | 0.18 |
| 218414_s_at | NDE1 | 54820 | NM_017668.1 | −8.42 | 0.18 |
| 213779_at | EMU1 | 129080 | AL031186 | −8.56 | 0.18 |
| 204198_s_at | RUNX3 | 864 | AA541630 | −8.85 | 0.18 |
| 211026_s_at | MGLL | 11343 | BC006230.1 | −9.01 | 0.18 |
| 219218_at | FLJ23058 | 79749 | NM_024696.1 | −9.61 | 0.18 |
| 206788_s_at | CBFB | 865 | AF294326.1 | −9.73 | 0.18 |
| 218927_s_at | CHST12 | 55501 | NM_018641.1 | −9.82 | 0.18 |
| 211031_s_at | CYLN2 | 7461 | BC006259.1 | −10.24 | 0.18 |
| 202370_s_at | CBFB | 865 | NM_001755.1 | −13.01 | 0.18 |
| 200675_at | CD81 | 975 | NM_004356.1 | −14.28 | 0.18 |

TABLE 32

Top 40 genes of cluster #10

| Probe Set ID | Gene symbol | Locus Link number | Accession number | Score SAM | q-value SAM (%) |
|---|---|---|---|---|---|
| 219145_at | FLJ11939 | 79732 | NM_024679.1 | 12.59 | 0.21 |
| 202551_s_at | CRIM1 | 51232 | BG546884 | 11.82 | 0.21 |
| 47560_at | FLJ11939 | 79732 | AI525402 | 11.75 | 0.21 |
| 209763_at | NRLN1 | 91851 | AL049176 | 8.99 | 0.21 |
| 200671_s_at | SPTBN1 | 6711 | NM_003128.1 | 8.75 | 0.21 |
| 213488_at | FLJ00133 | 25992 | AL050143.1 | 8.75 | 0.21 |
| 204004_at | — | — | AI336206 | 8.74 | 0.21 |
| 205933_at | SETBP1 | 26040 | NM_015559.1 | 8.63 | 0.21 |
| 213506_at | F2RL1 | 2150 | BE965369 | 8.53 | 0.21 |
| 41577_at | PPP1R16B | 26051 | AB020630 | 8.52 | 0.21 |
| 209679_s_at | LOC57228 | 57228 | BC003379.1 | 8.51 | 0.21 |
| 212558_at | GDAP1L1 | 78997 | BF508662 | 8.43 | 0.21 |
| 207788_s_at | SCAM-1 | 10174 | NM_005775.1 | 8.42 | 0.21 |
| 204083_at | TPM2 | 7169 | NM_003289.1 | 8.21 | 0.21 |
| 209487_at | RBPMS | 11030 | D84109.1 | 8.19 | 0.21 |
| 207836_s_at | RBPMS | 11030 | NM_006867.1 | 8.14 | 0.21 |
| 209282_at | PRKD2 | 25865 | AF309082.1 | 8.14 | 0.21 |
| 209436_at | SPON1 | 10418 | AB018305.1 | 8.12 | 0.21 |
| 204484_at | PIK3C2B | 5287 | NM_002646.1 | 8.11 | 0.21 |
| 212750_at | PPP1R16B | 26051 | AB020630.1 | 8.09 | 0.21 |
| 205330_at | MN1 | 4330 | NM_002430.1 | 8.03 | 0.21 |
| 209576_at | GNAI1 | 2770 | AL049933.1 | 8.02 | 0.21 |
| 220377_at | C14orf110 | 29064 | NM_014151.1 | 7.91 | 0.21 |
| 203756_at | P164RHOGEF | 9828 | NM_014786.1 | 7.89 | 0.21 |
| 200672_x_at | SPTBN1 | 6711 | NM_003128.1 | 7.88 | 0.21 |
| 212827_at | IGHM | 3507 | X17115.1 | 7.86 | 0.21 |
| 209437_s_at | SPON1 | 10418 | AB051390.1 | 7.74 | 0.21 |
| 204917_s_at | MLLT3 | 4300 | AV756536 | 7.59 | 0.21 |
| 204540_at | EEF1A2 | 1917 | NM_001958.1 | 7.57 | 0.21 |
| 208614_s_at | FLNB | 2317 | M62994.1 | 7.40 | 0.21 |
| 204581_at | CD22 | 933 | NM_001771.1 | 7.29 | 0.21 |
| 218086_at | NPDC1 | 56654 | NM_015392.1 | 7.25 | 0.21 |
| 209488_s_at | RBPMS | 11030 | D84109.1 | 7.21 | 0.21 |
| 218899_s_at | BAALC | 79870 | NM_024812.1 | 7.11 | 0.21 |
| 203796_s_at | BCL7A | 605 | AI950380 | 7.05 | 0.21 |
| 212071_s_at | SPTBN1 | 6711 | BE968833 | 6.93 | 0.21 |
| 206111_at | RNASE2 | 6036 | NM_002934.1 | -7.00 | 0.21 |
| 209906_at | C3AR1 | 719 | U62027.1 | -7.34 | 0.21 |
| 205382_s_at | DF | 1675 | NM_001928.1 | -7.63 | 0.21 |
| 214575_s_at | AZU1 | 566 | NM_001700.1 | -7.95 | 0.21 |

TABLE 33

Top 40 genes of cluster #11

| Probe Set ID | Gene symbol | Locus Link number | Accession number | Score SAM | q-value SAM (%) |
|---|---|---|---|---|---|
| 209079_x_at | PCDHGC3 | 5098 | AF152318.1 | -2.72 | 1.48 |
| 207076_s_at | ASS | 445 | NM_000050.1 | -2.74 | 1.48 |
| 218825_at | EGFL7 | 51162 | NM_016215.1 | -2.74 | 1.48 |
| 201522_x_at | SNRPN | 6638 | NM_003097.2 | -2.74 | 1.48 |
| 201601_x_at | IFITM1 | 8519 | NM_003641.1 | -2.75 | 1.48 |
| 206042_x_at | SNRPN | 6638 | NM_022804.1 | -2.80 | 1.48 |
| 209583_s_at | MOX2 | 4345 | AF063591.1 | -2.81 | 1.48 |
| 204385_at | KYNU | 8942 | NM_003937.1 | -2.84 | 1.48 |
| 218805_at | IAN4L1 | 55340 | NM_018384.1 | -2.90 | 1.48 |
| 214953_s_at | APP | 351 | X06989.1 | -2.90 | 1.48 |
| 203859_s_at | PALM | 5064 | NM_002579.1 | -2.97 | 1.48 |
| 203542_s_at | BTEB1 | 687 | BF438302 | -2.97 | 1.48 |
| 212171_x_at | VEGF | 7422 | H95344 | -3.03 | 1.48 |
| 218237_s_at | SLC38A1 | 81539 | NM_030674.1 | -3.05 | 1.48 |
| 219777_at | hIAN2 | 79765 | NM_024711.1 | -3.07 | 1.48 |
| 201656_at | ITGA6 | 3655 | NM_000210.1 | -3.13 | 1.48 |
| 208886_at | H1F0 | 3005 | BC000145.1 | -3.17 | 1.48 |
| 203139_at | DAPK1 | 1612 | NM_004938.1 | -3.18 | 1.48 |
| 31874_at | GAS2L1 | 10634 | Y07846 | -3.21 | 1.48 |
| 218966_at | MYO5C | 55930 | NM_018728.1 | -3.22 | 1.48 |
| 216033_s_at | FYN | 2534 | S74774.1 | -3.23 | 1.48 |
| 218589_at | P2RY5 | 10161 | NM_005767.1 | -3.24 | 1.48 |
| 217838_s_at | EVL | 51466 | NM_016337.1 | -3.25 | 1.48 |
| 201279_s_at | DAB2 | 1601 | BC003064.1 | -3.26 | 1.48 |
| 200762_at | DPYSL2 | 1808 | NM_001386.1 | -3.29 | 1.48 |
| 209723_at | SERPINB9 | 5272 | BC002538.1 | -3.34 | 1.48 |
| 205101_at | MHC2TA | 4261 | NM_000246.1 | -3.37 | 1.48 |
| 208873_s_at | DP1 | 7905 | BC000232.1 | -3.43 | 1.48 |
| 211675_s_at | HIC | 29969 | AF054589.1 | -3.49 | 1.48 |
| 200665_s_at | SPARC | 6678 | NM_003118.1 | -3.50 | 1.48 |
| 213848_at | DUSP7 | 1849 | AI655015 | -3.54 | 1.48 |
| 215116_s_at | DNM1 | 1759 | AF035321.1 | -3.56 | 1.48 |
| 203217_s_at | SIAT9 | 8869 | NM_003896.1 | -3.56 | 1.48 |
| 209543_s_at | CD34 | 947 | M81104.1 | -3.57 | 1.48 |
| 201425_at | ALDH2 | 217 | NM_000690.1 | -3.63 | 1.48 |
| 201559_s_at | CLIC4 | 25932 | AF109196.1 | -4.00 | 1.48 |
| 221223_x_at | CISH | 1154 | NM_013324.2 | -4.36 | 1.48 |
| 212658_at | LHFPL2 | 10184 | N66633 | -4.43 | 1.48 |
| 204401_at | KCNN4 | 3783 | NM_002250.1 | -4.70 | 1.48 |
| 201560_at | CLIC4 | 25932 | NM_013943.1 | -4.95 | 1.48 |

TABLE 34

Top 40 genes of cluster #12

| Probe Set ID | Gene symbol | Locus Link number | Accession number | Score SAM | q-value SAM (%) |
|---|---|---|---|---|---|
| 210997_at | HGF | 3082 | M77227.1 | 25.95 | 0.13 |
| 210998_s_at | HGF | 3082 | M77227.1 | 24.77 | 0.13 |
| 205110_s_at | FGF13 | 2258 | NM_004114.1 | 24.76 | 0.13 |
| 210794_s_at | MEG3 | 55384 | AF119863.1 | 23.54 | 0.13 |
| 204537_s_at | GABRE | 2564 | NM_004961.2 | 22.89 | 0.13 |
| 205614_x_at | MST1 | 4485 | NM_020998.1 | 20.74 | 0.13 |
| 205663_at | PCBP3 | 54039 | NM_020528.1 | 20.42 | 0.13 |
| 202260_s_at | STXBP1 | 6812 | NM_003165.1 | 19.36 | 0.13 |
| 216320_x_at | MST1 | 4485 | U37055 | 18.72 | 0.13 |
| 203074_at | ANXA8 | 244 | NM_001630.1 | 18.42 | 0.13 |
| 206634_at | SIX3 | 6496 | NM_005413.1 | 16.41 | 0.13 |
| 210755_at | HGF | 3082 | U46010.1 | 16.11 | 0.13 |
| 203397_s_at | GALNT3 | 2591 | BF063271 | 15.29 | 0.13 |
| 212732_at | MEG3 | 55384 | AI950273 | 15.24 | 0.13 |
| 207895_at | NAALADASEL | 10004 | NM_005468.1 | 14.64 | 0.13 |
| 218043_s_at | AZ2 | 64343 | NM_022461.1 | 14.17 | 0.13 |
| 209961_s_at | HGF | 3082 | M60718.1 | 13.51 | 0.13 |
| 209815_at | na | 349352 | U43148.1 | 12.71 | 0.13 |

TABLE 34-continued

Top 40 genes of cluster #12

| Probe Set ID | Gene symbol | Locus Link number | Accession number | Score SAM | q-value SAM (%) |
|---|---|---|---|---|---|
| 201276_at | RAB5B | 5869 | AF267863.1 | 12.44 | 0.13 |
| 212509_s_at | — | — | BF968134 | 12.27 | 0.13 |
| 207650_x_at | PTGER1 | 5731 | NM_000955.1 | 11.92 | 0.13 |
| 209960_at | HGF | 3082 | X16323.1 | 11.88 | 0.13 |
| 200770_s_at | LAMC1 | 3915 | J03202.1 | 11.57 | 0.13 |
| 212204_at | DKFZP564G2022 | 25963 | AF132733.1 | 11.55 | 0.13 |
| 207031_at | BAPX1 | 579 | NM_001189.1 | 11.44 | 0.13 |
| 211663_x_at | PTGDS | 5730 | M61900.1 | 11.33 | 0.13 |
| 206105_at | FMR2 | 2334 | NM_002025.1 | 11.28 | 0.13 |
| 214203_s_at | PRODH | 5625 | AA074145 | 11.27 | 0.13 |
| 200654_at | P4HB | 5034 | J02783.1 | 11.24 | 0.13 |
| 200656_s_at | P4HB | 5034 | NM_000918.1 | 11.23 | 0.13 |
| 210140_at | CST7 | 8530 | AF031824.1 | 11.16 | 0.13 |
| 200935_at | CALR | 811 | NM_004343.2 | 11.12 | 0.13 |
| 204153_s_at | MFNG | 4242 | NM_002405.1 | −11.33 | 0.13 |
| 202599_s_at | NRIP1 | 8204 | NM_003489.1 | −11.33 | 0.13 |
| 200931_s_at | VCL | 7414 | NM_014000.1 | −11.57 | 0.13 |
| 204362_at | SCAP2 | 8935 | NM_003930.1 | −11.76 | 0.13 |
| 202600_s_at | NRIP1 | 8204 | AI824012 | −11.86 | 0.13 |
| 204152_s_at | MFNG | 4242 | AI738965 | −12.02 | 0.13 |
| 203236_s_at | LGALS9 | 3965 | NM_009587.1 | −18.14 | 0.13 |
| 204425_at | ARHGAP4 | 393 | NM_001666.1 | −21.49 | 0.13 |

TABLE 35

Top 40 genes of cluster #13

| Probe Set ID | Gene symbol | Locus Link number | Accession number | Score SAM | q-value SAM (%) |
|---|---|---|---|---|---|
| 205529_s_at | CBFA2T1 (ETO) | 862 | NM_004349.1 | 60.36 | 0.14 |
| 205528_s_at | CBFA2T1 (ETO) | 862 | X79990.1 | 56.08 | 0.14 |
| 216831_s_at | CBFA2T1 (ETO) | 862 | AF018283.1 | 26.62 | 0.14 |
| 213194_at | ROBO1 | 6091 | BF059159 | 24.74 | 0.14 |
| 204811_s_at | CACNA2D2 | 9254 | NM_006030.1 | 23.53 | 0.14 |
| 206940_s_at | POU4F1 | 5457 | NM_006237.1 | 21.42 | 0.14 |
| 210744_s_at | IL5RA | 3568 | M75914.1 | 21.09 | 0.14 |
| 211517_s_at | IL5RA | 3568 | M96651.1 | 20.92 | 0.14 |
| 211341_at | POU4F1 | 5457 | L20433.1 | 20.66 | 0.14 |
| 204990_s_at | ITGB4 | 3691 | NM_000213.1 | 20.55 | 0.14 |
| 212097_at | CAV1 | 857 | AU147399 | 20.47 | 0.14 |
| 216832_at | CBFA2T1 | 862 | AF018283.1 | 17.51 | 0.14 |
| 206128_at | ADRA2C | 152 | AI264306 | 16.87 | 0.14 |
| 204874_x_at | BAIAP3 | 8938 | NM_003933.2 | 16.41 | 0.14 |
| 203065_s_at | CAV1 | 857 | NM_001753.2 | 16.07 | 0.14 |
| 212496_s_at | KIAA0876 | 23030 | AW237172 | 15.75 | 0.14 |
| 212492_s_at | KIAA0876 | 23030 | AW237172 | 15.66 | 0.14 |
| 218613_at | DKFZp761K1423 | 55358 | NM_018422.1 | 14.20 | 0.14 |
| 206622_at | TRH | 7200 | NM_007117.1 | 13.63 | 0.14 |
| 216356_x_at | BAIAP3 | 8938 | AB018277.1 | 13.48 | 0.14 |
| 201621_at | NBL1 | 4681 | NM_005380.1 | 13.45 | 0.14 |
| 213894_at | LOC221981 | 221981 | BF447246 | 13.05 | 0.14 |
| 203088_at | FBLN5 | 10516 | NM_006329.1 | 12.93 | 0.14 |
| 204396_s_at | GPRK5 | 2869 | NM_005308.1 | 12.66 | 0.14 |
| 201655_s_at | HSPG2 | 3339 | M85289.1 | 12.62 | 0.14 |
| 218742_at | HPRN | 64428 | NM_022493.1 | 12.59 | 0.14 |
| 214920_at | LOC221981 | 221981 | R33964 | 12.55 | 0.14 |
| 219686_at | HSA250839 | 55351 | NM_018401.1 | 12.44 | 0.14 |
| 204073_s_at | C11orf9 | 745 | NM_013279.1 | 12.35 | 0.14 |
| 209822_s_at | VLDLR | 7436 | L22431.1 | 12.29 | 0.14 |
| 206793_at | PNMT | 5409 | NM_002686.1 | 12.27 | 0.14 |
| 211685_s_at | NCALD | 83988 | AF251061.1 | 12.16 | 0.14 |
| 214946_x_at | FLJ10824 | 55747 | AV728658 | 12.03 | 0.14 |
| 210010_s_at | SLC25A1 | 6576 | U25147.1 | 11.84 | 0.14 |
| 203741_s_at | ADCY7 | 113 | NM_001114.1 | −11.89 | 0.14 |
| 208885_at | LCP1 | 3936 | J02923.1 | −12.03 | 0.14 |
| 204494_s_at | LOC56905 | 56905 | AW516789 | −12.21 | 0.14 |
| 208091_s_at | DKFZP564K0822 | 81552 | NM_030796.1 | −13.52 | 0.14 |
| 220560_at | C11orf21 | 29125 | NM_014144.1 | −14.30 | 0.14 |
| 221581_s_at | WBSCR5 | 7462 | AF257135.1 | −17.67 | 0.14 |

Table 36: Top40 genes of cluster #14
(No significant genes identified.)

TABLE 37

Top 40 genes of cluster #15

| Probe Set ID | Gene symbol | Locus Link number | Accession number | Score SAM | q-value SAM (%) |
|---|---|---|---|---|---|
| 206676_at | CEACAM8 | 1088 | M33326.1 | 7.20 | 1.66 |
| 204661_at | CDW52 | 1043 | NM_001803.1 | −3.44 | 1.07 |
| 211182_x_at | RUNX1 | 861 | AF312387.1 | −3.46 | 1.07 |
| 212827_at | IGHM | 3507 | X17115.1 | −3.47 | 1.07 |
| 203542_s_at | BTEB1 | 687 | BF438302 | −3.49 | 1.07 |
| 214835_s_at | SUCLG2 | 8801 | AF131748.1 | −3.51 | 1.07 |
| 209905_at | HOXA9 | 3205 | AI246769 | −3.56 | 1.07 |
| 201867_s_at | TBL1X | 6907 | NM_005647.1 | −3.59 | 1.07 |
| 204069_at | MEIS1 | 4211 | NM_002398.1 | −3.61 | 1.07 |
| 205600_x_at | HOXB5 | 3215 | AI052747 | −3.62 | 1.07 |
| 208962_s_at | FADS1 | 3992 | BE540552 | −3.63 | 1.07 |
| 205453_at | HOXB2 | 3212 | NM_002145.1 | −3.69 | 1.07 |
| 219256_s_at | FLJ20356 | 54436 | NM_018986.1 | −3.74 | 1.07 |
| 218627_at | FLJ11259 | 55332 | NM_018370.1 | −3.76 | 1.07 |
| 201719_s_at | EPB41L2 | 2037 | NM_001431.1 | −3.77 | 1.07 |
| 213150_at | HOXA10 | 3206 | NM_018951.1 | −3.77 | 1.07 |
| 209374_s_at | IGHM | 3507 | BC001872.1 | −3.89 | 1.07 |
| 210365_at | RUNX1 | 861 | D43967.1 | −3.90 | 1.07 |
| 214651_s_at | HOXA9 | 3205 | U41813.1 | −3.92 | 1.07 |
| 218552_at | FLJ10948 | 55268 | NM_018281.1 | −3.94 | 1.07 |
| 212906_at | na | 283158 | BE044440 | −3.97 | 1.07 |
| 213147_at | HOXA10 | 3206 | NM_018951.1 | −3.98 | 1.07 |
| 213400_s_at | TBL1X | 6907 | AV753028 | −4.01 | 1.07 |
| 200765_x_at | CTNNA1 | 1495 | NM_001903.1 | −4.02 | 1.07 |
| 202391_at | BASP1 | 10409 | NM_006317.1 | −4.07 | 1.07 |
| 217226_at | PMX1 | 5396 | M95929.1 | −4.09 | 1.07 |
| 217800_s_at | NDFIP1 | 80762 | NM_030571.1 | −4.26 | 1.07 |
| 201841_s_at | HSPB1 | 3315 | NM_001540.2 | −4.34 | 1.07 |
| 202236_s_at | SLC16A1 | 6566 | NM_003051.1 | −4.34 | 1.07 |
| 212314_at | KIAA0746 | 23231 | AB018289.1 | −4.43 | 1.07 |
| 215772_x_at | SUCLG2 | 8801 | AL050226.1 | −4.44 | 1.07 |
| 218847_at | IMP-2 | 10644 | NM_006548.1 | −4.46 | 1.07 |
| 212311_at | KIAA0746 | 23231 | AB018289.1 | −4.56 | 1.07 |
| 212459_x_at | SUCLG2 | 8801 | BF593940 | −4.63 | 1.07 |
| 209191_at | TUBB-5 | 84617 | BC002654.1 | −4.63 | 1.07 |
| 220974_x_at | BA108L7.2 | 81855 | NM_030971.1 | −4.75 | 1.07 |
| 217853_at | TEM6 | 64759 | NM_022748.1 | −5.09 | 1.07 |
| 218501_at | ARHGEF3 | 50650 | NM_019555.1 | −5.11 | 1.07 |
| 40489_at | DRPLA | 1822 | D31840 | −5.57 | 1.07 |
| 221737_at | GNA12 | 2768 | NM_007353.1 | −5.84 | 1.07 |

TABLE 38

Top 40 genes of cluster #16

| Probe Set ID | Gene symbol | Locus Link number | Accession number | Score SAM | q-value SAM (%) |
|---|---|---|---|---|---|
| 220057_at | GAGED2 | 9503 | NM_020411.1 | 22.48 | 0.27 |
| 219360_s_at | TRPM4 | 54795 | NM_017636.1 | 21.22 | 0.27 |
| 219414_at | CLSTN2 | 64084 | NM_022131.1 | 16.98 | 0.27 |
| 220116_at | KCNN2 | 3781 | NM_021614.1 | 16.31 | 0.27 |
| 216370_s_at | TKTL1 | 8277 | Z49258 | 15.76 | 0.27 |
| 205550_s_at | BRE | 9577 | NM_004899.1 | 15.55 | 0.27 |
| 211566_x_at | BRE | 9577 | U19178.1 | 15.11 | 0.27 |
| 214183_s_at | TKTL1 | 8277 | X91817.1 | 14.70 | 0.27 |
| 209031_at | IGSF4 | 23705 | NM_014333.1 | 13.62 | 0.27 |
| 212645_x_at | BRE | 9577 | AL566299 | 13.32 | 0.27 |
| 209030_s_at | IGSF4 | 23705 | NM_014333.1 | 13.30 | 0.27 |
| 213791_at | PENK | 5179 | NM_006211.1 | 13.25 | 0.27 |
| 206508_at | TNFSF7 | 970 | NM_001252.1 | 12.46 | 0.27 |
| 219506_at | FLJ23221 | 79630 | NM_024579.1 | 12.31 | 0.27 |
| 211421_s_at | RET | 5979 | M31213.1 | 12.03 | 0.27 |
| 203241_at | UVRAG | 7405 | NM_003369.1 | 11.99 | 0.27 |
| 213908_at | LOC339005 | 339005 | AI824078 | 11.94 | 0.27 |
| 207911_s_at | TGM5 | 9333 | NM_004245.1 | 11.78 | 0.27 |
| 214190_s_at | GGA2 | 23062 | AI799984 | 11.49 | 0.27 |
| 204561_x_at | APOC2 | 344 | NM_000483.2 | 11.38 | 0.27 |
| 209663_s_at | ITGA7 | 3679 | AF072132.1 | 11.27 | 0.27 |
| 214259_s_at | AKR7A2 | 8574 | AW074911 | 11.14 | 0.27 |
| 205472_s_at | DACH | 1602 | NM_004392.1 | 10.91 | 0.27 |
| 216331_at | ITGA7 | 3679 | AK022548.1 | 10.89 | 0.27 |
| 220010_at | KCNE1L | 23630 | NM_012282.1 | 10.78 | 0.27 |
| 213484_at | na | 151521 | AI097640 | 10.73 | 0.27 |
| 204497_at | ADCY9 | 115 | AB011092.1 | 10.48 | 0.27 |
| 215771_x_at | RET | 5979 | X15786.1 | 10.33 | 0.27 |
| 209032_s_at | IGSF4 | 23705 | AF132811.1 | 10.32 | 0.27 |
| 219714_s_at | CACNA2D3 | 55799 | NM_018398.1 | 10.21 | 0.27 |
| 219463_at | C20orf103 | 24141 | NM_012261.1 | 10.21 | 0.27 |
| 202139_at | AKR7A2 | 8574 | NM_003689.1 | 9.87 | 0.27 |
| 219143_s_at | FLJ20374 | 54913 | NM_017793.1 | 9.66 | 0.27 |
| 205996_s_at | AK2 | 204 | NM_013411.1 | 9.60 | 0.27 |
| 219288_at | HT021 | 57415 | NM_020685.1 | 9.57 | 0.27 |
| 215663_at | MBNL1 | 4154 | BC005296.1 | 9.42 | 0.27 |
| 213361_at | PCTAIRE2BP | 23424 | AW129593 | 9.23 | 0.27 |
| 210658_s_at | GGA2 | 23062 | BC000284.1 | 8.73 | 0.27 |
| 213772_s_at | GGA2 | 23062 | BF196572 | 8.59 | 0.27 |
| 212174_at | AK2 | 204 | AK023758.1 | 8.59 | 0.27 |

TABLE 39

PAM genes of prognostically important clusters (#13, #12, #9, #16, #10, #4, #15, #4 and #15, and FLT3ITD)

| Probe Set ID | Gene symbol | Locus Link number | Accession number | Abnormality |
|---|---|---|---|---|
| 205529_s_at | CBFA2T1 (ETO) | 862 | NM_004349.1 | AML and t (8; 21) |
| 205528_s_at | CBFA2T1 (ETO) | 862 | X79990.1 | AML and t (8; 21) |
| 213194_at | ROBO1 | 6091 | BF059159 | AML and t (8; 21) |
| 210997_at | HGF | 3082 | M77227.1 | AML and t (15; 17) |
| 210998_s_at | HGF | 3082 | M77227.1 | AML and t (15; 17) |
| 205110_s_at | FGF13 | 2258 | NM_004114.1 | AML and t (15; 17) |
| 201497_x_at | MYH11 | 4629 | NM_022844.1 | AML and inv (16) |
| 214183_s_at | TKTL1 | 8277 | X91817.1 | 11q23 (cluster 16) |
| 216370_s_at | TKTL1 | 8277 | Z49258 | 11q23 (cluster 16) |
| 220057_at | GAGED2 | 9503 | NM_020411.1 | 11q23 (cluster 16) |
| 209031_at | IGSF4 | 23705 | NM_014333.1 | 11q23 (cluster 16) |
| 209030_s_at | IGSF4 | 23705 | NM_014333.1 | 11q23 (cluster 16) |
| 219360_s_at | TRPM4 | 54795 | NM_017636.1 | 11q23 (cluster 16) |
| 216331_at | ITGA7 | 3679 | AK022548.1 | 11q23 (cluster 16) |

TABLE 39-continued

PAM genes of prognostically important clusters (#13, #12, #9, #16, #10, #4, #15, #4 and #15, and FLT3ITD)

| Probe Set ID | Gene symbol | Locus Link number | Accession number | Abnormality |
|---|---|---|---|---|
| 206508_at | TNFSF7 | 970 | NM_001252.1 | 11q23 (cluster 16) |
| 204561_x_at | APOC2 | 344 | NM_000483.2 | 11q23 (cluster 16) |
| 200989_at | HIF1A | 3091 | NM_001530.1 | 11q23 (cluster 16) |
| 219506_at | FLJ23221 | 79630 | NM_024579.1 | 11q23 (cluster 16) |
| 213791_at | PENK | 5179 | NM_006211.1 | 11q23 (cluster 16) |
| 205472_s_at | DACH | 1602 | NM_004392.1 | 11q23 (cluster 16) |
| 209629_s_at | NXT2 | 55916 | AF201942.1 | 11q23 (cluster 16) |
| 219288_at | HT021 | 57415 | NM_020685.1 | 11q23 (cluster 16) |
| 205471_s_at | DACH | 1602 | AW772082 | 11q23 (cluster 16) |
| 219463_at | C20orf103 | 24141 | NM_012261.1 | 11q23 (cluster 16) |
| 209628_at | NXT2 | 55916 | AK023289.1 | 11q23 (cluster 16) |
| 215571_at | — | — | AK021495.1 | 11q23 (cluster 16) |
| 209663_s_at | ITGA7 | 3679 | AF072132.1 | 11q23 (cluster 16) |
| 220010_at | KCNE1L | 23630 | NM_012282.1 | 11q23 (cluster 16) |
| 204885_s_at | MSLN | 10232 | NM_005823.2 | 11q23 (cluster 16) |
| 207911_s_at | TGM5 | 9333 | NM_004245.1 | 11q23 (cluster 16) |
| 209032_s_at | IGSF4 | 23705 | AF132811.1 | 11q23 (cluster 16) |
| 206277_at | P2RY2 | 5029 | NM_002564.1 | 11q23 (cluster 16) |
| 211421_s_at | RET | 5979 | M31213.1 | 11q23 (cluster 16) |
| 203241_at | UVRAG | 7405 | NM_003369.1 | 11q23 (cluster 16) |
| 209616_s_at | CES1 | 1066 | S73751.1 | 11q23 (cluster 16) |
| 219714_s_at | CACNA2D3 | 55799 | NM_018398.1 | 11q23 (cluster 16) |
| 213908_at | LOC339005 | 339005 | AI824078 | 11q23 (cluster 16) |
| 217520_x_at | na | 219392 | BG396614 | 11q23 (cluster 16) |
| 202551_s_at | CRIM1 | 51232 | BG546884 | EVI (cluster 10) |
| 213506_at | F2RL1 | 2150 | BE965369 | EVI (cluster 10) |
| 206111_at | RNASE2 | 6036 | NM_002934.1 | EVI (cluster 10) |
| 214575_s_at | AZU1 | 566 | NM_001700.1 | EVI (cluster 10) |
| 209679_s_at | LOC57228 | 57228 | BC003379.1 | EVI (cluster 10) |
| 41577_at | PPP1R16B | 26051 | AB020630 | EVI (cluster 10) |
| 212750_at | PPP1R16B | 26051 | AB020630.1 | EVI (cluster 10) |
| 204540_at | EEF1A2 | 1917 | NM_001958.1 | EVI (cluster 10) |
| 205330_at | MN1 | 4330 | NM_002430.1 | EVI (cluster 10) |
| 200671_s_at | SPTBN1 | 6711 | NM_003128.1 | EVI (cluster 10) |
| 207788_s_at | SCAM-1 | 10174 | NM_005775.1 | EVI (cluster 10) |
| 209576_at | GNAI1 | 2770 | AL049933.1 | EVI (cluster 10) |
| 218086_at | NPDC1 | 56654 | NM_015392.1 | EVI (cluster 10) |
| 204484_at | PIK3C2B | 5287 | NM_002646.1 | EVI (cluster 10) |
| 219145_at | FLJ11939 | 79732 | NM_024679.1 | EVI (cluster 10) |
| 212820_at | RC3 | 23312 | AB020663.1 | EVI (cluster 10) |
| 204004_at | — | — | AI336206 | EVI (cluster 10) |
| 209487_at | RBPMS | 11030 | D84109.1 | EVI (cluster 10) |
| 209543_s_at | CD34 | 947 | M81104.1 | EVI (cluster 10) |
| 205382_s_at | DF | 1675 | NM_001928.1 | EVI (cluster 10) |
| 47560_at | FLJ11939 | 79732 | AI525402 | EVI (cluster 10) |
| 212827_at | IGHM | 3507 | X17115.1 | EVI (cluster 10) |
| 217977_at | SEPX1 | 51734 | NM_016332.1 | EVI (cluster 10) |
| 212558_at | GDAP1L1 | 78997 | BF508662 | EVI (cluster 10) |
| 206429_at | F2RL1 | 2150 | NM_005242.2 | EVI (cluster 10) |
| 220377_at | C14orf110 | 29064 | NM_014151.1 | EVI (cluster 10) |
| 206851_at | RNASE3 | 6037 | NM_002935.1 | EVI (cluster 10) |
| 212012_at | D2S448 | 7837 | AF200348.1 | EVI (cluster 10) |
| 210844_x_at | CTNNA1 | 1495 | D14705.1 | cEBPalpha (cluster4) |
| 200765_x_at | CTNNA1 | 1495 | NM_001903.1 | cEBPalpha (cluster4) |
| 200764_s_at | CTNNA1 | 1495 | AI826881 | cEBPalpha (cluster4) |
| 214551_s_at | CD7 | 924 | NM_006137.2 | cEBPalpha (cluster4) |
| 214049_x_at | CD7 | 924 | AI829761 | cEBPalpha (cluster4) |
| 216191_s_at | TRD@ | 6964 | X72501.1 | cEBPalpha (cluster4) |
| 217143_s_at | TRD@ | 6964 | X06557.1 | cEBPalpha (cluster4) |
| 216286_at | — | — | AV760769 | cEBPalpha (cluster4) |
| 206232_s_at | B4GALT6 | 9331 | NM_004775.1 | cEBPalpha (cluster4) |
| 202241_at | C8FW | 10221 | NM_025195.1 | cEBPalpha (cluster4) |
| 219383_at | FLJ14213 | 79899 | NM_024841.1 | cEBPalpha (cluster4) |
| 209191_at | TUBB-5 | 84617 | BC002654.1 | cEBPalpha (cluster4) |
| 213830_at | TRD@ | 6964 | AW007751 | cEBPalpha (cluster4) |
| 206676_at | CEACAM8 | 1088 | M33326.1 | cEBPalpha (cluster15) |
| 210244_at | CAMP | 820 | U19970.1 | cEBPalpha (cluster15) |
| 202018_s_at | LTF | 4057 | NM_002343.1 | cEBPalpha (cluster15) |
| 217853_at | TEM6 | 64759 | NM_022748.1 | cEBPalpha (cluster15) |
| 204417_at | GALC | 2581 | NM_000153.1 | cEBPalpha (cluster15) |
| 204039_at | CEBPA | 1050 | NM_004364.1 | cEBPalpha (cluster15) |
| 211810_s_at | GALC | 2581 | D25284.1 | cEBPalpha (cluster15) |
| 210762_s_at | DLC1 | 10395 | AF026219.1 | cEBPalpha (cluster15) |
| 217800_s_at | NDFIP1 | 80762 | NM_030571.1 | cEBPalpha (cluster15) |

TABLE 39-continued

PAM genes of prognostically important clusters (#13, #12, #9, #16, #10, #4, #15, #4 and #15, and FLT3ITD)

| Probe Set ID | Gene symbol | Locus Link number | Accession number | Abnormality |
|---|---|---|---|---|
| 206726_at | PGDS | 27306 | NM_014485.1 | cEBPalpha (cluster15) |
| 202236_s_at | SLC16A1 | 6566 | NM_003051.1 | cEBPalpha (cluster15) |
| 202016_at | MEST | 4232 | NM_002402.1 | cEBPalpha (cluster15) |
| 212531_at | LCN2 | 3934 | NM_005564.1 | cEBPalpha (cluster15) |
| 218847_at | IMP-2 | 10644 | NM_006548.1 | cEBPalpha (cluster15) |
| 205692_s_at | CD38 | 952 | NM_001775.1 | cEBPalpha (cluster15) |
| 212459_x_at | SUCLG2 | 8801 | BF593940 | cEBPalpha (cluster15) |
| 201841_s_at | HSPB1 | 3315 | NM_001540.2 | cEBPalpha (cluster15) |
| 207329_at | MMP8 | 4317 | NM_002424.1 | cEBPalpha (cluster15) |
| 220974_x_at | BA108L7.2 | 81855 | NM_030971.1 | cEBPalpha (cluster15) |
| 207384_at | PGLYRP | 8993 | NM_005091.1 | cEBPalpha (cluster15) |
| 209191_at | TUBB-5 | 84617 | BC002654.1 | cEBPalpha (cluster15) |
| 202391_at | BASP1 | 10409 | NM_006317.1 | cEBPalpha (cluster15) |
| 215772_x_at | SUCLG2 | 8801 | AL050226.1 | cEBPalpha (cluster15) |
| 212314_at | KIAA0746 | 23231 | AB018289.1 | cEBPalpha (cluster15) |
| 221737_at | GNA12 | 2768 | NM_007353.1 | cEBPalpha (cluster15) |
| 214651_s_at | HOXA9 | 3205 | U41813.1 | cEBPalpha (cluster15) |
| 218501_at | ARHGEF3 | 50650 | NM_019555.1 | cEBPalpha (cluster15) |
| 202747_s_at | ITM2A | 9452 | NM_004867.1 | cEBPalpha (cluster15) |
| 213400_s_at | TBL1X | 6907 | AV753028 | cEBPalpha (cluster15) |
| 214049_x_at | CD7 | 924 | AI829961 | cEBPalpha (cluster15) |
| 209374_s_at | IGHM | 3507 | BC001872.1 | cEBPalpha (cluster15) |
| 212311_at | KIAA0746 | 23231 | AB018289.1 | cEBPalpha (cluster15) |
| 40489_at | DRPLA | 1822 | D31840 | cEBPalpha (cluster15) |
| 205453_at | HOXB2 | 3212 | NM_002145.1 | cEBPalpha (cluster15) |
| 214551_s_at | CD7 | 924 | NM_006137.2 | cEBPalpha (cluster15) |
| 206660_at | IGLL1 | 3543 | NM_020070.1 | cEBPalpha (cluster15) |
| 210844_x_at | CTNNA1 | 1495 | D14705.1 | CEBPalpha (cluster4 and 15) |
| 200765_x_at | CTNNA1 | 1495 | NM_001903.1 | CEBPalpha (cluster4 and 15) |
| 200764_s_at | CTNNA1 | 1495 | AI826881 | CEBPalpha (cluster4 and 15) |
| 214551_s_at | CD7 | 924 | NM_006137.2 | CEBPalpha (cluster4 and 15) |
| 214049_x_at | CD7 | 924 | AI829961 | CEBPalpha (cluster4 and 15) |
| 209191_at | TUBB-5 | 84617 | BC002654.1 | CEBPalpha (cluster4 and 15) |
| 217800_s_at | NDFIP1 | 80762 | NM_030571.1 | CEBPalpha (cluster4 and 15) |
| 217143_s_at | TRD@ | 6964 | X06557.1 | CEBPalpha (cluster4 and 15) |
| 216191_s_at | TRD@ | 6964 | X72501.1 | CEBPalpha (cluster4 and 15) |
| 219615_s_at | KCNK5 | 8645 | NM_003740.1 | FLT3 ITD |
| 204341_at | TRIM16 | 10626 | NM_006470.1 | FLT3 ITD |
| 201664_at | SMC4L1 | 10051 | AL136877.1 | FLT3 ITD |
| 201663_at | SMC4L1 | 10051 | NM_005496.1 | FLT3 ITD |
| 213110_s_at | COL4A5 | 1287 | AW052179 | FLT3 ITD |
| 213844_at | HOXA5 | 3202 | NM_019102.1 | FLT3 ITD |
| 204082_at | PBX3 | 5090 | NM_006195.1 | FLT3 ITD |
| 203151_at | MAP1A | 4130 | AW296788 | FLT3 ITD |
| 211269_s_at | IL2RA | 3559 | K03122.1 | FLT3 ITD |
| 203708_at | PDE4B | 5142 | NM_002600.1 | FLT3 ITD |
| 210425_x_at | GOLGIN-67 | 23015 | AF164622.1 | FLT3 ITD |
| 212070_at | GPR56 | 9289 | AL554008 | FLT3 ITD |
| 205366_s_at | HOXB6 | 3216 | NM_018952.1 | FLT3 ITD |
| 214039_s_at | LAPTM4B | 55353 | T15777 | FLT3 ITD |
| 203897_at | LOC57149 | 57149 | BE963444 | FLT3 ITD |
| 215806_x_at | TRGC2 | 6967 | M13231.1 | FLT3 ITD |
| 209813_x_at | — | — | M16768.1 | FLT3 ITD |
| 216920_s_at | TRGC2 | 6967 | M27331.1 | FLT3 ITD |
| 206945_at | LCT | 3938 | NM_002299.1 | FLT3 ITD |
| 208029_s_at | LAPTM4B | 55353 | NM_018407.1 | FLT3 ITD |
| 215288_at | TRPC2 | 7221 | AI769824 | FLT3 ITD |
| 203373_at | SOCS2 | 8835 | NM_003877.1 | FLT3 ITD |
| 209905_at | HOXA9 | 3205 | AI246769 | FLT3 ITD |
| 215623_x_at | SMC4L1 | 10051 | AK002200.1 | FLT3 ITD |
| 211144_x_at | TRGC2 | 6967 | M30894.1 | FLT3 ITD |
| 220813_at | CYSLTR2 | 57105 | NM_020377.1 | FLT3 ITD |
| 208767_s_at | LAPTM4B | 55353 | AW149681 | FLT3 ITD |
| 205227_at | IL1RAP | 3556 | NM_002182.1 | FLT3 ITD |
| 209014_at | MAGED1 | 9500 | AF217963.1 | FLT3 ITD |
| 206341_at | IL2RA | 3559 | NM_000417.1 | FLT3 ITD |
| 205453_at | HOXB2 | 3212 | NM_002145.1 | FLT3 ITD |
| 209392_at | ENPP2 | 5168 | L35594.1 | FLT3 ITD |
| 219304_s_at | SCDGF-B | 80310 | NM_025208.1 | FLT3 ITD |
| 208798_x_at | GOLGIN-67 | 23015 | AF204231.1 | FLT3 ITD |
| 211302_s_at | PDE4B | 5142 | L20966.1 | FLT3 ITD |
| 210839_s_at | ENPP2 | 5168 | D45421.1 | FLT3 ITD |
| 205600_x_at | HOXB5 | 3215 | AI052747 | FLT3 ITD |
| 208414_s_at | HOXB4 | 3214 | NM_002146.1 | FLT3 ITD |

TABLE 39-continued

PAM genes of prognostically important clusters (#13, #12, #9, #16, #10, #4, #15, #4 and #15, and FLT3ITD)

| Probe Set ID | Gene symbol | Locus Link number | Accession number | Abnormality |
|---|---|---|---|---|
| 208797_s_at | GOLGIN-67 | 23015 | AI829170 | FLT3 ITD |
| 210123_s_at | CHRNA7 | 1139 | U62436.1 | FLT3 ITD |
| 206289_at | HOXA4 | 3201 | NM_002141.1 | FLT3 ITD |
| 201069_at | MMP2 | 4313 | NM_004530.1 | FLT3 ITD |
| 213217_at | ADCY2 | 108 | AU149572 | FLT3 ITD |
| 214651_s_at | HOXA9 | 3205 | U41813.1 | FLT3 ITD |
| 211402_x_at | NR6A1 | 2649 | AF004291.1 | FLT3 ITD |
| 204044_at | QPRT | 23475 | NM_014298.2 | FLT3 ITD |
| 204438_at | MRC1 | 4360 | NM_002438.1 | FLT3 ITD |
| 206042_x_at | SNRPN | 6638 | NM_022804.1 | FLT3 ITD |
| 214953_s_at | APP | 351 | X06989.1 | FLT3 ITD |
| 201427_s_at | SEPP1 | 6414 | NM_005410.1 | FLT3 ITD |
| 209193_at | PIM1 | 5292 | M24779.1 | FLT3 ITD |
| 219218_at | FLJ23058 | 79749 | NM_024696.1 | FLT3 ITD |
| 200923_at | LGALS3BP | 3959 | NM_005567.2 | FLT3 ITD |
| 210424_s_at | GOLGIN-67 | 23015 | AF163441.1 | FLT3 ITD |
| 219602_s_at | FLJ23403 | 63895 | NM_022068.1 | FLT3 ITD |
| 201522_x_at | SNRPN | 6638 | NM_003097.2 | FLT3 ITD |

The invention claimed is:

1. A method for determining the prognosis for an AML-affected subject, said method comprising the steps of:
   determining, in a sample obtained from the subject, a level of expression of each of at least MYH11, CLIPR-59, ST18, NRP1 and CLECSF13 from cluster #9, corresponding to the AML class of inv(16);
   establishing the similarity of expression levels between the at least MYH11, CLIPR-59, ST18, NRP1 and CLECSF13 in the AML-affected subject and the at least MYH11, CLIPR-59, ST18, NRP1 and CLECSF13 in subjects selected from the inv(16) class; and
   assigning to the AML-affected subject a prognosis based on the established similarity of expression levels between the at least MYH11, CLIPR-59, ST18, NRP1 and CLECSF13 in the AML-affected subject and the at least MYH11, CLIPR-59, ST18, NRP1 and CLECSF13 in subjects selected from the inv(16) class.

2. A method for determining the prognosis for an AML-affected subject, said method comprising the steps of:
   determining, in a sample obtained from the subject, a level of expression of each of at least HGF, FGF13, MEG3, GABRE and MST1 from cluster #12, corresponding to the AML class of t(15; 17);
   establishing the similarity of expression levels between the at least HGF, FGF13, MEG3, GABRE and MST1 in the AML-affected subject and the at least HGF, FGF13, MEG3, GABRE and MST1 in subjects selected from the t(15; 17) class; and
   assigning to the AML-affected subject a prognosis based on the established similarity of expression levels between the at least HGF, FGF13, MEG3, GABRE and MST1 in the AML-affected subject and the at least HGF, FGF13, MEG3, GABRE and MST1 in subjects selected from the t(15; 17) class.

3. A method for determining the prognosis for an AML-affected subject, said method comprising the steps of:
   determining, in a sample obtained from the subject, a level of expression of each of at least CBFA2T1, ROBO1, CACNA2D2, POU4F1 and IL5RA from cluster #13, corresponding to the AML class of t(8;21);
   establishing the similarity of expression levels between the at least CBFA2T1, ROBO1, CACNA2D2, POU4F1 and IL5RA in the AML-affected subject and the at least CBFA2T1, ROBO1, CACNA2D2, POU4F1 and IL5RA in subjects selected from the t(8;21) class; and
   assigning to the AML-affected subject a prognosis based on the established similarity of expression levels between the at least CBFA2T1, ROBO1, CACNA2D2, POU4F1 and IL5RA in the AML-affected subject and the at least CBFA2T1, ROBO1, CACNA2D2, POU4F1 and IL5RA in subjects selected from the t(8;21) class.

4. The method according to claim 2, wherein determining the level of expression is performed with a gene chip.

5. The method according to claim 2, wherein the level of expression of each of at least eight cluster-specific genes from cluster #12 is determined.

6. The method according to claim 3, wherein determining the level of expression is performed with a gene chip.

7. The method according to claim 3, wherein the level of expression of each of at least eight cluster-specific genes from cluster #13 is determined.

8. The method according to claim 1, wherein determining the level of expression is performed with a gene chip.

9. The method according to claim 1, wherein the level of expression of each of at least eight cluster-specific genes from cluster #9 is determined.

* * * * *

```
                              SEQUENCE LISTING

<160> NUMBER OF SEQ ID NOS: 10

<210> SEQ ID NO 1
<211> LENGTH: 22
<212> TYPE: DNA
<213> ORGANISM: Artificial
<220> FEATURE:
<223> OTHER INFORMATION: Primer CBFbeta

<400> SEQUENCE: 1
aagactggat ggtatgggct gt                                            22

<210> SEQ ID NO 2
<211> LENGTH: 15
<212> TYPE: DNA
<213> ORGANISM: Artificial
<220> FEATURE:
<223> OTHER INFORMATION: Primer 126REV

<400> SEQUENCE: 2
cagggcccgc ttgga                                                    15

<210> SEQ ID NO 3
<211> LENGTH: 24
<212> TYPE: DNA
<213> ORGANISM: Artificial
<220> FEATURE:
<223> OTHER INFORMATION: Probe CBFbeta 6-FAM

<400> SEQUENCE: 3
tggagtttga tgaggagcga gccc                                          24

<210> SEQ ID NO 4
<211> LENGTH: 15
<212> TYPE: DNA
<213> ORGANISM: Artificial
<220> FEATURE:
<223> OTHER INFORMATION: Primer PML3-for

<400> SEQUENCE: 4
```
ccccaggagc cccgt                                                  15

<210> SEQ ID NO 5
<211> LENGTH: 20
<212> TYPE: DNA
<213> ORGANISM: Artificial
<220> FEATURE:
<223> OTHER INFORMATION: Primer PML-kbr

<400> SEQUENCE: 5
cctgcaggac ctcagctctt                                             20

<210> SEQ ID NO 6
<211> LENGTH: 21
<212> TYPE: DNA
<213> ORGANISM: Artificial
<220> FEATURE:
<223> OTHER INFORMATION: Primer RARA4-rev

<400> SEQUENCE: 6
aaagcaaggc ttgtagatgc g                                           21

<210> SEQ ID NO 7
<211> LENGTH: 20
<212> TYPE: DNA
<213> ORGANISM: Artificial
<220> FEATURE:
<223> OTHER INFORMATION: Probe RARA 6-FAM

<400> SEQUENCE: 7
agtgcccagc cctccctcgc                                             20

<210> SEQ ID NO 8
<211> LENGTH: 24
<212> TYPE: DNA
<213> ORGANISM: Artificial
<220> FEATURE:
<223> OTHER INFORMATION: Primer 821 For

<400> SEQUENCE: 8
tcactctgac catcactgtc ttca                                        24

<210> SEQ ID NO 9
<211> LENGTH: 25
<212> TYPE: DNA
<213> ORGANISM: Artificial
<220> FEATURE:
<223> OTHER INFORMATION: Primer 821 Rev

<400> SEQUENCE: 9
attgtggagt gcttctcagt acgat                                       25

<210> SEQ ID NO 10
<211> LENGTH: 21
<212> TYPE: DNA
<213> ORGANISM: Artificial
<220> FEATURE:
<223> OTHER INFORMATION: Probe ETO 6-FAM

<400> SEQUENCE: 10
acccaccgca agtcgccacc t                                           21